US008758771B2

(12) United States Patent
Finlay et al.

(10) Patent No.: US 8,758,771 B2
(45) Date of Patent: Jun. 24, 2014

(54) BACTERIAL VIRULENCE FACTORS AND USES THEREOF

(75) Inventors: Brett Finlay, Richmond (CA); Samantha Gruenheid, Montreal (CA); Wanyin Deng, Vancouver (CA); Bruce A. Vallance, Vancouver (CA); Jose L. Puente, Cuernavaca (MX)

(73) Assignees: The University of British Columbia, Vancouver, B.C. (CA); Universidad Nacional Autonoma de Mexico, Mexico, D.F. (MM)

( * ) Notice: Subject to any disclaimer, the term of this patent is extended or adjusted under 35 U.S.C. 154(b) by 1432 days.

(21) Appl. No.: 10/577,742

(22) PCT Filed: Oct. 29, 2004

(86) PCT No.: PCT/CA2004/001891
§ 371 (c)(1),
(2), (4) Date: Jul. 19, 2006

(87) PCT Pub. No.: WO2005/042746
PCT Pub. Date: May 12, 2005

(65) Prior Publication Data
US 2007/0041997 A1 Feb. 22, 2007

Related U.S. Application Data

(60) Provisional application No. 60/515,703, filed on Oct. 31, 2003.

(51) Int. Cl.
A61K 39/00 (2006.01)
A61K 39/02 (2006.01)
C07K 1/00 (2006.01)
C07K 14/00 (2006.01)
C07K 17/00 (2006.01)

(52) U.S. Cl.
USPC .................. 424/234.1; 424/184.1; 424/185.1; 530/350

(58) Field of Classification Search
None
See application file for complete search history.

(56) References Cited

U.S. PATENT DOCUMENTS

| | | | |
|---|---|---|---|
| 4,310,550 A | | 1/1982 | Wolff, III et al. |
| 4,708,871 A | | 11/1987 | Geysen |
| 4,744,984 A | | 5/1988 | Ragland |
| 5,151,267 A | | 9/1992 | Babiuk et al. |
| 5,370,989 A | * | 12/1994 | Stern et al. .................. 435/1.2 |
| 5,750,113 A | | 5/1998 | Cook |
| 5,951,988 A | | 9/1999 | Littel-van den Hurk et al. |
| 6,136,554 A | | 10/2000 | Bochner |
| 6,165,743 A | | 12/2000 | Rambach |
| 6,355,254 B1 | | 3/2002 | Finlay et al. |
| 6,365,723 B1 | | 4/2002 | Blattner et al. |
| 6,730,822 B1 | | 5/2004 | Ivarie et al. |
| 7,208,574 B1 | | 4/2007 | Finlay et al. |
| 7,531,315 B2 | | 5/2009 | Finlay et al. |
| 7,759,462 B2 | | 7/2010 | Finlay et al. |
| 8,586,057 B2 | | 11/2013 | Finlay et al. |
| 2002/0132788 A1 | | 9/2002 | Lewis et al. |
| 2002/0173478 A1 | | 11/2002 | Gewirtz |
| 2004/0180060 A1 | * | 9/2004 | Li et al. ................ 424/184.1 |
| 2007/0218518 A1 | | 9/2007 | Finlay et al. |
| 2009/0068230 A1 | | 3/2009 | Finlay et al. |

FOREIGN PATENT DOCUMENTS

| | | |
|---|---|---|
| JP | 2002355074 A2 | 12/2002 |
| JP | 2007-531511 A | 11/2007 |
| JP | 5100122 B2 | 10/2012 |
| WO | WO 97/40063 | 10/1997 |
| WO | WO 99/24576 | 5/1999 |
| WO | WO 02/053181 | 7/2002 |
| WO | WO 2005/042746 A1 | 5/2005 |

OTHER PUBLICATIONS

Horne et al. Expert Rev. Vaccines 1 (4), 483-493 (2002).*
Abbas et al. Cellular and Molecular Immunology 2000 Chapter 15 p. 360-362.*
Ellis, R.W. (Chapter 29 of "Vaccines" [Plotkin, S.A. et al. (eds) published by W. B. Saunders company (Philadelphia) in 1988.*
Colman et al (Research in Immunology 145: 33-36, 1994.*
Houghten et al. (New Approaches to Immunization, Vaccines 86, Cold Spring Harbor Laboratory, p. 21-25, 1986.*
Dziva et al. Veterinary Microbiology, 2007, 123:254-261.*
Van Diemen et al (Vet Immunol Immunopathol. Mar. 15, 2007; 116(1-2):47-58.*
Potter et al. Vaccine( 2004) 22:362-369.*
Felgner, Philip L., "Particulate systems and polymers for in vitro and in vivo delivery of polynucleotides," Advanced Drug Delivery Reviews, 1990, 5(3), pp. 163-187.
Van Dalen, F., et al., "Preparation and Characterization of Liposomes with Incorporated *Neisseria gonorrhoeae* Protein IB and Amphiphilic Adjuvants," Journal of Controlled Release, 1988, pp. 123-132, vol. 7.
Prager, M., Kodak Laboratory Chemicals Bulletin, 1986, 56(1), p. 1-5.
Abe, A. et al., "Enterpathogenic *Escherichia coli* traslocated intimin receptor, Tir, requires a specific chaperone for stable secretion," Mol. Microbiol., 1999, 33(6), p. 1162-1175.
Abe, A. et al., "Two enteropathogenic *Escherichia coli*, type III secreted proteins, EspA and EspB, are virulence factors," Journal of Experimental Medicine, 1998, 188, pp. 1907-1916.
Altschul, S.F., "Amino acid substitution matrices from an information theoretic perspective," Journal of Molecular Biology, 1991, 219, pp. 555-665.

(Continued)

Primary Examiner — Oluwatosin Ogunbiyi
(74) Attorney, Agent, or Firm — Fenwick & West LLP

(57) ABSTRACT

The invention relates to, in part, secreted proteins of bacterial pathogens and methods for their use. More specifically, the invention provides in part several new common secreted proteins for A/E pathogens. In some embodiments of the invention, these polypeptides and nucleic acid molecules encoding these polypeptides, or portions thereof, are useful as vaccines, diagnostics, or drug screening tools for A/E pathogenic infections, or as reagents.

17 Claims, 37 Drawing Sheets

(56) References Cited

OTHER PUBLICATIONS

Alymova, IV et al., "Immunogenicity and protective efficacy in mice of influenza B virus vaccines grown in mammalian cells or embyonated chicken eggs," J. Virol., 1998, vol. 72, No. 5, pp. 4472-4477.
Babiuk et al., "Protection of Cattle from Bovine Herpesvirus Type I (BHV-1) Infection by Immunization with Individual Viral Glycoprotiens," Virology, 1986, vol. 159, pp. 57-66.
Beuzon, C.R. et al., "Use of mixed infections with Salmonella strains to study virulence genes and their interactions in vivo," Microbes and Infection, 2001, vol. 3, pp. 1345-1352.
Brown, D., et al., "RNA Interference in Mammalian Cell Culture: Design, Execution and Analysis of the siRNA Effect," Ambion, The RNA Company, [online] retrieved from the internet on Sep. 26, 2007, 7 pages, Retrieved from Biocompare, The Buyer's Guide for Life Scientists, Technical Articles.
Brunder, W., et al., "EspP, a novel extracellular serine protease of enterohaemorrhagic Escherichia coli O157:H7 cleaves human coagulation factor V," Molecular Microbiology, 1997, pp. 767-778, vol. 24, No. 4.
Buchet, A., et al., "Positive co-regulation of the Escherichia coli carnitine pathway cai and fix operons by CRP and the CaiF activator," Molecular Microbiology, 1999, pp. 562-575, vol. 34, No. 3.
Buchrieser, C., et al., "The virulence plasmid pWR100 and the repertoire of proteins secreted by the type III secretion apparatus of Shigella flexneri," Molecular Microbiology, 2000, pp. 760-771, vol. 38(4).
Bustamante, V. H., et al., "Transcriptional regulation of type III secretion genes in enteropathogenic Escherichia coli: Ler antagonizes H-NS-dependent repression," Molecular Microbiology, 2001, pp. 664-678, vol. 39, No. 3.
Canil, C., et al., "Enteropathogenic Escherichia coli Decreases the Transepithelial Electrical Resistance of Polarized Epithelial Monolayers," Infection and Immunity, Jul. 1993, pp. 2755-2762, vol. 61, No. 7.
Celli, J., et al., "Enteropathogenic Escherichia coli mediates antiphagocytosis through the inhibition of PI 3-kinase-dependent pathways," The EMBO Journal, 2001, pp. 1245-1258, vol. 20, No. 6.
Chardin, P., et al., "Brefeldin A: The Advantage of Being Uncompetitive," Cell, Apr. 16, 1999, pp. 153-155, vol. 97.
Chernushevich, I. V., et al., "An introduction to quadrupole—time-of-flight mass spectrometry," Journal of Mass Spectrometry, 2001, pp. 849-865, vol. 36.
Clin. Exp. Immunol., 1989, 78(2), 256-262.
Cornelis, G. R., "Yersinia type III secretion: send in the effectors," The Journal of Cell Biology, Aug. 5, 2002, pp. 401-408, vol. 158, No. 3.
Dayhoff, M.O. et al., "A model of evolutionary change in proteins," Atlas of Protein Sequence and Structure, Dayhoff, M.O. (ed.), 1978, 5(3), pp. 345-352, National Biomedical Research Foundation, Washington.
Deng, W. et al., "Citrobacter rodentium translocated intimin receptor (Tir) is an essential virulence factor needed for actin condensation, intestinal colonization and colonic hyperplasia in mice," Mol. Microbiol., 2003, 48, pp. 95-115.
Deng, W. et al., "Dissecting virulence: Systematic and functional analyses of a pathogenicity island," PNAS, Mar. 2004, 101(10), pp. 3597-3602.
Deng, W. et al., "Locus of enterocyte effacement form Citrobacter rodentium: sequence analysis and evidence for horizontal transfer among attaching and effacing pathogens," Infect. Immun., 2001, 69(10), pp. 6323-6335.
Devinney, R. et al., "Enterohemorrhagic Escherichia coli O157:H7 produces Tir, which is translocated to the host cell membrane but is not tyrosine phosphorylated," Infect. Immun., 1999, 67(5), pp. 2389-2398.
Donnenberg, M.S. et al., "Construction of an eae deletion mutant of enteropathogenic Escherichia coli by using a positive-selection suicide vector," Infect. Immun., 1991, 59(12), pp. 4310-4317.
Edwards, R.A. et al., "Improved allelic exchange vectors and their use to analyze 987P fimbria gene expression," Gene, 1998, 207, pp. 149-157.
Esignberg, D. et al., "Analysis of membrane and surface protein sequences with the hydrophobic moment plot", J. Mol. Bio., Oct. 15, 1984 179(1), pp. 125-142, 184.
Elder, R.O. et al., "Correlation of enterohemorrhagic Escherichia coli O157 prevalence in feces, hides, and carcasses of beef cattle during processing", Proc. Natl. Acad. Sci. USA, Mar. 28, 2000, 97(7), pp. 2999-3003.
Elliot, S. J., et al., Identification of CesT, a chaperone for the type III secretion of Tir in enteropathogenic Escherichia coli, Molecular Microbiology, 1999, pp. 1176-1189, vol. 33, No. 6.
Elliot, S. J., et al., "EspG, a Novel Type III System-Secreted Protein from Enteropathogenic Escherichia coli with Similarities to VirA of Shigella flexneri," Infection and Immunity, Jun. 2001, pp. 4027-4033, vol. 69, No. 6.
Elliot, S. J., et al., "The complete sequence of the locus of enterocyte effacement (LEE) from enteropathogenic Escherichia coli E2348/69," Molecular Microbiology, 1998, pp. 1-4, vol. 28, No. 1.
Fey, P. D., et al., "Prevalence of Non-O157:PH7 Shiga Toxin-Producing Escherichia coli in Diarrheal Stool Samples from Nebraska," Emerging Infectious Diseases, Sep.-Oct. 2000, pp. 530-533, vol. 6, No. 5.
Frankel, G., et al., Enteropathogenic and enterohaemorrhagic Escherichia coli: more subversive elements, Molecular Microbiology, 1998, pp. 911-921, vol. 30, No. 5.
Galán, J. E., "Salmonella Interactions with Host Cells: Type III Secretion at Work," Annual Review of Cell Developmental Biology, 2001, pp. 53-86, vol. 17.
Gall, D., "The Adjuvant Activity of Aliphatic Nitrogenous Bases," Immunology, 1996, pp. 369-386, vol. 11.
Gauthier, A., et al., "Mechanical Fractionation Reveals Structural Requirements for Enteropathogenic Escherichia coli Tir Insertion into Host Membranes," Infection and Immunity, Jul. 2000, pp. 4344-4348, vol. 68, No. 7.
Goosney, D. L., et al., "Recruitment of Cytoskeletal and Signaling Proteins to Enteropathogenic and Enterohemorrhagic Escherichia coli pedestals," Infection and Immunity, May 2001, pp. 3315-3322, vol. 69, No. 5.
Griffin, P. M., et al., "Illness Associated with Escherichia coli O157:H7 Infections," Annals of Internal Medicine, Nov. 1988, pp. 705-712, vol. 109.
Gruenheid, S., et al., "Enteropathogenic E. coli Tir binds Nck to initiate actin pedestal formation in host cells," Nature Cell Biology, Sep. 2001, pp. 856-859, vol. 3.
Gruenheid, S., et al., "Identification and characterization of NleA, a non-Lee-encoded type III translocated virulence factor of enterohaemorrhagic Escherichia coli O157:H7," Molecular Microbiology, 2004, pp. 1233-1249, vol. 51, No. 5.
Gruenheid, S., et al., "Microbial pathogenesis and cytoskeletal function," Nature, 2003, pp. 775-781, vol. 422.
Guttman, D. S., et al., "A Functional Screen for the Type III (Hrp) Secretome of the Plant Pathogen Pseudomonas syrangae," Science, Mar. 1, 2002, pp. 1722-1726, vol. 295.
Hacker, J., et al. "Pathogenicity Islands and the Evolution of Microbes," Annual Review Microbiology, 2000, pp. 641-679, vol. 54.
Hammond, S. M., et al., "Post-Transcriptional Gene Silencing by Double-Stranded RNA," Nature Reviews, Genetics, Feb. 2001, pp. 110-119, vol. 2.
Hauf, N., et al., "Suppression of NF-κB Activation and Proinflammatory Cytokine Expression by Shiga Toxin-Producing Escherichia coli," The Journal of Immunology, 2003, pp. 2074-2082, vol. 170.
Henikoff, S., et al., "Performance Evaluation of Amino Acid Substitution Matrices," Proteins: Structure, Function and Genetics, 1993, pp. 49-61, vol. 17.
Henikoff, S., et al., "Amino acid substitution matrices from protein blocks," Proceedings of the National Academy of Sciences USA, Biochemistry, Nov. 1992, pp. 10915-10919, vol. 89.
Houthaeve, T. et al., "Automation of micro-preparation and enzymatic cleavage of gel electrophoretically separated proteins", FEBS Lett., 1995, 376, pp. 91-94.

(56) References Cited

OTHER PUBLICATIONS

Hsiao, W. et al., "IslandPath: aiding detection of genomic islands in prokaryotes," Bioinformatics, 2003, 19, pp. 418-420.
Hueck, C.J., "Type III protein secretion systems in bacterial pathogens of animals and plants," Microbiol. Mol. Biol. Rev., 1998, 62, 379-433.
Jarvis, K.G. et al., "Secretion of extracellular proteins by enterohemorrhagic *Escherichia coli* via a putative type III secretion system," Infect. Immun., 1996, 64, pp. 4826-4829.
Johnson, M.S. et al., "A Structural Basis of Sequence Comparisons: An evaluation of scoring methodologies," Journal of Molecular Biology, 1993, 233, pp. 716-738.
Kenny, B. et al., "Co-ordinate regulation of distinct host cell signaling pathways by multifunctional enteropathogenic *Escherichia coli* effector molecules," Mol. Microbiol., 2002, 44, pp. 1095-1107.
Kenny, B. et al., "Enteropathogenic *E. coli* (EPEC) transfers its receptor for intimate adherence into mammalian cells," Cell, 1997, 91, pp. 511-520.
Kenny, B. et al., "Targeting of an enteropathogenic *Escherichia coli* (EPEC) effector protein to host mitochondria," Cell Microbiol., 2000, 2, pp. 579-590.
Knodler, L.A. et al., "*Salmonella* effectors within a single pathogenicity island are differentially expressed and translocated by separate type III secretion systems," Mol. Microbiol., 2002, 43, pp. 1089-1103.
Knodler, L.A. et al., "*Salmonella* type III effectors PipB and PipB2 are targeted to detergent-resistant microdomains on internal host cell membranes," Mol. Microbiol., 2003, 49, pp. 685-704.
Kohler, G. et al., "Continuous cultures of fused cells secreting antibody of predefined specificity", Nature, 1975, 256(5517), pp. 495-497.
Kohler, G. et al., "Derivation of specific antibody-producing tissue culture and tumor lines by cell fusion", Eur. J. Immunol., 1976, 6(7), pp. 511-519.
Kohler, G. et al., "Fusion between immunoglobulin-secreting and nonsecreting myeloma cell lines", Eur. J. Immunol., 1976, 6(4), pp. 292-295.
Kresse, A.U. et al., "Characterization of SepL of Enterohemorrhagic *Escherichia coli*," J of Bacteriology, Nov. 2000, 182(22), pp. 6490-6498.
Kyte, J. et al., "A simple method for displaying the hydropathic character of a protein", J. Mol. Biol., 1982, 157(1), pp. 105-132.
Larsson, A. et al., "Chicken antibodies: taking advantage of evolution—a review," Poult Sci., 1993, 72(10), pp. 1807-1812.
Lee, N.S. et al., "Expression of small interfering RNAs targeted against HIV-1 rev transcripts in human cells", Nature Biotechnol., 2002, 20(5), pp. 500-505.
Levine, M.M. et al., "*Escherichia coli* strains that cause diarrhoea but do not produce heat-labile or heat-stable enterotoxins and are non-invasive," Lancet, 1978, 1, pp. 1119-1122.
Li, Y. et al., "Human response to *Escherichia coli* O157:H7 Infection: Antibodies to Secreted Virulence Factors," Infection and Immunity, Sep. 2000, 68(9), pp. 5090-5095.
Limpens, J. and Scheper, RJ, "Synergistic effects of locally administered cytostatic drugs and a surfactant on the development of delayed-type hypersensitivity to keyhole limpet haemocyanin in mice", Clin. Exp. Immunol., 1989, 78(2), pp. 256-262.
Marches, O. et al., "Enteropathogenic and enterohaemorrhagic *Escherichia coli* deliver a novel effector called Cif, which blocks cell cycle G2/M transition," Mol. Microbiol., Dec. 2003, 50(5), pp. 1553-1567.
Marches, O. et al., "Role of tir and intimin in the virulence of rabbit enteropathogenic *Escherichia coli* serotype O103:H2", Infect. Immun., 2000, 68(4), pp. 2171-2182.
McNamara, B.P. et al., "Translocated EspF protein from enteropathogenic *Escherichia coli* disrupts host intestinal barrier function," J. Clin. Invest., 2001, 107, pp. 621-629.
Mellies, J.L. et al., "Identification of CesT, a chaperone for the type III secretion of Tir in enteropathogenic *Escherichia coli*", Mol. Microbiol., 1999, 33(6), pp. 1176-1189.

Miller, S.I. et al., "A two-component regulatory system (phoP phoQ) controls *Salmonella* typhimurium virulence", Proc. Natl. Acad. Sci. USA, 1989, 86(13), pp. 5054-5058.
Miyagishi, M. et al., "U6 promoter-driven siRNAs with four uridine 3' overhangs efficiently suppress targeted gene expression in mammalian cells", Nature Biotechnol., 2002, 20(5), pp. 497-500.
Mundy, R. et al., "Identification of a Novel Citrobacter rodentium Type III Secreted Protein, EspI, and Roles of this and Other Secreted Proteins in Infection," Infect. Immun., Apr. 2004, 72(4), pp. 2288-2302.
Myers, E.W. et al., "Optimal alignments in linear space", CABIOS, 1988, 4(1), pp. 11-17.
Nataro, J.P. et al., "Diarrheagenic *Escherichia coli*," Clin Microbiol. Rev., 1998, 11, pp. 142-201.
Naylor, S.W. et al., "Lymphoid follicle-desne mucosa at the terminal rectum is the prinispal site of colonization of enterhemorrhagic *Escherichia coli* O157:H7 in the bovine host," Infect. Immun., 2003, 71, pp. 1505-1512.
O'Farrelly, C. et al., "Oral ingestion of egg yolk immunogloculin from hens immunized with an enterotoxigenic *Escherichia coli* strain prevents diarrhea in rabbits challenged with the same strain," Infect. Immun., 1992, 60(7), pp. 2593-2597.
Paddison, P.J. et al., "Short hairpin RNAs (shRNAs) induce sequence-specific silencing in mammalian cells", Genes & Dev., 2002, 16(8), pp. 948-958.
Paul, C.P. et al., "Effective expression of small interfering RNA in human cells", Nature Biotechnol., 2002, 20(5), pp. 505-508.
Peeters, J.E. et al., "Biotype, serotype, and pathogenicity of attaching and effacing enteropathogenic *Escherichia coli* strains isolated from diarrheic commercial rabbits," Infect. Immun., 1988, 56, pp. 1442-1448.
Perna, N.T. et al., "Genome Sequence of enterohaemorrhagic *Escherichia coli* O157:H7," Nature, 2001, 409, pp. 529-533.
Perna, N.T. et al., "Molecular evolution of a pathogenicity island from enterohemorrhagic *Escherichia coli* O157:H7," Infect. Immun., 1998, 66, pp. 3810-3817.
Petnicki-Ocwieja, T. et al., "Genomewide identification of proteins secreted by the Hrp type III protein secretion system of *Pseudomonas syringae* pv. tomato DC3000", Proc. Natl. Acad. Sci. USA, 2002, 99(11), pp. 7652-7657.
Puente, J.L. et al., "The bundle-forming pili of enteropathogenic *Escherichia coli*: transcriptional regulation by environmental signals", Mol. Microbiol., 1996, 20(1), pp. 87-100.
Romito, M. et al., "Eliciting antigen-specific egg-yold IgY with naked DNA," Biotechniques, 2001, 31(3), pp. 670,672,674-675.
Schauer, D.B. et al., "The eae gene of Ctrobacter freudii biotype 4280 is necessary for colonization in transmissible murine colonic hyperplasia," Infect. Immun., 1993, 61, pp. 4654-4661.
Schijns, V.E. et al., "Immunological concepts of vaccine adjuvant activity", Curr. Opi. Immunol., 2000, 12(4), pp. 456-463.
Sharp, P.A., "RNA interference—2001", Genes Dev., 2001, 15(5), pp. 485-490.
Smith, R.H. et al., Cyclophosphamide and dimethyl dioctadecyl ammonium bromide immunopotentiate the delayed-type hypersensitivity response to inactivated enveloped viruses, Immunology, 1986, 58(2), pp. 245-250.
Snippe, H. et al., "Adjuvanticity of dimethyl dioctadecyl ammonium bromide in guinea pigs. I. Skin test reactions", Int. Arch. Allergy Appl. Immunol., 1982, 68(3), pp. 201-208.
Sperandio, V. et al., "Quorum sensing controls expression of the type III secretion gene transcription and protein secretion in enterohemorrhagic and enteropathogenic *Escherichia coli*", Proc. Natl. Acad. Sci. USA, 1999, 96(26), pp. 15196-15201.
States, D.J. et al., "Improved Sensitivity of Nucleic Acid Databse Search Using Application-Specific Scoring Matrices," Methods: A Companion to Methods in Enzymology, 1991, 3(1), pp. 66-77.
Tauschek, M. et al., "Characterization and evidence of mobilization of the LEE pathogenicity island of rabbit-specific strains of enteropathogenic *Escherichia coli*," Mol. Microbiol., 2002, 44, pp. 1533-1550.
Tu, X. et al., "EspH, a new cytoskeleton-modulating effector of enterohaemorrhagic and enteropathogenic *Escherichia coli*," Mol. Microbiol., 2003, 47, pp. 595-606.

(56) References Cited

OTHER PUBLICATIONS

Vallance, B.A. et al., "Host susceptibility to the attaching and effacing bacterial pathogen Citrobacter rodentium," Infect. Immun., 2003, 71, pp. 3443-3453.

Vallance, B.A. et al., "Mice lacking T and B lymphocytes develop transient colitis and crypt hyperplasia yet suffer impaired bacterial clearance during Citrobacter rodentium infectio," Infect. Immun., 2002, 70, pp. 2070-2081.

Vallance, B.A. et al., "Modulation of inducible nitric oxide synthase expression by the attaching and effacing bacterial pathogen citrobacter rodentium in infected mice," Infect. Immun., 2002, 70, pp. 6424-6435.

Van Donkersgoed, J. et al., "Environmental sources and transmission of *Escherichia coli* O157 in feedlot cattle", Can Vet. J., 2001, 42(9), pp. 714-720.

Van Donkersgoed, J. et al., "The prevalence of verotoxins, *Escherichia coli* O157:H7, and *Salmonella* in the feces and rumen of cattle at processing", Can Vet. J., 1999, 40(5), pp. 332-338.

Vaughan, T.J. et al., "Human antibodies with sub-nanomolar affinities isolated from a large non-immunized phage display library", Nature Biotech, 1996, 14(3), pp. 309-314.

Yokoyama, H. et al., "Oral passive immunization against experimental salmonellosis in mice using chicken egg yolk antibodies specific for *Salmonella* enteritidis and S. typhimurium,"Vaccine, 1998, 16(4), pp. 388-393.

Yoshida, S. et al., "Shigella deliver an effector protein to trigger host microtubule destabilization, which promotes Rac1 activity and efficient bacterial internalization," Embo J., 2002, 21, pp. 2923-2935.

Yu, J.Y. et al., "RNA interference by expression of short-interfering RNAs and hairpin RNAs in mammalian cells", Proc. Natl. Acad. Sci. USA, 2002, 99(9), pp. 6047-6052.

Zhu, C. et al., "Complete nucleotide sequence and analysis of the locus of enterocyte Effacement from rabbit diarrheagenic *Escherichia coli* RDEC-1," Infect Immun., 2001, 69, pp. 2107-2115.

Ziegler, Z., "Ion traps come of age", Anal. Chem., 2002, 74(17), pp. 489A-492A.

Ziola, B. et al., "In vitro proliferation of lymphocytes from cyclophosphamide-pretreated mice immunized with antigen mixed with dimethyl dioctadecyl ammonium bromide", J. Immunol. Methods, 1987, 97(2), pp. 159-164.

Hypothetical protein Z6024 UniProt/TrEMBL, database Mar. 1, 2002 accession No. Q8XAJ5.

Sui, G., et al., "A DNA vector-based RNAI technology to suppress gene expression in mammalian cells," PNAS, Apr. 16, 2002, pp. 5515-5520, vol. 99, No. 8.

Karlin, S., et al., "Methods for assessing the statistical significance of molecular sequence features by using general scoring schemes," PNAS, Mar. 1990, pp. 2264-2268, vol. 87.

Hopp, T., et al., "Prediction of protein antigenic determinants from amino acid sequences," PNAS, Jun. 1981, pp. 3824-3828, vol. 78, No. 6.

Geysen, H., et al., "A Priori Delineation of a Peptide which Mimics a Discontinuous Antigenic Determinant," Molecular Immunology, 1986, pp. 709-715, vol. 23, No. 23.

Geysen, H., et al., "Use of peptide synthesis to probe viral antigens for epitopes to a resolution of a single amino acid," PNAS, Jul. 1984, pp. 3998-4002, vol. 81.

Caplen, N., et al., "Specific inhibition of gene espression by small double-stranded RNAs in invertebrate and vertebrate systems," PNAS, Aug. 14, 2001, pp. 9742-9747, vol. 98, No. 17.

Brummelkamp, T., et al., "A System for Stable Expression of Short Interfering RNAs in Mammalian Cells," Science, Apr. 19, 2002, vol. 296.

*Escherichia coli*, Accession No. AF071034, NCBI Sequence Viewer, Aug. 13, 1998, 24 pages.

*Escherichia coli*, Accession No. AE005174, NCBI Sequence Viewer, Jan. 27, 2005, 3 pages.

*Escherichia coli*, Accession No. NC002655, NCBI Sequence Viewer, Jul. 19, 2006, 2005, 2 pages.

*Escherichia coli*, Accession No. NC002695, NCBI Sequence Viewer, May 23, 2006, 2 pages.

*Escherichia coli*, Accession No. AE005594, NCBI Sequence Viewer, Mar. 21, 2001, 9 pages.

*Escherichia coli*, Accession No. AE005595, NCBI Sequence Viewer, Mar. 21, 2001, 7 pages.

*Escherichia coli*, Accession No. AP002566, NCBI Sequence Viewer, Mar. 20, 2004, 158 pages.

PCT International Search Report, PCT/CA2004/001891, Mar. 7, 2005, 4 pages.

PCT Written Opinion, PCT/CA2004/001891, Mar. 7, 2005, 8 pages.

Rankin, S. et al., "Macrophage-Induced Genes of *Legionella pneumophila*: Protection from Reactive Intermediates and Solute Imbalance During Intracellular Growth," Infection and Immunity, Jul. 2002, pp. 3637-3648, vol. 70, No. 7.

Tanaka, M. et al., "Quinolone Resistance Mutations in the GrlB Protein of *Staphylococcus aureus*," Antimicrobial Agents and Chemotherapy, 1998, pp. 3044-3046, vol. 42, No. 11.

United States Office Action, U.S. Appl. No. 13/182,334, May 22, 2012, 13 pages.

Australian Office Action, Australian Application No. 2011201889, Dec. 8, 2011, 3 pages.

Australian Office Action, Australian Application No. 2004286002, May 1, 2009, 3 pages.

Canadian Office Action, Requisition—Sequence Listing, Canadian Application No. 2,543,763, Nov. 28, 2013, 1 page.

Canadian Office Action, Canadian Application No. 2,543,763, Oct. 18, 2012, 4 pages.

Chinese First Office Action, Chinese Application No. 200910206659.1, Jan. 18, 2012, 17 pages.

Chinese Second Office Action, Chinese Application No. 200910206659.1, Oct. 19, 2012, 10 pages.

Chinese Third Office Action, Chinese Application No. 200910206659.1, Apr. 2, 2013, 9 pages.

Chinese First Office Action, Chinese Application No. 200480039568.9, Apr. 18, 2008, 18 pages.

Chinese Second Office Action, Chinese Application No. 200480039568.9, Dec. 12, 2008, 19 pages.

Chinese Third Office Action, Chinese Application No. 200480039568.9, Jun. 12, 2009, 5 pages.

Colombian Office Action, Colombian Application No. 06-052194, May 10, 2011, 1 page.

Colombian Office Action, Colombian Application No. 06-52194A, Aug. 24, 2012, 6 pages.

Colombian Office Action, Colombian Application No. 06-52194A, Feb. 29, 2012, 4 pages.

Elliott, S.J. et al., "The Locus of Enterocyte Effacement (LEE)-Encoded Regulator Controls Expression of Both LEE- and Non-LEE-Encoded Virulence Factors in Enteropathogenic and Enterohemorrhagic *Escherichia coli*," Infection and Immunity, Nov. 2000, pp. 6115-6126, vol. 68, No. 11.

European Examination Report, European Application No. 11175692.0, Jun. 18, 2012, 1 page.

European Extended Search Report, European Application No. 11184778.6, May 10, 2012, 12 pages.

European Examination Report, European Application No. 11184778.6, Feb. 25, 2013, 4 pages.

European Extended Search Report, European Application No. 11175692.0, Sep. 30, 2011, 7 pages.

European Supplementary Search Report, European Application No. 04789798.8, Feb. 28, 2007, 3 pages.

European Examination Report, European Application No. 04789798.8, Oct. 2, 2009, 4 pages.

European Examination Report, European Application No. 04789798.8, Apr. 29, 2011, 5 pages.

European Examination Report, European Application No. 04789798, Nov. 10, 2011, 4 pages.

GenBank Accession No. AAQ75736.1 (Mar. 24, 2004), NCBI Sequence Viewer v2.0, 5 pages, [online] [Retrieved on Dec. 17, 2013] Retrieved from the Internet at <URL: http://www.ncbi.nlm.nih.gov//protein/AAQ75736.1>.

(56) References Cited

OTHER PUBLICATIONS

Ghaem-Maghami, M. et al., "Intimin-Specific Immune Responses Prevent Bacterial Colonization by the Attaching-Effacing Pathogen Citrobacter rodentium," Infection and Immunity, Sep. 2001, pp. 5597-5605, vol. 69, No. 9.

Indian Notice of Hearing, Indian Application No. 2984/DELNP/2006, Jan. 10, 2012, 2 pages.

Indian Office Action, Indian Application No. 2984/DELNP/2006, Jul. 16, 2010, 3 pages.

Japanese Office Action, Japanese Application No. 2011-152074, Jan. 15, 2013, 9 pages.

Japanese Office Action, Japanese Application No. 2011-152074, May 14, 2013, 15 pages.

Japanese Office Action, Japanese Application No. 2006-537022, Aug. 24, 2010, 11 pages.

Japanese Office Action, Japanese Application No. 2006-537022, Feb. 8, 2011, 9 pages.

Japanese Office Action, Japanese Application No. 2006-537022, Apr. 3, 2012, 10 pages.

Kelly, M. et al., "Essential Role of the Type III Secretion System Effector NleB in Colonization of Mice by Citrobacter Rodentium," Infection and Immunity, Apr. 2006, pp. 2328-2337, vol. 74, No. 4.

Korean Office Action, Korean Application No. 10-2006-7010661, Jun. 20, 2011, 8 pages.

Korean Office Action, Korean Application No. 10-2006-7010661, Feb. 22, 2012, 6 pages.

Korean Office Action, Korean Application No. 10-2006-7010661, Nov. 20, 2013, 5 pages.

Korean Office Action, Korean Application No. 10-2013-7001391, May 1, 2013, 10 pages.

Korean Office Action, Korean Application No. 10-2011-7019259, Dec. 9, 2011, 7 pages.

Korean Office Action, Korean Application No. 10-2011-7019259, May 24, 2013, 5 pages.

Korean Office Action, Korean Application No. 10-2011-7019259, Jul. 25, 2012, 1 page.

Mexican Office Action, Mexican Application No. PA/a/2006/004858, Jun. 16, 2011, 3 pages.

Reece, S. et al., "Mutagenesis of Conserved Tryptophan Residues Within the Receptor-Binding Domain of Intimin: Influence on Binding Activity and Virulence," Microbiology, 2002, pp. 657-665, vol. 148, No. 3.

Russian Office Action, Russian Application No. 2010106639/10(009346), Jul. 22, 2011, 2 pages.

\* cited by examiner

*Citrobacter rodentium* NleA DNA Sequence

ATGAACATTCAACCGAACATACATTCCGGAATCACCACACAGAATAATCAACAACATCATCACGCAGAA
CAAGTGCCTGTCTCTAGCTCAATACCGCGATCAGATTTACCTCCAAATTGCGAAGCTGGATTTGTTGTG
CATATTCCAGAGGATATACAGCAACATGTACCGGAATGTGGTGAAACAACGGCTCTATTAAGCTTGATA
AAAGATGAAGGCCTGCTCTCAGGACTAGATAAATATCTTGCTCCTCACCTTGAAGAAGGCTCCCTTGGG
AAAAAAGCATTGGATACGTTTGGTTTATTCAATGTTACTCAAATGGCATTAGAGATACCCAGTTCCGTT
CCAGGCATATCTGGTAAATATGGTGTTCAGATGAACATTGTAAAACCAGACATACATCCAACAACCGGG
AACTATTTTTTACAGCTATTTCCTCTGCATGACGAAATAGGTTTTAACTTCAAAGATCTTCCTGGCCCA
TTAAAAAATGCATTAACCAACAGCAGTATATCGGCTACTGCATCGACTGTAGCCCCCACACCAAACGAC
CCAATGCCATGGTTTGGATTAACTGCTCAAGTGGTTCGTAATCATGGTGTAGAACTTCCTATAGTCAAA
ACCGAAAATGGATGGAAGCTTGTAGGGGAAACACCTCTTACTCCAGATGGCCCCAAAGCCAATTATACG
GAAGAATGGGTTATCAGGCCGGGAGAAGCAGATTTTAAATATGGAACATCGCCATTACAGGCAACTCTT
GGACTGGAGTTTGGTGCGCATTTTAAGTGGGATTTAGATAATCCTAATACCAAATATGCCATCCTTACC
AATGCTGCCGCAAATGCTATTGGTGCTGCTGGAGGGTTTGCGGTATCCAAAGTCCCCGGCATAGATCCA
ATGCTGTCCCCTCATGTCGGTGCAATGCTTGGGCAAGCAGCGGGGCATGCCGTACAATGTAATACCCCC
GGATTAAAGCCAGACACTATTTTATGGTGGGCAGGCGCGACATTTGGAGCTGCTGATTTAAATAAAGCC
GAATTTGATAAAGTGCGGTTCACTGACTACCCTCGTATATGGTTCCATGCACGGGAAGGAGCTTTATTC
CCAAATAAGCAAGACATTGCCCGTGTAACAGGCGCAGACATAAAAGCTATGGAAGAAGGCGTACCCGTT
GGACATCAACATCCAAAACCGGAGGATGTGGTCATCGATATCGAAGGTGGCAATTCACCACATCATAAT
CCATCAAATTATGTTGACACCTTTGAAATAATCCAAGAAACAAGGGTCTAA (SEQ ID NO:1)

FIG. 1A

*Citrobacter rodentium* NleA Protein Sequence

MNIQPNIHSGITTQNNQQHHHAEQVPVSSSIPRSDLPPNCEAGFVVHIPEDIQQHVPECGETTALLSLI
KDEGLLSGLDKYLAPHLEEGSLGKKALDTFGLFNVTQMALEIPSSVPGISGKYGVQMNIVKPDIHPTTG
NYFLQLFPLHDEIGFNFKDLPGPLKNALTNSSISATASTVAPTPNDPMPWFGLTAQVVRNHGVELPIVK
TENGWKLVGETPLTPDGPKANYTEEWVIRPGEADFKYGTSPLQATLGLEFGAHFKWDLDNPNTKYAILT
NAAANAIGAAGGFAVSKVPGIDPMLSPHVGAMLGQAAGHAVQCNTPGLKPDTILWWAGATFGAADLNKA
EFDKVRFTDYPRIWFHAREGALFPNKQDIARVTGADIKAMEEGVPVGHQHPKPEDVVIDIEGGNSPHHN
PSNYVDTFEIIQETRV (SEQ ID NO:22)

FIG. 1B

Enteropathogenic *E. coli* NleA DNA Sequence atgaacattcaaccgatcgtaacatccggaatcaccacacaaaacaatcgacatcatcacgcagaacaa
acgtcccctacacaaataccgcaatccgaattacctaatggatgcgaaacgggatttgttgttcatatc
ccagaggatatgcagcgacatgcaccggaatgcggtgaaacaacagctctactgagcttgataaaagat
gaaggtctgctctctgggctggataaatatcttgcacctcatcttgaagaaggctctgcaggaaaaaaa
gcattggatatgtttggtttattcaatgtctctcagatggcattagaaatacccagcaccgttccgggt
atctctggtaaatatggtgtccagctaaacattgtaaaaccagatattcatcctacatcaggtaattat
tttttacagatattccctttgcatgatgaaataggtattaattttaaagaccttcctggtccattaaaa
aatgcattaagcaacagcaatataccaaccactgtatcgactgctgcatccactattgcatcagccact
acttcgacggtaaccaccgcgtcaaaagacccaataccatggtttggattaacagctcaagtagttcgt
aatcatggtgtggaacttcctatagtcaaaactgaaatggatggaagcttgttggagaaactcctctt
actcctgatggccccaaagcaaattatactgaagagtgggtgatcagaccgggagaagcagattttaaa
tatggtgcatctccactacaggcaactctagggctggagtttggcgcacatttcaagtgggatttagat
aaccctaatactaaatatgccgttcttaccaatgctgccgcaaatgcgcttggtgctgtaggggganptt
gcagtatccagatttactggtacagatccaatgttaagtcctcatatcggtgcaatggttgggcaagca
gcggggcatgccatacagtataatacccccggattaaagccagacactattttatggtgggcaggtact
actcttggactggctgatttaaacaaggccgagtttggagaggccagattcactgactatcctcgtata
tggtggcatgcaagagaaggtgccatttttcccaaataaagcagatattgaacatgccacaggggctgat
atacgcgcaatggaagaaggtgtatctgttggacaacggcatccaaatccagaggatgtggtcatcaat
atcgaaagcaataactcaccacatcataacccatcaaattatgttgataccgttgatataatccaagaa
acaagagtctaa (SEQ ID NO:2)

FIG. 1C

Enteropathogenic *E. coli* NleA Protein Sequence

MNIQPIVTSGITTQNNRHHHAEQTSPTQIPQSELPNGCETGFVVHIPEDMQRHAPECGETTALLSLIKD
EGLLSGLDKYLAPHLEEGSAGKKALDMFGLFNVSQMALEIPSTVPGISGKYGVQLNIVKPDIHPTSGNY
FLQIFPLHDEIGINFKDLPGPLKNALSNSNIPTTVSTAASTIASATTSTVTTASKDPIPWFGLTAQVVR
NHGVELPIVKTENGWKLVGETPLTPDGPKANYTEEWVIRPGEADFKYGASPLQATLGLEFGAHFKWDLD
NPNTKYAVLTNAAANALGAVGGFAVSRFTGTDPMLSPHIGAMVGQAAGHAIQYNTPGLKPDTILWWAGT
TLGLADLNKAEFGEARFTDYPRIWWHAREGAIFPNKADIEHATGADIRAMEEGVSVGQRHPNPEDVVIN
IESNNSPHHNPSNYVDTVDIIQETRV (SEQ ID NO:23)

FIG. 1D

Enterohemorrhagic *E. coli* NleA DNA Sequence

ATGAACATTCAACCGACCATACAATCTGGAATCACCTCACAAAACAATCAACATCATCAAACAGAACAA
ATACCCTCTACACAAATACCGCAATCCGAATTACCTCTAGGATGCCAAGCTGGATTTGTTGTTAATATT
CCAGATGATATACAGCAACATGCACCGGAATGCGGTGAAACAACAGCTCTACTGAGCTTGATAAAAGAT
AAAGGTCTGCTCTCAGGGCTAGACGAATATATAGCTCCTCACCTTGAAGAAGGATCCATAGGAAAAAAA
ACATTGGATATGTTTGGTTTATTCAATGTTACCCAAATGGCATTAGAGATACCTAGTTCCGTTTCAGGC
ATCTCTGGTAAATATGGTGTCCAGCTAAACATTGTAAAACCAGATATTCATCCTACATCAGGTAATTAT
TTTTTACAGATATTCCCTCTGCATGATGAAATAGGTTTTAATTTTAAAGACCTTCCTGGCCCGTTAAAA
AATGCATTAAGCAACAGTAATATATCAACCACTGCAGTGTCGACTATTGCATCGACTGGAACATCAGCC
ACTACTTCGACGGTAACCACCGAGCCAAAAGACCCAATACCATGGTTTGGATTAACAGCTCAAGTGGTT
CGTAATCATGGTGTAGAACTTCCTATAGTCAAAACTGAAAATGGATGGAAGCTTGTTGGAGAAACACCA
CTTACTCCTGATGGGCCGAAAGCAAATTACACGGAGGAGTGGGTTATCAGACCGGGAGAAGCAGATTTT
AAATATGGTGCATCTCCATTACAGGCAACTCTAGGGCTGGAGTTTGGCGCACATTTCAAGTGGGATTTA
GATAACCCTAATACTAAATATGCCGTTCTTACCAATGCTGCCGCAAATGCGCTTGGTGCTTTAGGGGGA
TTTGCAGTATCCAGATTTGCTAGTACAGATCCAATGTTAAGTCCTCATATCGGTGCAATGGTTGGGCAA
GCAGCAGGGCATGCCATACAGTATAATACCCCTGGATTAAAGCCAGACACTATTTTATGGTGGGCTGGT
GCGACACTGGGGGCTGCCGATTTAAACAAGGCCGAGTTTGAAGTAGCTAGATTCACTGACTATCCTCGT
ATATGGTGGCACGCAAGAGAAGGAGCTATTTTCCCCAATAAAGCAGATATTGAACATGCCACAGGTGCT
GATATACGCGCAATGGAAGAAGGTATCCCTGTTGGACAGCGGCATCCAAATCCAGAGGATGTGGTAATC
GATATCGAAAGCAATGGCTTACCACATCATAATCCATCAAATCATGTTGATATCTTTGATATAATCCAA
GAAACAAGAGTCTAA (SEQ ID NO:3)

FIG. 1E

Enterohemorrhagic *E. coli* NleA Protein Sequence mniqptiqsgitsqnnqhhqteqipstqipqselplgcqagfvvnipddiqqhapecgettallslikd
kgllsgldeyiaphleegsigkktldmfglfnvtqmaleipssvsgisgkygvqlnivkpdihptsgny
flqifplhdeigfnfkdlpgplknalsnsnisttavstiastgtsattstvttepkdpipwfgltaqvv
rnhgvelpivktengwklvgetpltpdgpkanyteewvirpgeadfkygasplqatlglefgahfkwdl
dnpntkyavltnaaanalgalggfavsrfastdpmlsphigamvgqaaghaiqyntpglkpdtilwwag
atlgaadlnkaefevarftdypriwwharegaifpnkadiehatgadirameegipvgqrhpnpedvvi
diesnglphhnpsnhvdifdiiqetrv (SEQ ID NO:24)

FIG. 1F

*Citrobacter rodentium* NleB DNA Sequences tattcttttcagtggtttgaagcAAGGCCAGAGCGATACGGAAAAGGTGAAGTACCGATATTGAATAC
CAAAGAGCATCCGTATTTGAGCAATATTATAAATGCTGCAAAAATAGAAAATGAGCGcgTAATaGGAGT
ACTGGTAGACGGAGACTTTACTTATGAGCAAAGAAAAGAATTTCTCAGTCTTGAAGATGAACATCAAAA
TATAAAGATAATATATCGGGAAAATGTTGATTTCAGTATGTATGATAAAAAACTGTCTGATATTTATCT
TGAAAATATTCATGAACAAGAATCATATCCAGCGAGTGAGAGAGATAATTATCTGTTaGGcTTaTTAAG
AGAAGAGTTAAAAAATATTCCATACGGAAAGGACTCTTTGATTGAATCATATGCAGAAAAAAGAGGTCA
TACTTGGTTTGATTTTTTTAGAAACTTGGCGGTATTGAAGGGGGGGGGGGTTGTTTACAGAGACGGGTAA
AACTGGATGCCATAACATATCTCCATGTGGGGGATGTATATATCTTGATGCAGATATGATTATTACTGA
TAAATTAGGTGTCCTGTATGCTCCTGATGGTATCgctgtgcatgtagattgtaatgatgaga (SEQ
ID NO:4)

FIG. 2A

AAGGCCAGAGCGATACGGAAAAGGTGAAGTACCGATATTGAATACCAAAGAGCATCCGTATTTGAGCAA
TATTATAAATGCTGCAAAAATAGAAAATGAGCGTAATGGAGTACTGGTAGACGGAGACTTTACTTATGA
GCAAAGAAAAGAATTTCTCAGTCTTGAAGATGAACATCAAAATATAAAGATAATATATCGGGAAAATGT
TGATTTCAGTATGTATGATAAAAAACTGTCTGATATTTATCTTGAAAATATTCATGAACAAGAATCATA
TCCAGCGAGTGAGAGAGATAATTATCTGTTGGTTTTAAGAGAAGAGTTAAAAAATATTCCATACGGAAA
GGACTCTTTGATTGAATCATATGCAGAAAAAAGAGGTCATACTTGGTTTGATTTTTTTAGAAACTTGGC
GGTATTGAAGGGGGGGGGGTTGTTTACAGAGACGGGTAAAACTGGATGCCATAACATATCTCCATGTGG
GGATGTATATATCTTGATGCAGATATGATTATTACTGATAAATTAGGTGTCCTGTATGCTCCTGATGG
TAT (SEQ ID NO:5)

FIG. 2B

*Citrobacter rodentium* NleB Protein Sequences

*ILFQWFE*ARPERYGKGEVPILNTKEHPYLSNIINAAKIENERVIGVLVDGDFTYEQRKEFLSLEDEHQN
IKIIYRENVDFSMYDKKLSDIYLENIHEQESYPASERDNYLLGLLREELKNIPYGKDSLIESYAEKRGH
TWFDFFRNLAVLKGGGLFTETGKTGCHNISPCGGCIYLDADMIITDKLGVLYAPDG*IAVHVDCNDE*
(SEQ ID NO:25)

FIG. 2C

RPERYGKGEVPILNTKEHPYLSNIINAAKIENERVIGVLVDGDFTYEQRKEFLSLEDEHQNIKIIYREN
VDFSMYDKKLSDIYLENIHEQESYPASERDNYLLGLLREELKNIPYGKDSLIESYAEKRGHTWFDFFRN
LAVLKGGGLFTETGKTGCHNISPCGGCIYLDADMIITDKLGVLYAPDG (SEQ ID NO:26)

FIG. 2D

Enteropathogenic *E. coli* NleB DNA Sequence atgttatcttcattaaatgtccttcaatccagcttcagaggaaagacagctttatcaaatagtacactt
ctccagaaagtttcttttgctggaaaagaatattctctggaacctattgatgaagaaccccctattctt
tttcagtggtttgaagcaaggccagagcgatacgaaaaggagaagtaccaatattgaataccaaagaa
catccgtatttgagcaatattataaatgctgcaaaaatagaaatgagcgtataatcggtgtgctggta
gatggaaattttacttatgaacaaaaaaggaatttctcaatcttgaaaatgaacatcaaaatataaaa
ataatctaccgagcagatgtggatttcagcatgtatgataaaaaactatctgatatttaccttgaaaat
atccataaacaagaatcataccctgccagtgagagggataattatctgttaggcttattaagagaagag
ttaaaaaatatcccagaaggtaaggactctttgattgagtcatatgcagaaaaagagaacatacttgg
tttgattttttcaggaatttggccatattgaaggctggaagtttgtttacagagacgggaaaaactgga
tgccataacatatcgccctgtagcggatgtatatatcttgatgccgacatgattattaccgataaatta
ggagtcctgtatgctcctgatggtatcgctgtgcatgtagattgtaatgatgagataaaaagtcttgaa
aatggtgcgatagttgtcaatcgtagtaatcatccagcattacttgcaggcctcgatattatgaagagt
aaagttgacgctcatccatattatgatggtctaggaaagggtatcaagcggcattttaactattcatcg
ttacacaattataatgcttttgtgattttattgaatttaagcatgaaaatattataccgaataccagt
atgtataccagcagttcatggtaa (SEQ ID NO:6)

FIG. 2E

Enteropathogenic *E. coli* NleB Protein Sequence

MLSSLNVLQSSFRGKTALSNSTLLQKVSFAGKEYSLEPIDERTPILFQWFEARPERYEKGEVPILNTKE
HPYLSNIINAAKIENERIIGVLVDGNFTYEQKKEFLNLENEHQNIKIIYRADVDFSMYDKKLSDIYLEN
IHKQESYPASERDNYLLGLLREELKNIPEGKDSLIESYAEKREHTWFDFFRNLAILKAGSLFTETGKTG
CHNISPCSGCIYLDADMIITDKLGVLYAPDGIAVHVDCNDEIKSLENGAIVVNRSNHPALLAGLDIMKS
KVDAHPYYDGLGKGIKRHFNYSSLHNYNAFCDFIEFKHENIIPNTSMYTSSSW (SEQ ID NO:27)

FIG. 2F

Enterohemorrhagic *E. coli* NleB DNA Sequence

ATGTTATCTTCATTAAATGTCCTTCAATCCAGCTTCAGAGGAAAGACAGCTTTATCAAATAGTACACTT
CTCCAGAAAGTTTCTTTTGCTGGAAAAGAATATCCTCTGGAACCTATTGATGAAAAACCCCTATTCTT
TTTCAGTGGTTTGAAGCAAGGCCAGAGCGATACGAAAAGGAGAAGTACCAATATTGAATACCAAAGAA
CATCCGTATTTGAGCAATATTATAAATGCTGCAAAAATAGAAATGAGCGTATAATCGGTGTGCTGGTA
GATGGAAATTTTACTTATGAACAAAAAAGGAATTTCTCAGTCTTGAAAATGAATATCAAAATATAAAA
ATAATCTACCGAGCAGATGTGGATTTCAGCATGTATGATAAAAAACTATCTGATATTTACCTTGAAAAT
ATCCATAAACAAGAATCATACCCTGCCAGTGAGAGGGATAATTATCTGTTAGGCTTATTAAGAGAAGAG
TTAAAAAATATCCCAGAAGGTAAGGACTCTTTGATTGAGTCATATGCAGAAAAAGAGAACATACTTGG
TTTGATTTTTTCAGGAATTTGGCCATGTTGAAGGCTGGAAGTTTGTTTACAGAGACGGGAAAAACTGGA
TGCCATAACATATCGCCCTGTAGCGGATGTATATATCTTGATGCCGACATGATTATTACCGATAAATTA
GGAGTCCTGTATGCTCCTGATGGTATCGCTGTGCATGTAGATTGTAATGATGAGATAAAAAGTCTTGAA
AATGGTGCGATAGTTGTCAATCGTAGTAATCATCCAGCATTACTTGCAGGCCTCGATATTATGAAGAGT
AAAGTTGACGCTCATCCATATTATGATGGTCTAGGAAAGGGTATCAAGCGGCATTTTAACTATTCATCG
TTACACGATTATAATGCTTTTGTGATTTTATTGAATTTAAGCATGAAAATATTATACCGAATACCAGT
ATGTATACCTGCAGTTCATGGTAA (SEQ ID NO:7)

FIG. 2G

Enterohemorrhagic *E. coli* NleB Protein Sequences mlsslnvlqssfrgktalsnstllqkvsfagkeyplepidektpilfqwfearperyekgevpilntke
hpylsniinaakieneriigvlvdgnftyeqkkeflsleneyqnikiiyradvdfsmydkklsdiylen
ihkqesypaserdnyllgllreelknipegkdsliesyaekrehtwfdffrnlamlkagslftetgktg
chnispcsgciyldadmiitdklgvlyapdgiavhvdcndeikslengaivvnrsnhpallagldimks
kvdahpyydglgkgikrhfnysslhdynafcdfiefkheniipntsmytcssw (SEQ ID NO:28)

FIG. 2H

MLSPIRTTFHNSVNIVQSSPCQTVSFAGKEYELKVIDEKTPILFQWFEPNPERYKKDEVPIVNTKQHPY
LDNVTNAARIESDRMIGIFVDGDFSVNQKTAFSKLERDFENVMIIYREDVDFSMYDRKLSDIYHDIICE
QRLRTEDKRDEYLLNLLEKELREISKAQDSLISMYAKKRNHAWFDFFRNLALLKAGEIFRCTYNTKNHG
ISFGEGCIYLDMDMILTGKLGTIYAPDGISMHVDRRNDSVNIENSAIIVNRSNHPALLEGLSFMHSKVD
AHPYYDGLGKGVKKYFNFTPLHNYNHFCDFIEFNHPNIIMNTSQYTCSSW (SEQ ID NO:29)

FIG. 2I

Enterohemorrhagic *E. coli* NleB DNA Sequence atgctttcac cgataaggac aactttccat aactcagtaa atatagtgca gagttcaccc
tgtcaaacgg tttcttttgc aggaaaggaa tatgagttaa aggtcattga tgaaaaaacg
cctattcttt ttcagtggtt tgaacctaat cctgaacgat ataagaaaga tgaggttcca
atagttaata ctaagcagca tccctattta gataatgtca caaatgcggc aaggatagag
agtgatcgta tgataggtat ttttgttgat ggcgattttt cagtcaacca aaagactgct
ttttcaaaat tggaacgaga ttttgaaaat gtaatgataa tctatcggga agatgttgac
ttcagtatgt atgacagaaa actatcagat atttatcatg atattatatg tgaacaaagg
ttacgaactg aagacaaaag agatgaatac ttgttgaatc tgttagagaa agagctgagg
gaaatttcaa aggcgcagga ttcttttgatt tctatgtatg caaagaaaag aaatcatgca
tggtttgatt tcttcagaaa tttagcccta ttaaaagcag gagagatatt caggtgcaca
tataatacaa gaatcacgg tatttcattc ggggaggggt gtatctatct tgatatggat
atgatactta caggtaagct tggtacaata tatgctcctg atggaatttc aatgcatgtg
gatcgtcgta atgatagtgt aaatattgaa aatagtgcaa taattgttaa ccgtagtaat
catcctgctc tacttgaggg actttctttt atgcatagta agtagatgc tcatccatat
tatgatggtt tggggaaagg agttaagaaa tattttaatt ttacaccatt acataattat
aatcattttt gtgactttat tgagtttaac caccctaata taatcatgaa cacaagtcag
tatacatgca gttcatggta a (SEQ ID NO:60)

FIG. 2J

*Citrobacter rodentium* NleC DNA Sequence

ATGAAAATTCCCTCACTCCAGCCCAGCTTCAACTTTTTCGCCCCAGCAGGATACTCTGCTGCCGTTGCT
CCCAATCGTTCGGACAATGCCTATGCTGATTACGTATTGGATATAGGCAAGCGAATACCACTTTCCGCG
GAAGATTTAGGCAACCTATATGAAAATGTCATTCGCGCCGTTCGTGACAGCCGTAGCAAGCTCATAGAT
CAGCATACGGTCGATATGATTGGTAACACTATACTTGATGCTTTGAGCCGATCACAAACCTTTCGTGAT
GCCGTAAGCTATGGCATTCATAATAAGGAGGTACACATTGGTTGCATTAAATACAGAAACGAATACGAG
CTCAACGGAGAATCCCCCGTCAAAGTTGATGATATTCAATCACTAACCTGTACCGAATTATATGAATAC
GATGTCGGGCAAGAACCAATTTTACCCATTTGCGAGGCAGGAGAAAACGATAACGAAGAGCCTTATGTC
AGTTTTAGTGTTGCGCCAGATACTGACTCTTATGAGATGCCATCGTGGCAGGAAGGGCTGATTCACGAG
ATTATTCATCATGTGACTGGAGCTAGCGATCCGTCTGGAGATAGTAATATAGAGCTAGGACCCACGGAG
ATTCTCGCACGTCGTGTCGCTCAAGAGCTGGGATGGACTGTCCCCGACTTCATAGGATATGCAGAGCCA
GATCGTGAAGCTCATCTTAGGGGACGTAACCTGAATGCCCTTCGACAGGCGGCCATGCGACATGAAGAT
AATGAGAGGACTTTCTTCGAAAGGCTGGGTATGATCAGTGATCGATATGAGGCGAGTCCTGATTTCACA
GAGTATTCCGCTGTGTCTAACATAGAATATGGATTTATCCAGCAACATGATTTTCCCGGGTTGGCTATC
GACGATAATTTACAGGATGCAAATCAGATCCAACTCTATCATGGAGCACCTTATATCTTTACATTCGGG
GATGTGGACAAACACAATCAGCGCTGA (SEQ ID NO:8)

FIG. 3A

*Citrobacter rodentium* NleC Protein Sequence

MKIPSLQPSFNFFAPAGYSAAVAPNRSDNAYADYVLDIGKRIPLSAEDLGNLYENVIRAVRDSRSKLID
QHTVDMIGNTILDALSRSQTFRDAVSYGIHNKEVHIGCIKYRNEYELNGESPVKVDDIQSLTCTELYEY
DVGQEPILPICEAGENDNEEPYVSFSVAPDTDSYEMPSWQEGLIHEIIHHVTGASDPSGDSNIELGPTE
ILARRVAQELGWTVPDFIGYAEPDREAHLRGRNLNALRQAAMRHEDNERTFFERLGMISDRYEASPDFT
EYSAVSNIEYGFIQQHDFPGLAIDDNLQDANQIQLYHGAPYIFTFGDVDKHNQR (SEQ ID NO:30)

FIG. 3B

Enteropathogenic *E. coli* NleC DNA Sequence atgaaaattccctcattacagtccaacttcaacttttccgccccggcaggatactctgctcccattgct
cctaatcgtgctgaaaatgcctatgcggattacgttttggatataggtaagcgaataccactttccgca
gcagatttaagcaacgtatacgaaagtgtaatacgcgccgtccatgacagccgtagcaggcttatcgat
cagcatacagtcgatatgatcggcaacactgtacttgatgctttgagccgatcacagacatttcgtgat
gccgtaagctatggcattcataatgagaaggtacacattggttgcattaaatacagaaacgaatacgag
cttaacgaagaatcttctgtcaaaattgatgatattcaatcactaacctgtaacgaattatatgaatat
gatgtcgggcaagagccaatttttccccatttgcgaagcaggagaaaacgataacgaagagccttatgtc
agtttagtgttgcgccagatactgactcttatgagatgccatcgtggcaggaaggactgattcacgag
attattcatcatgttactggatctagcgatccatctggagatagtaatatagagttaggacccaccgag
attctcgcacgtcgtgtcgctcaagaactgggatggagtgttcccgacttcaaaggatatgcagagcca
gaacgtgaagctcatcttaggttacgtaacctgaatgcccttcgacaggctgccatgaggcatgaagag
aatgagagggctttcttcgaaaggctgggtacgatcagtgaccgatatgaggcgagtcctgatttcaca
gagtattccgctgtgtctaacataggatacggatttatccagcaacatgattttcctggattggctatc
aacgataatttacaggatgcaaatcagatccaactgtatcatggcgccccttatattttacatttggg
gatgtggacaaacacaatcagcgatga (SEQ ID NO:9)

FIG. 3C

Enteropathogenic *E. coli* NleC Protein Sequence

MKIPSLQSNFNFSAPAGYSAPIAPNRAENAYADYVLDIGKRIPLSAADLSNVYESVIRAVHDSRSRLID
QHTVDMIGNTVLDALSRSQTFRDAVSYGIHNEKVHIGCIKYRNEYELNEESSVKIDDIQSLTCNELYEY
DVGQEPIFPICEAGENDNEEPYVSFSVAPDTDSYEMPSWQEGLIHEIIHHVTGSSDPSGDSNIELGPTE
ILARRVAQELGWSVPDFKGYAEPEREAHLRLRNLNALRQAAMRHEENERAFFERLGTISDRYEASPDFT
EYSAVSNIGYGFIQQHDFPGLAINDNLQDANQIQLYHGAPYIFTFGDVDKHNQR (SEQ ID NO:31)

FIG. 3D

Enterohemorrhagic *E. coli* NleC DNA Sequence

ATGAAAATTCCCTCATTACAGTCCAACTTCAACTTTTCCGCCCCGGCAGGATACTCTGCTCCCATTGCT
CCTAATCGTGCTGAAAATGCCTATGCGGATTACGTTTTGGATATAGGTAAGCGAATACCACTTTCCGCA
GCAGATTTAAGCAACGTATACGAAAGTGTAATACGCGCCGTCCATGACAGCCGTAGCAGGCTTATCGAT
CAGCATACAGTCGATATGATCGGCAACACTGTACTTGATGCTTTGAGCCGATCACAGACATTTCGTGAT
GCCGTAAGCTATGGCATTCATAATGAGAAGGTACACATTGGTTGCATTAAATACAGAAACGAATACGAG
CTTAACGAAGAATCTTCTGTCAAAATTGATGATATTCAATCACTAACCTGTAACGAATTATATGAATAT
GATGTCGGGCAAGAGCCAATTTTCCCCATTTGCGAAGCAGGAGAAAACGATAACGAAGAGCCTTATGTC
AGTTTTAGTGTTGCGCCAGATACTGACTCTTATGAGATGCCATCGTGGCAGGAAGGACTGATTCACGAG
ATTATTCATCATGTTACTGGATCTAGCGATCCATCTGGAGATAGTAATATAGAGTTAGGACCCACCGAG
ATTCTCGCACGTCGTGTCGCTCAAGAACTGGGATGGAGTGTTCCCGACTTCAAAGGATATGCAGAGCCA
GAACGTGAAGCTCATCTTAGGCTACGTAACCTGAATGCCCTTCGACAGGCTGCCATGAGGCATGAAGAG
AATGAGAGGGCTTTCTTCGAAAGGCTGGGTACGATCAGTGACCGATATGAGGCGAGTCCTGATTTCACA
GAGTATTCCGCTGTGTCTAACATAGGATACGGATTTATCCAGCAACATGATTTTCCTGGATTGGCTATC
AACGATAATTTACAGGATGCAAATCAGATCCAACTGTATCATGGCGCCCCTTATATTTTTACATTTGGG
GATGTGGACAAACACAATCAGCAATGA (SEQ ID NO:10)

FIG. 3E

Enterohemorrhagic *E. coli* NleC Protein Sequence mkipslqsnfnfsapagysapiapnraenayadyvldigkriplsaadlsnvyesviravhdsrsrlid
qhtvdmigntvldalsrsqtfrdavsygihnekvhigcikyrneyelneessvkiddiqsltcnelyey
dvgqepifpiceagendneepyvsfsvapdtdsyempswqegliheiihhvtgssdpsgdsnielgpte
ilarrvaqelgwsvpdfkgyaepereahlrlrnlnalrqaamrheeneraffer lgtisdryeaspdft
eysavsnigygfiqqhdfpglaindnlqdanqiqlyhgapyiftfgdvdkhnqq (SEQ ID NO:32)

FIG. 3F

*Citrobacter rodentium* NleD DNA Sequence

ATGCGCCCTACATCCCTTAACCTGACATTACCTTCGTTACCTCTACCCTCATCTTCAAATTCAATTTCA
GCCACAGACATTCAATCTCTTGTAAAAATGTCGGGTGTGCGCTGGGTGAAAAACAACCAACAACTCTGT
TTCCACGGGACTGACCTTAAAATCTACCAGCATCTTGAAGCTGCCCTCGATAAGATCGAATCCACAGAC
ACTGGACGTACTCTTTTGAACTGTATTGAATTAACATCCCGACTCAAATCAGAAAAACTGGCAATACAT
CTCGATTCTGCTGAGTTAGGGGTGATAGCACACTGCAATGCGGATGCTGAAAACTCCCGAGGAACTGGC
TCCGACTTTCACTGTAATCTGAATGCAGTTGAATATCCCTGCGGGCAAGGAATTAGCCTGGTAGACTTT
CATGCATGCATTGTTTTCCATGAACTTCTCCACGTTTTCCACAATTTAAATGGAGAGCGCCTGAAAGTT
GAGAGTTCTCAACCAGAATTACAAACACACTCCCCACTTTTACTCGAAGAAGCCAGGACTGTTGGGTTG
GGTGCTTTTTCTGAAGAAGTTCTTTCAGAAAATAAATTTCGTGAAGAGATTGGGATGCCCCGCAGAACA
TTCTACCCGCACGATTCATCTCTCATTCATGATGACAATACAGTGACTCAGAGATTCCAGCGGAAAAAA
CTGCATCCGTTACTTTAG (SEQ ID NO:11)

FIG. 4A

*Citrobacter rodentium* NleD Protein Sequence

MRPTSLNLTLPSLPLPSSSNSISATDIQSLVKMSGVRWVKNNQQLCFHGTDLKIYQHLEAALDKIESTD
TGRTLLNCIELTSRLKSEKLAIHLDSAELGVIAHCNADAENSRGTGSDFHCNLNAVEYPCGQGISLVDF
HACIVFHELLHVFHNLNGERLKVESSQPELQTHSPLLLEEARTVGLGAFSEEVLSENKFREEIGMPRRT
FYPHDSSLIHDDNTVTQRFQRKKLHPLL (SEQ ID NO:33)

FIG. 4B

Enteropathogenic *E. coli* NleD DNA Sequence atgcgccctacgtccctcaacttggtattacatcagtcatcaacgtcgagctcaatgtcagatacagat
atcgagtctcttgtaaaagcatcgagcgttcaatggataaaaataatccgcaacttcgtttccagggg
actgatcataatatatatcagcagattgaagcagcactcgataagattggctctacagagacagggcgt
gtactcctgaatgctattgaatcaatatcccgacttaaatcagaaacagtggtaatacacctcaactct
tccagactaggagttatggcacatagagatatagatgctgagaaccatcggggggactggttccgatttt
cactgtaatctgaatgcagttgaatatccctgtggggaggggattagcgtggtggactttcatgcgact
attgtttttcatgagttgctccatgttttccacaatttaaatggggagcgtttgaaagttgagagttcc
cgaccagaatcacaaaaatactctccacttttactcgaagaagccaggactgttgggttgggggctttt
tcagaggaggtgctttcagaaaataaattccgcgaagagattgggatgccccgtagaacctcctacccg
cacgactcagctcttattcatgatgacaatacagtgagtctgggattccaacaggtaagactgcatcca
ttgctttag (SEQ ID NO:12)

FIG. 4C

Enteropathogenic *E. coli* NleD Protein Sequence

MRPTSLNLVLHQSSTSSSMSDTDIESLVKASSVQWIKNNPQLRFQGTDHNIYQQIEAALDKIGSTETGR
VLLNAIESISRLKSETVVIHLNSSRLGVMAHRDIDAENHRGTGSDFHCNLNAVEYPCGEGISVVDFHAT
IVFHELLHVFHNLNGERLKVESSRPESQKYSPLLLEEARTVGLGAFSEEVLSENKFREEIGMPRRTSYP
HDSALIHDDNTVSLGFQQVRLHPLL (SEQ ID NO:34)

FIG. 4D

Enterohemorrhagic *E. coli* NleD DNA Sequence

ATGCGCCCTACGTCCCTCAACTTGGTATTACATCAGTCATCAAGGTCGAGCTCAATGTCAGATACAGAT
ATCGAGTCTCTTGTAAAAGCATCGAGCGTTCAATGGATAAAAAATAATCCGCAACTTCGTTTCCAGGGG
ACTGATCATAATATATATCAGCAGATTGAAGCAGCACTCGATAAGATTGGCTCTACAGAGACAGGGCGT
GTACTCCTGAATGCTATTGAATCAATATCCCGACTTAAATCAGAAACAGTGGTAATACACCTCAACTCT
TCCAGACTAGGAGTTATGGCACATAGAGATATAGATGCTGAGAACCATCGGGGACTGGTTCCGATTTT
CACTGTAATCTGAATGCAGTTGAATATCCCTGTGGGGAGGGGATTAGCGTGGTGGACTTTCATGCGACT
ATTGTTTTTCATGAGTTGCTCCATGTTTTCCACAATTTAAATGGGGAGCGTTTGAAAGTTGAGAGTTCC
CGAGCAGAATCACAAAAATACTCTCCACTTTTACTCGAAGAAGCCAGGACTGTTGGGTTGGGGCTTTT
TCAGAGGAGGTGCTTTCAGAAAATAAATTCCACGAAGAGATTGGGATGCCCCGTAGAACCTCCTACCCG
CRCGACTCAGCTCTTATTCATGATGACAATACAGTGAGTCTGGGATTCCAACAGGTAAGACTGCATCCA
TTGCTTTAG (SEQ ID NO:13)

FIG. 4E

Enterohemorrhagic *E. coli* NleD Protein Sequence mrptslnlvlhqssrsssmsdtdieslvkassvqwiknnpqlrfqgtdhniyqqieaaldkigstetgr
vllnaiesisrlksetvvihlnssrlgvmahrdidaenhrgtgsdfhcnlnaveypcgegisvvdfhat
ivfhellhvfhnlngerlkvessraesqkysplllleeartvglgafseevlsenkfheeigmprrtsyp
xdsalihddntvslgfqqvrlhpll (SEQ ID NO:35)

FIG. 4F

*Citrobacter rodentium* NleE DNA Sequences tactttaatgaatcaccCAATGTATATGATAAGAAGTATATATCTGGCGTAACTAGAGGAGTAGCTGAA
CTAAAACAGGAAGGATTTATTAACGAGAAAGCCAGGCGACTTGCTTATATGCAAGCAATGTATTCTGTA
TGTCCGGAAGAGTTTAAACCTATTTCCAGAAACGAAGCTAGTACACCGGAAGGCAGCTGGCTAACAGTT
ATATCCGGAAAACGCCCAATGGGACAGTTTTCTGTAGATAGCTTATATCATCCTGACTTACATGCATTG
TGTGAGCTTCCGGATATTTGTTGCAAGATCTTCCCTAAAGAAAACAATGATTTTTGTATATAGTGATT
GTGTACAGAAATGACAGCCCTCTGGGAGAACAACGAGCAAATCGATTTATAGAATTATATAATATAAAA
AGAGACATCATGCAGGAATTAAATTATGAATCTCCAGAGTTAAAGGCTGTGAAATCTGAAATGATTATT
gcacgtgaaatgggagaaatctt (SEQ ID NO:14)

FIG. 5A

CAATGTATATGATAAGAAGTATATATCTGGCGTAACTAGAGGAGTAGCTGAACTAAAACAGGAAGGATT
TATTAACGAGAAAGCCAGGCGACTTGCTTATATGCAAGCAATGTATTCTGTATGTCCGGAAGAGTTTAA
ACCTATTTCCAGAAACGAAGCTAGTACACCGGAAGGCAGCTGGCTAACAGTTATATCCGGAAAACGCCC
AATGGGACAGTTTTCTGTAGATAGCTTATATCATCCTGACTTACATGCATTGTGTGAGCTTCCGGATAT
TTGTTGCAAGATCTTCCCTAAAGAAAACAATGATTTTTGTATATAGTGATTGTGTACAGAAATGACAG
CCCTCTGGGAGAACAACGAGCAAATCGATTTATAGAATTATATAATATAAAAAGAGACATCATGCAGGA
ATTAAATTATGAATCTCCAGAGTTAAAGGCTGTGAAATCTGAAATGATTATT (SEQ ID NO:15)

FIG. 5B

*Citrobacter rodentium* NleE Protein Sequences

*YFNES*PNVYDKKYISGVTRGVAELKQEGFINEKARRLAYMQAMYSVCPEEFKPISRNEASTPEGSWLTV
ISGKRPMGQFSVDSLYHPDLHALCELPDICCKIFPKENNDFLYIVIVYRNDSPLGEQRANRFIELYNIK
RDIMQELNYESPELKAVKSEMI*IAREMGEI* (SEQ ID NO:36)

FIG. 5C

NVYDKKYISGVTRGVAELKQEGFINEKARRLAYMQAMYSVCPEEFKPISRNEASTPEGSWLTVISGKRP
MGQFSVDSLYHPDLHALCELPDICCKIFPKENNDFLYIVIVYRNDSPLGEQRANRFIELYNIKRDIMQE
LNYESPELKAVKSEMI (SEQ ID NO:37)

FIG. 5D

Enteropathogenic *E. coli* NleE DNA Sequence atgattaatcctgttactaatactcagggcgtgtccctataaatactaaatatgctgaacatgtggtg
aaaaatatttacccgaaaattaaacatgattactttaatgaatcacccaatatatatgataagaagtat
atatccggtataaccagaggagtagctgaactaaaacaggaagaatttgttaacgagaaagccagacgg
ttttcttatatgaagactatgtattctgtatgtccagaagcgtttgaacctatttccagaaatgaagcc
agtacaccggaaggaagctggctaacagttatatccggaaaacgcccaatggggcagttttctgtagat
agtttatacaatcctgatttacatgcattatgtgagcttccggacatttgttgtaagatcttccctaaa
gaaaataatgatttttatacatagttgttgtgtacagaaatgacagccctctaggagaacaacgggca
aatagatttatagaattatataatataaaaagagatatcatgcaggaattaaattatgagttaccagag
ttaaaggcagtaaaatctgaaatgattatcgcacgtgaaatgggagaaatctttagctacatgcctggg
gaaatagacagttatatgaaatacataaataataaactttctaaaattgagtag (SEQ ID NO:16)

FIG. 5E

Enteropathogenic *E. coli* NleE Protein Sequence

MINPVTNTQGVSPINTKYAEHVVKNIYPKIKHDYFNESPNIYDKKYISGITRGVAELKQEEFVNEKARR
FSYMKTMYSVCPEAFEPISRNEASTPEGSWLTVISGKRPMGQFSVDSLYNPDLHALCELPDICCKIFPK
ENNDFLYIVVVYRNDSPLGEQRANRFIELYNIKRDIMQELNYELPELKAVKSEMIIAREMGEIFSYMPG
EIDSYMKYINNKLSKIE (SEQ ID NO:38)

FIG. 5F

Enterohemorrhagic *E. coli* NleE DNA Sequence

ATGATTAATCCTGTTACTAATACTCAGGGCGTGTCCCCTATAAATACTAAATATGCTGAACATGTGGTG
AAAAATATTTACCCGGAAATTAAACATGATTACTTTAATGAATCACCCAATATATATGATAAGAAGTAT
ATATCCGGTATAACCAGAGGAGTAGCTGAACTAAAACAGGAAGAATTTGTTAACGAGAAAGCCAGACGG
TTTTCTTATATGAAGACTATGTATTCTGTATGTCCAGAAGCGTTTGAACCTATTTCCAGAAATGAAGCC
AGTACACCGGAAGGAAGCTGGCTAACAGTTATATCCGGAAAACGCCCAATGGGGCAGTTTTCTGTAGAT
AGTTTATACAATCCTGATTTACATGCATTATGTGAGCTTCCGGACATTTGTTGTAAGATCTTCCCTAAA
GAAAATAATGATTTTTTATACATAGTTGTTGTGTACAGAAATGACAGCCCTCTAGGAGAACAACGGGCA
AATAGATTTATAGAATTATATAATATAAAAAGAGATATCATGCAGGAATTAAATTATGAGTTACCAGAG
TTAAAGGCAGTAAAATCTGAAATGATTATCGCACGTGAAATGGGAGAAATCTTTAGCTACATGCCTGGG
GAAATAGACAGTTATATGAAATACATAAATAATAAACTTTCTAAAATTGAGTAG (SEQ ID NO:17)

FIG. 5G

Enterohemorrhagic *E. coli* NleE Protein Sequence minpvtntqgvspintkyaehvvkniypeikhdyfnespniydkkyisgitrgvaelkqeefvnekarr
fsymktmysvcpeafepisrneastpegswltvisgkrpmgqfsvdslynpdlhalcelpdicckifpk
enndflyivvvyrndsplgeqranrfielynikrdimqelnyelpelkavksemiiaremgeifsympg
eidsymkyinnklskie (SEQ ID NO:39)

FIG. 5H

*Citrobacter rodentium* NleF DNA Sequences atgttaccaacaagtggttcttcAGCAAATCTTTACTCATGGATGTATATCTCAGGAAAAGAGAATCCT
TCGACTCCGGAATCAGTAAGTGAACTTAATCATAATCATTTTCTTTCTCCTGAATTACAGGAGAAACTG
GATGTTATGTTCGCCATATATTCATGTGCCAGAAACAATGATGAGCGTGAGAATATTTACCCGGAGCTA
AGGGATTTTGTAAGTAGCCTAATGGATAAGAGAAACAATGTGTTTGAGGTGATAAATGAAGATACTGAT
GAGGTGACCGGAGCTCTGAGAGCGGGAATGACGATAGAGGACAGGGATAGTTATATCAGGGATCTTTTT
TTTCTGCATTCATTGAAAGTAAAAATTGAGGAAAGCAGACAAGATAAAGAGGATTGGAAATGTAAAGTT
TATGATCTGCTATGTCCGCATCATTCTTCAGAGCTATATGGGGATCTACGGGCAATCAAATGCCTCGTT
GAAGGATGCAGTGATGATTTTAGTCCTTTTGATACTATTAAGGTGCCGGATCTTACTTAcaacaaagga
tctttacaatgtggatga (SEQ ID NO:18)

FIG. 6A

AGCAAATCTTTACTCATGGATGTATATCTCAGGAAAAGAGAATCCTTCGACTCCGGAATCAGTAAGTGA
ACTTAATCATAATCATTTTCTTTCTCCTGAATTACAGGAGAAACTGGATGTTATGTTCGCCATATATTC
ATGTGCCAGAAACAATGATGAGCGTGAGAATATTTACCCGGAGCTAAGGGATTTTGTAAGTAGCCTAAT
GGATAAGAGAAACAATGTGTTTGAGGTGATAAATGAAGATACTGATGAGGTGACCGGAGCTCTGAGAGC
GGGAATGACGATAGAGGACAGGGATAGTTATATCAGGGATCTTTTTTTTCTGCATTCATTGAAAGTAAA
AATTGAGGAAAGCAGACAAGATAAAGAGGATTGGAAATGTAAAGTTTATGATCTGCTATGTCCGCATCA
TTCTTCAGAGCTATATGGGGATCTACGGGCAATCAAATGCCTCGTTGAAGGATGCAGTGATGATTTTAG
TCCTTTTGATACTATTAAGGTGCCGGATCTTACTTA (SEQ ID NO:19)

FIG. 6B

*Citrobacter rodentium* NleF Protein Sequences

*MLPTSGSS*ANLYSWMYISGKENPSTPESVSELNHNHFLSPELQEKLDVMFAIYSCARNNDERENIYPEL
RDFVSSLMDKRNNVFEVINEDTDEVTGALRAGMTIEDRDSYIRDLFFLHSLKVKIEESRQDKEDWKCKV
YDLLCPHHSSELYGDLRAIKCLVEGCSDDFSPFDTIKVPDL*TYNKGSLQC* (SEQ ID NO:40)

FIG. 6C

ANLYSWMYISGKENPSTPESVSELNHNHFLSPELQEKLDVMFAIYSCARNNDERENIYPELRDFVSSLM
DKRNNVFEVINEDTDEVTGALRAGMTIEDRDSYIRDLFFLHSLKVKIEESRQDKEDWKCKVYDLLCPHH
SSELYGDLRAIKCLVEGCSDDFSPFDTIKVPDL (SEQ ID NO:41)

FIG. 6D

Enteropathogenic *E. coli* NleF DNA Sequence atgttaccaacaagtggttcttcagcaaatctttattcatggatgtatgtatcaggaagaggtaaccct
tcgactccggaatcagtaagtgagcttaatcataatcactttctttctcctgaattacaagataaactt
gatgttatggtctctatatattcatgtgccagaaataataatgagcttgaggaaattttcaagagcta
agtgcttttgtaagtgggctgatggataagagaaatagtgtatttgaggtgagaaatgaaaatactgat
gaggttgtcggagcgctgagggcgggaatgacgatagaggataggatagttatatcagggatctttt
tttctgcattcattgaaagtaaaaattgaggaaagtagacaaggcaagaagattcgaaatgtaagtt
tataatctgctatgtccgcatcactcttcagagctatatggtgatctacgagcaatgaaatgcctcgtg
gaaggatgcagtgatgattttaatccttttgatattattagggtaccagatcttacttacaacaaagga
tctttacaatgtggatga (SEQ ID NO:20)

FIG. 6E

Enteropathogenic *E. coli* NleF Protein Sequence

MLPTSGSSANLYSWMYVSGRGNPSTPESVSELNHNHFLSPELQDKLDVMVSIYSCARNNNELEEIFQEL
SAFVSGLMDKRNSVFEVRNENTDEVVGALRAGMTIEDRDSYIRDLFFLHSLKVKIEESRQGKEDSKCKV
YNLLCPHHSSELYGDLRAMKCLVEGCSDDFNPFDIIRVPDLTYNKGSLQCG (SEQ ID NO:42)

FIG. 6F

Enterohemorrhagic *E. coli* NleF DNA Sequence

ATGTTACCAACAAGTGGTTCTTCAGCAAATCTTTATTCATGGATGTATGTATCAGGAAGAGGTAACCCT
TCGACTCCGGAATCAGTAAGTGAGCTTAATCATAATCACTTTCTTTCTCCTGAATTACAAGATAAACTT
GATGTTATGGTCTCTATATATTCATGTGCCAGAAATAATAATGAGCTTGAGGAAATTTTTCAAGAGCTA
AGTGCTTTTGTAAGTGGGCTGATGGATAAGAGAAATAGTGTATTTGAGGTGAGAAATGAAAATACTGAT
GAGGTTGTCGGAGCGCTGAGGGCGGGAATGACGATAGAGGACAGGGATAGTTATATCAGGGATCTTTTT
TTTCTGCATTCATTGAAAGTAAAAATTGAGGAAAGTAGACAAGGCAAAGAAGATTCGAAATGTAAAGTT
TATAATCTGCTATGTCCGCATCACTCTTCAGAGCTATATGGTGATCTACGAGCAATGAAATGCCTCGTG
GAAGGATGCAGTGATGATTTTAATCCTTTTGATATTATTAGGGTACCAGATCTTACTTACAACAAAGGA
TCTTTACAATGTGGATGA (SEQ ID NO:21)

FIG. 6G

Enterohemorrhagic *E. coli* NleF Protein Sequence mlptsgssanlyswmyvsgrgnpstpesvselnhnhflspelqdkldvmvsiyscarnnneleeifqel
safvsglmdkrnsvfevrnentdevvgalragmtiedrdsyirdlfflhslkvkieesrqgkedskckv
ynllcphhsselygdlramkclvegcsddfnpfdiirvpdltynkgslqcg (SEQ ID NO:43)

FIG. 6H

```
                                                              *
SGH       MCPDNTHAKKQYLTPGNDIBYPGQTNHDACFIPVSVRQYA
CaiF      MCEG--------------------------------YV
GrlA      M-------------------ESKNSDYVIPDSVKNYN

**+++  *     +++*+    +*+  *+*     +*    ++
SGH       GEPLYIIVAHWCLLQQNWVQRNQIAEAFHITARRASYLIA
CaiF      EKPLYLLIAEWMMAENRWVIAREISIHFDIEHSKAVNTLT
GrlA      GEPLYILVSLWCKLQEKWISRNDIAEAFGINLRRASFIIT
                            Helix-turn-helix motif

*+        +      +       +     +   +     + +*
SGN       YLRSKTSRVVSICRHQTLPN-KARRYEIY-VIRVLDSPTP
CaiF      YILSEVTEISCEVKMIP-NKLEGRGCQCQRLVKVVDIDEQ
GrlA      YISRRKEKISFRVRYVSYGNLHYKRLEIF-IYNVNLEAAP

+       +            *+              *+  +
SGN       STRREKAGPP-----LVSKRRVGNGDRSM--ANELWNRLC
CaiF      IYARLRNNSREKLVGVRKTPRIPAVPLTELNREQKWQMM-
GrlA      TESHVSTGPK------RKTLRVGNGIVG---QSSIWNEM-

+++*  +        +
SGN       SNRNAGKILKKKEDEDDGT   (170 aa)
CaiF      ----LSKSMRR           (131 aa)
GrlA      -------IMRRKKE----S   (135 aa)
```

FIG. 7

A.
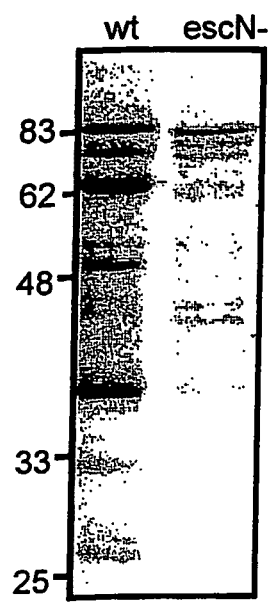
B.
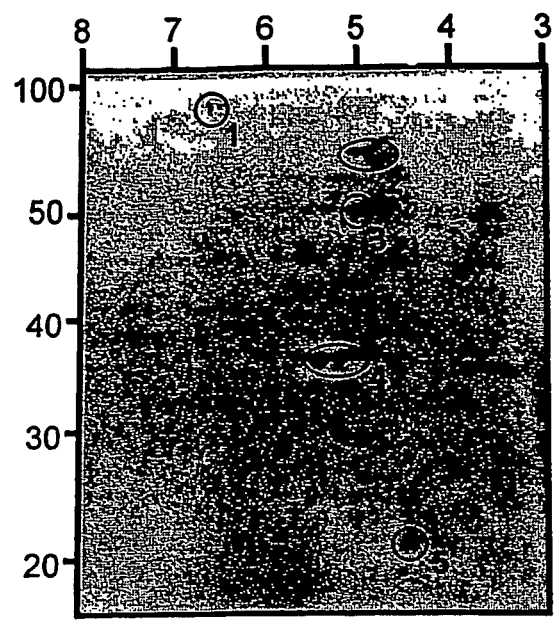
FIG. 10

A.

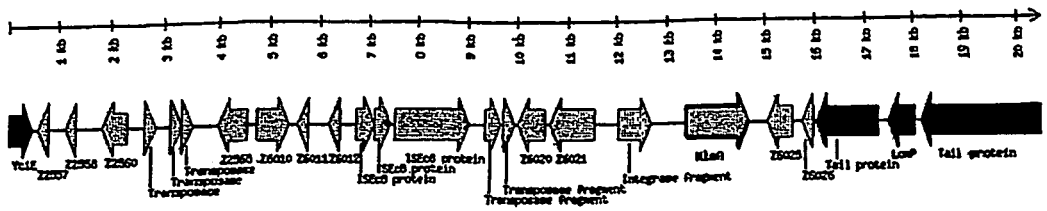

B.

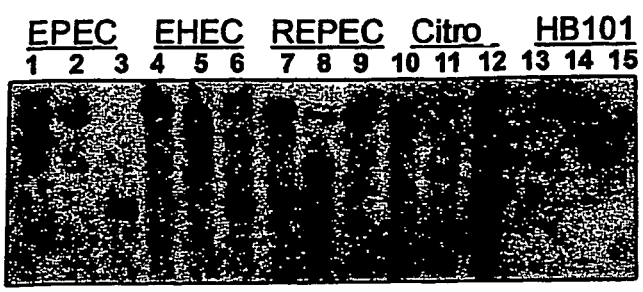

C.

```
EHEC        MNIQPTIQSGITSQNNQ-HHQTEQIPS-TQIPQSELPLGCQAGFVVNIPDDIQQHAPECG  58
O84_H4      .....IV.....T....-...R....P..........N..E..................  58
EPEC        .....IVT....T...R-..HA..TSP..........N..ET....H..E.M.R......  58
Citrobacter .....N.H....T....Q..HA..V.VSSS..R.D..PN.E......H..E.....V....  60

EHEC        ETTALLSLIKDKGLLSGLDEYIAPHLEEGSIGKKTLDMFGLFNVTQMALEIPSS-VSGIS   117
O84_H4      ...........................................T.PS..            118
EPEC        ............E.......K.........A...A........S........T-.P...  117
Citrobacter ............E.......K.L.......L...A..T...............-.P...  119

EHEC        GKYGVQLNIVKFDIHPTSGNYFLQIFPLHDEIGFNPKDLFGPLKNALSNSNISTTAVS--  175
O84_H4      ......H..........S...........................TI            178
EPEC        .............I....................P..VST--                 175
Citrobacter ......H.........T......L....................T..S..--------  172

EHEC        -----------------TIASTGTSATTSTVTTEPKDPIFWFGLTAQVVRNHGVELPIVK 218
O84_H4      ASAATSAATSAASTAVS........................................... 238
EPEC        ----------------A...IA.........AS...........................  217
Citrobacter  ---------------..A...AFT.N..H.................................  207

EHEC        TENGWKLVGETPLTPDGPKANYTEEWVIRFGEADFKYGASPLQATLGLEFGAHFKWDLDN 278
O84_H4      ........................................................... 298
EPEC        ........................................................... 277
Citrobacter ...............T........................................... 267

EHEC        FNTKYAVLTNAAANALGALGGPAVSRFASTDPMLSPHIGAMVGQAAGHAIQYNTPGLKPD 338
O84_H4      .......T..V..A......LPGV....A.....S.A....L...V.CY........ 358
EPEC        ..........V........TG................................... 337
Citrobacter ......I........I..A.....KVFGI.......V...L........V.C...... 327

EHEC        TILHWAGATLGAADLNKAEFEVARFTDYPRIWHHAREGAIFPNKADIEHATGADIRAMEE 398
O84_H4      .......T...L........G.....................S..AR........... 418
EPEC        .......T...L........GE.................................... 397
Citrobacter .........F..........DKV.........F.......L....Q..ARV.....K.... 387

EHEC        GIFVGQRHFNPEDVVIDIESNGLPHHNPSNHVDIFDIIQETRV 441
O84_H4      .V..DH...H..........S--..N....Y..TV...R.... 459
EPEC        .VS............N....NS.......Y..TV........ 440
Citrobacter .V...HQ..K..........GGNS.......Y..T.E....... 430
```

FIG. 11

A.
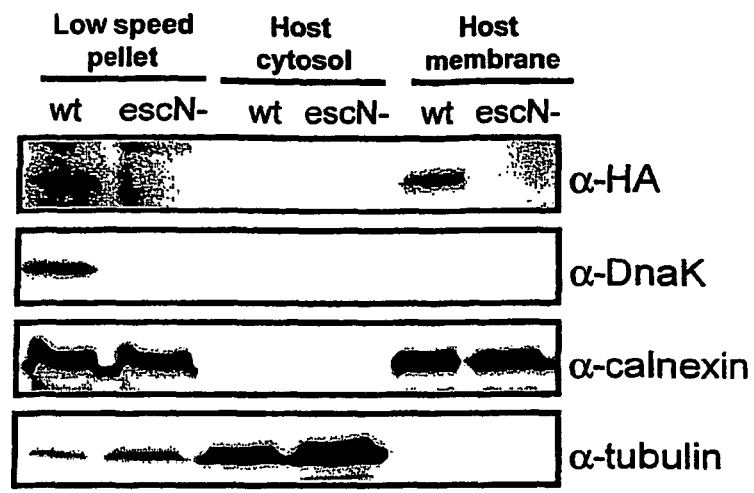
B.
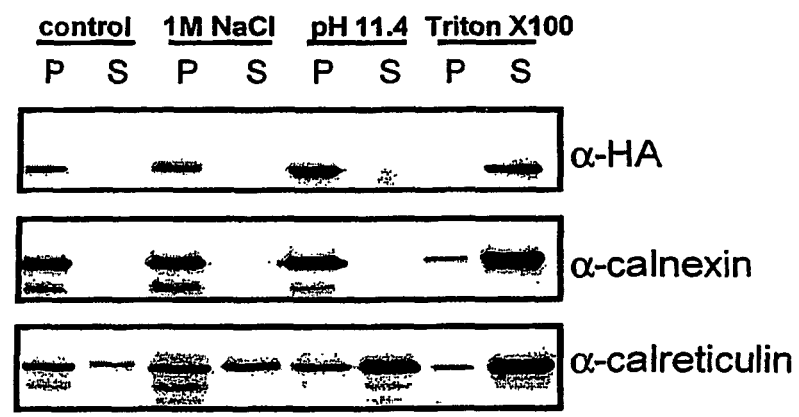
FIG. 14

Enterohemorrhagic *E. coli* NleG homolog Nucleotide Sequence

ATGAATGTCCTTCGAGCTCAAGTAGCATCTAGCGGTCGAGGGGAGTTTACATTAGGTAAT
GAGACTGTCAGCATTGTATTTAATGAAACCGATGGGCGTTTTCTATCCAGCGGCAGTAGT
GGGGGATTGCTTACTGAGTTATTCCTTTATGGGTTTAATAACGGCCCTGAAGCTCTTCGC
GATAGGATGCTCAGTATGCTTTCGGACTCAGGTGAAGCACAATCGCAAGAGAGTATTCAG
GACAAAATATCTCAATGTAAGTTTCCTGTTAGTTCAGGAAATTTCCAGTGCCCGCCAGAG
TCTATTCAGTGTCCAATTACACTAGAGAGACCCGAAGAAGGAGTGTTTGTCAAAAATTCA
GATAGTTCGGCAGTATGCTGCTTATTTGATTTTGATGCATTTCTCGTTTAGCTAGTGAA
GGCTCATATCATCCACTGACCCGAGAACCAATAACGGCATCAATGATTATAAGTCCTGAT
AAATGTGTTTATGATCCTATCAAGGGAAACTTCATTATAAAAGATAGTTAA
(SEQ ID NO: 61)

FIG. 16A

Enterohemorrhagic *E. coli* NleG homolog Protein Sequence

MNVLRAQVASSGRGEFTLGNETVSIVFNETDGRFLSSGSSGGLLTELFLYGFNNGPEALRDRMLSMLSD
SGEAQSQESIQDKISQCKFPVSSGNFQCPPESIQCPITLERPEEGVFVKNSDSSAVCCLFDFDAFSRLA
SEGSYHPLTREPITASMIISPDKCVYDPIKGNFIIKDS (SEQ ID NO: 73)

FIG. 16B

Enterohemorrhagic *E. coli* NleH1 Nucleotide Sequence

ATGTTATCGCCCTCTTCTATAAATTTGGGATGTTCATGGAATTCTTTAACCAGAAACCTG
ACTTCGCCTGATAATCGTGTTTTATCCTCTGTAAGGGATGCTGCTGTTCACTCTGATAGC
GGGACGCAAGTAACGGTTGGCAACAGAACATATCGTGTTGTGGTCACTGATAATAAGTTT
TGCGTTACAAGAGAAAGTCATAGTGGTTGTTTTACTAATCTGTTGCACAGGTTGGGATGG
CCTAAGGGAGAGATTAGCAGAAAAATTGAGGCTATGCTGAATACATCGCCAGTGAGCACG
ACTATAGAAAGAGGCTCTGTTCATTCGAACAGACCTGATTTACCTCCAGTGGATTATGCG
CAGCCGGAGTTACCTCCAGCGGATTATACTCAATCAGAGTTGCCGAGGGTTAGCAACAAT
AAATCACCCGTGCCAGGTAATGTTATTGGTAAAGGTGGTAATGCTGTCGTGTATGAAGAT
ATGGAAGATACAACAAAAGTGTTGAAGATGTTTACTATATCTCAAAGCCATGAAGAGGTG
ACAAGCGAAGTTCGTTGTTTCAATCAGTATTATGGTTCCGGGAGTGCAGAGAAAATATAT
AATGATAATGGAAATGTTATTGGTATTAGAATGAATAAAATAAATGGGGAATCTCTTTTG
GATATTCCATCATTACCAGCACAAGCTGAACAGGCTATTTACGATATGTTTGACAGACTG
GAGAAAAAAGGAATTCTTTTTGTTGATACAACAGAAACAAATGTTTTATATGATCGTATG
AGAAATGAATTTAATCCAATAGATATATCATCTTATAATGTTTCTGATATTTCATGGAGT
GAACATCAAGTCATGCAATCTTATCACGGAGGAAAGCTGGATCTTATTAGTGTAGTATTA
AGTAAGATATAA
  (SEQ ID NO: 62)

FIG. 17A

Enterohemorrhagic *E. coli* NleH1 Protein Sequence

MLSPSSINLGCSWNSLTRNLTSPDNRVLSSVRDAAVHSDSGTQVTVGNRTYRVVVTDNKF
CVTRESHSGCFTNLLHRLGWPKGEISRKIEAMLNTSPVSTTIERGSVHSNRPDLPPVDYA
QPELPPADYTQSELPRVSNNKSPVPGNVIGKGGNAVVYEDMEDTTKVLKMFTISQSHEEV
TSEVRCFNQYYGSGSAEKIYNDNGNVIGIRMNKINGESLLDIPSLPAQAEQAIYDMFDRL
EKKGILFVDTTETNVLYDRMRNEFNPIDISSYNVSDISWSEHQVMQSYHGGKLDLISVVL
SKI (SEQ ID NO: 74)

FIG. 17B

Enterohemorrhagic *E. coli* NleH2 Nucleotide Sequence

ATGTTATCGCCATATTCTGTAAATTTGGGATGTTCATGGAATTCTTTAACCAGAAACCTG
ACTTCGCCTGATAATCGTGTTTTATCCTCTGTAAGGGATGCTGCCGTTCATTCTGATAAT
GGGGCGCAAGTAAAGGTTGGCAACAGAACATATCGTGTTGTTGCCACCGATAATAAGTTT
TGCGTTACAAGAGAAAGTCATAGTGGTTGTTTTACTAATCTGTTGCACAGGCTGGGATGG
CCTAAGGGGGAGATTAGCAGGAAAATTGAGGTCATGCTGAATGCATCACCAGTGAGCGCT
GCTATGGAAAGAGGCATTGTTCATTCGAACAGACCTGATTTACCTCCTGTTGATTATGCA
CCGCCAGAGTTACCGAGTGTGGACTATAACAGGTTGTCAGTACCTGGTAATGTTATTGGC
AAAGGGGGGAACGCTGTAGTATATGAAGATGCTGAGGATGCAACAAAAGTCCTGAAGATG
TTTACTACATCTCAAAGCAATGAAGAGGTGACAAGCGAAGTTCGTTGCTTCAACCAATAT
TATGGTGCCGGGAGTGCAGAAAAAATATATGGCAATAATGGTGATATTATTGGTATTAGA
ATGGATAAAATAAATGGAGAATCGCTTTTAAATATTTCGTCCTTGCCAGCACAGGCTGAG
CATGCTATTTACGATATGTTTGATAGACTGGAGCAAAAAGGAATTCTTTTTGTCGATACA
ACAGAGACAAATGTCTTATATGACCGCGCGAAGAATGAGTTTAATCCAATAGATATATCA
TCTTATAATGTTTCCGACCGTTCATGGAGTGAAAGTCAAATAATGCAATCTTATCATGGC
GGAAAGCAAGATCTTATTAGTGTGGTATTAAGTAAAATTTAG (SEQ ID NO:63)

FIG. 18A

Enterohemorrhagic *E. coli* NleH2 Protein Sequence

MLSPYSVNLGCSWNSLTRNLTSPDNRVLSSVRDAAVHSDNGAQVKVGNRTYRVVATDNKF
CVTRESHSGCFTNLLHRLGWPKGEISRKIEVMLNASPVSAAMERGIVHSNRPDLPPVDYA
PPELPSVDYNRLSVPGNVIGKGGNAVVYEDAEDATKVLKMFTTSQSNEEVTSEVRCFNQY
YGAGSAEKIYGNNGDIIGIRMDKINGESLLNISSLPAQAEHAIYDMFDRLEQKGILFVDT
TETNVLYDRAKNEFNPIDISSYNVSDRSWSESQIMQSYHGGKQDLISVVLSKI (SEQ ID NO: 75)

FIG. 18B

Enterohemorrhagic *E. coli* Z2076 Nucleotide Sequence

ATGGTAATGCCTGGATTAGTATCATATATATCATCGACTTCATTCGCGAATGAGATGGCG
GAGATGCGTCAGCAGGTAATGGAAGGGCAGATTGGTGGATTTCTCCTGGGAGGGGAGAGA
GTTAGAGTTTCTTATTTATTTCAATTGCATTAA (SEQ ID NO: 64)

FIG. 19A

Enterohemorrhagic *E. coli* Z2076 Protein Sequence

MVMPGLVSYISSTSFANEMAEMRQQVMEGQIGGFLLGGERVRVSYLFQLH
  (SEQ ID NO: 76)

FIG. 19B

Enterohemorrhagic *E. coli* Z2149 Nucleotide Sequence

ATGCCATTAACCTCAGATATTAGATCACATTCATTTAATCTTGGGGTGGAGGTTGTTCGT
GCCCGAATTGTAGCCAATGGGCGCGGAGATATTACAGTCGGTGGTGAAACTGTCAGTATT
GTGTATGATTCTACTAATGGGCGCTTTTCATCCAGTGGCGGTAATGGCGGATTGCTTTCT
GAGTTATTGCTTTTGGGATTTAATAGTGGTCCTCGAGCCCTTGGTGAGAGAATGCTAAGT
ATGCTTTCGGACTCAGGTGAAGCACAATCGCAAGAGAGTATTCAGAACAAAATATCTCAA
TGTAAGTTTTCTGTTTGTCCAGAGAGACTTCAGTGCCCGCTTGAGGCTATTCAGTGTCCA
ATTACACTGGAGCAGCCTGAAAAAGGTATTTTTGTGAAGAATTCAGATGGTTCAGATGTA
TGTACTTTATTTGATGCCGCTGCATTTTCTCGTTTGGTTGGTGAAGGCTTACCCCACCCA
CTGACCCGGGAACCAATAACGGCATCAATAATTGTAAAACATGAAGAATGCATTTATGAC
GATACCAGAGGAAACTTCATTATAAAGGGTAATTGA (SEQ ID NO: 65)

FIG. 20A

Enterohemorrhagic *E. coli* Z2149 Protein Sequence

MPLTSDIRSHSFNLGVEVVRARIVANGRGDITVGGETVSIVYDSTNGRFSSSGGNGGLLS
ELLLLGFNSGPRALGERMLSMLSDSGEAQSQESIQNKISQCKFSVCPERLQCPLEAIQCP
ITLEQPEKGIFVKNSDGSDVCTLFDAAAFSRLVGEGLPHPLTREPITASIIVKHEECIYD
DTRGNFIIKGN (SEQ ID NO: 77)

FIG. 20B

Enterohemorrhagic *E. coli* Z2150 Nucleotide Sequence

```
atgcctgtta ccaccttaag tatcccaagt atatctcaat tatctcctgc aagagtacag
tctttgcagg atgcagccag acttgaaagt ggaataagaa tatccattgg tagtggccaa
tattctgttc actatgtcca actactggat ggattttcag ttgaaccggt gagaggaggc
ttactggata ggctattggg gcgtgagcat cgaatggata aagggctgt ggctctggaa
aggcaattaa atggaggtgt cgattttta agtagtgtta ataactattt tcagagtgtc
atggcagaac acagagaaaa taaaacaggt aataaaatat taatggaaaa aataaattct
tgtgtatttg gaacggattc taatcacttt tcttgcccgg agtcattttt gacatgcccg
ataacgctgg acacacctna gactggagtg ttcatgagaa actcacgagg tgctgagata
tgctctctat atgataagga tgcgttagtg caacttgttg aaactggtgg aactcatcct
ctgagtcgag aacctataac agaatcaatg attatgagaa aagacgaatg tcactttgat
gcaaaaagag aagctttttg ttgtaagtga
```
(SEQ ID NO: 66)

FIG. 21A

Enterohemorrhagic *E. coli* Z2150 Protein Sequence

MPVTTLSIPSISQLSPARVQSLQDAARLESGIRISIGSGQYSVHYVQLLDGFSVEPVRGGLLDRLLGRE
HRMDRRAVALERQLNGGVDFLSSVNNYFQSVMAEHRENKTGNKILMEKINSCVFGTDSNHFSCPESFLT
CPITLDTPXTGVFMRNSRGAEICSLYDKDALVQLVETGGTHPLSREPITESMIMRKDECHFDAKREAFC
CK (SEQ ID NO:78)

FIG. 21B

Enterohemorrhagic *E. coli* Z2151 Nucleotide Sequence

ATGCCTGTAGATTTAACGCCTTATATTTTACCTGGGGTTAGTTTTTTGTCTGACATTCCT
CAAGAAACCTTGTCTGAGATACGTAATCAGACTATTCGTGGAGAAGCTCAAGTAAGACTG
GGTGAGTTGATGGTGTCAATACGACCTATGCAGGTAAATGGATATTTTATGGGAAGTCTT
AACCAGGATGGTTTATCGAATGATAACATCCAGATTGGCCTTCAATATATAGAACATATT
GAACGTACACTTAATCATGGTAGTTTGACAAGCCGTGAAGTTACAGTACTGCGTGAAATT
GAGATGCTCGAAAATATGGAATTGCTTTCTAACTACCAGTTAGAGGAGTTGTTAGATAAA
ATTGAAGTATGTGCATTTAATGTGGAGCATGCACAATTGCAAGTGCCAGAGAGCTTACGA
ACATGCCCTGTTACATTATGTGAACCAGAAGATGGGGTATTTATGAGGAATTCAATGAAT
TCAAATGTTTGTATGTTGTATGATAAAATGTCATTAATATATCTTGTTAAAACAAGGGCG
GCTCATCCTTTGAGCAGGGAATCAATCGCAGTTTCAATGATTGTAGGAAGAGATAATTGT
GCTTTTGACTCTGACAGAGGTAACTTCGTTTTAAAAAATTAA (SEQ ID NO: 67)

FIG. 22A

Enterohemorrhagic *E. coli* Z2151 Protein Sequence

MPVDLTPYILPGVSFLSDIPQETLSEIRNQTIRGEAQVRLGELMVSIRPMQVNGYFMGSL
NQDGLSNDNIQIGLQYIEHIERTLNHGSLTSREVTVLREIEMLENMELLSNYQLEELLDK
IEVCAFNVEHAQLQVPESLRTCPVTLCEPEDGVFMRNSMNSNVCMLYDKMSLIYLVKTRA
AHPLSRESIAVSMIVGRDNCAFDSDRGNFVLKN (SEQ ID NO: 79)

FIG. 22B

Enterohemorrhagic *E. coli* Z2337 Nucleotide Sequence

ATGCCTGTAGATTTAACGCCTTATATTTTACCTGGGGTTAGTTTTTTGTCTGACATTCCT
CAAGAAACCTTGTCTGAGATACGTAATCAGACTATTCGTGGAGAAGCTCAAATAAGACTG
GGTGAGTTGATGGTGTCAATACGACCTATGCAGGTAAATGGATATTTTATGGGAAGTCTT
AACCAGGATGGTTTATCGAATGATAATATCCAGATTGGCCTTCAATATATAGAACATATT
GAACGTACACTTAATCATGGTAGTTTGACAAGCCGTGAAGTTACAGTACTGCGTGAAATT
GAGATGCTCGAAAATATGGATTTGCTTTCTAACTACCAGTTAGAGGAGTTGTTAGATAAA
ATTGAAGTATGTGCATTTAATGTGGAGCATGCACAATTGCAAGTGCCAGAGAGCTTACGA
ACATGCCCTGTTACATTATGTGAACCAGAAGATGGGGTATTTATGAGGAATTCAATGAAT
TCAAATGTTTGTATGTTGTATGATAAAATGGCATTAATACATCTTGTTAAAACAAGGGCG
GCTCATCCTTTGAGCAGGGAATCAATCGCAGTTTCAATGATTGTAGGAAGAGATAATTGT
GCTTTTGACCCTGACAGAGGTAACTTCGTTTTAAAAAATTAA (SEQ ID NO: 68)

FIG. 23A

Enterohemorrhagic *E. coli* Z2337 Protein Sequence

MPVDLTPYILPGVSFLSDIPQETLSEIRNQTIRGEAQIRLGELMVSIRPMQVNGYFMGSL
NQDGLSNDNIQIGLQYIEHIERTLNHGSLTSREVTVLREIEMLENMDLLSNYQLEELLDK
IEVCAFNVEHAQLQVPESLRTCPVTLCEPEDGVFMRNSMNSNVCMLYDKMALIHLVKTRA
AHPLSRESIAVSMIVGRDNCAFDPDRGNFVLKN (SEQ ID NO: 80)

FIG. 23B

Enterohemorrhagic *E. coli* Z2338 Nucleotide Sequence

ATGCCTGTTACCACCTTAAGTATCCCAAGTATATCTCAATTATCTCCTGCAGGAGTACAG
TCTTTGCAGGATGCTGCCAGACTTGAAAGTGGAATAAGAATATCCATTGGTAGTGGCCAA
TATTCTGTTCACTATGTCCAGCTACTGGATGGATTTTCAGTTGAACCGGTGAGAGGAGGC
TTACTGGATAGGCTATTGGGGCGTGAGCATCGAATGGAGAGAAGGGCTGTGGCTCTGGAA
AGGCAATTAAATGGAGGTGTCGATTTTTAAGTAGTGTTAATAACTATTTTCAGAGTGTC
ATGGCAGAACACAGAGAAAATAAAACAAGTAATAAAATATTAATGGAAAAAATAAATTCT
TGTTTATTTAGACCTGATTCTAATCACTTTTCTTGCCCGGAGTCATTTTGACATGCCCG
ATAACGCTGGACACACCTGAGACTGGGGTGTTCATGAGAAACTCACGAGGTGCTGAGATA
TGCTCTCTATATGATAAGGACGCGTTAGTGCAACTTGTTGAAACTGGTGGAGCTCATCCT
CTGAGTCGAGAACCTATAACAGAATCAATGATTATGAGAAAAGATGAATGTCACTTTGAT
ACAAAAAGAGAAGCTTTTTGTTGTAAGTGA (SEQ ID NO:69)

FIG. 24A

Enterohemorrhagic *E. coli* Z2338 Protein Sequence

MPVTTLSIPSISQLSPAGVQSLQDAARLESGIRISIGSGQYSVHYVQLLDGFSVEPVRGG
LLDRLLGREHRMERRAVALERQLNGGVDFLSSVNNYFQSVMAEHRENKTSNKILMEKINS
CLFRPDSNHFSCPESFLTCPITLDTPETGVFMRNSRGAEICSLYDKDALVQLVETGGAHP
LSREPITESMIMRKDECHFDTKREAFCCK (SEQ ID NO: 81)

FIG. 24B

Enterohemorrhagic *E. coli* Z2339 Nucleotide Sequence

ATGCCATTAACCTCAGATATTAGATCACATTCATTTAATCTTGGGGTGGAGGTTGTTCGT
GCCCGAATTGTAGCCAATGGGCGCGGAGATATTACAGTCGGTGGTGAAACTGTCAGTATT
GTGTATGATTCTACTAATGGGCGCTTTTCATCCAGTGGCGGTAATGGCGGATTGCTTTCT
GAGTTATTGCTTTTGGGATTTAATAGTGGTCCTCGAGCCCTTGGTGAGAGAATGCTAAGT
ATGCTTTCGGACTCAGGTGAAGCACAATCGCAAGAGAGTATTCAGAACAAAATATCTCAA
TGTAAGTTTTCTGTTTGTCCAGAGAGACTTCAGTGCCCGCTTGAGGCTATTCARTGTCCA
ATTACACTGGAGCAGCCTGAAAAAGGTATTTTTGTGAAGAATTCAGATGGTTCAGATGTA
TGTACTTTATTTGATGCCGCTGCATTTTCTCGTTTGGTTGGTGAAGGCTTACCCCACCCA
CTGACCCGGGAACCAATAACGGCATCAATAATTGTAAAACATGAAGAATGCATTTATGAC
GATACCAGAGGAAACTTCGTTATAAAGGGTAATTGA (SEQ ID NO: 70)

FIG. 25A

Enterohemorrhagic *E. coli* Z2339 Protein Sequence

MPLTSDIRSHSFNLGVEVVRARIVANGRGDITVGGETVSIVYDSTNGRFSSSGGNGGLLS
ELLLLGFNSGPRALGERMLSMLSDSGEAQSQESIQNKISQCKFSVCPERLQCPLEAIQCP
ITLEQPEKGIFVKNSDGSDVCTLFDAAAFSRLVGEGLPHPLTREPITASIIVKHEECIYD
DTRGNFVIKGN (SEQ ID NO: 82)

FIG. 25B

Enterohemorrhagic E. coli Z2560 Nucleotide Sequence

```
atggacgctt ttattgtaga tcctgttcaa ggggaactat attcgggttt aagccataca
gaactagccg atatcattag attggctgat tctgttgaaa atcaattgaa tggaggcaat
tcatttcttg atgtattcag tacatatatg gggcaggtta tttctgaatt tatgcatagt
aatgataaca gaattgaatt gttacagcgg cgattacatt catgttcatt tttagttaat
attgaagaaa tgtcttacat agatgaagca ttacagtgcc cgattacgct ggcaattcct
caacgaggtg ttttttaag aaatgctgaa ggttccagag tatgtagttt atatgatgaa
atggctcttt ctcgtataat taatgatggg atgcatcacc cactaagcag agagccaata
acattatcaa tgcttgtggc cagagagcag tgtgagtttg attgcagtat cggtcacttt
acggtgagga gtgattgtta ttcagtgtag (SEQ ID NO: 71)
```

FIG. 26A

Enterohemorrhagic E. coli Z2560 Protein Sequence

MDAFIVDPVQGELYSGLSHTELADIIRLADSVENQLNGGNSFLDVFSTYMGQVISEFMHSNDNRIELLQ
RRLHSCSFLVNIEEMSYIDEALQCPITLAIPQRGVFLRNAEGSRVCSLYDEMALSRIINDGMHHPLSRE
PITLSMLVAREQCEFDCSIGHFTVRSDCYSV (SEQ ID NO: 83)

FIG. 26B

Enterohemorrhagic *E. coli* Z2976 Nucleotide Sequence

ATGGCAGACCGCAAACAGCACCGCGCTATCGCGGAGCGTCGTCACATCCAGACTGAAATC
AACCGCAGACTTTCCCGCGCATCACGCGTCGCGCAAATCATGCACATCAATATGCTGCAT
GAGCGCAGCCACGCACTATCAAACATTTATTCCGCCTCTGTTTTCAGCTATCTGGCGGAT
GATCTGCACGAGTTTCAACAGCTCATCCAGCAGCAAAACAAACTCCATTAA (SEQ ID NO:72)

FIG. 27A

Enterohemorrhagic *E. coli* Z2976 Protein Sequence

MADRKQHRAIAERRHIQTEINRRLSRASRVAQIMHINMLHERSHALSNIYSASVFSYLAD
DLHEFQQLIQQQNKLH (SEQ ID NO:84)

FIG. 27B

BACTERIAL VIRULENCE FACTORS AND USES THEREOF

FIELD OF THE INVENTION

The invention relates to bacterial pathogens. More specifically, the invention relates to, in part, secreted proteins of bacterial pathogens and methods for their use.

BACKGROUND OF THE INVENTION

*Escherichia coli* is an extremely versatile organism. In addition to being a member of the normal intestinal flora, strains of *E. coli* also cause bladder infections, meningitis, and diarrhea. Diarrheagenic *E. coli* include at least five types of *E. coli*, which cause various symptoms ranging from cholera-like diarrhea to extreme colitis. Each type of diarrheagenic *E. coli* possesses a particular set of virulence factors, including adhesins, invasins, and/or toxins, which are responsible for causing a specific type of diarrhea.

Enteropathogenic *E. coli* (EPEC), is a predominant cause of infantile diarrhea worldwide. EPEC disease is characterized by watery diarrhea of varying severity, with vomiting and fever often accompanying the fluid loss. In addition to isolated outbreaks in daycares and nurseries in developed countries, EPEC poses a major endemic health threat to young children (<6 months) in developing countries. Worldwide, EPEC is the leading cause of bacterial mediated diarrhea in young children, and it has been estimated that EPEC kills several hundred thousand children per year.

Enterohemorrhagic *E. coli* (EHEC), also called Shiga toxin producing *E. coli* (STEC) or Vero toxin producing *E. coli* (VTEC), causes a more severe diarrhea than EPEC (enteric colitis) and in approximately 10% of cases, this disease progresses to an often fatal kidney disease, hemolytic uremic syndrome (HUS). EHEC O157:H7 is the most common serotype in Canada and the United States, and is associated with food and water poisoning (3). Other serotypes of EHEC also cause significant problems in Asia, Europe, and South America, and to a lesser extent in North America. EHEC colonizes cattle and causes A/E lesions, but does not cause disease in adult animals, and instead sheds organisms into the environment. This however causes serious health problems as a relatively few EHEC are necessary to infect humans.

Unlike other *E. coli* diarrheas, such as enterotoxigenic *E. coli*, diarrhea caused by EHEC and EPEC is not mediated by a toxin. Instead, EPEC and EHEC bind to intestinal surfaces (EPEC the small bowel, EHEC the large bowel) and cause a characteristic histological lesion, called the attaching and effacing (A/E) lesion (8). A/E lesions are marked by dissolution of the intestinal brush border surface and loss of epithelial microvilli (effacement) at the sites of bacterial attachment. Once bound, bacteria-reside upon cup-like projections or pedestals. Underlying this pedestal in the epithelial cell are several cytoskeletal components, including actin and actin associated cytoskeletal proteins. Formation of A/E lesions and actin-rich pedestals beneath attaching bacteria is the histopathological hallmark of A/E pathogens (1, 2). This pathology can be recapitulated in cultured cells in vitro, and pedestal formation can be viewed by a fluorescent actin staining assay (2, 11). Formation of the A/E lesion may be responsible for disruption of the brush border and microvilli, fluid secretion, and diarrhea.

EPEC and EHEC belong to a family of A/E pathogens, including several EPEC-like animal pathogens that cause disease in rabbits (REPEC), pigs (PEPEC), and mice (*Citrobacter rodentium*). These pathogens contain pathogenicity islands (PAIs) that encode specialized secretion systems and secreted virulence factors critical for disease. The genes required for the formation of A/E lesions are thought to be clustered together in a single chromosomal pathogenicity island known as the locus for enterocyte effacement (LEE), which includes regulatory elements, a type III secretion system (TTSS), secreted effector proteins, and their cognate chaperones (4-8).

The LEE contains 41 genes, making it one of the more complex PAIs. The main function of the LEE TTSS is to deliver effectors into host cells, where they subvert host cell functions and mediate disease (9, 10, 34). Five LEE-encoded effectors (Tir, EspG, EspF, Map, and EspH) have been identified (35-40). Tir (for translocated intimin receptor) is translocated into host cells where it binds host cytoskeletal and signaling proteins and initiates actin polymerization at the site of bacterial attachment (31, 44), resulting in formation of actin pedestal structures underneath adherent bacteria, which directly interact with the extracellular loop of Tir via the bacterial outer membrane protein intimin. CesT plays a role as a chaperone for Tir stability and secretion (18, 19).

Four other LEE-encoded TTSS-translocated effectors have been characterized in A/E pathogens: EspH enhances elongation of actin pedestals (40); EspF plays a role in disassembly of tight junctions between intestinal epithelial cells (38); EspG is related to the Shigella microtubule-binding effector VirA (36, 55); and Map localizes to mitochondria (37), but also has a role in actin dynamics (48). Ler (for LEE encoded regulator) is the only LEE encoded regulator identified.

SUMMARY OF THE INVENTION

This invention is based, in part, on the identification of several new common secreted proteins of A/E pathogens.

The invention provides, in one aspect, compositions including a polypeptide or fragment or variant thereof, or a cell culture supernatant including such a polypeptide where the substantially pure polypeptide includes an amino acid sequence substantially identical to the sequence of any one or more of SEQ ID NOs: 22-43, 59, or 73-84 or fragments or variants thereof. The invention also provides compositions including a nucleic acid molecule, where the nucleic acid molecule includes a nucleotide sequence substantially identical to the sequence of any one or more of SEQ ID NOs: 1-21 or 60-72; and compositions including a nucleotide sequence encoding a polypeptide substantially identical to the sequence of any one or more of SEQ ID NO: 22-43, or fragments thereof. The compositions may further include a physiologically acceptable carrier, or may further include an adjuvant. The compositions may also include a polypeptide or nucleic acid molecule such as EspA, EspB, EspD, EspP, Tir, Shiga toxin 1, Shiga toxin 2, or intimin. The polypeptides or nucleic acid molecules may be substantially pure.

The invention also provides, in alternative aspects, a bacterium or a preparation thereof, where the bacterium includes a mutation in a gene such as nleA, nleB, nleC, nleD, nleE, nleF, nleG, nleH, or a homologue thereof, or includes a mutation in the bacterial genome in a nucleotide sequence that is substantially identical to SEQ ID NOs: 1-21 or 60-72. In some embodiments, the bacterium may be an A/E pathogen, such as enterohemorrhagic *E. coli* (EHEC; e.g., EHEC O157:H7 or EHEC O157:NM), enteropathogenic *E. coli* (EPEC; e.g., EPEC O127:H6), or *Citrobacter rodentium*. In some embodiments, the mutation may attenuate virulence, or may occur in a nucleotide sequence in the genome of the A/E pathogen that is substantially identical to a sequence selected from the group consisting of SEQ ID NOs: 1-21 or 60-72. The bacterium may be provided as a composition, in combination with an adjuvant. In some embodiments, the bacterium may be live. In some embodiments, the bacterium may be killed. The mode of administration may be oral or parenteral.

The invention also provides, in alternative aspects, a method of detecting the presence of an A/E pathogen in a sample, by providing a sample; and detecting the presence of: a nucleotide sequence substantially identical to a sequence selected from SEQ ID NOs: 1-21 or 60-72 or a fragment or variant thereof; a nucleotide sequence encoding a polypeptide sequence substantially identical to a sequence selected from SEQ ID NOs: 22-43, 59, or 13-84, or a polypeptide including an amino acid sequence substantially identical to a sequence selected from SEQ ID NOs: 22-43, 59, or 73-84 or a fragment or variant thereof, where the presence of the nucleotide sequence or the amino acid sequence indicates the presence of an A/E pathogen in the sample (e.g., egg, feces, blood, or intestine). The detecting may include contacting the nucleotide sequence with a probe or primer substantially identical to a sequence selected from the group consisting of SEQ ID NOs: 1-21 or 60-72, or a nucleotide sequence encoding a polypeptide sequence substantially identical to a sequence selected from the group consisting of SEQ ID NOs: 22-43, 59, or 73-84, or a portion thereof, or may include contacting the amino acid sequence with an antibody that specifically binds a sequence selected from the group consisting of SEQ ID NOs: 22-43, 59, or 73-84 or a fragment or variant thereof.

The invention also provides, in alternative aspects, methods for eliciting an immune response against an A/E pathogen or component thereof, or for reducing colonization or shedding of an A/E pathogen in a animal (e.g., a human; a ruminant, such as sheep (ovine subject), goats, cattle (bovine subject), etc.; or any other animal, e.g., pigs, rabbits, poultry (e.g., ducks, chicken, turkeys) etc.), by identifying a animal infected with, or at risk for infection by, an A/E pathogen; and administering to the animal an effective amount of a composition including a polypeptide including an amino acid sequence substantially identical to the sequence of any one or more of SEQ ID NOs: 22-43, 59, or 73-84-43; a nucleotide sequence encoding a polypeptide sequence substantially identical to a sequence selected from SEQ ID NOs: 22-43, 59, or 73-84; a nucleic acid molecule including a nucleotide sequence substantially identical to the sequence of any one or more of SEQ ID NOs: 1-21 or 60-72; or a cell culture supernatant including such polypeptides, thus eliciting an immune response, or reducing colonization or shedding of the A/E pathogen in the animal.

The invention also provides, in alternative aspects, a method of attenuating the virulence of an A/E pathogen, by providing an A/E pathogen; and mutating a gene such as nleA, nleB, nleC, nleD, nleE, nleF, nleG, or nleH, or a homologue thereof in the A/E pathogen, or mutating one or more of a nucleotide sequence in the genome of the A/E pathogen, where the nucleotide sequence is selected from SEQ ID NOs: 1-21 or 60-72, thereby attenuating virulence.

The invention also provides, in alternative aspects, a method of screening for a compound that attenuates the virulence of an A/E pathogen, by providing a system (e.g., a cell, such as a EHEC, EPEC, or *C. rodentium* cell, an animal model, or an in vitro system) including: a polypeptide including an amino acid sequence substantially identical to the sequence of any one or more of SEQ ID NOs: 22-43, 59, or 73-84 or a fragment or variant thereof; a nucleotide sequence encoding a polypeptide sequence substantially identical to a sequence selected from SEQ ID NOs: 22-43, 59, or 73-84 or a fragment or variant thereof 3; or a nucleic acid molecule including a nucleotide sequence substantially identical to the sequence of any one or more of SEQ ID NOs: 1-21 or 60-72 or a fragment or variant thereof; providing a test compound; and determining whether the test compound modulates the expression, secretion, or biological activity of the polypeptide or the nucleic acid molecule, where a change, e.g., decrease in the expression, secretion, or biological activity of the polypeptide or the nucleic acid molecule indicates a compound that attenuates the virulence of an A/E pathogen.

The invention also provides, in alternative aspects, a method of producing a A/E pathogen virulence factor by providing a recombinant cell including a polypeptide including an amino acid sequence substantially identical to the sequence of any one of SEQ ID NOs: 22-43, 59, or 73-84 or a fragment or variant thereof; a nucleotide sequence encoding a polypeptide sequence substantially identical to a sequence selected from the group consisting of SEQ ID NOs: 22-43, 59, or 73-84 or a fragment or variant thereof; or a nucleic acid molecule including a nucleotide sequence substantially identical to the sequence of any one of SEQ ID NOs: 1-21 or 60-72 or a fragment or variant thereof; growing the recombinant cell under conditions that permit expression and/or secretion of the polypeptide, and optionally, isolating the polypeptide. In some embodiments, the polypeptide may be secreted from the cell.

The invention also provides, in alternative aspects, a method of treating or preventing infection by an A/E pathogen, by identifying a mammal having, or at risk for, an A/E pathogen infection; and administering to the mammal an effective amount of a compound that attenuates the virulence of an A/E pathogen, where the compound inhibits the expression or secretion of a polypeptide including an amino acid sequence substantially identical to the sequence of any one of SEQ ID NOs: 22-43, 59, or 73-84 or a fragment or variant thereof. In some embodiments, the compound may be an antisense nucleic acid molecule that is complementary to a nucleotide sequence substantially identical to the sequence of any one of SEQ ID NOs: 1-21 or 60-72 or a fragment or variant thereof, or may be a siRNA.

The invention also provides, in alternative aspects, a recombinant polypeptide including an amino acid sequence substantially identical to the sequence of SEQ ID NOs: 22-43, 59, or 73-84, or an isolated nucleic acid molecule including a nucleotide sequence substantially identical to the sequence of SEQ ID NOs: 1-21 or 60-72; and/or a vector including such nucleotide sequences; and or a host cell (e.g., an A/E pathogen such as enterohemorrhagic *E. coli* (EHEC), enteropathogenic *E. coli* (EPEC), or *Citrobacter rodentium*, including such vectors. The vector may be capable or incapable of integrating into the genome of an A/E pathogen.

In alternative aspects, the invention also provides uses of the compositions, bacteria, polypeptides, or the nucleic acid molecules according to the invention, for the preparation of a medicament for eliciting an immune response against an A/E pathogen, or component thereof, or for reducing shedding or colonization of an A/E pathogen in an animal.

In alternative aspects, the invention also provides kits including a reagent for detecting an A/E pathogen in a sample and a package insert with instructions for detecting the A/E pathogen in the sample. The reagent may include a probe or primer probe or primer substantially identical to: a nucleotide sequence selected from the group consisting of one or more of SEQ ID NOs: 1-21 or 60-72 or a fragment or variant thereof, or a nucleotide sequence encoding a polypeptide substantially identical to one or more of SEQ ID NO: 22-43, 59, 73-84 or a fragment or variant thereof, or an antibody that specifically binds a sequence selected from the group consisting of one or more of SEQ ID NOs: 22-43, 59, 73-84 or a fragment or variant thereof.

An "A/E pathogen" is a pathogen, for example a pathogenic *E. coli* bacterium, that can bind to the intestinal surfaces of an animal, for example, a mammal, e.g., cattle, sheep, goats, pigs, rabbits, dogs, cats, etc., or an avian species e.g., chickens, ducks, turkeys, etc., and cause a characteristic histological lesion, called the attaching and effacing (A/E) lesion (8). In general, an A/E pathogenic infection may result in diarrhea, enteric colitis, kidney disease (such as hemolytic uremic syndrome). However, infection with an A/E pathogen need not necessarily manifest in disease symptoms; a host mammal infected with an A/E pathogen may be a carrier of the pathogen and remain healthy and free of disease. Thus, mammals infected with, or at risk for infection by, an A/E pathogen include animals, e.g., farm animals, such as poultry animals, e.g, chickens, turkeys, ducks, or ruminants, e.g., cattle, sheep, goats, etc. or other farm animals, e.g., pigs, that do not manifest symptoms of disease, as well as include humans, who are susceptible to severe enteric disease as a result of A/E pathogenic infection.

Exemplary A/E pathogens include, without limitation, enterohemorrhagic *E. coli* (EHEC) (also known as Shiga toxin producing *E. coli* (STEC) or Vero toxin producing *E. coli* (VTEC), for example EHEC serotypes O157 (e.g., EHEC O157:H7, the genomic sequence of which is described in Accession Nos. AE005594, AE005595, AP002566, AE 005174, NC_002695, or NC_002655), or O158, O5, O8, O18, O26, O45, O48, O52, O55, O75, O76, O78, O84, O91, O103, O104, O111, O113, O114, O116, O118, O119, O121, O125, O28, O145, O146, O163, O165; enteropathogenic *E. coli* (EPEC); as well as pathogenic *E. coli* that infect mice (e.g., *Citrobacter rodentium*); rabbits (e.g. RDEC-1 strains, such as O15:H⁻); pigs; sheep; dogs; and other mammals. Many strains of A/E pathogens are commercially available, for example, through the American Type Culture Collection (ATCC), Manassus, VA, USA. A/E pathogens may also be isolated from infected individuals for example, by direct plating on sorbitol MacConkey agar supplemented with cefixime and tellurite or immunomagnetic enrichment followed by plating on the same media (72, 107, 108).

A "protein," "peptide" or "polypeptide" is any chain of two or more amino acids, including naturally occurring or non-naturally occurring amino acids or amino acid analogues, regardless of post-translational modification (e.g., glycosylation or phosphorylation). An "amino acid sequence", "polypeptide", "peptide" or "protein" of the invention may include peptides or proteins that have abnormal linkages, cross links and end caps, non-peptidyl bonds or alternative modifying groups. Such modified peptides are also within the scope of the invention. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the core peptidic structure). For example, the modifying group can be coupled to the amino-terminus or carboxy-terminus of a peptidic structure, or to a peptidic or peptidomimetic region flanking the core domain. Alternatively, the modifying group can be coupled to a side chain of at least one amino acid residue of a peptidic structure, or to a peptidic or peptidomimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

The terms "nucleic acid" or "nucleic acid molecule" encompass both RNA (plus and minus strands) and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. One example of a modified RNA included within this term is phosphorothioate RNA. By "DNA" is meant a sequence of two or more covalently bonded, naturally occurring or modified deoxyribonucleotides. By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector. By "complementary" is meant that two nucleic acids, e.g., DNA or RNA, contain a sufficient number of nucleotides which are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex. A nucleic acid molecule is "complementary" to another nucleic acid molecule if it hybridizes, under conditions of high stringency, with the second nucleic acid molecule.

A "cell culture supernatant," as used herein, refers generally to a supernatant derived from culturing a bacterium or other organism (e.g., yeast) or cell (e.g., insect cell) that is capable of secreting one or more of a polypeptide comprising an amino acid sequence substantially identical to the sequence of any one of SEQ ID NOs: 22-43, 59, 73-84 or a fragment or variant thereof, or an immunogenic portion thereof, into the cell culture medium. In some embodiments, the cell culture supernatant is substantially pure, i.e., substantially free of bacterial cells or the lysate of such cells. In some embodiments, the cell culture supernatant may also contain one or more of the EspA, EspB, EspD, Tir, intimin, Shiga toxin 1 or 2, or EspP polypeptides, or fragments or aggregates thereof.

The bacterium may be an A/E pathogen, for example, EHEC, EPEC, or *Citrobacter rodentium* that, in some embodiments, may be modified or mutated to preferentially express or secrete the proteins described herein, or may be some other bacterium, for example, a non-pathogenic bacterium, e.g., a non-pathogenic *E. coli* such as HB101, or a non-A/E pathogen, that has been modified or mutated, for example, by recombinant or other techniques, such that it secretes one or more of a protein described herein, for example, a polypeptide comprising an amino acid sequence substantially identical to the sequence of any one of SEQ ID NOs: 22-43, 59, 73-84 or a fragment or variant thereof, or an immunogenic portion thereof, into the cell culture medium.

In some embodiments, the bacterium is not EHEC or EPEC. In some embodiments, where the bacterium is an A/E pathogen, it may also carry a further modification that impairs its ability to express or secrete a polypeptide (for example, EspA, EspB, EspD, Tir, intimin, Shiga toxin 1 or 2, or EspP) that it would normally secrete in the absence of the modification. In some embodiments, the other organism (e.g., yeast) or cell (e.g., insect cell) has been modified or mutated, for example, by recombinant or other techniques, such that it secretes one or more of a protein described herein, for example, a polypeptide comprising an amino acid sequence substantially identical to the sequence of any one of SEQ ID NOs: 22 through 43, or an immunogenic portion thereof, into the cell culture medium.

A compound is "substantially pure" or "isolated" when it is separated from the components that naturally accompany it. Typically, a compound is substantially pure when it is at least 10%, 20%, 30%, 40%, 50%, or 60%, or more generally at least 70%, 75%, 80%, 85%, 90%, 95%, or 99% by weight, of the total material in a sample. Thus, for example, a polypeptide that is chemically synthesised or produced by recombinant technology will be generally be substantially free from its naturally associated components. A polypeptide will also generally be substantially pure if it is separated from its naturally associated components by physical techniques, such as centrifugation, precipitation, column chromatography, gel electrophoresis, HPLC, etc.

A nucleic acid molecule will generally be substantially pure or "isolated" when it is not immediately contiguous with (i.e., covalently linked to) the coding sequences with which it is normally contiguous in the naturally occurring genome of the organism from which the DNA of the invention is derived. Therefore, an "isolated" gene or nucleic acid molecule is intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. The term therefore includes, e.g., a recombinant nucleic acid incorporated into a vector, such as an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant nucleic acid which is part of a hybrid gene encoding additional polypeptide sequences. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue, such as peripheral blood), such as by Northern blot analysis.

A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc. A substantially pure preparation of a cell, for example, a bacterial cell, is a preparation of cells in which contaminating cells that do not have the desired mutant genotype, or do not express or secrete the desired polypeptide in sufficient quantities, constitute less than 10%, 20%, 30%, 40%, 50%, 60%, 70%, 80%, or 90%, of the total number of cells in the preparation.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

As used herein, "heterologous" in reference to a nucleic acid or protein is a molecule that has been manipulated by human intervention so that it is located in a place other than the place in which it is naturally found. For example, a nucleic acid sequence from one species may be introduced into the genome of another species, or a nucleic acid sequence from one genomic locus may be moved to another genomic or extrachromasomal locus in the same species. A heterologous protein includes, for example, a protein expressed from a heterologous coding sequence or a protein expressed from a recombinant gene in a cell that would not naturally express the protein.

A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be any integer from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical at the amino acid or nucleotide level to the sequence used for comparison using, for example, the Align Program (96) or FASTA. For polypeptides, the length of comparison sequences may be at least 2, 5, 10, or 15 amino acids, or at least 20, 25, or 30 amino acids. In alternate embodiments, the length of comparison sequences may be at least 35, 40, or 50 amino acids, or over 60, 80, or 100 amino acids. For nucleic acid molecules, the length of comparison sequences may be at least 5, 10, 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, or as described herein). Examples of useful software include the programs Pile-up and PrettyBox. Such software matches similar sequences by assigning degrees of homology to various substitutions, deletions, substitutions, and other modifications.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology (61).

A substantially identical sequence may for example be an amino acid sequence that is substantially identical to the sequence of any one of SEQ ID NOs: 2243, 59, or 73-84, or a fragment or variant thereof, or a nucleotide sequence substantially identical to the sequence of any one of SEQ ID NOs: 1-21 or 60-72 or a fragment or variant thereof. In some embodiments, a substantially identical sequence may for example be a nucleotide sequence that is complementary to or hybridizes with the sequence of any one of SEQ ID NOs: 1-21 or 60-72 or a fragment or variant thereof. In some embodiments, a substantially identical sequence may be derived from an A/E pathogen.

A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes or primers specific for the nucleic acid sequences described herein, or portions thereof, may vary in length by any integer from at least 8 nucleotides to over 500 nucleotides, including any value in between, depending on the purpose for which, and conditions under which, the probe or primer is used. For example, a probe or primer may be at least 8, 10, 15, 20, or 25 nucleotides in length, or may be at least 30, 40, 50, or 60 nucleotides in length, or may be over 100, 200, 500, or 1000 nucleotides in length. Probes or primers specific for the nucleic acid molecules described herein can be any integer from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical to the nucleic acid sequences described herein using for example the Align program (96).

Probes or primers can be detectably-labeled, either radioactively or non-radioactively, by methods that are known to those skilled in the art. Probes or primers can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are known to those skilled in the art. Probes or primers may be derived from genomic DNA or cDNA, for example, by amplification, or from cloned DNA segments, or may be chemically synthesized.

A "mutation" includes any alteration in the DNA sequence, i.e. genome, of an organism, when compared with the parental strain. The alterations may arise spontaneously or by exposing the organism to a mutagenic stimulus, such as a mutagenic chemical, energy, radiation, recombinant techniques, mating, or any other technique use to alter DNA. A mutation may include an alteration in any of the nucleotide sequences described herein, or may include an alteration in a nucleotide sequence encoding any of the polypeptides described herein.

A mutation may "attenuate virulence" if, as a result of the mutation, the level of virulence of the mutant cell is decreased by at least 10%, 20%, 30%, 40%, 50%, 60%, 70%, 80%, 90%, or 100%, when compared with the parental strain. Decrease in virulence may also be measured by a decrease of at least 10%, 20%, 30%, 40%, 50%, 60%, 70%, 80%, 90%, or 100% in the expression of a polypeptide, for example, a polypeptide including an amino acid sequence substantially identical to the sequence of any one of SEQ ID NOs: 22-43, 59, or 73-84, or a fragment or variant thereof, in the mutant strain when compared with the parental strain. Virulence of an A/E pathogen may be measured as described herein or as known in the art. Decrease in virulence may also be measured by a change of at least 10%, 20%, 30%, 40%, 50%, 60%, 70%, 80%, 90%, or 100% in the biological activity of a polypeptide, for example, a polypeptide including an amino acid sequence substantially identical to the sequence of any one of SEQ ID NOs: 22-43, 59, or 73-84, or a fragment or variant thereof.

"Modulating" or "modulates" means changing, by either increase or decrease. The increase or decrease may be a change of any integer value between 10% and 90%, or of any integer value between 30% and 60%, or may be over 100%, when compared with a control or reference sample or compound.

A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as any of the polypeptides or nucleic acid molecules described herein by, for example, interfering with virulence, or by interfering with any biological response induced by the known compound.

Generally, a test compound can exhibit any value between 10% and 200%, or over 500%, modulation when compared to a reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

A "vector" is a DNA molecule derived, for example, from a plasmid, bacteriophage, or mammalian or insect virus, or artificial chromosome, into which a nucleic acid molecule, for example, a nucleotide sequence substantially identical to the sequence of any one of SEQ ID NOs: 1-21 or 60-72 or a fragment or variant thereof, may be inserted. A vector may contain one or more unique restriction sites and may be capable of autonomous replication in a defined host or vehicle organism such that the cloned sequence is reproducible. A vector may be a DNA expression vector, i.e, any autonomous element capable of directing the synthesis of a recombinant polypeptide, and thus may be used to express a polypeptide, for example a polypeptide comprising an amino acid sequence substantially identical to the sequence of any one of SEQ ID NOs: 22-43, 59, or 73-84, or a fragment or variant thereof, in a host cell. DNA expression vectors include bacterial plasmids and phages and mammalian and insect plasmids and viruses. A vector may be capable of integrating into the genome of the host cell, such that any modification introduced into the genome of the host cell by the vector becomes part of the genome of the host cell. A vector may be incapable of integrating into the genome of the host cell, and therefore remain as an autonomously replicating unit, such as a plasmid.

An antibody "specifically binds" an antigen when it recognises and binds the antigen, for example, a polypeptide including an amino acid sequence substantially identical to the sequence of any one of SEQ ID NOs: 22-43, 59, or 73-84, or a fragment or variant thereof, but does not substantially recognise and bind other molecules in a sample. Such an antibody has, for example, an affinity for the antigen which is at least 10, 100, 1000 or 10000 times greater than the affinity of the antibody for another reference molecule in a sample.

A "sample" can be any organ, tissue, cell, or cell extract isolated from a subject, such as a sample isolated from an animal infected with an A/E pathogen, or an animal to which one or more of the polypeptides or nucleic acid molecules of the invention, or immunogenic fragments thereof, have been administered. For example, a sample can include, without limitation, tissue (e.g., from a biopsy or autopsy), cells, blood, serum, milk, urine, stool, saliva, feces, eggs, mammalian cell culture or culture medium, or any other specimen, or any extract thereof, obtained from a patient (human or animal), test subject, or experimental animal. A sample may also include, without limitation, products produced in cell culture by normal or transformed cells (e.g., via recombinant DNA or monoclonal antibody technology). A "sample" may also be a cell or cell line created under experimental conditions, that are not directly isolated from a subject. A sample can also be cell-free, artificially derived or synthesised.

The sample may be analyzed to detect the presence of a gene, genome, polypeptide, nucleic acid molecule derived from an A/E pathogen, or to detect a mutation in a gene derived from an A/E pathogen, or to detect expression levels of a gene or polypeptide derived from an A/E pathogen, or to determine the biological function of a gene or polypeptide derived from an A/E pathogen, using methods that are known in the art and/or described herein. For example, methods such as sequencing, single-strand conformational polymorphism (SSCP) analysis, or restriction fragment length polymorphism (RFLP) analysis of PCR products derived from a sample can be used to detect a mutation in a gene; ELISA or western blotting can be used to measure levels of polypeptide or antibody affinity; northern blotting can be used to measure mRNA levels, or PCR can be used to measure the level of a nucleic acid molecule.

An "immune response" includes, but is not limited to, one or more of the following responses in a mammal: induction of antibodies, B cells, T cells (including helper T cells, suppressor T cells, cytotoxic T cells, γδ T cells) directed specifically to the antigen(s) in a composition or vaccine, following administration of the composition or vaccine. An immune response to a composition or vaccine thus generally includes the development in the host mammal of a cellular and/or antibody-mediated response to the composition or vaccine of interest. In general, the immune response will result in prevention or reduction of infection by an A/E pathogen; resistance of the intestine to colonization by the A/E pathogen; or reduction in shedding of the A/E pathogen.

An "immunogenic fragment" of a polypeptide or nucleic acid molecule refers to an amino acid or nucleotide sequence that elicits an immune response. Thus, an immunogenic fragment may include, without limitation, any portion of any of the sequences described herein, or a sequence substantially identical thereto, that includes one or more epitopes (the site recognized by a specific immune system cell, such as a T cell or a B cell). For example, an immunogenic fragment may include, without limitation, peptides of any value between 6 and 60, or over 60, amino acids in length, e.g., peptides of any value between 10 and 20 amino acids in length, or between 20 and 40 amino acids in length, derived from any one or more of the sequences described herein. Such fragments may be identified using standard methods known to those of skill in the art, such as epitope mapping techniques or antigenicity or hydropathy plots using, for example, the Omiga version 1.0 program from Oxford Molecular Group (see, for example, U.S. Pat. No. 4,708,871)(76, 77, 81, 92, 73,).

BRIEF DESCRIPTION OF THE DRAWINGS

FIGS. 1A-F show nucleotide and amino acid sequences of NleA from C. rodentium, EPEC, and EHEC (SEQ ID NOs: 1-3 & 22-24).

FIGS. 2A-J show nucleotide and amino acid sequences of NleB and NleB2 from C. rodentium, EPEC, and EHEC (SEQ ID NOs: 4-7 & 25-29 & 60).

FIGS. 3A-F show nucleotide and amino acid sequences of NleC from C. rodentium, EPEC, and EHEC (SEQ ID NOs: 8-10 & 30-32).

FIGS. 4A-F show nucleotide and amino acid sequences of NleD from *C. rodentium*, EPEC, and EHEC (SEQ ID NOs: 11-13 & 33-35).

FIGS. 5A-H show nucleotide and amino acid sequences of NleE from *C. rodentium*, EPEC, and EHEC (SEQ ID NOs: 14-17 & 36-39).

FIGS. 6A-H show nucleotide and amino acid sequences of NleF from *C. rodentium*, EPEC, and EHEC (SEQ ID NOs: 18-21 & 40-43).

FIG. 7 shows an amino acid sequence alignment of *C. rodentium* Orf11/GrlA (SEQ ID NO: 56) with a positive transcriptional regulator, CaiF (SEQ ID NO: 57), and with the deduced amino acid sequence of an uncharacterized *Salmonella* protein (SEQ ID NO: 58). Underlined is the predicted helix-turn-helix motif characteristic of DNA binding proteins. Identical amino acid residues are indicated by *, while conserved changes are marked by +.

FIGS. 10A-B show proteomic analysis of EHEC secreted proteins. A. 1-dimensional SDS-PAGE gel of total secreted proteins from wild type EHEC (wt) and the type III secretion mutant (escN-). Migration of molecular weight markers (in kDa) is indicated at the left of the gel. B. 2-dimensional gel of total secreted proteins from wild type EHEC. Migration of molecular weight markers (in kDa) is indicated at the left, and approximate pI values are shown on the top of the gel. Protein spots analyzed by mass spectroscopy (see Table I) are circled and numbered.

FIGS. 11A-C show NleA genomic organization, distribution and conservation. A. Graphic representation of the region surrounding nleA in the EHEC genome. Transcriptional direction of each ORF is indicated with an arrowhead. Annotation of ORFs is modified from (3). NleA is highlighted in bold. B. Southern blot analysis of genomic DNA from EPEC, EHEC, REPEC, *Citrobacter rodentium*(Citro.), and the non-pathogenic *E. coli* strain HB101. Each genomic DNA sample was digested with BamHI (lanes 1, 4, 7, 10, 13), EcoRI (lanes 2, 5, 8, 11, 14), and PstI (lanes 3, 6, 9, 12, 15). C. Multiple protein sequence alignment of NleA from EHEC, the prophage of an intimin-positive, non-O157 EHEC strain (O84:H4), EPEC, and *Citrobacter rodentium*. Identical residues are represented by a dot (.), amino acids absent from a particular sequence are represented with a dash (-). Two hydrophobic stretches that could be putative transmembrane domains are highlighted in bold in the EHEC sequence.

FIGS. 14A-B show Western blot analysis of infected host cell fractions. A. HeLa cells were infected with wildtype (wt) or escN-EHEC expressing HA-tagged NleA and subjected to subcellular fractionation by differential centrifugation. Fractions analyzed were: bacteria, unbroken cells and cytoskeleton (low speed pellet), host cell cytosol (host cytosol), and host cell membranes (host membrane). Fractions were analysed by Western blot using anti-HA, anti-DnaK, anti-Calnexin, and anti-tubulin antibodies. B. Membrane fractions from cells infected with wildtype EHEC expressing HA-tagged NleA were isolated. Membrane fractions were then extracted on ice under high salt (1M NaCl), high pH (pH 11.4), neutral pH and isotonic salt (control), or neutral pH and isotonic salt containing 1% triton x100 (Triton X100) and recentrifuged to obtain soluble (S) and insoluble (P) membrane fractions. These fractions were subjected to Western blot analysis with anti-HA (top panel), anti-calnexin (middle panel), and anti-calreticulin (bottom panel) antibodies.

FIGS. 16A-B show nucleotide and amino acid sequences of NleG homolog from EHEC (SEQ ID NOs: 61 & 73).

FIGS. 17A-B show nucleotide and amino acid sequences of NleH1 from EHEC (SEQ ID NOs: 62 & 74).

FIGS. 18A-B show nucleotide and amino acid sequences of NleH2 from EHEC (SEQ ID NOs: 63 & 75).

FIGS. 19A-B show nucleotide and amino acid sequences of Z2076 from EHEC (SEQ ID NOs: 64 & 76).

FIGS. 20A-B show nucleotide and amino acid sequences of Z2149 from EHEC (SEQ ID NOs: 65 & 77).

FIGS. 21A-B show nucleotide and amino acid sequences of Z2150 from EHEC (SEQ ID NOs: 66 & 78).

FIGS. 22A-B show nucleotide and amino acid sequences of Z2151 from EHEC (SEQ ID NOs: 67 & 79).

FIGS. 23A-B show nucleotide and amino acid sequences of Z2337 from EHEC (SEQ ID NOs: 68 & 80).

FIGS. 24A-B show nucleotide and amino acid sequences of Z2338 from EHEC (SEQ ID NOs: 69 & 81).

FIGS. 25A-B show nucleotide and amino acid sequences of Z2339 from EHEC (SEQ ID NOs: 70 & 82).

FIGS. 26A-B show nucleotide and amino acid sequences of Z2560 from EHEC (SEQ ID NOs: 71 & 83).

FIGS. 27A-B show nucleotide and amino acid sequences of Z2976 from EHEC (SEQ ID NOs: 72 & 84).

DETAILED DESCRIPTION OF THE INVENTION

Figure 8:
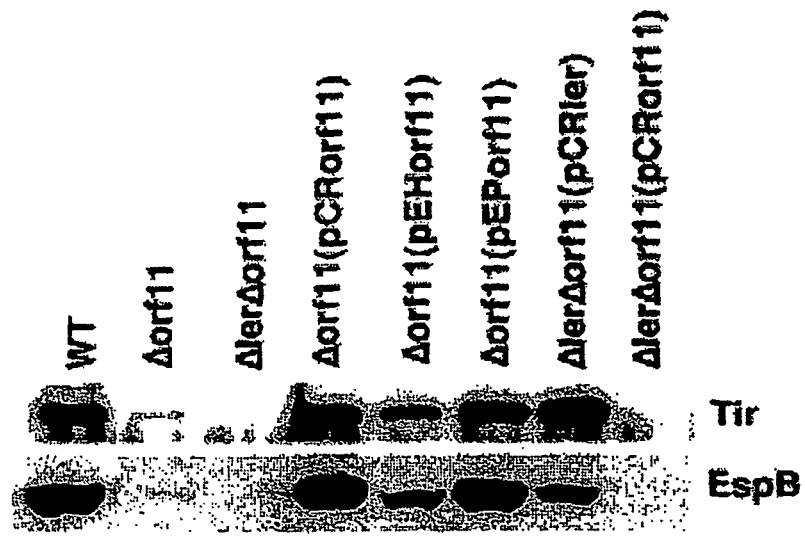
FIG. 8 shows complementation of *C. rodentium* Δorf11 by orf11 from *C. rodentium* (pCRorf11), EHEC (pEHorf11), or EPEC (pEPorf11), and complementation of *C. rodentium* Δler-Δorf11 double mutant by *C. rodentium* ler or orf11.

We have identified several new common secreted proteins for A/E pathogens (Table 2) using a positive LEE regulator (Global Regulator of LEE Activator, or GrlA) which can be used to increase secretion significantly, and has allowed us to functionally screen for proteins secreted via the LEE-encoded TTSS using a proteomics-based approach. These new proteins, termed Nle (non-LEE-encoded effector) A through H, are present in LEE-containing pathogens, and is absent from non-pathogenic strains of E. coli and from non-LEE pathogens are encoded outside the LEE by 3 PAIs that are present in A/E pathogens and have co-evolved with the LEE (3, 8). Identification of these proteins has, in some cases, enabled the assignment of function to ORFs of previously unknown function. An exemplary protein, NleA (p54), is a type III effector in A/E pathogens, including C. rodentium, EPEC, and EHEC, and plays a critical role in virulence. NleA is encoded in a phage-associated pathogenicity island within the EHEC genome, distinct from the LEE. The LEE-encoded TTSS directs translocation of NleA into host cells, where it localizes to the Golgi apparatus. nleA is present in LEE-containing pathogens, and is absent from non-pathogenic strains of E. coli and from non-LEE pathogens.

In some embodiments of the invention, these polypeptides and nucleic acid molecules encoding these polypeptides, or portions thereof, may be useful as vaccines, therapeutics, diagnostics, or drug screening tools for A/E pathogenic infections, or as reagents.

Polypeptides and Test Compounds

Compounds according to the invention include, without limitation, the polypeptides and nucleic acid molecules described in, for example, SEQ ID NOs: 1-56, 59-84, and fragments, analogues and variants thereof. Compounds according to the invention also include the products of the orf11/grlA, nleA, nleB, nleB2, nleC, nleD, nleE, nleF, nleG, nleH (nleH1, and/or nle H2) genes, or homologues thereof. Compounds according to the invention also include polypeptides and nucleic acid molecules described in, for example, the EHEC genome sequence (e.g. AE005174) as numbers Z0985 (NleB2), Z0986 (NleC), Z0990 (NleD), Z6020 (NleF), Z6024 (NleA), Z4328 (NleB), Z4329 (NleE), Z6025 (NleG homolog), Z6021 (NleH1), Z0989 (NleH2), Z2076, Z2149, Z2150, Z2151, Z2337, Z2338, Z2339, Z2560, Z2976, or L0043 (Orf11/GrlA)(Accession No. AF071034), and fragments, analogues and variants thereof.

Compounds can be prepared by, for example, replacing, deleting, or inserting an amino acid residue at any position of a polypeptide described herein, with other conservative amino acid residues, i.e., residues having similar physical, biological, or chemical properties, and screening, for example, for the ability of the compound to attenuate virulence. In some embodiments of the invention, compounds of the invention include antibodies that specifically bind to the polypeptides described herein, for example, SEQ ID NOs: 22 - 43, 59, or 73-84.

It is well known in the art that some modifications and changes can be made in the structure of a polypeptide without substantially altering the biological function of that peptide, to obtain a biologically equivalent polypeptide. In one aspect of the invention, polypeptides of the present invention also extend to biologically equivalent peptides or "variants" that differ from a portion of the sequence of the polypeptides of the present invention by conservative amino acid substitutions, or differ by non-conservative substitutions that do not affect biological function e.g., virulence. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

As used herein, the term "amino acids" means those L-amino acids commonly found in naturally occurring proteins, D-amino acids and such amino acids when they have been modified. Accordingly, amino acids of the invention may include, for example: 2-Aminoadipic acid; 3-Aminoadipic acid; beta-Alanine; beta-Aminopropionic acid; 2-Aminobutyric acid; 4-Aminobutyric acid; piperidinic acid; 6-Aminocaproic acid; 2-Aminoheptanoic acid; 2-Aminoisobutyric acid; 3-Aminoisobutyric acid; 2-Aminopimelic acid; 2,4 Diaminobutyric acid; Desmosine; 2,2'-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; sarcosine; N-Methylisoleucine; 6-N-methyllysine; N-Methylvaline; Norvaline; Norleucine; and Ornithine.

In some embodiments, conserved amino acid substitutions may be made where an amino acid residue is substituted for another having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conservative amino acid substitutions may be made where an amino acid residue is substituted for another having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conservative amino acid substitutions may be made using publicly available families of similarity matrices (60, 70, 102, 103, 94, 104, 86) The PAM matrix is based upon counts derived from an evolutionary model, while the Blosum matrix uses counts derived from highly conserved blocks within an alignment. A similarity score of above zero in either of the PAM or Blosum matrices may be used to make conservative amino acid substitutions.

In alternative embodiments, conservative amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (71). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —$NO_2$, —NO, —$NH_2$, —NHR, —NRR, —C(O)R, —C(O)OH, —C(O)OR, —C(O)$NH_2$, —C(O)NHR, —C(O)NRR, etc., where R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl, or substituted ($C_1$-$C_6$) alkynyl) or isostere of an amide linkage (for example, —$CH_2$NH—, —$CH_2$S, —$CH_2CH_2$—, —CH═CH— (cis and trans), —C(O)$CH_2$—, —CH(OH)$CH_2$—, or —$CH_2$SO—).

The compound can be covalently linked, for example, by polymerisation or conjugation; to form homopolymers or heteropolymers. Spacers and linkers, typically composed of small neutral molecules, such as amino acids that are uncharged under physiological conditions, can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used. The compound can also be linked to a another compound that can for example modulate an immunogenic response. The compound can also be constrained, for example, by having cyclic portions.

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods such as those described in, for example, Sambrook, et al. (110) or Ausubel et al. (111). In general, candidate compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein; Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, Mass., USA. In addition, natural and synthetically produced libraries of, for example, A/E pathogen polypeptides, are produced, if desired, according to methods known in the art, e.g., by standard extraction and fractionation methods. Furthermore, if desired, any library or compound is readily modified using standard chemical, physical, or biochemical methods.

When a crude extract is found to modulate virulence, further fractionation of the positive lead extract is necessary to isolate chemical constituents responsible for the observed effect. Thus, the goal of the extraction, fractionation, and purification process is the careful characterization and identification of a chemical entity within the crude extract having virulence modulatory properties. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using a *Citrobacter* or bovine model for A/E pathogenic infection, or any other animal model for A/E pathogenic infection.

Vaccines

A "vaccine" is a composition that includes materials that elicit a desired immune response. A vaccine may select, activate or expand memory B and T cells of the immune system to, for example, enable the elimination of infectious agents, such as A/E pathogens, or components thereof. In some embodiments, a vaccine includes a suitable carrier, such as an adjuvant, which is an agent that acts in a non-specific manner to increase the immune response to a specific antigen, or to a group of antigens, enabling the reduction of the quantity of antigen in any given vaccine dose, or the reduction of the frequency of dosage required to generate the desired immune response. A desired immune response may include full or partial protection against shedding of (presence in feces of an infected animal, e.g., mammal) or colonization (presence in the intestine of an infected animal, e.g., mammal) by an A/E pathogen. For example, a desired immune response may include any value from between 10% to 100%, e.g., 10%, 20%, 30%, 40%, 50%, 60%, 70%, 80%, 90%, 100%, protection against shedding of or colonization by an A/E pathogen in a vaccinated animal when compared to a non-vaccinated animal.

Vaccines according to the invention may include the polypeptides and nucleic acid molecules described herein, or immunogenic fragments thereof, and may be administered using any form of administration known in the art or described herein. In some embodiments of the invention, the vaccine may include a live A/E pathogen, a killed A/E pathogen, or components thereof. Live A/E pathogens, which may be administered in the form of an oral vaccine, may contain non-revertible genetic alterations that affect the virulence of the A/E pathogen, but not its induction of an immune response. A live vaccine may be capable of colonizing the intestines of the inoculated animal, e.g., mammal.

In some embodiments, the polypeptides and nucleic acid molecules described herein, or immunogenic fragments thereof, or the mutated bacteria (e.g., attenuated bacteria) described herein may be administered to poultry, e.g., chicken, ducks, turkeys, etc., so as to elicit an immune response e.g., raise antibodies, in the poultry. Eggs, or products thereof, obtained from such poultry, that exhibit an immune response against the polypeptides and nucleic acid molecules described herein, or immunogenic fragments thereof, may be administered to an animal, e.g., humans, cattle, goats, sheep, etc., to elicit an immune response to the polypeptides and nucleic acid molecules described herein, or immunogenic fragments thereof, in the animal. Methods of raising antibodies in poultry, and administering such antibodies, are described in for example, U.S. Pat. No. 5,750,113 issued to Cook, May 12, 1998; U.S. Pat. No. 6,730,822 issued to Ivarie, et al. May 4, 2004; and publications 113-117 cited herein.

The vaccines according to the invention may be further supplemented by the addition of recombinant or purified antigens such as EspA, EspB, EspD, EspP, Tir, Shiga toxin 1 or 2, and/or intimin, using standard techniques known in the art. For example, the recombinant production and use of EHEC O157:H7 proteins such as EspA, Tir, EspB, and intimin have been described (PCT Publication No. WO 97/40063; PCT Publication No. WO 99/24576; 51).

Cell Culture

A/E pathogens may be grown according to any methods known in the art or described herein. For example, A/E pathogens may be first grown in Luria-Bertani (LB) medium for a period of about 8 to 48 hours, or about 12 to 24 hours, and then diluted about 1:5 to 1:100, e.g., 1:67, or about 1:5 to 1:25, or about 1:10, into M-9 minimal medium supplemented with 20-100 mM $NaHCO_2$ or $NaHCO_3$, or about 30-50 mM, or about 44 mM $NaHCO_2$ or $NaHCO_3$; 4-20 mM $MgSO_4$, or about 5-10 mM; or about 0.8 mM to 8 mM $MgSO_4$, 0.1 to 1.5% glucose, or about 0.2 to 1%, or about 0.4% glucose and 0.05 to 0.5% Casamino Acids, or about 0.07 to 0.2%, or about 0.1% Casamino Acids. Cultures are generally maintained at about 37 degrees C., optionally in 2-10% $CO_2$, or optionally in about 5% $CO_2$, and grown to an optical density of about 600 nm of 0.7 to 0.8. Whole cells are then removed by any suitable means, e.g., microfiltration or centrifugation and the supernatant can be concentrated, e.g., 10-1000 fold or more, such as 100-fold, using dialysis, ultrafiltration and the like. Total protein is easily determined using methods well known in the art.

Cell culture supernatants may be produced using cultures of any A/E pathogen, for example, EHEC, as described herein or known to those of skill in the art, including wild type or mutant A/E pathogens. Generally, the A/E pathogen is cultured in a suitable medium, under conditions that favor type III antigen secretion (U.S. Pat. Nos. 6,136,554 and 6,165, 743)(51, 74).

Isolation and Identification of Additional Genes

Based on the nucleotide and amino acid sequences described herein, for example, in SEQ ID NOs: 1-56 or 59-84, the isolation and identification of additional genes is made possible using standard techniques. Any A/E pathogen can serve as the source for such genes.

In some embodiments, the nucleic acid sequences described herein may be used to design probes or primers, including degenerate oligonucleotide probes or primers, based upon the sequence of either DNA strand. The probes or primers may then be used to screen genomic or cDNA libraries for genes from other A/E pathogens, using standard amplification or hybridization techniques.

In some embodiments, the amino acid sequences described herein may be used to generate antibodies or other reagents that be used to screen for polypeptides from A/E pathogens that bind these antibodies.

In some embodiments, binding partners may be identified by tagging the polypeptides of the invention (e.g., those substantially identical to SEQ ID NOs; 22-43, 59, or 73-84) with an epitope sequence (e.g., FLAG or 2HA), and delivering it into host cells, either by transfection with a suitable vector containing a nucleic acid sequence encoding a polypeptide of the invention, or by endogenous bacterial type III delivery, followed by immunoprecipitation and identification of the binding partner. HeLa cells may be infected with strains expressing the FLAG or 2HA fusions, followed by lysis and immunoprecipitation with anti-FLAG or anti-2HA antibodies. Binding partners may be identified by mass spectroscopy. If the polypeptide of the invention is not produced in sufficient quantities, such a method may not deliver enough tagged protein to identify its partner. As part of a complementary approach, each polypeptide of the invention may be cloned into a mammalian transfection vector fused to, for example, 2HA, GFP and/or FLAG. Following transfection, HeLa cells may be lysed and the tagged polypeptide immunoprecipitated. The binding partner may be identified by SDS PAGE followed by mass spectroscopy.

In some embodiments, polypeptides of the invention may be tagged, overproduced, and used on affinity columns and in immunoprecipitations to identify and/or confirm identified target compounds. FLAG, HA, and/or His tagged proteins can be used for such affinity columns to pull out host cell factors from cell extracts, and any hits may be validated by standard binding assays, saturation curves, and other methods as described herein or known to those of skill in the art.

In some embodiments, a bacterial two hybrid system may be used to study protein-protein interactions. The nucleic acid sequences described herein, or sequences substantially identical thereto, can be cloned into the pBT bait plasmid of the two hybrid system, and a commercially available murine spleen library of $5\times10^6$ independent clones, may be used as the target library for the baits. Potential hits may be further characterized by recovering the plasmids and retransforming to reduce false positives resulting from clonal bait variants and library target clones which activate the reporter genes independent of the cloned bait. Reproducible hits may be studied further as described herein.

In some embodiments, an A/E pathogenic strain expressing GrlA, for example, an EHEC O157 strain expressing a cloned GrlA, may be used for proteomic analysis of A/E type III secreted proteomes, using for example, 2D gel analysis of the supernatants. In addition, complete A/E pathogen (e.g., EHEC arrays) may be used to define which genes are regulated by GrlA. Virulence may be assayed as described herein or as known to those of skill in the art.

Once coding sequences have been identified, they may be isolated using standard cloning techniques, and inserted into any suitable vector or replicon for, for example, production of polypeptides. Such vectors and replicons include, without limitation, bacteriophage X (*E. coli*), pBR322 (*E. coli*), pACYC177 (*E. coli*), pKT230 (gram-negative bacteria), pGV1 106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) or bovine papilloma virus (mammalian cells).

In general, the polypeptides of the invention may be produced in any suitable host cell transformed or transfected with a suitable vector (69). The method of transformation or transfection and the choice of expression vehicle will depend on the host system selected. A wide variety of expression systems may be used, and the precise host cell used is not critical to the invention. For example, a polypeptide according to the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or COS cells). Such cells are available from a wide range of sources (e.g., the American Type Culture Collection, Manassus, Va.). Bacterial expression systems for polypeptide production include the *E. coli* pET expression system (Novagen, Inc., Madison, Wis.), and the pGEX expression system (Pharmacia).

Assays

Candidate compounds, including polypeptides, nucleic acid molecules, and small molecules, can be screened and tested using a variety of techniques described herein or known to those of skill in the art. A compound that reduces the level of expression of any of the polypeptides or nucleic acid molecules of the invention may be useful, for example, as a therapeutic against an A/E pathogenic infection.

Screening assays may be conducted, for example, by measuring gene expression by standard Northern blot analysis, using any appropriate nucleic acid fragment according to the invention as a hybridization probe, where the level of gene expression in the presence of the candidate compound is compared to the level of gene expression in the absence of the candidate compound. Alternatively, or additionally, the effect of a candidate compound may be determined at the level of polypeptide expression or secretion, using for example immunoprecipitation or Western blotting approaches.

Other assays may be conducted as follows:

Confirmation of Type III Secretion and Translocation into Host Cells

To determine which of the candidate compounds require the TTSS for secretion, each gene or portion thereof may be fused to a FLAG at its C terminus, and supernatants collected from WT and TTSS mutants, for example, WT EHEC and the isogenic escN type III mutant as described herein or known in the art. Alternate methods to determine secretion include examination of supernatants for loss of secreted product in the mutant strain, or raising antibodies to the protein and using Western analysis of WT and type III supernatants. To confirm that none of the proteins of interest are TTSS components, supernatants from each of the candidate compounds, grown under type III inducing conditions may be examined for type III secretion. The LEE TTSS secretes two classes of proteins: the translocon (EspA, B, and D) which is assembled on the bacterial cell surface, and effectors, which are translocated directly into host cells. Candidate compounds may be tested to determine whether they are effectors or translocators. For example, FLAG-tagged putative effectors in EHEC or other A/E pathogens may be used to infect cultured HeLa epithelial cells, and examined by immunofluorescence microscopy after staining with anti-FLAG antibodies. Such visualization usually demonstrates bacterial delivery into the host cell, and often indicates which organelle the effector is targeted to (e.g. Tir to membrane, NleA to Golgi). Antibodies to various cellular compartments can be used these to confirm the localization. To complement the visualization, infected HeLa cells can be fractionated into cytosol, insoluble, and membrane fractions using known fractionation methods (30), and Western analysis performed using anti-FLAG antibodies to define which cellular fraction the effector is targeted to. As a control, cells may be infected with the tagged effector expressed in a TTSS defective strain. If targeted to the membrane fraction, high salt or alkaline pH treatment can be used to determine if it is an integral membrane protein. If the candidate compound is expressed at a low level, and detecting translocation by immunofluorescence is difficult, genetic fusions can be made to adenlyate cyclase, an enzyme which requires a mammalian cytoplasmic cofactor (calmodulin) for activity (87).

Effects on Pedestal Formation and Uptake.

Given that actin condensation and pedestal formation are hallmarks of A/E pathogens, candidate compounds can be screened for actin accumulation and pedestal formation in, for example, cultured HeLa epithelial cells.

EPEC and EHEC invasion is another cell culture phenotype that is readily measured, and gives an indication of interactions with cultured epithelial cells and ability to alter host cytoskeleton (type III mutants do not invade, nor do strains lacking Tir and intimin). The invasion levels of various candidate compounds may be compared in wt and type III mutant A/E pathogen, for example, WT and TTSS mutant EHEC in HeLa cells, using a gentamicin protection assay.

In addition, the ability of the candidate compounds to block cultured macrophage phagocytosis can be tested, as EPEC and EHEC inhibit phagocytosis in cultured macrophages by inhibiting host PI 3-kinase activity in a type III dependent manner (Celli, J., M. Olivier, and B. B. Finlay. 2001. Enteropathogenic *Escherichia coli* mediates antiphagocytosis through the inhibition of PI 3-kinase-dependent pathways. Embo J 20:1245-58). If any candidate compounds are unable to inhibit phagocytosis, a secondary assay of PI-3 kinase inhibition can be performed.

Effects on Polarized Epithelial Monolayers.

Junctional integrity plays a key role in diarrhea. In addition to pedestal formation, A/E pathogens cause other LEE type III effects on polarized epithelial cells, including loss of microvilli (microvilli effacement) and loss of transmonolayer electrical resistance, a measure of tight junctions. Using polarized human intestinal monolayers of Caco-2 cells, high resolution scanning electron microscopy may be performed on monolayers infected with WT A/E pathogen (e.g, WT EHEC), TTSS mutant A/E pathogen, e.g, EHEC escN, and each of the candidate compounds. Monolayers can be infected for various times, washed, and processed for SEM using standard techniques (66) and screened for loss of electrical resistance after infecting polarized Caco-2 cells.

Effects on Innate Immunity and Inflammation

A rapidly emerging theme among pathogens is the ability to inhibit innate immunity and inflammatory responses. Such effects have been reported for A/E pathogens such as EHEC and EPEC, and these assays may be used to examine candidate compounds in WT and TTSS mutant A/E pathogen strains. For example, EHEC causes inhibition of NF-κβ, resulting in suppression of several cytokines such as Il-8, Il-6, and Il-1α in HeLa cells (80), and this process requires the LEE TTSS. Candidate compounds may assayed for inhibition of these factors following, for example, infection of HeLa cells, using standard methods such as RT-PCR (real time PCR), and commercially available ELISA assays.

Functional Studies Based on Localization Information

In addition to phenotypic assays, candidate compounds may be assayed depending on their localization with a host cell. For example, if a candidate compounds localizes to the Golgi, it can be assayed to determine if it affects Golgi function, including biochemical studies examining glycosylation, and functional Golgi assays in yeast expressing the candidate compounds. If the candidate compounds localizes to mitochondria, assays on apoptosis and other mitochondrial functions can be utilized. If the candidate compounds targets to the endoplasmic reticulum, protein synthesis and secretion assays can be designed. If nuclear targeting occurs, transcriptional studies may be conducted.

Role in Nirulence

Competitive indices (CI) have been used extensively to determine the role of minor virulence factors, as well as whether two virulence factors belong to the same virulence "pathway" (63). Briefly, two strains, marked with different antibiotic resistances, are coinfected into an animal, and following appropriate incubation times, bacteria harvested and a ratio of the two strains determined. A value of 1 indicates equal virulence. If identified compounds have an effect on virulence, their CI compared to WT may be determined. CI may also be used to determine which virulence pathways the candidate compounds belong to. For example, CIs may be done comparing mutants of two virulence factors, in addition to comparing each one to WT. When comparing the single mutants and to a double mutant, a CI ratio of 1 indicates they belong to the same general virulence pathway, while anything other than 1 indicates they are on different virulence "paths".

Microscopy Studies

Microscopy techniques may be used to characterize A/E pathogen disease, including transmission electron microscopy (TEM) and scanning electron microscopy (SEM) to examine lymphoid follicles in distal ileal Peyer's patches from REPEC infected rabbits to confirm A/E lesion formation (63), confocal microscopy to show delivery into murine villi, and histological analysis of the disease process in infected mice.

These techniques may be used to assay candidate compounds in suitable animal models, for example, mice infected with various *Citrobacter* strains carrying mutations in the candidate sequences. For each candidate compounds, a comprehensive study may be undertaken to follow the disease progression (or lack of) in this system. In addition, the level of colonization of these mutants on intestinal surfaces may be determined. Antibiotic marked strains may be used to infect animals, followed by harvesting of intestinal tissue. Tissue may be homogenized and bacteria quantitated by plate counting on selective plates.

A major feature of A/E pathogenic infection, e.g., *Citrobacter* infection, is extensive inflammation. The cellular events of inflammation may be followed by confocal microscopy for various mutants in candidate compounds. By labeling tissues with antibodies or lectins followed by confocal microscopy, the inflammatory cells that are recruited to the site of infection by the mutants may be defined, compared to the parental strain. Antibodies to several innate response factors are available and may also be used to analyze the mutant phenotypes during infection, examining innate response factors and cells such as macrophages, neutrophils, iNOS production, dendritic cells, etc.

Histological Studies

Histological studies of stained tissue may be conducted. For example, hematoxylin and eosin-stained ileal sections of rabbits infected with REPEC and strains with deletions in candidate compounds may be studied to compare the inflammation and tissue damage and characterize A/E pathogen infections (58). Similar staining may be done with *Citrobacter* strains lacking candidate compounds in mice. Several other histological stains are available that may further define the inflammation associated with *Citrobacter* and isogenic mutants, including Giemsa and Toluidine Blue O (for general morphology), Periodic Acid-Schiff (stains carbohydrates, allowing examination of the intestinal mucus layer and goblet cells), Gram stain, chloroacetate esterase (an inflammatory cell stain), and a caspase assay (for apoptosis). Immunohistochemistry allows utilization of antibodies directed against bacterial and mammalian cell antigens.

Antibodies

The compounds of the invention can be used to prepare antibodies to the polypeptides of the invention, using standard techniques of preparation (45), or known to those skilled in the art.

For example, a coding sequence for a polypeptide of the invention may be purified to the degree necessary for immunization of rabbits. To attempt to minimize the potential problems of low affinity or specificity of antisera, two or three polypeptide constructs may be generated for each protein, and each construct is injected into at least two rabbits. Antisera may be raised by injections in a series, preferably including at least three booster injections. Primary immunizations may be carried out with Freund's complete adjuvant and subsequent immunizations with Freund's incomplete adjuvant. Antibody titres may be monitored by Western blot and immunoprecipitation analyses using the purified protein. Immune sera may be affinity purified using CNBr-Sepharose-coupled protein. Antiserum specificity may be determined using a panel of unrelated proteins. Alternatively or additionally, peptides corresponding to relatively unique immunogenic regions of a polypeptide of the invention may be generated and coupled to keyhole limpet hemocyanin (KLH) through an introduced C-terminal lysine. Antiserum to each of these peptides may be affinity purified on peptides conjugated to BSA, and specificity tested in ELISA and Western blots using peptide conjugates and by Western blot and immunoprecipitation.

Alternatively, monoclonal antibodies which specifically bind any one of the polypeptides of the invention are prepared according to standard hybridoma technology (91, 90, 89, 78). Once produced., monoclonal antibodies may also be tested for specific recognition by Western blot or immunoprecipitation. Antibodies which specifically bind the polypeptide of the invention are considered to be useful; such antibodies may be used., e.g., in an immunoassay. Alternatively monoclonal antibodies may be prepared using the polypeptide of the invention described above and a phage display library (112).

In some embodiments, antibodies may be produced using polypeptide fragments that appear likely to be immunogenic, by criteria such as high frequency of charged residues. Antibodies can be tailored to minimise adverse host immune response by, for example, using chimeric antibodies contain an antigen binding domain from one species and the Fc portion from another species, or by using antibodies made from hybridomas of the appropriate species.

In some embodiments, antibodies against any of the polypeptides described herein may be employed to treat or prevent infection by an A/E pathogen.

Animal Models

Compounds can be rapidly screened in various animal models of A/E pathogen infection.

The *Citrobacter* murine infection model is a naturally occurring disease model, and the adult bovine EHEC shedding model, a natural non-disease carriage model (cattle are not sick, yet EHEC is not part of the normal flora). For the *Citrobacter* model, mutants can be screened for virulence in mice as described herein. Knock out (KO)/mutant mice may be used to study the role of candidate sequences in infection. Several KO mouse lines have been developed, including defining the role of iNOS (20), T and B cells (106), Tlr-4 and establishing a range of host susceptibility (54), as well as Nck.

For the bovine model, the EHEC mutants can be screened in yearling cattle (see, for example, PCT Publication No. WO 02/053181). Briefly, $10^8$ CFU of mutant or WT O157 are delivered to cattle via oral-gastric intubation. 14 days post-inoculation fecal shedding is monitored by selective plating, and colonies verified by mutliplex PCR, shedding levels, and histological and microscopic analyses of the perianal region where EHEC concentrates (97). Another model is the bovine intestinal loop model in which intestinal loops are injected with EHEC and at various times examined histologically and microscopically, as well as quantitating adherent bacteria by plating.

A natural rabbit infection model of RDEC-1 infection may be conducted as follows: Overnight bacterial cultures are collected by centrifugation and resuspended in one ml of phosphate-buffered saline. New Zealand white rabbits (weight 1.0 to 1.6 kg) are fasted overnight, then five ml of 2.5% sterile sodium bicarbonate and one ml of RDEC-1 or candidate sequence mutant strains ($2:-5 \times 10^1$) are inoculated into the stomach using orogastric tubes. The same dosage of bacteria is inoculated into each rabbit the following day. Each rabbit is weighed daily and fecal shedding of bacteria is collected by rectal swabs and from stool pellets. Rectal swabs are rolled over one half of the surface of MacConkey plates containing nalidixic acid. Five stool pellets or same amount of liquid stool are collected from each rabbit and resuspended in three ml phosphate-buffered saline and 0.1 ml of each stool suspension is plated onto MacConkey plate containing nalidixic acid. The growth of nalidixic resistant colonies is scored as follows: 0, no growth; 1, widely spaced colonies; 2, closely spaced colonies; 3, confluent growth of colonies. Tissues are excised immediately following sacrifice by intravenous injection of ketamine and overdosing with sodium phenobarbital. The amount of bacterial colonization in intestinal tissues us assayed as follows: The intestinal segments (10 cm), except cecum, are doubly ligated at their proximal and distal ends, and dissected between the double ligated parts, then flushed with 10 ml of ice-cold phosphate-buffered saline. One gram of viscous contents from the cecum is added to 9 ml phosphate-buffered saline. The resulting phosphate-buffered saline suspensions are diluted and plated on MacConkey plates containing nalidixic acid. Tissue samples are excised using a 9 mm diameter cork punch, washed three times with phosphate-buffered saline, added to two ml of ice-cold phosphate-buffered saline, and homogenized with a homogenizer, then serial diluted samples are plated onto MacConkey plates. The numbers of bacteria adherent to each tissue per square centimeter are calculated as follows: CFU/cm2=the bacterial number/plate×dilution factor×2 ml/−0.452.

Therapeutics and Diagnostics

The polypeptide and nucleic acid molecules described herein may be used as therapeutics, for example, for the preparation of vaccine or therapeutic compositions, or the construction of A/E pathogens that are attenuated in virulence. Such A/E pathogens may be constructed as described herein by, for example, designing primers based on the nucleic acid sequences described herein, and using a sacB gene-based allelic exchange technique (29). The polypeptides and nucleic acid molecules may be used alone or in combination with each other or other suitable molecules, such as EspA, EspB, EspD, EspP, Tir, Shiga toxin 1, Shiga toxin 2, or intimin molecules.

In some embodiments, the nucleic acid molecules described herein may be used in antisense techniques. By "antisense," as used herein in reference to nucleic acids, is meant a nucleic acid sequence that is complementary to the coding strand of a nucleic acid molecule, for example, a gene, such as a nleA nleB, nleC, nleD, nleE, or nleF gene, or that is complementary to a nucleotide sequence substantially identical to the sequence of any one of SEQ ID NOs: 1-21 or 60-72 or a fragment or variant thereof. In some embodiments, an antisense nucleic acid molecule is one which is capable of lowering the level of polypeptide encoded by the complementary gene when both are expressed in a cell. In some embodiments, the polypeptide level is lowered by any integer from at least 10% to at least 25%, or by any integer from at least 25% to at least 50%, or by any integer from at least 50% to at least 75%, or by any integer from at least 75% to 100%, as compared to the polypeptide level in a cell expressing only the gene, and not the complementary antisense nucleic acid molecule.

In some embodiments, expression of a gene or coding or non-coding region of interest may be inhibited or prevented using RNA interference (RNAi) technology, a type of post-transcriptional gene silencing. RNAi may be used to create a functional "knockout", i.e. a system in which the expression of a gene or coding or non-coding region of interest is reduced, resulting in an overall reduction of the encoded product. As such, RNAi may be performed to target a nucleic acid of interest or fragment or variant thereof, to in turn reduce its expression and the level of activity of the product which it encodes. Such a system may be used for functional studies of the product, as well as to treat infection by an A/E pathogen. RNAi is described in for example published US patent applications 20020173478 (Gewirtz; published Nov. 21, 2002) and 20020132788 (Lewis et al.; published Nov. 7, 2002)(79, 67). Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the Rnase III family of dsRNA-specific ribonucleases. Alternatively, RNAi may be effected via directly introducing into the cell, or generating within the cell by introducing into the cell a suitable precursor (e.g. vector, etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA (64), for which suitable RNA molecules may chemically synthesized using known methods. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts combined to form an RNA duplex which is introduced into a target cell of interest. Other vectors may be used, which express small hairpin RNAs (shRNAs) which can be processed into siRNA-like molecules. Various vector-based methods are known in the art (65, 93, 95, 98, 99, 105, 109). Various methods for introducing such vectors into cells, either in vitro or in vivo (e.g. gene therapy) are known in the art.

Accordingly, in an embodiment expression of a polypeptide including an amino acid sequence substantially identical to the sequence of any one of SEQ ID NOs: 22 through 43 may be inhibited by introducing into or generating within a cell an siRNA or siRNA-like molecule corresponding to a nucleic acid molecule encoding the polypeptide or fragment thereof, or to an nucleic acid homologous thereto. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecules are about 21-23 nucleotides in length. In an embodiment, siRNA or siRNA-like molecules comprise and 19-21 bp duplex portion, each strand having a 2 nucleotide 3' overhang. In embodiments, the siRNA or siRNA-like molecule is substantially identical to a nucleic acid encoding the polypeptide or a fragment or variant (or a fragment of a variant) thereof. Such a variant is capable of encoding a protein having the activity of a polypeptide encoded by SEQ ID NOs: 22-43. In embodiments, the sense strand of the siRNA or siRNA-like molecule is substantially identical to SEQ ID NOs: 1-21 or a fragment thereof (RNA having U in place of T residues of the DNA sequence).

In some embodiments, antibodies raised against the polypeptides of the invention may be used as therapy against infection by an A/E pathogen.

In some embodiments, the polypeptide and nucleic acid molecules of the invention may be used to detect the presence of an A/E pathogen in a sample. The nucleic acid molecules may be used to design probes or primers that could, for example, hybridize to the DNA of an A/E pathogen in a sample, or could be used to amplify the DNA of an A/E pathogen in a sample using, for example, polymerase chain reaction techniques. The polypeptides could be used for example to raise antibodies that specifically bind to a polypeptide expressed by an A/E pathogen. Such probes or primers or antibodies may be detectably labelled. By "detectably labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling such as, enzymatic labelling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labeled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

Pharmaceutical & Veterinary Compositions, Dosages and Administration

Compounds include the polypeptide and nucleic acid molecules described herein, as well as compounds identified using the methods of the invention. Compounds according to the invention can be provided alone or in combination with other compounds (for example, nucleic acid molecules, small molecules, polypeptides, peptides, or peptide analogues), in the presence of a liposome, an adjuvant, or any pharmaceutically acceptable carrier, in a form suitable for administration to mammals, for example, humans, cattle, sheep, etc. If desired, treatment with a compound according to the invention may be combined with more traditional and existing therapies for an A/E pathogen infection Conventional pharmaceutical practice may be employed to provide suitable formulations or compositions to administer the compounds to subjects infected by an A/E pathogen. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Formulations may be in the form of liquid solutions or suspensions; tablets or capsules; powders, nasal drops, or aerosols.

Methods are well known in the art for making formulations (57). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the compounds are administered to an individual in an amount sufficient to stop or slow an A/E pathogen infection.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as reduction of colonization by or shedding of an A/E pathogen. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as prevention of colonization by an A/E pathogen. Typically, a prophylactic dose is used in subjects prior to or at an earlier stage of disease, so that a prophylactically effective amount may be less than a therapeutically effective amount. A preferred range for therapeutically or prophylactically effective amounts of a compound may be any integer from 0.1 nM-0.1M, 0.1 nM-0.05M, 0.05 nM-15 µM or 0.01 nM-10 µM.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of vaccine formulations, an effective amount of a compound of the invention can be provided, alone or in combination with other compounds, and with one or more of an immunological adjuvant to induce an immune response. Adjuvants according to the invention may include emulsifiers, muramyl dipeptides, pyridine, aqueous adjuvants such as aluminum hydroxide, chitosan-based adjuvants, saponins, oils, Amphigen®, LPS, bacterial cell wall extracts, bacterial DNA, bacterial complexes, synthetic oligonucleotides and combinations thereof (100). The adjuvant may include a *Mycobacterium phlei* (*M. phlei*) cell wall extract (MCWE) (U.S. Pat. No. 4,744,984), a *M. phlei* DNA (M-DNA), or a Mycobacterial cell wall complex (MCC). Emulsifiers include natural and synthetic emulsifying agents. Synthetic emulsifying agents include anionic agents (e.g., potassium, sodium and ammonium salts of lauric and oleic acid, the calcium, magnesium and aluminum salts of fatty acids, i.e., metallic soaps, and organic sulfonates, such as sodium lauryl sulfate), cationic agents (e.g., cetyltrimethylammonium bromide), and nonionic agents (e.g, glyceryl esters such as glyceryl monostearate, polyoxyethylene glycol esters and ethers, and the sorbitan fatty acid esters such as sorbitan monopalmitate and their polyoxyethylene derivatives, e.g., polyoxyethylene sorbitan monopalmitate). Natural emulsifying agents include acacia, gelatin, lecithin and cholesterol. Other suitable adjuvants include an oil, such as a single oil, a mixture of oils, an oil-in-water emulsion (e.g, EMULSIGEN™, EMULSIGEN PLUS™ or VSA3), or a non-oil-in-water emulsion (e.g., an oil emulsion, a water-in-oil emulsion, or a water-in-oil-in-water emulsion). The oil may be a mineral oil, a vegetable oil, or an animal oil. Suitable animal oils include, for example, cod liver oil, halibut oil, menhaden oil, orange roughly oil or shark liver oil, all of which are available commercially. Suitable vegetable oils, include, without limitation, canola oil, almond oil, cottonseed oil, corn oil, olive oil, peanut oil, safflower oil, sesame oil, or soybean oil. Alternatively, a number of aliphatic nitrogenous bases may be used as adjuvants with the vaccine formulations. For example, known immunologic adjuvants include amines, quaternary ammonium compounds, guanidines, benzamidines and thiouroniums (75). Specific adjuvant compounds include dimethyldioctadecyl ammonium bromide (DDA) (U.S. Pat. No. 5,951,988) (88, 59, 85, 68, 84, 82, 83) and N,N-dioctadecyl-N,N-bis (2 hydroxyethyl) propanediamine ("pyridine") (U.S. Pat. No. 4,310,550, U.S. Pat. No. 5,151,267)(62). An adjuvant according to the invention may for example include a mineral oil and dimethyldioctadecylammonium bromide.

Vaccine compositions may be prepared using standard techniques including, but not limited to, mixing, sonication and microfluidation. The adjuvant may be comprise about 10 to 50% (v/v) of the vaccine, or about 20 to 40% (v/v) or about 20 to 30% or 35% (v/v), or any value within these ranges. The compound may also be linked with a carrier molecule, such as bovine serum albumin or keyhole limpet hemocyanin to enhance immunogenicity.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

The following examples are intended to illustrate embodiments of the invention, and should not be construed as limitations on the scope of the invention.

EXAMPLE 1

Generation of Mutants

Bacterial strains used are as follows: EHEC O157:H7 strain 86//24 (32), EHEC EDL933 (wildtype *E. coli* O127:H7 isolate; 3); EHEC escN- (47), wild type EPEC E2348/69 (wildtype *E. coli* O127:H6 isolate; 50), *C. rodentium* DBS100 (ATCC 51459; 53), REPEC 0103:K-:H2 85/150 (52), *E. coli* HB101.

Plasmids used were as follows:

| Plasmid | Description and Relevant Phenotype | Reference |
|---|---|---|
| pRE118 | sacB-based suicide vector for allelic exchange, Kan$^r$ | 4 |
| pKD46 | Plasmid expression λ red recombinase, AMP$^r$ | 5 |
| pACYC184 | Cloning Vector, CM$^r$ Tet$^r$ | NEB |
| pCR2.1-TOPO | PCR cloning vector, Amp$^r$ Kan$^r$ | Invitrogen |
| pTOPO-2HA | pCR2.1-TOPO based, Plac-driven expression cassette for C-terminal 2HA tagging, Amp$^r$ Kan$^r$ | |
| pCRespG-2HA/BglII | pACYC184 based, Citrobacter espG promoter-driven expression cassette for C-terminal 2HA tagging Cm$^r$ | |
| pCR1er | *C. rodentium* ler in pCR2.1-TOPO | |
| pCRorf11 | *C. rodentium* orf11/grla in pCR2.1-TOPO | |
| pEHorf11 | EHEC orf11/grlA in pCR2.1-TOPO | |
| pEPorf11 | EPEC orf11/grlA in pCR2.1-TOPO | |
| pKK232-8 | pBR322 derivative containing a promoterless cat gene | Pharmacia |
| pLEE1-CAT | pKK232-8 derivative carrying *C. rodentium* LEE1 (Ler)-cat transcriptional fusion from nucleotides −162 to +216. | |
| pLEE5-CAT | pKK232-8 derivative carrying *C. rodentium* LEE5 (Tir)-cat transcriptional fusion from nucleotides −262 to +201. | |

For PCR and inverse PCR, the proof-reading ELONGASE Amplification System (GIBCO BRL/Life Technologies) was routinely used to minimize PCR error rate. PCR products were cloned using the TOPO TA Cloning Kit from Invitrogen with either pCR2. 1-TOPO or pCRII-TOPO. DNA sequence was determined using the Taq Dye-terminator method and an automated 373A DNA Sequencer (Applied Biosystems). For routine cloning, transformation, and infections, bacteria were grown in Luria-Bertani (LB) agar or LB broth supplemented with appropriate antibiotics at 37° C. Various antibiotics were used at the following concentrations, ampicillin 100 µg/ml, carbenicillin 100 µg/ml, kanamycin 50 µg/ml, and chloramphenicol 30 µg/ml. Growth in Dullbecco's modified Eagle's medium (DMEM) was used for induction of LEE gene expression and type III protein secretion.

The sacB gene-based allelic exchange (14) and the lambda Red recombinase system (17), were used to generate the mutants. In general, 75% or more of the internal portion of each gene was deleted to ensure the disruption of the function of the gene. The ler gene was mutated by the lambda red recombinase method and the ler, orf11/grlA, and cesT genes were mutated by the sacB gene-based allelic exchange method. The double mutant of ler/orf11 was also generated using the sacB-based method. The generation of the tir and escD mutants was described elsewhere (20, 56). The mutants were in-frame deletion mutants, with the introduction of a restriction enzyme site (either Nhe I, Bam HI, or Sal I) at the site of deletion as follows:

| LEE mutant name | Protein length (aa) | Codons deleted (from # to #) | Features introduced at the deletion site | Deletion methods employed |
|---|---|---|---|---|
| Δler | 129 | 23-97 or 9-122 | NheI or aphT cassette | SacB or Lambda Red |
| Δorf11/grlA | 135 | 23-115 | NheI | SacB |
| ΔcesT | 156 | 25-147 | NheI | SacB |

These mutants were verified by multiple PCR reactions. Complementation was tested for the Δtir, Δler, and Δorf11 mutants by supplying the respective gene on a plasmid. All of these mutants can be complemented, confirming that the mutations generated by both allelic exchange methods did not affect the function of downstream genes and are therefore non-polar.

To make EHEC-pNleA-HA, the coding region of nleA was amplified using the proof-reading ELONGASE Amplification System (Invitrogen) and the following primers: Z6024F: 5'AGATCTGAAGGAGATATTATGAACAT-TCAACCGACCATAC (SEQ ID NO:44); Z6024R: 5'CTC-GAGGACTCTTGTTCTTCGATTATATCAAAG (SEQ ID NO:45). PCR products were cloned using the TOPO TA Cloning Kit (Invitrogen) and the DNA sequence was verified using the Taq Dye-terminator method and an automated 373A DNA Sequencer (Applied Biosystems). The product was then subcloned into pCRespG-2HA/BglII, a pACYC-derived plasmid engineered to drive protein expression from a *C. rodentium*EspG promoter and to add two influenza hemagglutinin (HA) to the C-terminus of the expressed protein. The plasmid constructs were then introduced into wildtype EHEC and EHEC escN- by electroporation.

A deletion mutant in nleA in a nalidixic acid resistant strain of EHEC was created by sacB gene-based allelic exchange (29). Two DNA fragments that flank nleA were PCR amplified using EHEC chromosomal DNA as template.

Fragment A was PCR amplified using primer NT10 5'CCGGTACCTCTAACCATTGACGCACTCG (SEQ ID NO:46) and primer NT11 5'AACCTGCAGAACTAGG-TATCTCTAATGCC (SEQ ID NO:47) to generate a 1.3 kb product.

Fragment B was amplified using primer NT12 5'AACCT-GCAGCTGACTATCCTCGTATATGG (SEQ ID NO:48) and primer NT13 5'CCGAGCTCAGGTAATGAGACTGT-CAGC (SEQ ID NO:49) to generate a 1.3 kb product.

Fragments A and B were then digested with PstI for 1 hr and then the enzyme was heat inactivated for 20 minutes at 65° C. Approximately 50 ng of each digested fragment was ligated with T4 DNA ligase for 1 hr at room temperature. The ligation reaction was diluted 1/10 and 1 μl was added to a PCR using primers NT10 and NT13. The resulting 2.3 kb PCR product was then digested with SacI and KpnI, ligated to the corresponding sites of pRE112 (14) and transformed into DH5αλpir to generate pNT225. pNT225 was transformed into the conjugative strain SM10λpir which served as the donor strain in a conjugation with wild type EHEC. Nalidixic acid and chloramphenicol resistant exoconjugants were selected on LB agar. The exoconjugants were then plated onto LB agar containing 5% (w/v) sucrose, and no NaCl. The resulting colonies were then screened for sensitivity to chloramphenicol, followed by PCR to identify isolates with the nleA deletion and loss of plasmid sequences. A nleA deletion mutant was then isolated and used for further work. A *C. rodentium* nleA mutant was generated using PCR was used to create, in pRE118 (14), a suicide vector bearing an internal deletion of nleA.

The following primers were used: del1F: 5'GGTACCAC-CACACAGAATAATC (SEQ ID NO:50); del2R: 5'CGCTAGCCTATATACTGCTGTTGGTT (SEQ ID NO:51); del2F: 5'GCTAGCTGACAGGCAACTCTTG-GACTGG (SEQ ID NO:52); del2R: 5'GAGCTCAACAT-AATTTGATGGATTATGAT (SEQ ID NO:53). The resulting plasmid was introduced into *C. rodentium* by electroporation to create a antibiotic-resistant merodiploid strain. Loss of plasmid sequences through a second recombination event was selected for as described above. Antibiotic-sensitive, sucrose-resistant colonies were verified for the proper recombination event by PCR utilizing primers flanking the deleted region. The absence of NleA was verified by Western blotting whole cell lysates with polyclonal anti-NleA antisemm.

Assaying Total and Secreted Proteins/Proteomics

Secreted proteins were prepared as previously described (51).

*C. rodentium* strains were grown overnight in a shaker in 4 ml of Luria broth (LB) at 37° C. The cultures were subcultured 1 to 50 into 4 ml of Dulbecco's modified Eagle's medium (DMEM) which was pre-incubated in a tissue culture incubator (with 5% $CO_2$) overnight, and grown standing for 6 hours in the same incubator to induce LEE gene expression. The cultures were centrifuged twice at 13,000 rpm for 10 min. to remove the bacteria, and the supernatant was precipitated with 10% trichloroacetic acid (TCA) to concentrate proteins secreted into the culture media. The bacterial pellet was dissolved in 2X SDS-PAGE buffer and designated as total bacterial proteins. The secreted proteins precipitated from the supernatant were also dissolved in 2X SDS-PAGE buffer and the residual TCA was neutralized with 1 μl of saturated Tris. The volumes of buffer used to re-suspend the bacterial pellet as well as the secreted proteins were normalized to the OD600 of the cultures to ensure equal loading of the samples. The secreted proteins were analyzed in 12% or 17% SDS-PAGE, and stained with 0.1% Coomassie Blue G250. For Western blot analysis, total or secreted proteins were separated in 10% SDS-PAGE, and transferred onto nitrocellulose membrane (Bio-Rad). The antibodies used were rat polyclonal antibodies against the His-tagged *Citrobacter* Tir, and mouse monoclonal antibody against EPEC EspB. Standard ECL Western blotting protocols were followed (Amersham Life Science).

Wildtype EHEC and EHEC CVD451 were grown overnight in LB medium. Cultures were then diluted 1:100 into M-9 minimal medium supplemented with 44 mM NaHCO3, 8 mM MgSO4, 0.4% glucose and 0.1% Casamino acids and grown standing at 37° C. in 5% $CO_2$ to an OD600 of 0.6 to 0.8.

Secreted proteins were harvested by centrifuging cultures at 8000 g for 30 minutes, thus separating the supernatants from the pellets. Supernatants were filtered through 0.45 micron filters and the protein concentration determined by BCA assay (Sigma). Proteins were prepared for electrophoresis by precipitation with 1/9 volume 100% cold TCA, on ice for 45 to 120 min, followed by centrifugation at 17600 g for 30 min. The pellets were rinsed in cold 100% acetone and solubilized in 1X laemmli buffer (for 1-dimensional SDS-PAGE gels) or 2D sample buffer for 2D gels (8M urea, 2M thiourea, 4% CHAPS, 20 mM Tris, 0.002% bromophenol blue). For 2D gels, DTT was added to 6 mg/ml, and IPG buffer (pH 3-10: Amersham Biosciences) to 0.5% before loading. 18 cm Immobiline Dry Strips (pH 3-10: Amersham) were rehydrated in the sample overnight at 20° C. Samples were then focused at 15° C. for 65,000 Vh. After focusing, strips were equilibrated in EB+10 mg/ml DTT for 15 minutes, and then EB+25 mg/ml Iodoacetamide for 15 minutes (EB is 50 mM Tris, 6M Urea, 30% glycerol, 2% SDS, pH8.8). Equilibrated strips were sealed onto the top of large format SDS-PAGE gels (12% or 14% acrylamide) using 0.5% agarose in SDS-PAGE running buffer+0.002% bromophenol blue and the gels were run until the dye front ran off the gel.

Gels were stained with Sypro Ruby as per the manufacturers instructions (BioRad) and visualized on a UV lightbox or by MS/MS on a LCQ Deca Ion Trap Mass Spectrometer (Thermo Finnigan) equipped with a Nanoflow Liquid Chromatography system (LC Packings-Dionex). For gels visualized on a UV lightbox, spots of interest were excised manually. In-gel digestion of proteins was performed on the Investigator ProGest Robot (Genomic Solutions, Ann Arbor, Mich.) as described (23). Samples of high protein abundance were analyzed by an LC-MS system consisting of a Nanoflow Liquid Chromatography system equipped with FAMOS Autosampler (LC Packings-Dionex, San Francisco, Calif.), and an LCQ Deca Ion Trap Mass Spectrometer (Thermo Finnigan, San Jose, Calif.)(24).

Reversed-phase PicoFrit Columns PFC7515-PP18-5 (New Objective, Woburn, Mass., USA) were used for peptide separation and the column effluent was sprayed directly into the Mass Spectrometer. A flow rate of 200 nL/min was used and the total acquisition time was equal to 45 min per sample.

Low protein abundance samples were analyzed on an API QSTAR Pulsar Hybrid MS/MS Mass Spectrometer (Applied Biosystems/MDS SCIEX, Concord, Canada)(12) equipped with a Nanospray Ion Source (Proxeon, Odense, Denmark). Prior to the analysis, samples were purified and concentrated on ZipTips (Millipore, Billerica, Mass.). The API QSTAR Pulsar was also used for de novo peptide sequencing.

Spectra were searched against the NCBI (Bethesda, Md.) DataBase with Mascot (Matrixscience) or Sonar (Proteometrics Canada Ltd.) search engines.

Construction of Cat Transcriptional Fusions and Cat Assay

PCR fragments carrying the promoters and all the upstream regulatory elements of *Citrobacter* ler (LEE1) and tir (LEE5) were digested with Bam HI and Hind III, and cloned into plasmid pKK232-8, which contains a promoterless cat gene. The positions spanned by the cloned fragments are as indicated herein. The CAT activity directed by these fusions in different *Citrobacter* strains was determined as described previously (21, 22). Samples were collected at different time points from bacterial cultures grow in DMEM as described above.

Sequence Analysis and Bioinformatics Tools

DNA and protein sequence analysis and homology search by BLASTN, TBLASTN, and BLASTP were carried out using programs available from the NCBI website. Databases used include those from the NCBI site, the Sanger Genome Centre website, and the SwissProt website. The positions of the LEE PAI as well as the prophages in the EHEC genome were obtained from data generated by the IslandPath program (13).

Southern Blot Analysis

Genomic DNA samples for Southern blot analysis were prepared using DNeasy Tissue kit (Qiagen). Probe was prepared by digesting pNleA-HA with SalI and BglII enzymes to obtain a 500 bp fragment, which was labeled using BrightStar Psoralen-Biotin Nonisotopic Labeling Kit (Ambion).

Five micrograms of each genomic DNA sample were fully digested with 25 units of BamHI, EcoRI, and PstI overnight. The samples were resolved by electrophoresis on 1% agarose gel, and transferred overnight to BrightStar-Plus nylon membrane (Ambion) by passive, slightly alkaline downward elution. The DNA was cross-linked to the membrane by exposing the membrane to UV light for 2 min, followed by 30 min of baking at 80° C.

The membrane was prehybridized by washing it in 10 ml of ULTRAhyb Ultrasensitive Hybridization Buffer (Ambion) at 42° C. for 30 min. Ten microliters of the prepared probe were then added to the prehybridized membrane in buffer and the probe was hybridized to the membrane overnight at 42° C. Membrane was washed 2 times 5 min in low stringency wash buffer (Ambion) and 2 times 15 min in high stringency wash buffer (Ambion) at room temperature. The hybridized probe was detected using BrightStar BioDetect Nonisotopic Detection Kit (Ambion), followed by exposure to Kodak film.

Generation of Anti-NleA Antiserum

The coding portion of nleA was amplified from EHEC genomic DNA and cloned into a his-tagged expression vector (pET28a, Novagen) using following primers: 5'TTCCATAT-GAACATTCAACCGACC (SEQ ID NO:54) and 5'GGAAT-TCAATAATAGCTGCCATCC (SEQ ID NO:55). This plasmid was introduced into BL21 (λDE3), grown to an optical density (A600) of 0.8 and induced with 0.5 mM IPTG for 16 h at 20° C. His-tagged protein was purified on a Ni-NTA column as per the manufacturers' instructions (Qiagen). The NleA containing fractions were pooled and thrombin was added (500:1) and the protein was dialysed overnight against 20 mM tris pH 8. 2, 50 mM NaCl. The next day the protein was loaded on a monoQ FPLC column and the column was developed with a linear gradient from 50 to 500 mM NaCl. NleA containing fractions were pooled. The protein was >90% pure after this step. Purified protein was used to immunize two male Sprague Dawley rats, 300 µg protein/rat using Freund's complete adjuvant (Sigma), and the resulting antisera was affinity purified using the activated immunoaffinity support Affi-Gel 15 as per the manufacturer's instructions (BioRad). For immunofluorescence experiments, antiserum was further purified by absorption against acetone powders prepared from HeLa cells and from EHEC. NleA as described in (45). Specificity of antiserum was confirmed by Western blotting of cell extracts from wildtype EHEC and EHEC. NleA.

Immunoblot Analysis

Samples for Western blot analysis were resolved by SDS-PAGE (9% to 12% polyacrylamide). Proteins were transferred to nitrocellulose and immunoblots were blocked in 5% nonfat dried milk (NFDM) in TBS, pH 7.2, containing 0.1% Tween 20 (TBST) overnight at 4° C., and then incubated with primary antibody in 1% NFDM TBST for 1 hr at room temperature (RT). Membranes were washed 6 times in TBST, and then incubated with a 1:5000 dilution of horseradish peroxidase-conjugated goat anti-mouse (H+ L) antibody (Jackson ImmunoResearch Laboratories Inc.) for 1 hr at RT. Membranes were then washed as described above. Antigen-antibody complexes were visualized with enhanced chemiluminescence detection kit (Amersham), followed by exposure to Kodak film (Perkin Elmer). The following primary antibodies were utilized: anti-HA.11 (Covance), anti-DnaK (Stressgen), anti-EHEC Tir, anti-NleA (this study), anti-Calnexin (Stressgen), anti-Calreticulin (Affinity Bioreagents), anti-tubulin (Sigma).

Immunofluorescence

HeLa cells were grown on glass coverslips in 24 well tissue culture plates and infected for 6 hours with 1 ul (EHEC) of a standing overnight culture of OD ~0.4. At 6 hours postinfection, cells were washed 3 times in PBS containing $Ca^{2+}$ and $Mg^{2+}$, and fixed in 2.5% paraformaldehyde in PBS for 15 minutes at room temperature. Cells were permeabilized in 0.1% saponin in PBS, blocked in 5% goat serum or 5% BSA in PBS+0.1% saponin, and incubated with the following primary antibodies diluted in blocking solution for 1 hour at room temperature: anti-EHEC Tir, 1:1000; anti-*E. coli* O157 (Difco), 1:200; affinity-purified rat polyclonal anti-NleA (this study), 1:100; anti-mannosidase II (kindly provided by Dr. Marilyn Farquhar, UCSD), 1:1000. After 3 washes in PBS/saponin, cells were incubated in secondary antibodies (Alexa-488 or -568-conjugated anti-mouse, rabbit, rat (Molecular Probes) 1:400), for 30 minutes at room temperature, washed 3 times in PBS/saponin and once in PBS, and mounted onto glass slides using mowiol+DABCO. For visualization of polymerized actin, Alexa-488-conjugated phalloidin (Molecular Probes) was included with the secondary antibodies at a 1:100 dilution. Where indicated, cells were incubated with 5 µg/ml brefeldin A (Boehringer Mannheim) for 30 minutes before fixation. Images were detected using a Zeiss Axioskop microscope, captured with an Empix DVC1300 digital camera and analyzed using Northern Eclipse imaging software, or on a BioRad Radiance Plus confocal microscope using Lasersharp software.

Fractionation of Infected Host Cells

For each sample, two confluent 100 mm dishes of HeLa cells were infected with wildtype EHEC-pNleA-HA or EHECescN-pNleA-HA using an intial MOI of 1:10. At 6 hours post-infection, cells were washed three times with ice-cold PBS and subjected to biochemical fractionation as previously described (30, 49). Briefly, cells were resuspended in 300 μL homogenization buffer (3 mM imidazole, 250 mM sucrose, 0.5 mM EDTA, pH 7.4) supplemented with COMPLETE protease inhibitor cocktail (Roche) and mechanically disrupted by passage through a 22-gauge needle. The homogenate was centrifuged at low speed (3000 g) for 15 minutes at 4° C. to pellet unbroken cells, bacteria, nuclei and cytoskeletal components (low speed pellet). The supernatant was subject to high speed ultracentrifugation (41,000 g) for 20 minutes at 4° C. in a TLS55 rotor in a TL100 centrifuge (Beckman) to separate host cell membranes (pellet) from cytoplasm (supernatant). The pellets were resuspended in 300 μL 1X laemmli buffer, and the supernatant was made up to 1X laemmli buffer using a 5X stock. Equal volumes of all fractions were resolved by SDS-PAGE (9% polyacrylamide) and transferred to nitrocellulose and assayed by Western blot.

For extraction studies of membrane associated NleA, two 100 mm dishes of infected HeLa cells were fractionated as described above for each extraction condition. The high speed pellets (host membrane fraction) were resuspended in 300 μL of one of the following extraction buffers: (i) 10 mM Tris, 5 mM $MgCl_2$, pH 7.4; (ii) 10 mM Tris, 5 mM $MgCl_2$, 1 M NaCl, pH 7.4; (iii) 0.2 M $NaHCO_3$, 5 mM $MgCl_2$, pH 11.4; (iv) 10 mM Tris, 5 mM $MgCl_2$, 1% Triton X-100 pH 7.4. Extraction was performed on ice by pipetting the samples up and down every 5 minutes for 30 minutes and the samples were recentrifuged at 100,000 g for 30 minutes. The pellet (insoluble fraction) was resuspended in 300 μL 1X laemmli buffer, the supernatant (soluble fraction) was precipitated in 10% trichloroacetic acid on ice for 30 minutes, washed in 100% acetone and resuspended in 300 μL 1X laemmli buffer. Equal volumes were resolved by SDS-PAGE (9% polyacrylamide) and transferred to nitrocellulose and assayed by Western blot.

Infection Analysis of *C. rodentium* in Mice 5 week old C3H/HeJ mice (Jackson Laboratory) and outbred NIH Swiss mice (Harlan Sprague-Dawley) were housed in the animal facility at the University of British Columbia in direct accordance with guidelines drafted by the University of British Columbia's Animal Care Committee and the Canadian Council on the Use of Laboratory Animals. Wild-type *C. rodentium* and the nleA deletion mutant were grown in LB broth overnight in a shaker at 200 rpm and 100 μl of the cultures was used to infect mice by oral gavage. Inoculum was titred by serial dilution and plating and was calculated to be 4×108 cfu/mouse for both groups. For infection of the highly susceptible C3H/HeJ mice by *C. rodentium*, the survival of infected mice were assessed daily over the course of the infection. When any mouse became moribund, it was immediately sacrificed. For bacterial virulence assays using NIH Swiss mice, animals were sacrificed at day 10 post infection. To score colonic hyperplasia, the first 4 cm of the distal colon starting from the anal verge was collected and weighed after any fecal pellets were removed. To assay bacterial colonization, colonic tissues plus fecal pellets were homogenized in PBS using a Polytron Tissue Homogenizer, and serially diluted before being plated on MacConkey agar (Difco Laboratories). Colonic tissue and fecal pellets were combined to determine the total bacterial burden in the mouse colon at the time of sacrifice. MacConkey agar is selective for Gram-negative bacteria, on which *C. rodentium* forms colonies with a highly distinctive and identifiable morphology not typical of *E. coli* (26). For histological analysis, the last 0.5 cm of the colon of infected mice was fixed in 10% neutral buffered formalin, processed, cut into 3 μm sections and stained with hematoxylin and eosin. Histology analysis was done by the Morphological Services Laboratory at the Department of Pathology and Laboratory Medicine of the University of British Columbia.

EXAMPLE 2

Analysis of Regulation of LEE Gene Expression

To address which genes in the LEE regulate LEE gene expression in *C. rodentium*, we analyzed LEE mutants for expression of EspB and Tir, which are encoded by the LEE4 and LEE5 (Tir) operons, respectively. Total cell lysates of bacteria grown in DMEM were analyzed by Western blot with anti-Tir and anti-EspB sera. Our results confirmed Ler's essential role in LEE expression, since no Tir and EspB were produced in Δler. As expected, Δtir and ΔespB did not produce Tir and EspB, respectively. No Tir was visible in ΔcesT, consistent with CesT's role as the chaperone for Tir stability and secretion (18, 19). Surprisingly, another LEE-encoded protein, Orf11, was also required for the expression of Tir and EspB. Expression of Tir and EspB in Δorf11 was complemented by a plasmid carrying only *Citrobacter* orf11 (FIG. 8). The orf11 gene is highly conserved among A/E pathogens, and both EHEC and EPEC orf11 complemented *Citrobacter* Δorf11 (FIG. 8), indicating that Orf11 is functionally equivalent in positive regulation of LEE gene expression in A/E pathogens.

Sequence analysis indicated that Orf11/GrlA shows 23% identity to CaiF, a transcriptional activator of the cai and fix operons of the Enterobacteriaceae (15), and 37% identity to the deduced amino acid sequence of a uncharacterized *Salmonella* product encoded by a gene located downstream of the std fimbrial operon (16) (FIG. 7). This *Salmonella* homologue is indicated as SGH (Salmonella GrlA Homologue) in the figure. All three proteins contain a predicted helix-turn-helix motif characteristic of DNA binding proteins.

To address the hierarchy of Orf11 and Ler in regulating LEE gene expression, we created a double mutant of ler and orf11 in *C. rodentium*. While Tir and EspB expression in Δler Δorf11 can be partially restored by expressing Ler in trans, similarly expressed Orf11 had no such effect (FIG. 8), suggesting that Orf11 acts upstream of Ler in the regulatory cascade. Primer extension analysis confirmed this regulatory hierarchy by showing that the *Citrobacter* ler promoter is similar to that of EPEC ler and its expression was reduced in Δorf11.

The role of Orf11 in regulating ler expression was further demonstrated by monitoring the activities of transcriptional fusions between the regulatory regions of the LEE1 (Ler) (pLEE1-CAT) or LEE5 (Tir)(pLEE5-CAT) operons and the cat reporter gene in *Citrobacter* WT, Δler, and Δorf11 strains grown in Dulbecco's Modified Essential Medium (DMEM) for 6 hrs. The activity of LEE1-cat fusion was decreased in Δorf11, and that of the LEE5-cat fusions was dramatically reduced in both Δler and Δorf11. These results indicate that Orf11 is a novel positive regulator of the expression of Ler, which subsequently facilitates the expression of other LEE operons. Since Orf11 acts upstream of Ler in the regulatory cascade, it was named GrlA (for global regulator of LEE-activator).

EXAMPLE 3

Identification of Effectors Secreted by LEE-Encoded TTSS

A/E pathogens secrete several proteins into tissue culture or minimal media, but the secreted proteins are predominantly the translocators EspA, EspB, and EspD. Secreted proteins were concentrated by TCA precipitation from supernatants of bacterial cultures grown in DMEM and analyzed by 12% SDS-PAGE followed by Coomassie Blue staining. *C. rodentium* carrying a plasmid containing orf11/grlA secreted at least 300% more EspA, EspB, and EspD than the WT strain.

To define the effectors encoded by the *Citrobacter* LEE, we tagged various LEE-encoded proteins that are not involved in TTS and host cell adhesion with a double hemaglutinin (2HA) epitope at the carboxy terminus, and analyzed their secretion in WT and mutant *C. rodentium*. Only Tir, EspG, EspF, EspH, and Map were secreted by the LEE-encoded TTSS in *C. rodentium*, suggesting that the LEE encodes only 5 effectors. A previously unrecognized 54 kDa protein (p54) was readily detected by Coomassie staining in a mutant that also had greatly enhanced secretion of Tir, suggesting that it represents a novel putative effector encoded outside the LEE.

To identify p54 and to determine whether additional effectors are encoded outside the LEE in *C. rodentium*, we took advantage of the ability of GrlA to increase LEE gene expression and/or type III secretion, and introduced the grlA plasmid into mutants that secreted effectors, but not translocators. Over-expression of GrlA greatly enhanced (by more than 400%) the secretion of Tir in these mutants, with no translocators being secreted. At least 6 additional secreted proteins were observed, indicating that the LEE-encoded TTSS secretes several additional non-LEE-encoded proteins.

To identify these proteins, the secreted proteins were analyzed by 2-D gels. Since some of the LEE-encoded effectors (EspF, EspH, and Map) have predicted basic pI values, with EspF having an extreme pI of 11.00, the secreted proteins were first focused in Immobiline Dry Strips with both acidic (pH 3-10) and basic (pH 6-11) gradients, and then resolved in 12% and 14% SDS-PAGE, respectively. Gels were stained with Sypro Ruby, and selected protein spots were excised manually and analyzed by mass spectrometry and de novo peptide equencing.

This analysis confirmed that the LEE-encoded Tir, EspF, EspG, EspH, and Map were type III secreted (Table 2).

TABLE 2

Effectors and Putative effectors secreted by the LEE-encoded TTSS in *C. rodentium*.

| Serial number | Proposed name | Estimated MW | Estimated pI | Gene location | Homologues in EHEC and other pathogens |
|---|---|---|---|---|---|
| 5 | Tir | 68 | 5.0 | LEE | Tir, conserved in all A/E pathogens. |
| 10 | EspG | 44 | 7.3 | LEE | EspG, conserved in all A/E pathogens. |
| C1&C2 | Map | 23 | 9.0 | LEE | Map, conserved in all A/E pathogens. |
| C3 | EspF | 31 | 11.0 | LEE | EspF, conserved in all A/E pathogens. |
| C5&C6 | EspH | 21 | 8.7 | LEE | EspH, conserved in all A/E pathogens. |
| 7 | NleA | 54 | 5.8 | Non-LEE | EHEC Z6024 in O-island 71 near prophage CP-933P. |
| 12 | NleB | 39 | 5.9 | Non-LEE | EHEC Z4328 in O-island 122, REPEC LEE-associated RorfE, and *S. typhimurium* STMF1. Also has homology to Z0985 of O-island 36. |
| 13 | NleC | 40 | 4.6 | Non-LEE | EHEC Z0986 in O-island 36 near prophage CP-933K. |
| 14 | NleD | 28 | 7.1 | Non-LEE | EHEC Z0990 in O-island 36, in the same O-island as Z0985 and Z0986. Also has similarities to *P. syringae* pv. tomato effector HopPtoH. |
| 17 | NleE | 27 | 6.3 | Non-LEE | EHEC Z4329 in the same O-island 122 as Z4328. REPEC LEE-associated RorfD, and *S. flexneri* ORF122. |
| 19 | NleF | 24 | 4.7 | Non-LEE | EHEC Z6020, in the same O-island 71 as Z6024. Some similarities to hypothetical proteins in *Yersinia pestis* and *Helicobacter pylori*. |
| 20 | NleG | 26 | 5.8 | Non-LEE | Peptide sequence identified: QQENAPSS(I/L)QTR. No homologue found in the database. |

Figure 9:
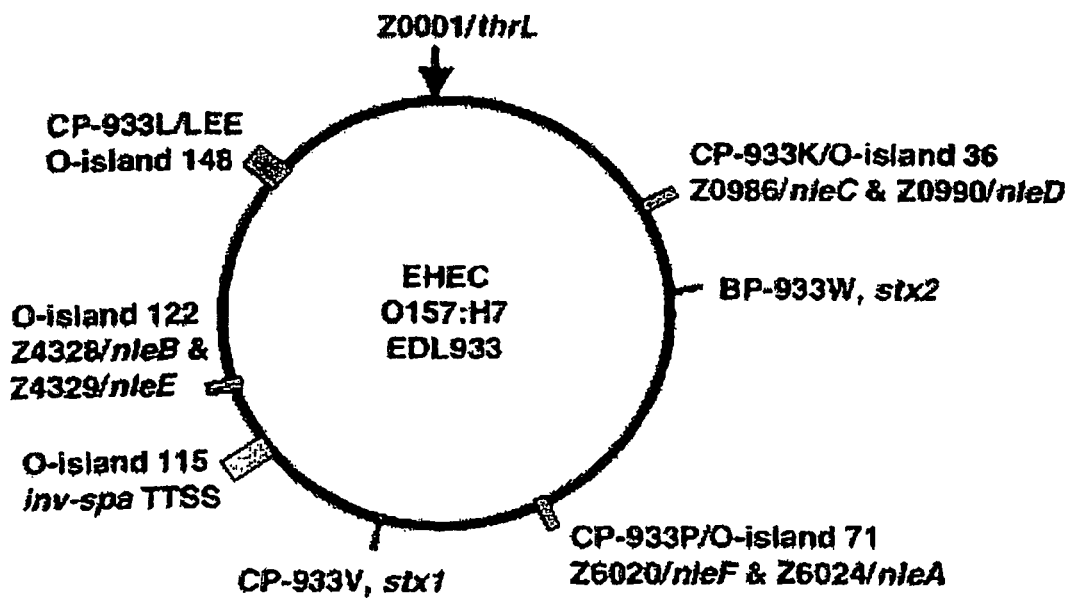
FIG. 9 is a schematic diagram showing the relative locations of the O-islands containing the 6 newly identified effector genes in the EHEC O157:H7 genome. Also shown are the locations of the Shiga toxin genes (stx), the LEE, and the inv-spa TTSS. Note the association of many of these genes with prophages (CP-933 and BP-933).

In addition to the five LEE-encoded effectors, we identified seven non-LEE-encoded secreted proteins that are likely effectors. These secreted proteins encoded outside the LEE were therefore designated NleA (p54), NleB, NleC, NleD, NleE, NleF, and NleG (QQENAPSS(I/L)QTR; SEQ ID NO: 59) (for non-LEE-encoded effectors) to distinguish them from LEE-encoded secreted proteins/effectors (Esp) (Table 2). Among the seven proteins identified, only NleG was unique to *C. rodentium*, and the other 6 proteins have highly conserved homologues in EHEC O157 (Table 2). The EHEC homologues are encoded by genes clustered in three discrete regions in the genome, with each region encoding at least two proteins that show homology to the *C. rodentium* secreted proteins (Table 2). The genes Z6024 and Z6020 encoding the homologues of NleA and NleF are located in EHEC O-island 71 associated with prophage CP-933P. Similarly, the genes Z4328 and Z4329 encoding the NleB and NleE homologues are located in O-island 122, and those encoding the NleC and NleD homologues (Z0986 and Z0990) are in O-island 36 (Table 2, FIG. 9). Furthermore, Z4328 (O-island 122) has strong homology to Z0985, a gene located next to Z0986 in O-island 36.

Homologues of all six new EHEC effector genes are also present and similarly organized in EPEC, whose genome is being sequenced (http://www.sanger.ac.uk/Projects/Microbes/). Except for Z6024, which showed 89% nucleotide identity to an EPEC gene, the other 5 EHEC genes showed greater than 95% identity to their homologues in EPEC. Moreover, some of these effectors are also highly conserved in other pathogenic bacteria. NleD/Z0990 has similarity to the type III effector HopPtoH of *P. syringae* pv. tomato (41, 42). NleE/Z4329 has significant homology to RorfD of rabbit EPEC (REPEC) and Orf212 of *S. flexneri* (8, 33), while NleB/Z4328 has strong homology to RorfE of REPEC and two hypothetical *S. typhimurium* proteins. The genes for Z4328 and Z4329 are located adjacent in EHEC, similar to the gene arrangement of rorfD and rorfE in REPEC (8). However, rorfD and rorfE are located next to the LEE in REPEC, while their counterparts in EHEC reside in a region (O-island 122) distant from the LEE. EHEC O-island 122 carrying Z4328 and Z4329 also contains genes encoding two cytotoxins as well as a homologue of PagC, an important PhoP/PhoQ-regulated virulence factor in *S. enterica* (3, 43). The three O-islands in EHEC that encode the new effectors have dinucleotide bias and low GC % contents, hallmarks of PAIs (9). In addition, they are either associated with a prophage or flanked by mobile insertion sequences, and are not present in the genome of non-pathogenic *E. coli* (3), suggesting horizontal transfer of these genes. Collectively, this suggests the importance of these islands and the newly identified *Citrobacter* and EHEC effectors in virulence. It also indicates that, as they diverge from each other, related pathogens maintain a surprisingly conserved set of PAIs despite the varied locations of the PAIs in the bacterial chromosome.

EXAMPLE 4

Identification of NleA

Although type III-secretion is generally thought to be contact-dependent (46), defined in vitro culture conditions can induce EHEC to secrete type III effectors into the extracellular medium during growth in liquid culture (28, 51). Culture supernatants were prepared from wildtype EHEC (wt) and a type III secretion mutant (escN-), grown in type III-secretion-inducing conditions. Analysis of the secreted proteins by SDS-PAGE revealed one abundant high molecular weight protein common to the secreted proteins from both the wildtype and escN- samples, and several other abundant proteins unique to the wildtype sample (FIG. 10A). The secreted proteins were separated by 2-dimensional gel electrophoresis and the abundant separated protein spots were excised from the gel and analyzed by mass spectrometry (FIG. 10B, Table I).

Spot #1 which was present in both wildtype and escN- culture supernatants was identified as EspP, a plasmid-encoded protein of EHEC that is secreted by an autotransporter mechanism which is independent of type III secretion (25). Four major spots (#2, 3, 4, 5) were unique to the wildtype supernatants. Three of these spots were identified as known type III secreted proteins encoded within the LEE: Tir (spot #2), EspB (spot #4), and EspA (spot #5) (FIG. 10B, Table I). Spot #3 was identified as a protein of predicted molecular weight of 48 kDa encoded by an open reading frame within the EHEC genome but outside the LEE (FIG. 10C). We called this protein NleA, for Non-LEE-encoded effector A.

EXAMPLE 5

Characterization of the Locus Containing nleA

The nleA gene is encoded in an O-island: a region of the EHEC genome absent from the genome of the non-pathogenic *E. coli* strain K-12 (3). The region between the last gene conserved in the *E. coli* K12 backbone (YciE) and genes encoding phage structural proteins contained several putative transposase fragments and one putative site-specific recombinase fragment (FIG. 11A). Analysis of this region with Islandpath, a program designed to identify PAIs (13), revealed that all ORFs within this region have a dinucleotide bias and a GC content divergent from the EHEC genome mean. 10 ORFs within the region have a GC content at least 1 standard deviation lower than the EHEC genome mean, while 2 of the 6 ORFs have GC content at least 1 standard deviation higher than the EHEC genome mean. Together, these results suggest that nleA is localized to a PAI containing horizontally-transferred genes. Several other ORFs within this region have features suggestive of roles in virulence including a putative chaperone (Z2565) and two proteins with similarity to type III-secreted proteins of other pathogens (Z6021, Z6020).

To investigate further the nature and distribution of the nleA gene, a nleA probe was prepared and Southern blots were performed on a panel of genomic DNA from other A/E pathogens and a non-pathogenic *E. coli* strain. As shown in FIG. 11B, the nleA gene was present in all A/E pathogens examined, but absent from non-pathogenic *E. coli*. Analysis of the in-progress EPEC genome sequence revealed that nleA is present in close proximity to a phage insertion site in the EPEC genome. nleA is also present within a prophage of an intimin-positive, non-O157 EHEC strain, O84:H4, but absent from non-pathogenic strains of *E coli*, uropathogenic *E. coli*, which does not contain the LEE. nleA is also absent from other TTSS-containing pathogens such as *Salmonella* and *Shigella* species. Thus, nleA appears to have been specifically acquired or retained in A/E pathogens. A multiple sequence alignment of nleA gene sequences from *C. rodentium*, EPEC,

TABLE I

| Spot number | ID | e value | # of peptides | predicted mw (kDa) | experimental mw (kDa) | predicted pI | experimental pI |
|---|---|---|---|---|---|---|---|
| 1 | EspP | 5.60E−4 | 4 | 105 | 95 | 5.9 | 6.5 |
| 2a | Tir | 2.50E−39 | 14 | 58 | 68 | 5 | 5 |
| 2b | Tir | 2.10E−29 | 10 | 58 | 65 | 5 | 4.8 |
| 3 | NleA | 7.70E−11 | 6 | 48 | 50 | 5 | 5 |
| 4a | EspB | 8.60E−53 | 19 | 33 | 38 | 5.1 | 5.2 |
| 4b | EspB | 2.00E−06 | 2 | 33 | 38 | 5.1 | 5.1 |
| 5 | EspA | 1.30E−37 | 16 | 21 | 18 | 4.8 | 5 |

EHEC, and O84:H4 reveals a high degree of sequence conservation in these four A/E pathogens (FIG. 11C).

EXAMPLE 6

NleA is Secreted by the LEE-Encoded Type III Secretion System

Figure 12:
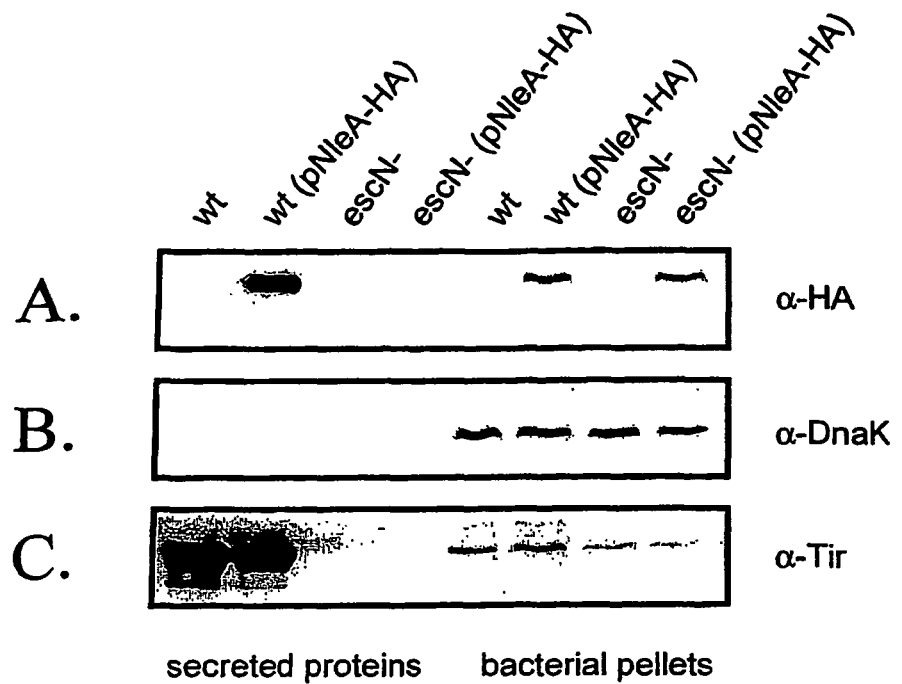
FIG. 12 shows a Western blot analysis of secreted proteins (left lanes) and bacterial pellets (right lanes) of wildtype (wt) EHEC and the type III secretion mutant (escN-) expressing pNleA-HA and the untransformed controls. Blots were probed with anti-HA (A.), anti-DnaK (B.), anti-Tir (C.).

EHEC and EPEC effectors of the LEE-encoded TTSS described to date are encoded within the LEE, in close proximity to the genes encoding the secretion apparatus itself. To determine whether secretion of NleA was dependent on the LEE-encoded TTSS, an epitope-tagged version of NleA was expressed from a plasmid in wildtype EHEC and an escN- strain, which is deficient for type III secretion (47). As shown in FIG. 12A, while HA-tagged NleA was expressed to similar levels in wildtype and escN- EHEC, the protein was only secreted into the extracellular media by the NleA-HA-transformed wildtype bacteria. DnaK, a non-secreted bacterial protein, was used as a control for the absence of non-secreted proteins in the secreted protein samples (FIG. 12B). Tir was secreted in the untransformed and NleA-HA-transformed wildtype strains, but not secreted by the escN- strains (FIG. 12C), verifying the expected TTSS phenotypes. Similar results were obtained for expression of epitope-tagged NleA in wildtype EPEC and several type III-secretion mutants of EPEC, indicating that NleA can also be secreted by the EPEC TTSS.

EXAMPLE 7

NleA is Translocated into Host Cells

Figure 13:
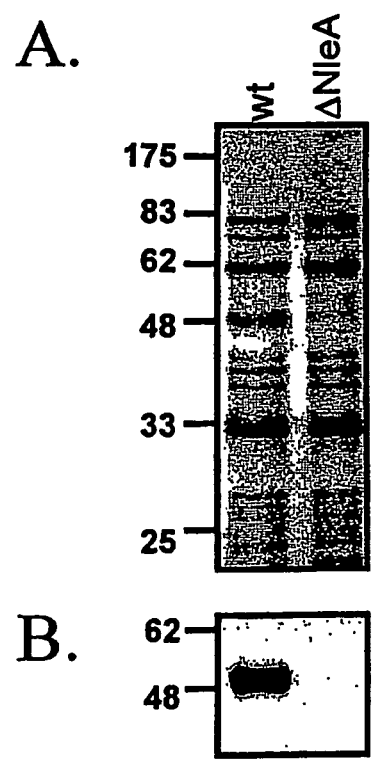
FIGS. 13A-B show Type III secretion and translocation in ΔnleA EHEC. A. SDS-PAGE gel of total secreted proteins from wildtype EHEC (wt) and the ΔnleA mutant. Migration of molecular weight markers (in kDa) is indicated at the left of the gel. B. Western blot analysis of secreted proteins from wildtype EHEC (wt) and the ΔnleA mutant with anti-NleA antiserum. Migration of molecular weight markers (in kDa) is indicated at the left of the gel.
Figure 15:
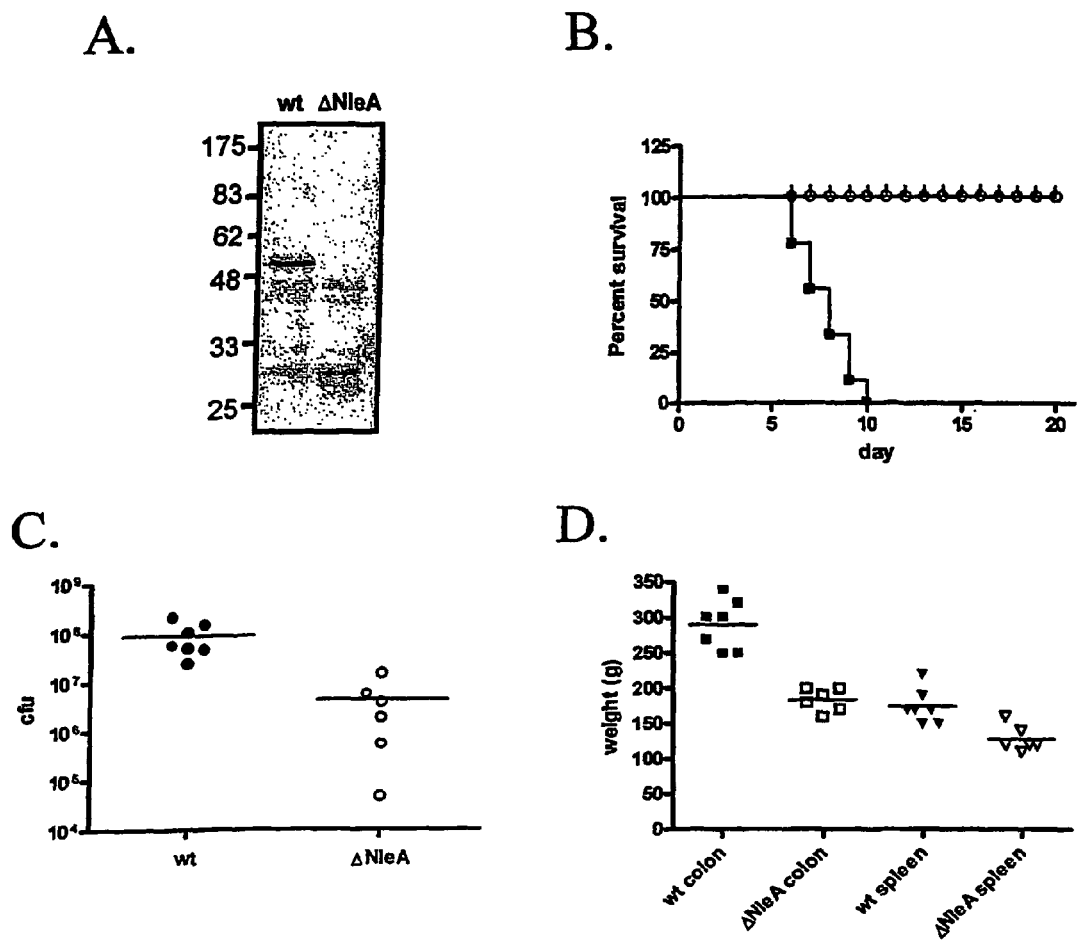
FIGS. 15A-D shows *Citrobacter rodentium* virulence studies in mice. A. Western blot of total bacterial extracts from wildtype *C. rodentium* (wt) and the ΔnleA mutant, probed with anti-NleA antiserum. Migration of molecular weight markers (in kDa) is indicated at the left of the gel. B. Survival plots for C3H/HeJ mice infected with wildtype *C. rodentium* (black squares), ΔnleA *C. rodentium*(open circles), and mice previously infected with the ΔnleA mutant and subsequently challenged with wildtype *C. rodentium*(vertical bars). Mice were monitored daily during the course of infection and when any mice became moribund they were sacrificed immediately. Percentage of the starting number of mice in each group that were viable on each day is shown. C. *C. rodentium* titres from infected NIH swiss mice colons. Mice were infected with wildtype *C. rodentium*(black circles) or the ΔnleA strain (open circles) and sacrificed at day 10 post infection. Colonic tissue and fecal pellets were homogenized and plated on MacConkey agar to determine the total *C. rodentium* burden in the mouse colon at the time of sacrifice. Each mouse in the experiment is represented by a single point. The mean of each group is indicated on the graph by horizontal bars. D. Colon and spleen weights of infected NIH swiss mice. Mice were infected with wildtype *C. rodentium*(black squares and triangles) or the ΔnleA strain (open squares and triangles) and sacrificed at day 10 post infection. Colons (squares) and spleens (triangles) were dissected and weighed. Each mouse in the experiment is represented by a single point. The mean of each group is indicated on the graph by horizontal bars.

When EHEC is grown under type III secretion-inducing conditions, two types of proteins are secreted into the extracellular medium. To determine whether NleA was a translocator or a translocated effector, we investigated type III secretion and translocation in the absence of NleA by generating a deletion mutant strain. Secreted protein profiles from wildtype and a ΔnleA mutant EHEC strains were analyzed. The wildtype sample contained an abundant protein of approximately 50 kDa which was absent from the ΔnleA secreted proteins (FIG. 13A). Western blot analysis with antisera directed against NleA demonstrated that 50 kDa NleA was present in the wildtype secreted proteins and absent in ΔnleA sample (FIG. 13B). However, other than the presence or absence of NleA, the secreted protein profiles of the wildtype and ΔnleA strains were identical (FIG. 13A). Thus, NleA is not required for secretion of other type III-secreted effectors. To determine whether NleA is required for translocation of other type III effectors into host cells, HeLa cells were infected with wildtype EHEC and EHEC ΔnleA, and Tir translocation and function were monitored by immunofluorescent staining of infected cells. Pedestal formation by wildtype EHEC and the ΔnleA mutant was examined by subjecting infected cells to immunofluorescence with anti-EHEC and anti-Tir antibodies, and visualizing filamentous actin using phalloidin. The results indicated that EHEC ΔnleA adhered to HeLa cells at similar levels to wildtype EHEC. Immunofluorescent staining revealed that Tir was translocated into host cells and focused under infecting bacteria in both the wildtype and ΔnleA EHEC strains. To confirm functional Tir translocation, infected cells were stained with fluorescent phalloidin to visualize polymerized actin involved in pedestal formation underneath adherent bacteria. Actin pedestals were evident in cells infected with either wildtype or ΔnleA EHEC, indicating that translocation and function of other type III effectors can proceed in the absence of NleA. These results also indicate that NleA is not required for pedestal formation.

As NleA did not appear to play a role in the secretion or translocation of other effectors, we investigated whether NleA was translocated itself. HeLa cells were infected for 6 hours with wildtype or escN- EHEC expressing HA-tagged NleA and subjected to subcellular fractionation and Western blot analysis with an anti-HA antibody. As indicated in FIG. 14A, NleA is translocated into host cells where it associates with the host cell membrane fraction. Translocation of NleA is not observed during infection of cells with a type III secretion mutant expressing HA-tagged NleA, indicating that NleA translocation and host membrane association is TTSS-dependent. Western blotting of the fractions with antibodies to proteins specific to each fraction confirmed the absence of cross-contamination of the fractions. Calnexin, a host cell integral membrane protein, was absent from the host cytoplasmic fraction; and tubulin, a host cell cytoplasmic protein, was absent from the host membrane fraction. DnaK, a non-secreted bacterial protein, was present only in the low-speed pellet, demonstrating a lack of bacterial contamination of the host membrane and cytosolic fractions. NleA and DnaK were absent from the low speed pellet in the type-III mutant-infected cells due to the type III dependence of EHEC adherencE. To control for the artifactual absence of NleA in type III mutant-infected samples due to the type III-dependence of EHEC adherence, we also performed similar experiments expressing and delivering NleA-HA by wildtype and type III mutant EPEC, since EPEC adherence to HeLa cells is independent of type III secretion. NleA was present in the membrane fraction of cells infected with wildtype, but not type III mutant EPEC strain. Both NleA and DnaK were present in the low-speed pellet fractions of both wildtype and type III mutant EPEC infected cells.

To investigate the nature of NleA association with host cell membranes, infected host cell membrane fractions containing HA-tagged NleA were extracted on ice under several conditions and recentrifuged to obtain soluble and insoluble membrane fractions (FIG. 14B). These fractions were subjected to Western blot analysis with anti-HA antibody to detect HA-tagged NleA. Treatment with high salt (1M NaCl) or alkaline pH (0.2M Na2CO3, pH 11.4) removes proteins that are peripherally associated with membranes via electrostatic or hydrophilic interactions respectively. The association of NleA with host cell membranes resisted disruption with these treatments (FIG. 14B, top panel), as did calnexin, an integral membrane protein (FIG. 14B, middle panel). In contrast, a significant proportion of calreticulin, a peripheral membrane protein, was extracted from the membrane fraction during both high salt and alkaline pH treatment (FIG. 14B, bottom panel). Treatment of membrane fractions with the non-ionic detergent Triton X-100, which solublizes integral membrane proteins such as calnexin (FIG. 14B, middle panel), almost completely solubilized NleA, resulting in a shift of the HA-tagged NleA protein from the insoluble to soluble fraction (FIG. 14B, top panel). These results indicate that NleA is translocated into host cells where it behaves as an integral membrane protein. Indeed, analysis of the NleA protein sequence by several transmembrane domain prediction programs predicts one or two putative transmembrane domains within the sequence (FIG. 11C).

EXAMPLE 8

NleA Localizes to the Host Golgi Apparatus

The subcellular localization of NleA within host cells was then determined. HeLa cells were infected with wildtype EHEC or EHEC ΔnleA and subjected to immunofluorescence with antibodies directed against NleA and mannosidase II. Some samples were treated with brefeldin A for 30 minutes prior to fixation. Two-color overlays of the NleA and mannosidase II staining were performed. HeLa cells were transfected with an expression construct encoding a GFP-NleA fusion protein, and subjected to immunofluorescence with an antibody directed against mannosidase II. Immunofluorescent staining of HeLa cells infected with wildtype EHEC, using the anti-NleA antibody, resulted in a perinuclear pattern of staining that was absent in cells infected with EHECΔnleA, or uninfected cells. This pattern did not resemble staining obtained with markers for late endosomes, lysosomes, ER, mitochondria, or the nucleus. However, a very similar pattern of staining was observed when cells were co-stained with anti-NleA and antibodies to markers of the Golgi apparatus, including mannosidase II, where the two proteins colocalized extensively. To confirm Golgi-localization of NleA, infected cells were incubated with brefeldin A, a fungal metabolite that disrupts Golgi structure (27), before fixation and immunofluorescencE. Brefeldin A treatment caused a diffusion of both mannosidase II and NleA staining, as expected for Golgi-localized proteins. Colocalization of NleA was observed with several other markers of the Golgi apparatus, and Golgi localization was also observed in experiments examining epitope-tagged NleA stained with anti-tag antibodies, utilizing both HA and FLAG epitope tags. To determine if Golgi localization of NleA required other bacterial factors or was an inherent property of NleA, cells were transfected with an expression construct encoding a GFP-NleA fusion protein. Transfected NleA GFP also localized to the Golgi, where it overlapped with mannosidase II staining.

Thus, our results indicate that NleA localizes to the Golgi. The observation that a transfected NleA-GFP fusion protein localizes to the Golgi suggests that the NleA protein contains Golgi-targeting information, and does not require other bacterial factors to get to this destination. Bacterially-delivered NleA is also Golgi-localized.

EXAMPLE 9

NleA is Required for Virulence

The high degree of sequence conservation of NleA in A/E pathogens (FIG. 11C) suggests that NleA plays a similar role in infection. *C. rodentium* is a natural pathogen of mice (53), and has been used as a model system to study A/E pathogenesis. In susceptible strains, *C. rodentium* infection is fatal, and typically causes death of infected mice between days 6-10 of infection (54). More resistant mouse strains do not die from *C. rodentium* infection, but become colonized and develop intestinal inflammation and colonic hyperplasia (54).

To test the role of NleA in virulence, we created a nleA-deleted *C. rodentium* strain and verified the absence of NleA by Western blotting total bacterial extracts with the NleA antiserum (FIG. 16A). Mice were infected with equal numbers of wildtype or ΔnleA bacteria by oral gavage. In *C. rodentium*-susceptible C3H-HeJ mice, NleA was absolutely required for virulence. All C3H-HeJ mice infected with wildtype *C. rodentium* died between day 6 and 10 of the infection (n=9), whereas all ΔnleA-infected mice (n=13) displayed some mild disease symptoms such as soft stools but still gained weight and were active throughout the infection and survived indefinitely (FIG. 16B). Furthermore, the ΔnleA-infected mice were resistant to subsequent challenge with wildtype *C. rodentium*(n=5, FIG. 16B). Thus, while the ΔnleA strain is non-pathogenic in susceptible mice, it interacts sufficiently with the host to stimulate protective immunity.

In contrast to C3H/HeJ mice, *C. rodentium* infection is not lethal for outbred NIH swiss mice. In these mice, *C. rodentium* colonization of the large intestine leads to intestinal inflammation, colonic hyperplasia and mild diarrheal symptoms. NIH swiss mice were infected with wildtype *C. rodentium* or the ΔnleA strain and sacrificed at day 10 post infection. The mice infected with the ΔnleA strain had, on average, a 20-fold lower *C. rodentium* titre in the colon at day 10 (FIG. 16C).

Histological analysis of infected NIH swiss mouse colons was performed by infecting mice with wildtype *C. rodentium* or the ΔnleA strain and sacrificing them at day 10 post infection. The last 0.5 cm of the colon of infected mice was fixed in 10% neutral buffered formalin, processed, cut into 3 μm sections and stained with hematoxylin and eosin. Tissue sections for all mice were observed and photographed using the 5X and 63X objectives. The results indicated that, in histological analyses of biopsies taken from the anal verge of infected mice, numerous bacteria were evident in the wildtype-infected tissue, but bacteria were scarce in the ΔnleA-infected samples. All animals infected with wildtype *C. rodentium* displayed pathological signs of colonic hyperplasia, whereas all ΔnleA-infected mice had no signs of hyperplasia. The wildtype-infected samples showed severe inflammation and hyperplasia to the extent that the intestinal lumen was no longer apparent and the external muscle layer was visibly distended, to accommodate the increased volume of epithelium. In contrast, the ΔnleA-infected samples displayed relatively normal histology. The relative degree of intestinal inflammation and hyperplasia was also evident in the difference in colon weights at the time of sacrifice in the two groups of mice (FIG. 16D). The wildtype infected mice also had larger spleens than the ΔnleA-infected mice as reflected in splenic weights (FIG. 16D).

Thus, we have demonstrated a striking effect of NleA on virulence in a mouse model of disease. In the susceptible mice, the presence of functional NleA in *C. rodentium* leads to a lethal infection within 10 days. Mice infected with a strain lacking NleA exhibit few symptoms and survive the infection indefinitely. In a more resistant mouse strain where *C. rodentium* infection is non-lethal, NleA is required for the development of colonic hyperplasia, and at day 10 of infection, there are less nleA mutant bacteria present in the host intestine. These studies indicate a clear effect of NleA in *C. rodentium* virulence. Our results from EHEC infection of HeLa cells demonstrate that in vitro, NleA does not affect adherence of bacteria to host cells or translocation of other effectors, suggesting that NleA may act at the level of resisting host clearance rather than enhancing bacterial adherence. Furthermore, the resistance of ΔnleA-infected mice to subsequent challenge with wildtype *C. rodentium* provides evidence that a nle mutant strain colonizes and interacts with the host sufficiently to stimulate host immunity. This is in contrast to type III-mutants of *C. rodentium*, that do not colonize the host, and provide no protection from subsequent challenge. Thus, nleA mutant strains may be used as an attenuated vaccine strain.

REFERENCES

The following publications are incorporated by reference.
1. Nataro, J. P., and Kaper, J. B. (1998) Diarrheagenic *Escherichia coli*. Clin Microbiol Rev 11: 142-201.
2. Frankel, G., Phillips, A. D., Rosenshine, I., Dougan, G., Kaper, J. B. and Knutton, S. (1998) Enteropathogenic and enterohaemorrhagic *Escherichia coli*: more subversive elements. *Mol Microbiol* 30: 911-921.
3. Pema, N. T., Plunkeft, G., 3rd, Burland, V., Mau, B., Glasner, J. D. Rose, D. J., Mayhew, G. F., Evans, P. S., Gregor, J., Kirkpatrick, H. A., Posfai, G., Hackett, J., Klink, S., Boutin, A., Shao, Y., Miller, L., Grotbeck, E. J., Davis, N. W., Lim, A., Dimalanta, E. T., Potamousis, K., D., Apodaca, J., Anantharaman, T. S., Lin, J., Yen, G., Schwartz, D. C. Welch, R. A., and Blattner, F. R. (2001) Genome sequence of enterohaemorrhagic *Escherichia coli* O157: H7. *Nature* 409: 529-533.
4. Elliott, S. J., Wainwright, L. A., McDaniel, T. K., Jarvis, K. G., Deng, Y. K., Lai, L. C., McNamara, B. P., Donnenberg, M. S., and Kaper, J. B. (1998) The complete sequence of the locus of enterocyte effacement (LEE) from enteropathogenic *Escherichia coli* E2348/69. *Mol Microbiol* 28: 1-4.
5. Pema, N. T., Mayhew, G. F., Posfai, G., Elliott, S., Donnenberg, M. S., Kaper, J. B., and Blattner, F. R. (1998) Molecular evolution of a pathogenicity island from enterohemorrhagic *Escherichia coli* O157:H7. *Infect Immuii* 66: 3810-3817.
6. Zhu, C., Agin, T. S., Elliott, S. J., Johnson, L. A., Thate, T. E., Kaper, J. B., and Boedeker, E. C. (2001) Complete nucleotide sequence and analysis of the locus of enterocyte Effacement from rabbit diarrheagenic *Escherichia coli* RDEC-1. *Infect Immun* 69: 2107-2115.
7. Deng, W., Li, Y., Vallance, B. A., and Finlay, B. B. (2001) Locus of enterocyte effacement from *Citrobacter rodentium*: sequence analysis and evidence for horizontal transfer among attaching and effacing pathogens. *Infect Immun* 69: 6323-6335.
8. Tauschek, M., Strugnell, R. A., and Robins-Browne, R. M. (2002) Characterization and evidence of mobilization of the LEE pathogenicity island of rabbit-specific strains of enteropathogenic *Escherichia coli*. *Mol Microbiol* 44: 1533-1550.
9. Hacker, J., and Kaper, J. B. (2000) Pathogenicity islands and the evolution of microbes. *Annu Rev Microbiol* 54: 641-679.
10. G. R. Cornelis, *J. Cell. Biol.* 158, 401(2002).
11. S. Gruenheid, B. B. Finlay, *Nature* 422, 775 (2003).
12. I. Chemushevich, A. Loboda, B. Thomson, *J. Mass Spectrom.* 36, 849 (2001).
13. Hsiao, W., Wan, I., Jones, S. J., and Brinkman, F. S. (2003) IslandPath: aiding detection of genomic islands in prokaryotes. *Bioinformatics* 19: 418-420.
14. Edwards, R. A., Keller, L. H., and Schifferli, D. M. (1998) Improved allelic exchange vectors and their use to analyze 987P fimbria gene expression. *Gene* 207: 149-157.
15. V. Sperandio, J. L. Mellies, W. Nguyen, S. Shin, J. B. Kaper, *ProC. Natl. Acad. Sci. USA* 96, 15196 (1999).
16. J. L. Mellies, S. J. Elliott, V. Sperandio, M. S. Donnenberg, J. B. Kaper, *Mol. Microbiol.* 33, 296 (1999).
17. K. A. Datsenko, B. L. Wanner, *ProC. Natl. Acad. Sci. USA* 97, 6640 (2000).
18. A. Abe et al., *Mol. Microbiol.* 33, 1162 (1999).
19. S. J. Elliott et al., *Mol. Microbiol.* 33, 1176 (1999).
20. Vallance, B. A., Deng, W., De Grado, M., Chan, C., Jacobson, K., and Finlay, B. B. (2002b) Modulation of inducible nitric oxide synthase expression by the attaching and effacing bacterial pathogen *citrobacter* rodentium in infected micE. *Infect Immun* 70: 6424-6435.
21. V. H. Bustamante, F. J. Santana, E. Calva, J. L. Puente, Mol. Microbiol. 39, 664 (2001).
22. J. L. Puente, D. Bieber, S. W. Ramer, W. Murray, G. K. Schoolnik, *Mol. Microbiol.* 20, 87 (1996).
23. T. Houthaeve, H. Gausepohl, M. Mann, K. Ashman, *FEBS Lett.* 376, 91 (1995)
24. Z. Ziegler, Anal. Chem. 74, 489A (2002).
25. Brunder, W., Schmidt, H., and Karch, H. (1997) EspP, a novel extracellular serine protease of enterohaemorrhagic *Escherichia coli* O157:H7 cleaves human coagulation factor V. *Mol Microbiol* 24: 767-778.
26. Buchet, A., Nasser, W., Eichler, K., and Mandrand-Berthelot, M. A. (1999) Positive co-regulation of the *Escherichia coli* camitine pathway cai and fix operons by CRP and the CaiF activator. *Mol Microbiol* 34: 562-575.
27. Chardin, P., and McCormick, F. (1999) Brefeldin A: the advantage of being uncompetitivE. *Cell* 97: 153-155.
28. DeVinney, R., Stein, M., Reinscheid, D., Abe, A., Ruschkowski, S., and Finlay, B. B. (1999) Enterohemorrhagic *Escherichia coli* O157:H7 produces Tir, which is translocated to the host cell membrane but is not tyrosine phosphorylated. *Infect Immun* 67: 2389-2398.
29. Donnenberg, M. S., and Kaper, J. B. (1991) Construction of an eae deletion mutant of enteropathogenic *Escherichia coli* by using a positive-selection suicide vector. *Infect Immun* 59: 4310-4317.
30. Gauthier, A., de Grado, M., and Finlay, B. B. (2000) Mechanical fractionation reveals structural requirements for enteropathogenic *Escherichia coli* Tir insertion into host membranes. *Infect Immun* 68: 4344-4348.
31. Goosney, D. L., DeVinney, R., and Finlay, B. B. (2001) Recruitment of cytoskeletal and signaling proteins to enteropathogenic and enterohemorrhagic *Escherichia coli* pedestals. *Infect Immun* 69: 3315-3322.
32. Griffin, P. M., Ostroff, S. M., Tauxe, R. V., Greene, K. D., Wells, J. G., Lewis, J. H., and Blake, P. A. (1988) Illnesses associated with *Escherichia coli* O157:H7 infections. A broad clinical spectrum. *Ann Intern Med* 109: 705-712.
33. C. Buchrieser et al., *Mol. Microbiol.* 38, 760 (2000).
34. Galan, J. E. (2001) *Salmonella* interactions with host cells: type III secretion at work. *Annu Rev Cell Dev Biol* 17: 53-86.
35. Kenny, B., DeVinney, R., Stein, M., Reinscheid, D. J., Frey, E. A., and Finlay, B. B. (1997) Enteropathogenic *E. coli* (EPEC) transfers its receptor for intimate adherence into mammalian cells. *Cell* 91: 511-520.
36. Elliott, S. J., Krejany, E. O., Mellies, J. L., Robins-Browne, R. M. Sasakawa, C., and Kaper, J. B. (2001) EspG, a novel type III system-secreted protein from enteropathogenic *Escherichia coli* with similarities to VirA of *Shigella flexneri*. *Infect Immun* 69: 4027-4033.
37. Kenny, B., and Jepson, M. (2000) Targeting of an enteropathogenic *Escherichia coli* (EPEC) effector protein to host mitochondria. *Cell Microbiol* 2: 579-590.
38. McNamara, B. P., Koutsouris, A., O'Connell, C. B., Nougayrede, J. P. Donnenberg, M. S., and Hecht, G. (2001) Translocated EspF protein from enteropathogenic *Escherichia coli* disrupts host intestinal barrier function. *J Clin Invest* 107: 621-629.
39. O. Marches et al., *Infect. Immun.* 68, 2171 (2000).
40. Tu, X., Nisan, I., Yona, C., Hanski, E., and Rosenshine, I. (2003) EspH, a new cytoskeleton-modulating effector of enterohaemorrhagic and enteropathogenic *Escherichia coli*. *Mol Microbiol* 47: 595-606.
41. D. S. Guttman et al., *Science* 295, 1722 (2002).
42. T. Petnicki-Ocwieja et al., *ProC. Natl. Acad. Sci. USA* 99, 7652 (2002).
43. S. I. Miller, A. M. Kukral, J. J. Mekalanos, *ProC. Natl. Acad. Sci. USA* 86, 5054 (1989).
44. Gruenheid, S., DeVinney, R., Bladt, F., Goosney, D., Gelkop, S., Gish, G. D., Pawson, T., and Finlay, B. B.

(2001) Enteropathogenic *E. coli* Tir binds Nck to initiate actin pedestal formation in host cells. *Nat Cell Biol* 3: 856-859.

45. Harlow, E., and Lane, D. (1988) *Antibodies: a laboratory manual*. Cold Spring Harbor, N.Y.: Cold Spring Harbor Laboratory.
46. Hueck, C. J. (1998) Type III protein secretion systems in bacterial pathogens of animals and plants. *Microbiol Mol Biol Rev* 62: 379-433.
47. Jarvis, K. G., and Kaper, J. B. (1996) Secretion of extracellular proteins by enterohemorrhagic *Escherichia coli* via a putative type III secretion system. *Infect Immun* 64: 4826-4829.
48. Kenny, B., Ellis, S., Leard, A. D., Warawa, J., Mellor, H., and Jepson, M. A. (2002) Co-ordinate regulation of distinct host cell signalling pathways by multifunctional enteropathogenic *Escherichia coli* effector molecules. *Mol Microbiol* 44: 1095-1107.
49. Knodler, L. A., Vallance, B. A., Hensel, M., Jackel, D., Finlay, B. B. and Steele-Mortimer, O. (2003) *Salmonella* type III effectors PipB and PipB2 are targeted to detergent-resistant microdomains on internal host cell membranes. *Mol Microbiol* 49:685-704.
50. Levine, M. M., Bergquist, E. J., Nalin, D. R., Waterman, D. H. Hornick, R. B., Young, C. R., and Sotman, S. (1978) *Escherichia coli* strains that cause diarrhoea but do not produce heat-labile or heat-stable enterotoxins and are non-invasive. *Lancet* 1: 1119-1122.
51. Li, Y., Frey, E., Mackenzie, A. M., and Finlay, B. B. (2000) Human response to *Escherichia coli* O157:H7 infection: antibodies to secreted virulence factors. *Infect Immun* 68: 5090-5095.
52. Peeters, J. E., Geeroms, R., and Orskov, F. (1988) Biotype, serotype, and pathogenicity of attaching and effacing enteropathogenic *Escherichia coli* strains isolated from diarrheic commercial rabbits. *Infect Immun* 56: 1442-1448.
53. Schauer, D. B., and Falkow, S. (1993) The eae gene of *Citrobacter freundii* biotype 4280 is necessary for colonization in transmissible murine colonic hyperplasia. *Infect Immun* 61: 4654-4661.
54. Vallance, B. A., Deng, W., Jacobson, K., and Finlay, B. B. (2003) Host susceptibility to the attaching and effacing bacterial pathogen *Citrobacter rodentium*. *Infect Immun* 71: 3443-3453.
55. Yoshida, S., Katayama, E., Kuwae, A., Mimuro, H., Suzuki, T., and Sasakawa, C. (2002) Shigella deliver an effector protein to trigger host microtubule destabilization, which promotes Rac1 activity and efficient bacterial internalization. *Embo J* 21: 2923-2935.
56. Deng, W., Vallance, B. A., Li, Y., Puente, J. L., and Finlay, B. B. (2003) *Citrobacter rodentium* translocated intimin receptor (Tir) is an essential virulence factor needed for actin condensation, intestinal colonization and colonic hyperplasia in micE. *Mol Microbiol* 48: 95-115.
57. "Remington's Pharmaceutical Sciences" (19th edition), ed. A. Gennaro, 1995, Mack Publishing Company, Easton, Pa.
58. Abe, A., U. Heczko, R. Hegele, and B. Finlay. 1998. Two enteropathogenic *Escherichia coli* type III secreted proteins, EspA and EspB, are virulence factors. Journal of Experimental Medicine 188:1907-1916
59. Adv. Drug Deliv. Rev. 5 (3): 163-187 (1990)
60. Altschul, S. F. 1991. "Amino acid substitution matrices from an information theoretic perspective." Journal of Molecular Biology, 219: 555-665
61. Ausubel et al., Current Protocols in Molecular Biology, John Wiley & Sons, New York, N.Y., 1998
62. Babiuk et al. (1986) Virology 159: 57-66).
63. Beuzon, C. R., and D. W. Holden. 2001. Use of mixed infections with *Salmonella* strains to study virulence genes and their interactions in vivo. Microbes Infect 3:1345-52.
64. Brown D, et al. (2002) *TechNotes* 9: 3-5
65. Brummelkamp T R, et al. (2002) *Science* 296:550-553
66. Canil, C., I. Rosenshine, S. Ruschkowski, M. S. Donnenberg, J. B. Kaper, and B. B. Finlay. 1993. Enteropathogenic *Escherichia coli* decreases the transepithelial electrical resistance of polarized epithelial monolayers. Infect Immun 61:2755-62
67. Caplen N J, et al. (2001) *Proc. Natl. Acad. Sci. USA* 98: 9746-9747
68. Clin. Exp. Immunol. 78 (2): 256-262 (1989)
69. Cloning Vectors: A Laboratory Manual (P. H. Pouwels et al., 1985, Supp. 1987
70. Dayhoff, M. O., Schwartz, R. M., Orcutt, B. C. 1978. "A model of evolutionary change in proteins." In "Atlas of Protein Sequence and Structure" 5(3) M. O. Dayhoff (ed.), 345-352, National Biomedical Research Foundation, Washington
71. Eisenberg et al. (*J. Mol. Bio.* 179:125-142, 184
72. Elder et al., Proc. Natl. Acad. Sci. USA (2000) 97: 2999
73. Epitope Mapping Protocols in Methods in Molecular Biology, Vol. 66 (Glenn E. Morris, Ed., 1996) Humana Press, Totowa, N.J.
74. Fey et al., Emerg. Infect. Dis. (2000) Volume 6
75. Gall, D. (1966) Immunology 11: 369-386
76. Geysen et al. (1984) Proc. Natl. Acad. Sci. USA 81: 3998-4002
77. Geysen et al. (1986) Molec. Immunol. 23:709-715
78. Hammerling et al., In Monoclonal Antibodies and T Cell Hybridomas, Elsevier, N.Y., 1981
79. Hammond S M; et al. (2001) *Nature Rev Gen* 2: 110-119
80. Hauf, N., and T. Chakraborty. 2003. Suppression of NF-kappa B activation and proinflammatory cytokine expression by Shiga toxin-producing *Escherichia coli*. J Immunol 170:2074-82
81. Hopp et al., Proc. Natl. Acad. Sci USA (1981) 78:3824-3828
82. Immunology 58 (2): 245-250 (1986)
83. Int. Arch. Allergy Appl. Immunol. 68 (3): 201-208 (1982)
84. J. Immunol. Methods 97 (2): 159-164 (1987)
85. J. Controlled Release 7: 123-132 (1988)
86. Karlin, S. and Altschul, S. F. 1990. "Methods for assessing the statistical significance of molecular sequence features by using general scoring schemes" Proc. Natl. Acad. Sci. USA. 87: 2264-2268.
87. Knodler, L. A., J. Celli, W. D. Hardt, B. A. Vallance, C. Yip, and B. B. Finlay. 2002. *Salmonella* effectors within a single pathogenicity island are differentially expressed and translocated by separate type III secretion systems. Mol Microbiol 43:1089-103
88. Kodak Laboratory Chemicals Bulletin 56 (1): 1-5 (1986)
89. Kohler et al., Eur. J. Immunol. 6:292, 1976
90. Kohler et al., Eur. J. Immunol. 6:511, 1976
91. Kohler et al., Nature 256:495, 1975
92. Kyte et al., J: Mol. Biol. (1982) 157: 105-132).
93. Lee N S, et al. (2002) *Nature Biotechnol.* 20:500-505
94. M. S. Johnson and J. P. Overington. 1993. "A Structural Basis of Sequence Comparisons: An evaluation of scoring methodologies." Journal of Molecular Biology. 233: 716-738.
95. Miyagishi M, and Taira K. (2002) *Nature Biotechnol.* 20:497-500

96. Myers and Miller, CABIOS, 1989, 4:11-17
97. Naylor, S. W., J. C. Low, T. E. Besser, A. Mahajan, G. J. Gunn, M. C. Pearce, I. J. McKendrick, D. G. Smith, and D. L. Gally. 2003. Lymphoid follicle-dense mucosa at the terminal rectum is the principal site of colonization of enterohemorrhagic *Escherichia coli* O157:H7 in the bovine host. Infect Immun 71:1505-12
98. Paddison P J, et al. (2002). *Genes & Dev.* 16:948-958
99. Paul C P, et al. (2002) *Nature Biotechnol.* 20:505-508
100. Schijns et al., Curr. Opi. Immunol. (2000) 12: 456
101. Sharp P A. (2001) *Genes Dev* 15: 485-490
102. States, D. J., Gish, W., Altschul, S. F. 1991. "Improved Sensitivity of Nucleic Acid Database Search Using Application-Specific Scoring Matrices" Methods: A companion to Methods in Enzymology 3(1): 66-77
103. Steven Henikoff and Jorja G. Henikoff. 1992 "Amino acid substitution matrices from protein blocks." Proc. Natl. Acad. Sci. USA. 89(biochemistry): 10915-10919
104. Steven Henikoff and Jorja G. Henikoff. 1993. "Performance Evaluation of Amino Acid Substitution Matrices." Proteins: Structure, Function, and Genetics. 17: 49-61
105. Sui G, et al. (2002) *Proc. Natl. Acad. Sci. USA* 99:5515-5520
106. Vallance, B. A., W. Deng, L. A. Knodler, and B. B. Finlay. 2002. Mice lacking T and B lymphocytes develop transient colitis and crypt hyperplasia yet suffer impaired bacterial clearance during *Citrobacter rodentium* infection. Infect Immun 70:2070-81
107. Van Donkersgoed et al., Can. Vet. J. (1999) 40: 332
108. Van Donkersgoed et al., Can. Vet. J. (2001) 42: 714
109. Yu J-Y, et al. (2002) *Proc. Natl. Acad. Sci. USA* 99:6047-6052
110. Sambrook et al., Molecular Cloning: A Laboratory Manual. 2nd ed., Cold Spring Harbor Laboratory, Cold Spring Harbor Laboratory Press, Cold Spring Harbor, N.Y., 1989
111. Ausubel et al., Current Protocols in Molecular Biology, John Wiley & Sons, 1994
112. Vaughan et al., Nature Biotech 14:309-314, 1996
113. Larsson A et al Chicken antibodies: taking advantage of evolution—a review. Poult Sci. 1993 October;72(10): 1807-12.
114. Alymova I V, Kodihalli S, Govorkova E A, Fanget B, Gerdil C, Webster R G. Immunogenicity and protective efficacy in mice of influenza B virus vaccines grown in mammalian cells or embryonated chicken eggs. J. Virol. 1998 May;72(5):4472-7.
115. O'Farrelly C, Branton D, Wanke C A. Oral ingestion of egg yolk immunoglobulin from hens immunized with an enterotoxigenic *Escherichia coli* strain prevents diarrhea in rabbits challenged with the same strain. Infect Immun. 1992 July;60(7):2593-7.
116. Romito M, Viljoen G J, Du Plessis D H. Eliciting antigen-specific egg-yolk IgY with naked DNA. Biotechniques. 2001 September;31(3):670, 672, 674-5.
117. Yokoyama H, Umeda K, Peralta R C, Hashi T, Icatlo F C Jr, Kuroki M, Ikemori Y, Kodama Y. Oral passive immunization against experimental salmonellosis in mice using chicken egg yolk antibodies specific for *Salmonella enteritidis* and *S. typhimurium*. Vaccine. 1998 February;16(4): 388-93.

OTHER EMBODIMENTS

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Accession numbers, as used herein, refer to Accession numbers from multiple databases, including GenBank, the European Molecular Biology Laboratory (EMBL), the DNA Database of Japan (DDBJ), or the Genome Sequence Data Base (GSDB), for nucleotide sequences, and including the Protein Information Resource (PIR), SWISSPROT, Protein Research Foundation (PRF), and Protein Data Bank (PDB) (sequences from solved structures), as well as from translations from annotated coding regions from nucleotide sequences in GenBank, EMBL, DDBJ, or RefSeq, for polypeptide sequences. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for eliciting an immune response against an A/E pathogen, wherein the A/E pathogen is enterohemorrhagic *E. coli* (EHEC), enteropathogenic *E. coli* (EPEC), or *Citrobacter rodentium*, or component thereof, in a ruminant comprising administering to the ruminant an effective amount of a recombinant polypeptide which comprises an amino acid sequence selected from one or more of the group consisting of SEQ ID NOs: 22-24 thereby eliciting an immune response in the ruminant.

2. A method for reducing colonization of an A/E pathogen, wherein the A/E pathogen is enterohemorrhagic *E. coli* (EHEC), enteropathogenic *E. coli* (EPEC), or *Citrobacter rodentium*, in a ruminant, the method comprising administering to the ruminant an effective amount of a recombinant polypeptide which comprises an amino acid sequence selected from one or more of the group consisting of SEQ ID NOs: 22-24 thereby reducing colonization of the A/E pathogen in the ruminant.

3. A method for reducing shedding of an A/E pathogen, wherein the A/E pathogen is enterohemorrhagic *E. coli* (EHEC), enteropathogenic *E. coli* (EPEC), or *Citrobacter rodentium*, in a ruminant comprising administering to the ruminant an effective amount of a recombinant polypeptide which comprises an amino acid sequence selected from one or more of the group consisting of SEQ ID NOs: 22-24 thereby reducing shedding of the A/E pathogen in the ruminant.

4. The method of claim 1, wherein the ruminant is a bovine or ovine subject.

5. The method of claim 2, wherein the ruminant is a bovine or ovine subject.

6. The method of claim 3, wherein the ruminant is a bovine or ovine subject.

7. The method of claim 1, wherein the EHEC is EHEC O157:H7 or EHEC O157:NM or wherein the EPEC is EPEC O127:H6.

8. The method of claim 2 wherein the EHEC is EHEC O157:H7 or EHEC O157:NM.

9. The method of claim 3 wherein the EHEC is EHEC O157:H7 or EHEC O157:NM or wherein the EPEC is EPEC O127:H6.

10. The method of claim 1, wherein the recombinant polypeptide is provided in combination with a physiologically acceptable carrier.

11. The method of claim 1, wherein the recombinant polypeptide is provided in a composition that further comprises a EspA, EspB, EspD, EspP, Tir, or intimin polypeptide.

12. The method of claim 1, wherein the recombinant polypeptide is provided in combination with an adjuvant.

13. The method of claim 2, wherein the recombinant polypeptide is provided in combination with an adjuvant.

14. The method of claim 3, wherein the recombinant polypeptide is provided in combination with an adjuvant.

15. The method of claim 1, wherein the EHEC is EHEC O158, O5, O8, O18, O26, O45, O48, O52, O55, O75, O76, O78, O84, O91, O103, O104, O111, O113, O114, O116, O118, O119, O121, O125, O28, O145, O146, O163, or O165.

16. The method of claim 2, wherein the EHEC is EHEC O158, O5, O8, O18, O26, O45, O48, O52, O55, O75, O76, O78, O84, O91, O103, O104, O111, O113, O114, O116, O118, O119, O121, O125, O28, O145, O146, O163, or O165.

17. The method of claim 3, wherein the EHEC is EHEC O158, O5, O8, O18, O26, O45, O48, O52, O55, O75, O76, O78, O84, O91, O103, O104, O111, O113, O114, O116, O118, O119, O121, O125, O28, O145, O146, O163, or O165.

* * * * *

SEQUENCE LISTING

```
<160> NUMBER OF SEQ ID NOS: 84

<210> SEQ ID NO 1
<211> LENGTH: 1293
<212> TYPE: DNA
<213> ORGANISM: Citrobacter rodentium

<400> SEQUENCE: 1
atgaacattc aaccgaacat acattccgga atcaccacac agaataatca acaacatcat      60
cacgcagaac aagtgcctgt ctctagctca ataccgcgat cagatttacc tccaaattgc     120
gaagctggat ttgttgtgca tattccagag gatatacagc aacatgtacc ggaatgtggt     180
gaaacaacgg ctctattaag cttgataaaa gatgaaggcc tgctctcagg actagataaa     240
```

```
tatcttgctc ctcaccttga agaaggctcc cttgggaaaa aagcattgga tacgtttggt       300
ttattcaatg ttactcaaat ggcattagag atacccagtt ccgttccagg catatctggt       360
aaatatggtg ttcagatgaa cattgtaaaa ccagacatac atccaacaac cgggaactat       420
tttttacagc tatttcctct gcatgacgaa ataggtttta acttcaaaga tcttcctggc       480
ccattaaaaa atgcattaac caacagcagt atatcggcta ctgcatcgac tgtagccccc       540
acaccaaacg acccaatgcc atggtttgga ttaactgctc aagtggttcg taatcatggt       600
gtagaacttc ctatagtcaa aaccgaaaat ggatggaagc ttgtagggga acacctctt       660 actccagatg gccccaaagc caattatacg gaagaatggg ttatcaggcc gggagaagca       720
gattttaaat atggaacatc gccattacag gcaactcttg gactggagtt tggtgcgcat       780
tttaagtggg atttagataa tcctaatacc aaatatgcca tccttaccaa tgctgccgca       840
aatgctattg gtgctgctgg agggtttgcg gtatccaaag tccccggcat agatccaatg       900
ctgtcccctc atgtcggtgc aatgcttggg caagcagcgg ggcatgccgt acaatgtaat       960 accccccggat taaagccaga cactatttta tggtgggcag gcgcgacatt tggagctgct      1020
gatttaaata agccgaatt tgataaagtg cggttcactg actaccctcg tatatggttc       1080
catgcacggg aaggagcttt attcccaaat aagcaagaca ttgcccgtgt aacaggcgca      1140
gacataaaag ctatggaaga aggcgtaccc gttggacatc aacatccaaa accggaggat      1200
gtggtcatcg atatcgaagg tggcaattca ccacatcata atccatcaaa ttatgttgac      1260
acctttgaaa taatccaaga aacaagggtc taa                                   1293

<210> SEQ ID NO 2
<211> LENGTH: 1323
<212> TYPE: DNA
<213> ORGANISM: Enteropathogenic E. coli

<400> SEQUENCE: 2
atgaacattc aaccgatcgt aacatccgga atcaccacac aaaacaatcg acatcatcac       60
gcagaacaaa cgtcccctac acaaataccg caatccgaat tacctaatgg atgcgaaacg      120
ggatttgttg ttcatatccc agaggatatg cagcgacatg caccggaatg cggtgaaaca      180
acagctctac tgagcttgat aaaagatgaa ggtctgctct ctgggctgga taaatatctt      240
gcacctcatc ttgaagaagg ctctgcagga aaaaaagcat tggatatgtt tggtttattc      300
aatgtctctc agatggcatt agaaataccc agcaccgttc cgggtatctc tggtaaatat      360
ggtgtccagc taaacattgt aaaaccagat attcatccta catcaggtaa ttatttttta      420
cagatattcc ctttgcatga tgaaataggt attaatttta aagaccttcc tggtccatta      480
aaaaatgcat taagcaacag caatatacca accactgtat cgactgctgc atccactatt      540
gcatcagcca ctacttcgac ggtaaccacc gcgtcaaaag acccaatacc atggtttgga      600
ttaacagctc aagtagttcg taatcatggt gtggaacttc ctatagtcaa aactgaaaat      660
ggatggaagc ttgttggaga aactcctctt actcctgatg gccccaaagc aaattatact      720
gaagagtggg tgatcagacc gggagaagca gattttaaat atggtgcatc tccactacag      780
gcaactctag ggctggagtt tggcgcacat ttcaagtggg atttagataa ccctaatact      840
aaatatgccg ttcttaccaa tgctgccgca aatgcgcttg gtgctgtagg gggatttgca      900
gtatccagat ttactggtac agatccaatg ttaagtcctc atatcggtgc aatggttggg      960
caagcagcgg ggcatgccat acagtataat accccggat taaagccaga cactatttta      1020
tggtgggcag gtactactct tggactggct gatttaaaca aggccgagtt tggagaggcc      1080
```

| | |
|---|---:|
| agattcactg actatcctcg tatatggtgg catgcaagag aaggtgccat tttcccaaat | 1140 |
| aaaagcagata ttgaacatgc cacaggggct gatatacgcg caatggaaga aggtgtatct | 1200 |
| gttggacaac ggcatccaaa tccagaggat gtggtcatca atatcgaaag caataactca | 1260 |
| ccacatcata acccatcaaa ttatgttgat accgttgata taatccaaga aacaagagtc | 1320 |
| taa | 1323 |

<210> SEQ ID NO 3
<211> LENGTH: 1326
<212> TYPE: DNA
<213> ORGANISM: Enterohemorrhagic E. coli

<400> SEQUENCE: 3

| | |
|---|---:|
| atgaacattc aaccgaccat acaatctgga atcacctcac aaaacaatca acatcatcaa | 60 |
| acagaacaaa taccctctac acaaataccg caatccgaat tacctctagg atgccaagct | 120 |
| ggatttgttg ttaatattcc agatgatata cagcaacatg caccggaatg cggtgaaaca | 180 |
| acagctctac tgagcttgat aaaagataaa ggtctgctct cagggctaga cgaatatata | 240 |
| gctcctcacc ttgaagaagg atccatagga aaaaaaacat tggatatgtt tggtttattc | 300 |
| aatgttaccc aaatggcatt agagatacct agttccgttt caggcatctc tggtaaatat | 360 |
| ggtgtccagc taaacattgt aaaaccagat attcatccta catcaggtaa ttatttttta | 420 |
| cagatattcc ctctgcatga tgaaataggt tttaatttta aagaccttcc tggcccgtta | 480 |
| aaaaatgcat taagcaacag taatatatca accactgcag tgtcgactat tgcatcgact | 540 |
| ggaacatcag ccactacttc gacggtaacc accgagccaa aagacccaat accatggttt | 600 |
| ggattaacag ctcaagtggt tcgtaatcat ggtgtagaac ttcctatagt caaaactgaa | 660 |
| aatggatgga agcttgttgg agaaacacca cttactcctg atgggccgaa agcaaattac | 720 |
| acggaggagt gggttatcag accgggagaa gcagattta aatatggtgc atctccatta | 780 |
| caggcaactc tagggctgga gtttggcgca catttcaagt gggatttaga taaccctaat | 840 |
| actaaatatg ccgttcttac caatgctgcc gcaaatgcgc ttggtgcttt agggggattt | 900 |
| gcagtatcca gatttgctag tacagatcca atgttaagtc ctcatatcgg tgcaatggtt | 960 |
| gggcaagcag cagggcatgc catacagtat aataccctg gattaaagcc agacactatt | 1020 |
| ttatggtggg ctggtgcgac actggggggct gccgatttaa acaaggccga gtttgaagta | 1080 |
| gctagattca ctgactatcc tcgtatatgg tggcacgcaa gagaaggagc tattttcccc | 1140 |
| aataaagcag atattgaaca tgccacaggt gctgatatac gcgcaatgga agaaggtatc | 1200 |
| cctgttggac agcggcatcc aaatccagag gatgtggtaa tcgatatcga agcaatggc | 1260 |
| ttaccacatc ataatccatc aaatcatgtt gatatctttg atataatcca agaaacaaga | 1320 |
| gtctaa | 1326 |

<210> SEQ ID NO 4
<211> LENGTH: 614
<212> TYPE: DNA
<213> ORGANISM: Citrobacter rodentium

<400> SEQUENCE: 4

| | |
|---|---:|
| tattctttt cagtggtttg aagcaaggcc agagcgatac ggaaaaggtg aagtaccgat | 60 |
| attgaatacc aaagagcatc cgtatttgag caatattata aatgctgcaa aaatagaaaa | 120 |
| tgagcgcgta ataggagtac tggtagacgg agactttact tatgagcaaa gaaaagaatt | 180 |
| tctcagtctt gaagatgaac atcaaaatat aaagataata tatcgggaaa atgttgattt | 240 |

```
cagtatgtat gataaaaaac tgtctgatat ttatcttgaa atattcatg aacaagaatc    300 atatccagcg agtgagagag ataattatct gttaggctta ttaagagaag agttaaaaaa    360
tattccatac ggaaaggact ctttgattga atcatatgca gaaaaagag gtcatacttg    420 gtttgatttt tttagaaact tggcggtatt gaagggggg gggttgttta cagagacggg    480
taaaactgga tgccataaca tatctccatg tgggggatgt atatatcttg atgcagatat    540
gattattact gataaattag gtgtcctgta tgctcctgat ggtatcgctg tgcatgtaga    600
ttgtaatgat gaga                                                      614

<210> SEQ ID NO 5
<211> LENGTH: 555
<212> TYPE: DNA
<213> ORGANISM: Citrobacter rodentium

<400> SEQUENCE: 5
aaggccagag cgatacggaa aaggtgaagt accgatattg aataccaaag agcatccgta     60
tttgagcaat attataaatg ctgcaaaaat agaaatgag cgtaatggag tactggtaga    120
cggagacttt acttatgagc aaagaaaaga atttctcagt cttgaagatg aacatcaaaa    180
tataaagata atatatcggg aaaatgttga tttcagtatg tatgataaaa aactgtctga    240
tatttatctt gaaatattc atgaacaaga atcatatcca gcgagtgaga gagataatta    300
tctgttggtt ttaagagaag agttaaaaaa tattccatac ggaaaggact ctttgattga    360
atcatatgca gaaaaagag gtcatacttg gtttgatttt tttagaaact tggcggtatt    420 gaagggggg gggttgttta cagagacggg taaaactgga tgccataaca tatctccatg    480
tgggggatgt atatatcttg atgcagatat gattattact gataaattag gtgtcctgta    540
tgctcctgat ggtat                                                    555

<210> SEQ ID NO 6
<211> LENGTH: 990
<212> TYPE: DNA
<213> ORGANISM: Enteropathogenic E. coli

<400> SEQUENCE: 6
atgttatctt cattaaatgt ccttcaatcc agcttcagag gaaagacagc tttatcaaat     60
agtacacttc tccagaaagt ttcttttgct ggaaaagaat attctctgga acctattgat    120
gaaagaaccc ctattctttt tcagtggttt gaagcaaggc cagagcgata cgaaaaagga    180
gaagtaccaa tattgaatac caagaacat ccgtatttga gcaatattat aaatgctgca    240
aaaatagaaa atgagcgtat aatcggtgtg ctggtagatg gaaattttac ttatgaacaa    300 aaaaggaat ttctcaatct tgaaaatgaa catcaaaata taaaataat ctaccgagca    360 gatgtggatt tcagcatgta tgataaaaa ctatctgata tttaccttga aaatatccat    420
aaacaagaat catacccctgc cagtgagagg gataattatc tgttaggctt attaagagaa    480
gagttaaaaa atatcccaga aggtaaggac tctttgattg agtcatatgc agaaaaaaga    540
gaacatactt ggtttgattt tttcaggaat ttggccatat gaaggctgg aagtttgttt    600 acagagacgg gaaaaactgg atgccataac atatcgccct gtagcggatg tatatatctt    660
gatgccgaca tgattattac cgataaatta ggagtcctgt atgctcctga tggtatcgct    720
gtgcatgtag attgtaatga tgagataaaa agtcttgaaa atggtgcgat agttgtcaat    780
cgtagtaatc atccagcatt acttgcaggc ctcgatatta tgaagagtaa agttgacgct    840
catccatatt atgatggtct aggaaagggt atcaagcggc attttaacta ttcatcgtta    900
```

| | |
|---|---:|
| cacaattata atgcttttg tgatttatt gaatttaagc atgaaaatat tataccgaat | 960 |
| accagtatgt ataccagcag ttcatggtaa | 990 |

```
<210> SEQ ID NO 7
<211> LENGTH: 990
<212> TYPE: DNA
<213> ORGANISM: Enterohemorrhagic E. coli

<400> SEQUENCE: 7
```

| | |
|---|---:|
| atgttatctt cattaaatgt ccttcaatcc agcttcagag gaaagacagc tttatcaaat | 60 |
| agtacacttc tccagaaagt ttcttttgct ggaaaagaat atcctctgga acctattgat | 120 |
| gaaaaaccc ctattctttt tcagtggttt gaagcaaggc cagagcgata cgaaaaagga | 180 |
| gaagtaccaa tattgaatac caaagaacat ccgtatttga gcaatattat aaatgctgca | 240 |
| aaaatagaaa atgagcgtat aatcggtgtg ctggtagatg gaaattttac ttatgaacaa | 300 |
| aaaaaggaat ttctcagtct tgaaaatgaa tatcaaaata taaaaataat ctaccgagca | 360 |
| gatgtggatt tcagcatgta tgataaaaaa ctatctgata tttaccttga aaatatccat | 420 |
| aaacaagaat cataccctgc cagtgagagg gataattatc tgttaggctt attaagagaa | 480 |
| gagttaaaaa atatcccaga aggtaaggac tctttgattg agtcatatgc agaaaaaaga | 540 |
| gaacatactt ggtttgattt tttcaggaat ttggccatgt tgaaggctgg aagtttgttt | 600 |
| acagagacgg gaaaaactgg atgccataac atatcgccct gtagcggatg tatatatctt | 660 |
| gatgccgaca tgattattac cgataaatta ggagtcctgt atgctcctga tggtatcgct | 720 |
| gtgcatgtag attgtaatga tgagataaaa agtcttgaaa atggtgcgat agttgtcaat | 780 |
| cgtagtaatc atccagcatt acttgcaggc ctcgatatta tgaagagtaa agttgacgct | 840 |
| catccatatt atgatggtct aggaaagggt atcaagcggc atttaacta ttcatcgtta | 900 |
| cacgattata atgcttttg tgatttatt gaatttaagc atgaaaatat tataccgaat | 960 |
| accagtatgt atacctgcag ttcatggtaa | 990 |

```
<210> SEQ ID NO 8
<211> LENGTH: 993
<212> TYPE: DNA
<213> ORGANISM: Citrobacter rodentium

<400> SEQUENCE: 8
```

| | |
|---|---:|
| atgaaaattc cctcactcca gcccagcttc aactttttcg ccccagcagg atactctgct | 60 |
| gccgttgctc ccaatcgttc ggacaatgcc tatgctgatt acgtattgga tataggcaag | 120 |
| cgaataccac tttccgcgga agatttaggc aacctatatg aaaatgtcat tcgcgccgtt | 180 |
| cgtgacagcc gtagcaagct catagatcag catacggtcg atatgattgg taacactata | 240 |
| cttgatgctt tgagccgatc acaaaccttt cgtgatgccg taagctatgg cattcataat | 300 |
| aaggaggtac acattggttg cattaaatac agaaacgaat acgagctcaa cggagaatcc | 360 |
| cccgtcaaag ttgatgatat tcaatcacta acctgtaccg aattatatga atacgatgtc | 420 |
| gggcaagaac caattttacc catttgcgag gcaggagaaa acgataacga agagccttat | 480 |
| gtcagttta gtgttgcgcc agatactgac tcttatgaga tgccatcgtg gcaggaaggg | 540 |
| ctgattcacg agattattca tcatgtgact ggagctagcg atccgtctgg atatagtaat | 600 |
| atagagctag gacccacgga gattctcgca cgtcgtgtcg ctcaagagct gggatggact | 660 |
| gtccccgact tcataggata tgcagagcca gatcgtgaag ctcatcttag gggacgtaac | 720 |
| ctgaatgccc ttcgacaggc ggccatgcga catgaagata atgagaggac tttcttcgaa | 780 |

-continued

| aggctgggta tgatcagtga tcgatatgag gcgagtcctg atttcacaga gtattccgct | 840 |
| gtgtctaaca tagaatatgg atttatccag caacatgatt ttcccgggtt ggctatcgac | 900 |
| gataatttac aggatgcaaa tcagatccaa ctctatcatg gagcacctta tatctttaca | 960 |
| ttcggggatg tggacaaaca caatcagcgc tga | 993 |

<210> SEQ ID NO 9
<211> LENGTH: 993
<212> TYPE: DNA
<213> ORGANISM: Enteropathogenic E. coli

<400> SEQUENCE: 9

| atgaaaattc cctcattaca gtccaacttc aacttttccg ccccggcagg atactctgct | 60 |
| cccattgctc ctaatcgtgc tgaaaatgcc tatgcggatt acgttttgga tataggtaag | 120 |
| cgaataccac tttccgcagc agatttaagc aacgtatacg aaagtgtaat acgcgccgtc | 180 |
| catgacagcc gtagcaggct tatcgatcag catacagtcg atatgatcgg caacactgta | 240 |
| cttgatgctt tgagccgatc acagacattt cgtgatgccg taagctatgg cattcataat | 300 |
| gagaaggtac acattggttg cattaaatac agaaacgaat acgagcttaa cgaagaatct | 360 |
| tctgtcaaaa ttgatgatat tcaatcacta acctgtaacg aattatatga atatgatgtc | 420 |
| gggcaagagc caattttccc catttgcgaa gcaggagaaa acgataacga agagccttat | 480 |
| gtcagtttta gtgttgcgcc agatactgac tcttatgaga tgccatcgtg gcaggaagga | 540 |
| ctgattcacg agattattca tcatgttact ggatctagcg atccatctgg agatagtaat | 600 |
| atagagttag gacccaccga gattctcgca cgtcgtgtcg ctcaagaact gggatggagt | 660 |
| gttcccgact tcaaaggata tgcagagcca gaacgtgaag ctcatcttag gttacgtaac | 720 |
| ctgaatgccc ttcgacaggc tgccatgagg catgaagaga atgagagggc tttcttcgaa | 780 |
| aggctgggta cgatcagtga ccgatatgag gcgagtcctg atttcacaga gtattccgct | 840 |
| gtgtctaaca taggatacgg atttatccag caacatgatt ttcctggatt ggctatcaac | 900 |
| gataatttac aggatgcaaa tcagatccaa ctgtatcatg gcgcccctta tattttaca | 960 |
| tttggggatg tggacaaaca caatcagcga tga | 993 |

<210> SEQ ID NO 10
<211> LENGTH: 993
<212> TYPE: DNA
<213> ORGANISM: Enterohemorrhagic E. coli

<400> SEQUENCE: 10

| atgaaaattc cctcattaca gtccaacttc aacttttccg ccccggcagg atactctgct | 60 |
| cccattgctc ctaatcgtgc tgaaaatgcc tatgcggatt acgttttgga tataggtaag | 120 |
| cgaataccac tttccgcagc agatttaagc aacgtatacg aaagtgtaat acgcgccgtc | 180 |
| catgacagcc gtagcaggct tatcgatcag catacagtcg atatgatcgg caacactgta | 240 |
| cttgatgctt tgagccgatc acagacattt cgtgatgccg taagctatgg cattcataat | 300 |
| gagaaggtac acattggttg cattaaatac agaaacgaat acgagcttaa cgaagaatct | 360 |
| tctgtcaaaa ttgatgatat tcaatcacta acctgtaacg aattatatga atatgatgtc | 420 |
| gggcaagagc caattttccc catttgcgaa gcaggagaaa acgataacga agagccttat | 480 |
| gtcagtttta gtgttgcgcc agatactgac tcttatgaga tgccatcgtg gcaggaagga | 540 |
| ctgattcacg agattattca tcatgttact ggatctagcg atccatctgg agatagtaat | 600 |
| atagagttag gacccaccga gattctcgca cgtcgtgtcg ctcaagaact gggatggagt | 660 |

```
gttcccgact tcaaaggata tgcagagcca gaacgtgaag ctcatcttag gctacgtaac      720
ctgaatgccc ttcgacaggc tgccatgagg catgaagaga atgagagggc tttcttcgaa      780
aggctgggta cgatcagtga ccgatatgag gcgagtcctg atttcacaga gtattccgct      840
gtgtctaaca taggatacgg atttatccag caacatgatt ttcctggatt ggctatcaac      900
gataatttac aggatgcaaa tcagatccaa ctgtatcatg gcgcccctta tattttaca       960 tttggggatg tggacaaaca caatcagcaa tga                                   993
```

<210> SEQ ID NO 11
<211> LENGTH: 708
<212> TYPE: DNA
<213> ORGANISM: Citrobacter rodentium

<400> SEQUENCE: 11

```
atgcgcccta catcccttaa cctgacatta ccttcgttac ctctacctc atcttcaaat       60 tcaatttcag ccacagacat tcaatctctt gtaaaaatgt cgggtgtgcg ctgggtgaaa     120
aacaaccaac aactctgttt ccacgggact gaccttaaaa tctaccagca tcttgaagct     180
gccctcgata agatcgaatc cacagacact ggacgtactc ttttgaactg tattgaatta     240
acatcccgac tcaaatcaga aaaactggca atacatctcg attctgctga gttaggggtg     300
atagcacact gcaatgcgga tgctgaaaac tcccgaggaa ctggctccga cttttcactgt    360 aatctgaatg cagttgaata tccctgcggg caaggaatta gcctggtaga ctttcatgca     420
tgcattgttt tccatgaact tctccacgtt tccacaatt taaatggaga gcgcctgaaa      480
gttgagagtt ctcaaccaga attacaaaca cactccccac ttttactcga agaagccagg     540
actgttgggt tgggtgcttt ttctgaagaa gttctttcag aaaataaatt tcgtgaagag     600
attgggatgc cccgcagaac attctacccg cacgattcat ctctcattca tgatgacaat     660
acagtgactc agagattcca gcggaaaaaa ctgcatccgt actttag                   708
```

<210> SEQ ID NO 12
<211> LENGTH: 699
<212> TYPE: DNA
<213> ORGANISM: Enteropathogenic E. coli

<400> SEQUENCE: 12

```
atgcgcccta cgtccctcaa cttggtatta catcagtcat caacgtcgag ctcaatgtca      60
gatacagata tcgagtctct tgtaaaagca tcgagcgttc aatggataaa aaataatccg     120
caacttcgtt tccaggggac tgatcataat atatatcagc agattgaagc agcactcgat     180
aagattggct ctacagagac agggcgtgta ctcctgaatg ctattgaatc aatatcccga     240
cttaaatcag aaacagtggt aatacacctc aactcttcca gactaggagt tatggcacat     300
agagatatag atgctgagaa ccatcggggg actggttccg attttcactg taatctgaat     360
gcagttgaat atccctgtgg ggagggggatt agcgtggtgg actttcatgc gactattgtt     420
tttcatgagt tgctccatgt tttccacaat ttaaatgggg agcgtttgaa agttgagagt     480
tcccgaccag aatcacaaaa atactctcca cttttactcg aagaagccag gactgttggg     540
ttgggggctt tttcagagga ggtgctttca gaaaataaat tccgcgaaga gattgggatg     600
ccccgtagaa cctcctaccc gcacgactca gctcttattc atgatgacaa tacagtgagt     660
ctgggattcc aacaggtaag actgcatcca ttgctttag                            699
```

<210> SEQ ID NO 13
<211> LENGTH: 699
<212> TYPE: DNA

<213> ORGANISM: Enterohemorrhagic E. coli

<400> SEQUENCE: 13

```
atgcgcccta cgtccctcaa cttggtatta catcagtcat caaggtcgag ctcaatgtca    60
gatacagata tcgagtctct tgtaaaagca tcgagcgttc aatggataaa aaataatccg   120
caacttcgtt tccaggggac tgatcataat atatatcagc agattgaagc agcactcgat   180
aagattggct ctacagagac agggcgtgta ctcctgaatg ctattgaatc aatatcccga   240
cttaaatcag aaacagtggt aatacacctc aactcttcca gactaggagt tatggcacat   300
agagatatag atgctgagaa ccatcggggg actggttccg attttcactg taatctgaat   360
gcagttgaat atccctgtgg ggagggaatt agcgtggtgg actttcatgc gactattgtt   420
tttcatgagt tgctccatgt tttccacaat ttaaatgggg agcgtttgaa agttgagagt   480
tcccgagcag aatcacaaaa atactctcca cttttactcg aagaagccag gactgttggg   540
ttggggcctt tttcagagga ggtgctttca gaaaataaat ccacgaaga gattgggatg   600
ccccgtagaa cctcctaccc gcrcgactca gctcttattc atgatgacaa tacagtgagt   660
ctgggattcc aacaggtaag actgcatcca ttgctttag                          699
```

<210> SEQ ID NO 14
<211> LENGTH: 506
<212> TYPE: DNA
<213> ORGANISM: Citrobacter rodentium

<400> SEQUENCE: 14

```
tactttaatg aatcacccaa tgtatatgat aagaagtata tatctggcgt aactagagga    60
gtagctgaac taaaacagga aggatttatt aacgagaaag ccaggcgact tgcttatatg   120
caagcaatgt attctgtatg tccggaagag tttaaaccta tttccagaaa cgaagctagt   180
acaccggaag gcagctggct aacagttata tccggaaaac gcccaatggg acagttttct   240
gtagatagct tatatcatcc tgacttacat gcattgtgtg agcttccgga tatttgttgc   300
aagatcttcc ctaaagaaaa caatgatttt ttgtatatag tgattgtgta cagaaatgac   360
agccctctgg gagaacaacg agcaaatcga tttatagaat tatataatat aaaaagagac   420
atcatgcagg aattaaatta tgaatctcca gagttaaagg ctgtgaaatc tgaaatgatt   480
attgcacgtg aaatgggaga aatctt                                        506
```

<210> SEQ ID NO 15
<211> LENGTH: 466
<212> TYPE: DNA
<213> ORGANISM: Citrobacter rodentium

<400> SEQUENCE: 15

```
caatgtatat gataagaagt atatatctgg cgtaactaga ggagtagctg aactaaaaca    60
ggaaggatt attaacgaga aagccaggcg acttgcttat atgcaagcaa tgtattctgt   120
atgtccggaa gagtttaaac ctatttccag aaacgaagct agtacaccgg aaggcagctg   180
gctaacagtt atatccggaa aacgcccaat gggacagttt tctgtagata gcttatatca   240
tcctgactta catgcattgt gtgagcttcc ggatatttgt tgcaagatct ccctaaaga   300
aaacaatgat ttttgtata tagtgattgt gtacagaaat gacagccctc tgggagaaca   360
acgagcaaat cgatttatag aattatataa tataaaaaga gacatcatgc aggaattaaa   420
ttatgaatct ccagagttaa aggctgtgaa atctgaaatg attatt                  466
```

<210> SEQ ID NO 16

```
<211> LENGTH: 675
<212> TYPE: DNA
<213> ORGANISM: Enteropathogenic E. coli

<400> SEQUENCE: 16
atgattaatc ctgttactaa tactcagggc gtgtcccta taaatactaa atatgctgaa      60
catgtggtga aaatattta cccgaaaatt aaacatgatt actttaatga atcacccaat     120
atatatgata agaagtatat atccggtata accagaggag tagctgaact aaaacaggaa    180
gaatttgtta acgagaaagc cagacggttt tcttatatga agactatgta ttctgtatgt   240
ccagaagcgt ttgaacctat ttccagaaat gaagccagta caccggaagg aagctggcta   300
acagttatat ccggaaaacg cccaatgggg cagttttctg tagatagttt atacaatcct   360
gatttacatg cattatgtga gcttccggac atttgttgta agatcttccc taaagaaaat  420
aatgattttt tatacatagt tgttgtgtac agaaatgaca gccctctagg agaacaacgg   480
gcaaatagat ttatagaatt atataatata aaaagagata tcatgcagga attaaattat   540
gagttaccag agttaaaggc agtaaaatct gaaatgatta tcgcacgtga atgggagaa    600 atctttagct acatgcctgg ggaaatagac agttatatga aatacataaa taataaactt   660
tctaaaattg agtag                                                     675

<210> SEQ ID NO 17
<211> LENGTH: 675
<212> TYPE: DNA
<213> ORGANISM: Enterohemorrhagic E. coli

<400> SEQUENCE: 17
atgattaatc ctgttactaa tactcagggc gtgtcccta taaatactaa atatgctgaa      60
catgtggtga aaatattta cccgaaaatt aaacatgatt actttaatga atcacccaat     120
atatatgata agaagtatat atccggtata accagaggag tagctgaact aaaacaggaa    180
gaatttgtta acgagaaagc cagacggttt tcttatatga agactatgta ttctgtatgt   240
ccagaagcgt ttgaacctat ttccagaaat gaagccagta caccggaagg aagctggcta   300
acagttatat ccggaaaacg cccaatgggg cagttttctg tagatagttt atacaatcct   360
gatttacatg cattatgtga gcttccggac atttgttgta agatcttccc taaagaaaat  420
aatgattttt tatacatagt tgttgtgtac agaaatgaca gccctctagg agaacaacgg   480
gcaaatagat ttatagaatt atataatata aaaagagata tcatgcagga attaaattat   540
gagttaccag agttaaaggc agtaaaatct gaaatgatta tcgcacgtga atgggagaa    600 atctttagct acatgcctgg ggaaatagac agttatatga aatacataaa taataaactt   660
tctaaaattg agtag                                                     675

<210> SEQ ID NO 18
<211> LENGTH: 570
<212> TYPE: DNA
<213> ORGANISM: Citrobacter rodentium

<400> SEQUENCE: 18
atgttaccaa caagtggttc ttcagcaaat ctttactcat ggatgtatat ctcaggaaaa    60
gagaatcctt cgactccgga atcagtaagt gaacttaatc ataatcattt tctttctcct   120
gaattacagg agaaactgga tgttatgttc gccatatatt catgtgccag aaacaatgat   180
gagcgtgaga atatttaccc ggagctaagg gattttgtaa gtagcctaat ggataagaga   240
aacaatgtgt ttgaggtgat aaatgaagat actgatgagg tgaccggagc tctgagagcg   300
```

```
ggaatgacga tagaggacag ggatagttat atcagggatc ttttttttct gcattcattg    360
aaagtaaaaa ttgaggaaag cagacaagat aaagaggatt ggaaatgtaa agtttatgat    420
ctgctatgtc cgcatcattc ttcagagcta tatggggatc tacgggcaat caaatgcctc    480
gttgaaggat gcagtgatga ttttagtcct tttgatacta ttaaggtgcc ggatcttact    540
tacaacaaag gatctttaca atgtggatga                                     570
```

<210> SEQ ID NO 19
<211> LENGTH: 519
<212> TYPE: DNA
<213> ORGANISM: Citrobacter rodentium

<400> SEQUENCE: 19

```
agcaaatctt tactcatgga tgtatatctc aggaaaagag aatccttcga ctccggaatc     60
agtaagtgaa cttaatcata atcattttct ttctcctgaa ttacaggaga aactggatgt    120
tatgttcgcc atatattcat gtgccagaaa caatgatgag cgtgagaata tttacccgga    180
gctaagggat tttgtaagta gcctaatgga taagagaaac aatgtgtttg aggtgataaa    240
tgaagatact gatgaggtga ccggagctct gagagcggga atgacgatag aggacaggga    300
tagttatatc agggatcttt ttttttctgca ttcattgaaa gtaaaaattg aggaaagcag    360
acaagataaa gaggattgga aatgtaaagt ttatgatctg ctatgtccgc atcattcttc    420
agagctatat ggggatctac gggcaatcaa atgcctcgtt gaaggatgca gtgatgattt    480
tagtcctttt gatactatta aggtgccgga tcttactta                           519
```

<210> SEQ ID NO 20
<211> LENGTH: 570
<212> TYPE: DNA
<213> ORGANISM: Enteropathogenic E. coli

<400> SEQUENCE: 20

```
atgttaccaa caagtggttc ttcagcaaat ctttattcat ggatgtatgt atcaggaaga     60
ggtaaccctt cgactccgga atcagtaagt gagcttaatc ataatcactt tctttctcct    120
gaattacaag ataaacttga tgttatggtc tctatatatt catgtgccag aaataataat    180
gagcttgagg aaattttttca agagctaagt gcttttgtaa gtgggctgat ggataagaga    240
aatagtgtat tgaggtgag aaatgaaaat actgatgagg ttgtcggagc gctgagggcg    300
ggaatgacga taggggatag ggatagttat atcagggatc ttttttttct gcattcattg    360
aaagtaaaaa ttgaggaaag tagacaaggc aaagaagatt cgaaatgtaa agtttataat    420
ctgctatgtc cgcatcactc ttcagagcta tatggtgatc tacgagcaat gaaatgcctc    480
gtggaaggat gcagtgatga ttttaatcct tttgatatta ttagggtacc agatcttact    540
tacaacaaag gatctttaca atgtggatga                                     570
```

<210> SEQ ID NO 21
<211> LENGTH: 570
<212> TYPE: DNA
<213> ORGANISM: Enterohemorrhagic E. coli

<400> SEQUENCE: 21

```
atgttaccaa caagtggttc ttcagcaaat ctttattcat ggatgtatgt atcaggaaga     60
ggtaaccctt cgactccgga atcagtaagt gagcttaatc ataatcactt tctttctcct    120
gaattacaag ataaacttga tgttatggtc tctatatatt catgtgccag aaataataat    180
gagcttgagg aaattttttca agagctaagt gcttttgtaa gtgggctgat ggataagaga    240
```

-continued

```
aatagtgtat tgaggtgag aaatgaaaat actgatgagg ttgtcggagc gctgagggcg      300
ggaatgacga tagaggacag ggatagttat atcaggatc ttttttttct gcattcattg      360
aaagtaaaaa ttgaggaaag tagacaaggc aaagaagatt cgaaatgtaa agtttataat    420
ctgctatgtc cgcatcactc ttcagagcta tatggtgatc tacgagcaat gaaatgcctc    480
gtggaaggat gcagtgatga ttttaatcct tttgatatta ttagggtacc agatcttact    540
tacaacaaag gatctttaca atgtggatga                                      570
```

<210> SEQ ID NO 22
<211> LENGTH: 430
<212> TYPE: PRT
<213> ORGANISM: Citrobacter rodentium

<400> SEQUENCE: 22

```
Met Asn Ile Gln Pro Asn Ile His Ser Gly Ile Thr Thr Gln Asn Asn
1               5                   10                  15

Gln Gln His His His Ala Glu Gln Val Pro Val Ser Ser Ile Pro
            20                  25                  30

Arg Ser Asp Leu Pro Pro Asn Cys Glu Ala Gly Phe Val Val His Ile
        35                  40                  45

Pro Glu Asp Ile Gln Gln His Val Pro Glu Cys Gly Glu Thr Thr Ala
    50                  55                  60

Leu Leu Ser Leu Ile Lys Asp Glu Gly Leu Leu Ser Gly Leu Asp Lys
65                  70                  75                  80

Tyr Leu Ala Pro His Leu Glu Glu Gly Ser Leu Gly Lys Lys Ala Leu
                85                  90                  95

Asp Thr Phe Gly Leu Phe Asn Val Thr Gln Met Ala Leu Glu Ile Pro
            100                 105                 110

Ser Ser Val Pro Gly Ile Ser Gly Lys Tyr Gly Val Gln Met Asn Ile
        115                 120                 125

Val Lys Pro Asp Ile His Pro Thr Thr Gly Asn Tyr Phe Leu Gln Leu
    130                 135                 140

Phe Pro Leu His Asp Glu Ile Gly Phe Asn Phe Lys Asp Leu Pro Gly
145                 150                 155                 160

Pro Leu Lys Asn Ala Leu Thr Asn Ser Ser Ile Ser Ala Thr Ala Ser
                165                 170                 175

Thr Val Ala Pro Thr Pro Asn Asp Pro Met Pro Trp Phe Gly Leu Thr
            180                 185                 190

Ala Gln Val Val Arg Asn His Gly Val Glu Leu Pro Ile Val Lys Thr
        195                 200                 205

Glu Asn Gly Trp Lys Leu Val Gly Glu Thr Pro Leu Thr Pro Asp Gly
    210                 215                 220

Pro Lys Ala Asn Tyr Thr Glu Glu Trp Val Ile Arg Pro Gly Glu Ala
225                 230                 235                 240

Asp Phe Lys Tyr Gly Thr Ser Pro Leu Gln Ala Thr Leu Gly Leu Glu
                245                 250                 255

Phe Gly Ala His Phe Lys Trp Asp Leu Asp Asn Pro Asn Thr Lys Tyr
            260                 265                 270

Ala Ile Leu Thr Asn Ala Ala Ala Asn Ala Ile Gly Ala Ala Gly Gly
        275                 280                 285

Phe Ala Val Ser Lys Val Pro Gly Ile Asp Pro Met Leu Ser Pro His
    290                 295                 300

Val Gly Ala Met Leu Gly Gln Ala Ala Gly His Ala Val Gln Cys Asn
305                 310                 315                 320
```

```
Thr Pro Gly Leu Lys Pro Asp Thr Ile Leu Trp Trp Ala Gly Ala Thr
                325                 330                 335

Phe Gly Ala Ala Asp Leu Asn Lys Ala Glu Phe Asp Lys Val Arg Phe
            340                 345                 350

Thr Asp Tyr Pro Arg Ile Trp Phe His Ala Arg Glu Gly Ala Leu Phe
        355                 360                 365

Pro Asn Lys Gln Asp Ile Ala Arg Val Thr Gly Ala Asp Ile Lys Ala
    370                 375                 380

Met Glu Glu Gly Val Pro Val Gly His Gln His Pro Lys Pro Glu Asp
385                 390                 395                 400

Val Val Ile Asp Ile Glu Gly Gly Asn Ser Pro His His Asn Pro Ser
                405                 410                 415

Asn Tyr Val Asp Thr Phe Glu Ile Ile Gln Glu Thr Arg Val
            420                 425                 430

<210> SEQ ID NO 23
<211> LENGTH: 440
<212> TYPE: PRT
<213> ORGANISM: Enteropathogenic E. coli

<400> SEQUENCE: 23

Met Asn Ile Gln Pro Ile Val Thr Ser Gly Ile Thr Thr Gln Asn Asn
1               5                   10                  15

Arg His His His Ala Glu Gln Thr Ser Pro Thr Gln Ile Pro Gln Ser
            20                  25                  30

Glu Leu Pro Asn Gly Cys Glu Thr Gly Phe Val Val His Ile Pro Glu
        35                  40                  45

Asp Met Gln Arg His Ala Pro Glu Cys Gly Glu Thr Thr Ala Leu Leu
    50                  55                  60

Ser Leu Ile Lys Asp Glu Gly Leu Leu Ser Gly Leu Asp Lys Tyr Leu
65                  70                  75                  80

Ala Pro His Leu Glu Gly Ser Ala Gly Lys Lys Ala Leu Asp Met
                85                  90                  95

Phe Gly Leu Phe Asn Val Ser Gln Met Ala Leu Glu Ile Pro Ser Thr
            100                 105                 110

Val Pro Gly Ile Ser Gly Lys Tyr Gly Val Gln Leu Asn Ile Val Lys
        115                 120                 125

Pro Asp Ile His Pro Thr Ser Gly Asn Tyr Phe Leu Gln Ile Phe Pro
    130                 135                 140

Leu His Asp Glu Ile Gly Ile Asn Phe Lys Asp Leu Pro Gly Pro Leu
145                 150                 155                 160

Lys Asn Ala Leu Ser Asn Ser Asn Ile Pro Thr Thr Val Ser Thr Ala
                165                 170                 175

Ala Ser Thr Ile Ala Ser Ala Thr Thr Ser Thr Val Thr Thr Ala Ser
            180                 185                 190

Lys Asp Pro Ile Pro Trp Phe Gly Leu Thr Ala Gln Val Val Arg Asn
        195                 200                 205

His Gly Val Glu Leu Pro Ile Val Lys Thr Glu Asn Gly Trp Lys Leu
    210                 215                 220

Val Gly Glu Thr Pro Leu Thr Pro Asp Gly Pro Lys Ala Asn Tyr Thr
225                 230                 235                 240

Glu Glu Trp Val Ile Arg Pro Gly Glu Ala Asp Phe Lys Tyr Gly Ala
                245                 250                 255

Ser Pro Leu Gln Ala Thr Leu Gly Leu Glu Phe Gly Ala His Phe Lys
            260                 265                 270
```

-continued

Trp Asp Leu Asp Asn Pro Asn Thr Lys Tyr Ala Val Leu Thr Asn Ala
            275                 280                 285

Ala Ala Asn Ala Leu Gly Ala Val Gly Gly Phe Ala Val Ser Arg Phe
290                 295                 300

Thr Gly Thr Asp Pro Met Leu Ser Pro His Ile Gly Ala Met Val Gly
305                 310                 315                 320

Gln Ala Ala Gly His Ala Ile Gln Tyr Asn Thr Pro Gly Leu Lys Pro
                325                 330                 335

Asp Thr Ile Leu Trp Trp Ala Gly Thr Thr Leu Gly Leu Ala Asp Leu
            340                 345                 350

Asn Lys Ala Glu Phe Gly Glu Ala Arg Phe Thr Asp Tyr Pro Arg Ile
        355                 360                 365

Trp Trp His Ala Arg Glu Gly Ala Ile Phe Pro Asn Lys Ala Asp Ile
370                 375                 380

Glu His Ala Thr Gly Ala Asp Ile Arg Ala Met Glu Glu Gly Val Ser
385                 390                 395                 400

Val Gly Gln Arg His Pro Asn Pro Glu Asp Val Val Ile Asn Ile Glu
                405                 410                 415

Ser Asn Asn Ser Pro His His Asn Pro Ser Asn Tyr Val Asp Thr Val
            420                 425                 430

Asp Ile Ile Gln Glu Thr Arg Val
        435                 440

<210> SEQ ID NO 24
<211> LENGTH: 441
<212> TYPE: PRT
<213> ORGANISM: Enterohemorrhagic E. coli

<400> SEQUENCE: 24

Met Asn Ile Gln Pro Thr Ile Gln Ser Gly Ile Thr Ser Gln Asn Asn
1               5                   10                  15

Gln His His Gln Thr Glu Gln Ile Pro Ser Thr Gln Ile Pro Gln Ser
            20                  25                  30

Glu Leu Pro Leu Gly Cys Gln Ala Gly Phe Val Val Asn Ile Pro Asp
        35                  40                  45

Asp Ile Gln Gln His Ala Pro Glu Cys Gly Glu Thr Thr Ala Leu Leu
    50                  55                  60

Ser Leu Ile Lys Asp Lys Gly Leu Leu Ser Gly Leu Asp Glu Tyr Ile
65                  70                  75                  80

Ala Pro His Leu Glu Glu Gly Ser Ile Gly Lys Lys Thr Leu Asp Met
                85                  90                  95

Phe Gly Leu Phe Asn Val Thr Gln Met Ala Leu Glu Ile Pro Ser Ser
            100                 105                 110

Val Ser Gly Ile Ser Gly Lys Tyr Gly Val Gln Leu Asn Ile Val Lys
        115                 120                 125

Pro Asp Ile His Pro Thr Ser Gly Asn Tyr Phe Leu Gln Ile Phe Pro
    130                 135                 140

Leu His Asp Glu Ile Gly Phe Asn Phe Lys Asp Leu Pro Gly Pro Leu
145                 150                 155                 160

Lys Asn Ala Leu Ser Asn Ser Asn Ile Ser Thr Thr Ala Val Ser Thr
                165                 170                 175

Ile Ala Ser Thr Gly Thr Ser Ala Thr Thr Ser Thr Val Thr Thr Glu
            180                 185                 190

Pro Lys Asp Pro Ile Pro Trp Phe Gly Leu Thr Ala Gln Val Val Arg
        195                 200                 205

```
Asn His Gly Val Glu Leu Pro Ile Val Lys Thr Glu Asn Gly Trp Lys
    210                 215                 220

Leu Val Gly Glu Thr Pro Leu Thr Pro Asp Gly Pro Lys Ala Asn Tyr
225                 230                 235                 240

Thr Glu Glu Trp Val Ile Arg Pro Gly Glu Ala Asp Phe Lys Tyr Gly
                245                 250                 255

Ala Ser Pro Leu Gln Ala Thr Leu Gly Leu Glu Phe Gly Ala His Phe
            260                 265                 270

Lys Trp Asp Leu Asp Asn Pro Asn Thr Lys Tyr Ala Val Leu Thr Asn
        275                 280                 285

Ala Ala Ala Asn Ala Leu Gly Ala Leu Gly Gly Phe Ala Val Ser Arg
    290                 295                 300

Phe Ala Ser Thr Asp Pro Met Leu Ser Pro His Ile Gly Ala Met Val
305                 310                 315                 320

Gly Gln Ala Ala Gly His Ala Ile Gln Tyr Asn Thr Pro Gly Leu Lys
                325                 330                 335

Pro Asp Thr Ile Leu Trp Trp Ala Gly Ala Thr Leu Gly Ala Ala Asp
            340                 345                 350

Leu Asn Lys Ala Glu Phe Glu Val Ala Arg Phe Thr Asp Tyr Pro Arg
        355                 360                 365

Ile Trp Trp His Ala Arg Glu Gly Ala Ile Phe Pro Asn Lys Ala Asp
    370                 375                 380

Ile Glu His Ala Thr Gly Ala Asp Ile Arg Ala Met Glu Glu Gly Ile
385                 390                 395                 400

Pro Val Gly Gln Arg His Pro Asn Pro Glu Asp Val Val Ile Asp Ile
                405                 410                 415

Glu Ser Asn Gly Leu Pro His His Asn Pro Ser Asn His Val Asp Ile
            420                 425                 430

Phe Asp Ile Ile Gln Glu Thr Arg Val
        435                 440

<210> SEQ ID NO 25
<211> LENGTH: 204
<212> TYPE: PRT
<213> ORGANISM: Citrobacter rodentium

<400> SEQUENCE: 25

Ile Leu Phe Gln Trp Phe Glu Ala Arg Pro Glu Arg Tyr Gly Lys Gly
1               5                   10                  15

Glu Val Pro Ile Leu Asn Thr Lys Glu His Pro Tyr Leu Ser Asn Ile
            20                  25                  30

Ile Asn Ala Ala Lys Ile Glu Asn Glu Arg Val Ile Gly Val Leu Val
        35                  40                  45

Asp Gly Asp Phe Thr Tyr Glu Gln Arg Lys Glu Phe Leu Ser Leu Glu
50                  55                  60

Asp Glu His Gln Asn Ile Lys Ile Ile Tyr Arg Glu Asn Val Asp Phe
65                  70                  75                  80

Ser Met Tyr Asp Lys Lys Leu Ser Asp Ile Tyr Leu Glu Asn Ile His
                85                  90                  95

Glu Gln Glu Ser Tyr Pro Ala Ser Glu Arg Asp Asn Tyr Leu Leu Gly
            100                 105                 110

Leu Leu Arg Glu Glu Leu Lys Asn Ile Pro Tyr Gly Lys Asp Ser Leu
        115                 120                 125

Ile Glu Ser Tyr Ala Glu Lys Arg Gly His Thr Trp Phe Asp Phe Phe
    130                 135                 140
```

Arg Asn Leu Ala Val Leu Lys Gly Gly Gly Leu Phe Thr Glu Thr Gly
145                 150                 155                 160

Lys Thr Gly Cys His Asn Ile Ser Pro Cys Gly Gly Cys Ile Tyr Leu
                165                 170                 175

Asp Ala Asp Met Ile Ile Thr Asp Lys Leu Gly Val Leu Tyr Ala Pro
            180                 185                 190

Asp Gly Ile Ala Val His Val Asp Cys Asn Asp Glu
        195                 200

<210> SEQ ID NO 26
<211> LENGTH: 186
<212> TYPE: PRT
<213> ORGANISM: Citrobacter rodentium

<400> SEQUENCE: 26

Arg Pro Glu Arg Tyr Gly Lys Gly Glu Val Pro Ile Leu Asn Thr Lys
1               5                   10                  15

Glu His Pro Tyr Leu Ser Asn Ile Ile Asn Ala Ala Lys Ile Glu Asn
            20                  25                  30

Glu Arg Val Ile Gly Val Leu Val Asp Gly Asp Phe Thr Tyr Glu Gln
        35                  40                  45

Arg Lys Glu Phe Leu Ser Leu Glu Asp Glu His Gln Asn Ile Lys Ile
    50                  55                  60

Ile Tyr Arg Glu Asn Val Asp Phe Ser Met Tyr Asp Lys Lys Leu Ser
65                  70                  75                  80

Asp Ile Tyr Leu Glu Asn Ile His Glu Gln Glu Ser Tyr Pro Ala Ser
                85                  90                  95

Glu Arg Asp Asn Tyr Leu Leu Gly Leu Leu Arg Glu Glu Leu Lys Asn
            100                 105                 110

Ile Pro Tyr Gly Lys Asp Ser Leu Ile Glu Ser Tyr Ala Glu Lys Arg
        115                 120                 125

Gly His Thr Trp Phe Asp Phe Phe Arg Asn Leu Ala Val Leu Lys Gly
    130                 135                 140

Gly Gly Leu Phe Thr Glu Thr Gly Lys Thr Gly Cys His Asn Ile Ser
145                 150                 155                 160

Pro Cys Gly Gly Cys Ile Tyr Leu Asp Ala Asp Met Ile Ile Thr Asp
                165                 170                 175

Lys Leu Gly Val Leu Tyr Ala Pro Asp Gly
            180                 185

<210> SEQ ID NO 27
<211> LENGTH: 329
<212> TYPE: PRT
<213> ORGANISM: Enteropathogenic E. coli

<400> SEQUENCE: 27

Met Leu Ser Ser Leu Asn Val Leu Gln Ser Ser Phe Arg Gly Lys Thr
1               5                   10                  15

Ala Leu Ser Asn Ser Thr Leu Leu Gln Lys Val Ser Phe Ala Gly Lys
            20                  25                  30

Glu Tyr Ser Leu Glu Pro Ile Asp Glu Arg Thr Pro Ile Leu Phe Gln
        35                  40                  45

Trp Phe Glu Ala Arg Pro Glu Arg Tyr Glu Lys Gly Glu Val Pro Ile
    50                  55                  60

Leu Asn Thr Lys Glu His Pro Tyr Leu Ser Asn Ile Ile Asn Ala Ala
65                  70                  75                  80

Lys Ile Glu Asn Glu Arg Ile Ile Gly Val Leu Val Asp Gly Asn Phe

```
                     85                  90                  95
Thr Tyr Glu Gln Lys Lys Glu Phe Leu Asn Leu Glu Asn Glu His Gln
                100                 105                 110
Asn Ile Lys Ile Ile Tyr Arg Ala Asp Val Asp Phe Ser Met Tyr Asp
            115                 120                 125
Lys Lys Leu Ser Asp Ile Tyr Leu Glu Asn Ile His Lys Gln Glu Ser
        130                 135                 140
Tyr Pro Ala Ser Glu Arg Asp Asn Tyr Leu Leu Gly Leu Leu Arg Glu
145                 150                 155                 160
Glu Leu Lys Asn Ile Pro Glu Gly Lys Asp Ser Leu Ile Glu Ser Tyr
                165                 170                 175
Ala Glu Lys Arg Glu His Thr Trp Phe Asp Phe Arg Asn Leu Ala
            180                 185                 190
Ile Leu Lys Ala Gly Ser Leu Phe Thr Glu Thr Gly Lys Thr Gly Cys
        195                 200                 205
His Asn Ile Ser Pro Cys Ser Gly Cys Ile Tyr Leu Asp Ala Asp Met
    210                 215                 220
Ile Ile Thr Asp Lys Leu Gly Val Leu Tyr Ala Pro Asp Gly Ile Ala
225                 230                 235                 240
Val His Val Asp Cys Asn Asp Glu Ile Lys Ser Leu Glu Asn Gly Ala
                245                 250                 255
Ile Val Val Asn Arg Ser Asn His Pro Ala Leu Leu Ala Gly Leu Asp
            260                 265                 270
Ile Met Lys Ser Lys Val Asp Ala His Pro Tyr Tyr Asp Gly Leu Gly
        275                 280                 285
Lys Gly Ile Lys Arg His Phe Asn Tyr Ser Ser Leu His Asn Tyr Asn
    290                 295                 300
Ala Phe Cys Asp Phe Ile Glu Phe Lys His Glu Asn Ile Ile Pro Asn
305                 310                 315                 320
Thr Ser Met Tyr Thr Ser Ser Trp
                325

<210> SEQ ID NO 28
<211> LENGTH: 329
<212> TYPE: PRT
<213> ORGANISM: Enterohemorrhagic E. coli

<400> SEQUENCE: 28

Met Leu Ser Ser Leu Asn Val Leu Gln Ser Ser Phe Arg Gly Lys Thr
1               5                   10                  15
Ala Leu Ser Asn Ser Thr Leu Leu Gln Lys Val Ser Phe Ala Gly Lys
            20                  25                  30
Glu Tyr Pro Leu Glu Pro Ile Asp Glu Lys Thr Pro Ile Leu Phe Gln
        35                  40                  45
Trp Phe Glu Ala Arg Pro Glu Arg Tyr Glu Lys Gly Glu Val Pro Ile
    50                  55                  60
Leu Asn Thr Lys Glu His Pro Tyr Leu Ser Asn Ile Ile Asn Ala Ala
65                  70                  75                  80
Lys Ile Glu Asn Glu Arg Ile Ile Gly Val Leu Val Asp Gly Asn Phe
                85                  90                  95
Thr Tyr Glu Gln Lys Lys Glu Phe Leu Ser Leu Glu Asn Glu Tyr Gln
                100                 105                 110
Asn Ile Lys Ile Ile Tyr Arg Ala Asp Val Asp Phe Ser Met Tyr Asp
            115                 120                 125
Lys Lys Leu Ser Asp Ile Tyr Leu Glu Asn Ile His Lys Gln Glu Ser
```

```
            130                 135                 140
Tyr Pro Ala Ser Glu Arg Asp Asn Tyr Leu Leu Gly Leu Leu Arg Glu
145                 150                 155                 160

Glu Leu Lys Asn Ile Pro Glu Gly Lys Asp Ser Leu Ile Glu Ser Tyr
                    165                 170                 175

Ala Glu Lys Arg Glu His Thr Trp Phe Asp Phe Arg Asn Leu Ala
                180                 185                 190

Met Leu Lys Ala Gly Ser Leu Phe Thr Glu Thr Gly Lys Thr Gly Cys
                195                 200                 205

His Asn Ile Ser Pro Cys Ser Gly Cys Ile Tyr Leu Asp Ala Asp Met
210                 215                 220

Ile Ile Thr Asp Lys Leu Gly Val Leu Tyr Ala Pro Asp Gly Ile Ala
225                 230                 235                 240

Val His Val Asp Cys Asn Asp Glu Ile Lys Ser Leu Glu Asn Gly Ala
                    245                 250                 255

Ile Val Val Asn Arg Ser Asn His Pro Ala Leu Leu Ala Gly Leu Asp
                260                 265                 270

Ile Met Lys Ser Lys Val Asp Ala His Pro Tyr Tyr Asp Gly Leu Gly
                275                 280                 285

Lys Gly Ile Lys Arg His Phe Asn Tyr Ser Ser Leu His Asp Tyr Asn
290                 295                 300

Ala Phe Cys Asp Phe Ile Glu Phe Lys His Glu Asn Ile Ile Pro Asn
305                 310                 315                 320

Thr Ser Met Tyr Thr Cys Ser Ser Trp
                    325
```

<210> SEQ ID NO 29
<211> LENGTH: 326
<212> TYPE: PRT
<213> ORGANISM: Enterohemorrhagic E. coli

<400> SEQUENCE: 29

```
Met Leu Ser Pro Ile Arg Thr Thr Phe His Asn Ser Val Asn Ile Val
1               5                   10                  15

Gln Ser Ser Pro Cys Gln Thr Val Ser Phe Ala Gly Lys Glu Tyr Glu
                20                  25                  30

Leu Lys Val Ile Asp Glu Lys Thr Pro Ile Leu Phe Gln Trp Phe Glu
                35                  40                  45

Pro Asn Pro Glu Arg Tyr Lys Lys Asp Glu Val Pro Ile Val Asn Thr
                50                  55                  60

Lys Gln His Pro Tyr Leu Asp Asn Val Thr Asn Ala Ala Arg Ile Glu
65                  70                  75                  80

Ser Asp Arg Met Ile Gly Ile Phe Val Asp Gly Asp Phe Ser Val Asn
                85                  90                  95

Gln Lys Thr Ala Phe Ser Lys Leu Glu Arg Asp Phe Glu Asn Val Met
                100                 105                 110

Ile Ile Tyr Arg Glu Asp Val Asp Phe Ser Met Tyr Asp Arg Lys Leu
                115                 120                 125

Ser Asp Ile Tyr His Asp Ile Ile Cys Glu Gln Arg Leu Arg Thr Glu
                130                 135                 140

Asp Lys Arg Asp Glu Tyr Leu Leu Asn Leu Leu Glu Lys Glu Leu Arg
145                 150                 155                 160

Glu Ile Ser Lys Ala Gln Asp Ser Leu Ile Ser Met Tyr Ala Lys Lys
                165                 170                 175

Arg Asn His Ala Trp Phe Asp Phe Phe Arg Asn Leu Ala Leu Leu Lys
```

```
                180               185               190
Ala Gly Glu Ile Phe Arg Cys Thr Tyr Asn Thr Lys Asn His Gly Ile
            195                 200                 205
Ser Phe Gly Glu Gly Cys Ile Tyr Leu Asp Met Asp Met Ile Leu Thr
210                 215                 220
Gly Lys Leu Gly Thr Ile Tyr Ala Pro Asp Gly Ile Ser Met His Val
225                 230                 235                 240
Asp Arg Arg Asn Asp Ser Val Asn Ile Glu Asn Ser Ala Ile Ile Val
            245                 250                 255
Asn Arg Ser Asn His Pro Ala Leu Leu Glu Gly Leu Ser Phe Met His
        260                 265                 270
Ser Lys Val Asp Ala His Pro Tyr Tyr Asp Gly Leu Gly Lys Gly Val
        275                 280                 285
Lys Lys Tyr Phe Asn Phe Thr Pro Leu His Asn Tyr Asn His Phe Cys
        290                 295                 300
Asp Phe Ile Glu Phe Asn His Pro Asn Ile Ile Met Asn Thr Ser Gln
305                 310                 315                 320
Tyr Thr Cys Ser Ser Trp
            325

<210> SEQ ID NO 30
<211> LENGTH: 330
<212> TYPE: PRT
<213> ORGANISM: Citrobacter rodentium

<400> SEQUENCE: 30

Met Lys Ile Pro Ser Leu Gln Pro Ser Phe Asn Phe Ala Pro Ala
1               5                   10                  15
Gly Tyr Ser Ala Ala Val Ala Pro Asn Arg Ser Asp Asn Ala Tyr Ala
            20                  25                  30
Asp Tyr Val Leu Asp Ile Gly Lys Arg Ile Pro Leu Ser Ala Glu Asp
        35                  40                  45
Leu Gly Asn Leu Tyr Glu Asn Val Ile Arg Ala Val Arg Asp Ser Arg
    50                  55                  60
Ser Lys Leu Ile Asp Gln His Thr Val Asp Met Ile Gly Asn Thr Ile
65                  70                  75                  80
Leu Asp Ala Leu Ser Arg Ser Gln Thr Phe Arg Asp Ala Val Ser Tyr
                85                  90                  95
Gly Ile His Asn Lys Glu Val His Ile Gly Cys Ile Lys Tyr Arg Asn
            100                 105                 110
Glu Tyr Glu Leu Asn Gly Glu Ser Pro Val Lys Val Asp Asp Ile Gln
        115                 120                 125
Ser Leu Thr Cys Thr Glu Leu Tyr Glu Tyr Asp Val Gly Gln Glu Pro
    130                 135                 140
Ile Leu Pro Ile Cys Glu Ala Gly Glu Asn Asp Asn Glu Glu Pro Tyr
145                 150                 155                 160
Val Ser Phe Ser Val Ala Pro Asp Thr Asp Ser Tyr Glu Met Pro Ser
                165                 170                 175
Trp Gln Glu Gly Leu Ile His Glu Ile Ile His Val Thr Gly Ala
            180                 185                 190
Ser Asp Pro Ser Gly Asp Ser Asn Ile Glu Leu Gly Pro Thr Glu Ile
        195                 200                 205
Leu Ala Arg Arg Val Ala Gln Glu Leu Gly Trp Thr Val Pro Asp Phe
    210                 215                 220
Ile Gly Tyr Ala Glu Pro Asp Arg Glu Ala His Leu Arg Gly Arg Asn
```

```
              225                 230                 235                 240
Leu Asn Ala Leu Arg Gln Ala Ala Met Arg His Glu Asp Asn Glu Arg
                    245                 250                 255

Thr Phe Phe Glu Arg Leu Gly Met Ile Ser Asp Arg Tyr Glu Ala Ser
                260                 265                 270

Pro Asp Phe Thr Glu Tyr Ser Ala Val Ser Asn Ile Glu Tyr Gly Phe
            275                 280                 285

Ile Gln Gln His Asp Phe Pro Gly Leu Ala Ile Asp Asp Asn Leu Gln
        290                 295                 300

Asp Ala Asn Gln Ile Gln Leu Tyr His Gly Ala Pro Tyr Ile Phe Thr
305                 310                 315                 320

Phe Gly Asp Val Asp Lys His Asn Gln Arg
                325                 330

<210> SEQ ID NO 31
<211> LENGTH: 330
<212> TYPE: PRT
<213> ORGANISM: Enteropathogenic E. coli

<400> SEQUENCE: 31

Met Lys Ile Pro Ser Leu Gln Ser Asn Phe Asn Phe Ser Ala Pro Ala
1               5                   10                  15

Gly Tyr Ser Ala Pro Ile Ala Pro Asn Arg Ala Glu Asn Ala Tyr Ala
            20                  25                  30

Asp Tyr Val Leu Asp Ile Gly Lys Arg Ile Pro Leu Ser Ala Ala Asp
        35                  40                  45

Leu Ser Asn Val Tyr Glu Ser Val Ile Arg Ala Val His Asp Ser Arg
    50                  55                  60

Ser Arg Leu Ile Asp Gln His Thr Val Asp Met Ile Gly Asn Thr Val
65                  70                  75                  80

Leu Asp Ala Leu Ser Arg Ser Gln Thr Phe Arg Asp Ala Val Ser Tyr
                85                  90                  95

Gly Ile His Asn Glu Lys Val His Ile Gly Cys Ile Lys Tyr Arg Asn
            100                 105                 110

Glu Tyr Glu Leu Asn Glu Glu Ser Val Lys Ile Asp Asp Ile Gln
        115                 120                 125

Ser Leu Thr Cys Asn Glu Leu Tyr Glu Tyr Asp Val Gly Gln Glu Pro
    130                 135                 140

Ile Phe Pro Ile Cys Glu Ala Gly Glu Asn Asp Asn Glu Glu Pro Tyr
145                 150                 155                 160

Val Ser Phe Ser Val Ala Pro Asp Thr Asp Ser Tyr Glu Met Pro Ser
                165                 170                 175

Trp Gln Glu Gly Leu Ile His Glu Ile His His Val Thr Gly Ser
            180                 185                 190

Ser Asp Pro Ser Gly Asp Ser Asn Ile Glu Leu Gly Pro Thr Glu Ile
        195                 200                 205

Leu Ala Arg Arg Val Ala Gln Glu Leu Gly Trp Ser Val Pro Asp Phe
    210                 215                 220

Lys Gly Tyr Ala Glu Pro Glu Arg Glu Ala His Leu Arg Leu Arg Asn
225                 230                 235                 240

Leu Asn Ala Leu Arg Gln Ala Ala Met Arg His Glu Glu Asn Glu Arg
                245                 250                 255

Ala Phe Phe Glu Arg Leu Gly Thr Ile Ser Asp Arg Tyr Glu Ala Ser
            260                 265                 270

Pro Asp Phe Thr Glu Tyr Ser Ala Val Ser Asn Ile Gly Tyr Gly Phe
```

Ile Gln Gln His Asp Phe Pro Gly Leu Ala Ile Asn Asp Asn Leu Gln
290                 295                 300

Asp Ala Asn Gln Ile Gln Leu Tyr His Gly Ala Pro Tyr Ile Phe Thr
305                 310                 315                 320

Phe Gly Asp Val Asp Lys His Asn Gln Arg
                325                 330

<210> SEQ ID NO 32
<211> LENGTH: 330
<212> TYPE: PRT
<213> ORGANISM: Enterohemorrhagic E. coli

<400> SEQUENCE: 32

Met Lys Ile Pro Ser Leu Gln Ser Asn Phe Asn Phe Ser Ala Pro Ala
1               5                   10                  15

Gly Tyr Ser Ala Pro Ile Ala Pro Asn Arg Ala Glu Asn Ala Tyr Ala
                20                  25                  30

Asp Tyr Val Leu Asp Ile Gly Lys Arg Ile Pro Leu Ser Ala Ala Asp
            35                  40                  45

Leu Ser Asn Val Tyr Glu Ser Val Ile Arg Ala Val His Asp Ser Arg
50                  55                  60

Ser Arg Leu Ile Asp Gln His Thr Val Asp Met Ile Gly Asn Thr Val
65                  70                  75                  80

Leu Asp Ala Leu Ser Arg Ser Gln Thr Phe Arg Asp Ala Val Ser Tyr
                85                  90                  95

Gly Ile His Asn Glu Lys Val His Ile Gly Cys Ile Lys Tyr Arg Asn
                100                 105                 110

Glu Tyr Glu Leu Asn Glu Glu Ser Ser Val Lys Ile Asp Asp Ile Gln
            115                 120                 125

Ser Leu Thr Cys Asn Glu Leu Tyr Glu Tyr Asp Val Gly Gln Glu Pro
130                 135                 140

Ile Phe Pro Ile Cys Glu Ala Gly Glu Asn Asp Asn Glu Glu Pro Tyr
145                 150                 155                 160

Val Ser Phe Ser Val Ala Pro Asp Thr Asp Ser Tyr Glu Met Pro Ser
                165                 170                 175

Trp Gln Glu Gly Leu Ile His Glu Ile His His Val Thr Gly Ser
                180                 185                 190

Ser Asp Pro Ser Gly Asp Ser Asn Ile Glu Leu Gly Pro Thr Glu Ile
            195                 200                 205

Leu Ala Arg Arg Val Ala Gln Glu Leu Gly Trp Ser Val Pro Asp Phe
210                 215                 220

Lys Gly Tyr Ala Glu Pro Glu Arg Glu Ala His Leu Arg Leu Arg Asn
225                 230                 235                 240

Leu Asn Ala Leu Arg Gln Ala Ala Met Arg His Glu Glu Asn Glu Arg
                245                 250                 255

Ala Phe Phe Glu Arg Leu Gly Thr Ile Ser Asp Arg Tyr Glu Ala Ser
                260                 265                 270

Pro Asp Phe Thr Glu Tyr Ser Ala Val Ser Asn Ile Gly Tyr Gly Phe
            275                 280                 285

Ile Gln Gln His Asp Phe Pro Gly Leu Ala Ile Asn Asp Asn Leu Gln
                290                 295                 300

Asp Ala Asn Gln Ile Gln Leu Tyr His Gly Ala Pro Tyr Ile Phe Thr
305                 310                 315                 320

Phe Gly Asp Val Asp Lys His Asn Gln Gln 325                 330

<210> SEQ ID NO 33
<211> LENGTH: 235
<212> TYPE: PRT
<213> ORGANISM: Citrobacter rodentium

<400> SEQUENCE: 33

Met Arg Pro Thr Ser Leu Asn Leu Thr Leu Pro Ser Leu Pro Leu Pro
1               5                   10                  15

Ser Ser Ser Asn Ser Ile Ser Ala Thr Asp Ile Gln Ser Leu Val Lys
            20                  25                  30

Met Ser Gly Val Arg Trp Val Lys Asn Asn Gln Gln Leu Cys Phe His
        35                  40                  45

Gly Thr Asp Leu Lys Ile Tyr Gln His Leu Glu Ala Ala Leu Asp Lys
    50                  55                  60

Ile Glu Ser Thr Asp Thr Gly Arg Thr Leu Leu Asn Cys Ile Glu Leu
65                  70                  75                  80

Thr Ser Arg Leu Lys Ser Glu Lys Leu Ala Ile His Leu Asp Ser Ala
                85                  90                  95

Glu Leu Gly Val Ile Ala His Cys Asn Ala Asp Ala Glu Asn Ser Arg
            100                 105                 110

Gly Thr Gly Ser Asp Phe His Cys Asn Leu Asn Ala Val Glu Tyr Pro
        115                 120                 125

Cys Gly Gln Gly Ile Ser Leu Val Asp Phe His Ala Cys Ile Val Phe
    130                 135                 140

His Glu Leu Leu His Val Phe His Asn Leu Asn Gly Glu Arg Leu Lys
145                 150                 155                 160

Val Glu Ser Ser Gln Pro Glu Leu Gln Thr His Ser Pro Leu Leu Leu
                165                 170                 175

Glu Glu Ala Arg Thr Val Gly Leu Gly Ala Phe Ser Glu Glu Val Leu
            180                 185                 190

Ser Glu Asn Lys Phe Arg Glu Glu Ile Gly Met Pro Arg Arg Thr Phe
        195                 200                 205

Tyr Pro His Asp Ser Ser Leu Ile His Asp Asp Asn Thr Val Thr Gln
    210                 215                 220

Arg Phe Gln Arg Lys Lys Leu His Pro Leu Leu
225                 230                 235

<210> SEQ ID NO 34
<211> LENGTH: 232
<212> TYPE: PRT
<213> ORGANISM: Enteropathogenic E. coli

<400> SEQUENCE: 34

Met Arg Pro Thr Ser Leu Asn Leu Val Leu His Gln Ser Ser Thr Ser
1               5                   10                  15

Ser Ser Met Ser Asp Thr Asp Ile Glu Ser Leu Val Lys Ala Ser Ser
            20                  25                  30

Val Gln Trp Ile Lys Asn Asn Pro Gln Leu Arg Phe Gln Gly Thr Asp
        35                  40                  45

His Asn Ile Tyr Gln Gln Ile Glu Ala Ala Leu Asp Lys Ile Gly Ser
    50                  55                  60

Thr Glu Thr Gly Arg Val Leu Leu Asn Ala Ile Glu Ser Ile Ser Arg
65                  70                  75                  80

Leu Lys Ser Glu Thr Val Val Ile His Leu Asn Ser Ser Arg Leu Gly
                85                  90                  95

```
Val Met Ala His Arg Asp Ile Asp Ala Glu Asn His Arg Gly Thr Gly
            100                 105                 110

Ser Asp Phe His Cys Asn Leu Asn Ala Val Glu Tyr Pro Cys Gly Glu
        115                 120                 125

Gly Ile Ser Val Val Asp Phe His Ala Thr Ile Val Phe His Glu Leu
    130                 135                 140

Leu His Val Phe His Asn Leu Asn Gly Glu Arg Leu Lys Val Glu Ser
145                 150                 155                 160

Ser Arg Pro Glu Ser Gln Lys Tyr Ser Pro Leu Leu Glu Glu Ala
            165                 170                 175

Arg Thr Val Gly Leu Gly Ala Phe Ser Glu Glu Val Leu Ser Glu Asn
            180                 185                 190

Lys Phe Arg Glu Glu Ile Gly Met Pro Arg Arg Thr Ser Tyr Pro His
        195                 200                 205

Asp Ser Ala Leu Ile His Asp Asp Asn Thr Val Ser Leu Gly Phe Gln
        210                 215                 220

Gln Val Arg Leu His Pro Leu Leu
225                 230

<210> SEQ ID NO 35
<211> LENGTH: 232
<212> TYPE: PRT
<213> ORGANISM: Enterohemorrhagic E. coli
<220> FEATURE:
<221> NAME/KEY: MISC_FEATURE
<222> LOCATION: (208)..(208)
<223> OTHER INFORMATION: Xaa = Arg or His

<400> SEQUENCE: 35

Met Arg Pro Thr Ser Leu Asn Leu Val Leu His Gln Ser Ser Arg Ser
1               5                   10                  15

Ser Ser Met Ser Asp Thr Asp Ile Glu Ser Leu Val Lys Ala Ser Ser
            20                  25                  30

Val Gln Trp Ile Lys Asn Asn Pro Gln Leu Arg Phe Gln Gly Thr Asp
        35                  40                  45

His Asn Ile Tyr Gln Gln Ile Glu Ala Ala Leu Asp Lys Ile Gly Ser
    50                  55                  60

Thr Glu Thr Gly Arg Val Leu Leu Asn Ala Ile Glu Ser Ile Ser Arg
65                  70                  75                  80

Leu Lys Ser Glu Thr Val Val Ile His Leu Asn Ser Ser Arg Leu Gly
                85                  90                  95

Val Met Ala His Arg Asp Ile Asp Ala Glu Asn His Arg Gly Thr Gly
            100                 105                 110

Ser Asp Phe His Cys Asn Leu Asn Ala Val Glu Tyr Pro Cys Gly Glu
        115                 120                 125

Gly Ile Ser Val Val Asp Phe His Ala Thr Ile Val Phe His Glu Leu
    130                 135                 140

Leu His Val Phe His Asn Leu Asn Gly Glu Arg Leu Lys Val Glu Ser
145                 150                 155                 160

Ser Arg Ala Glu Ser Gln Lys Tyr Ser Pro Leu Leu Glu Glu Ala
            165                 170                 175

Arg Thr Val Gly Leu Gly Ala Phe Ser Glu Glu Val Leu Ser Glu Asn
            180                 185                 190

Lys Phe His Glu Glu Ile Gly Met Pro Arg Arg Thr Ser Tyr Pro Xaa
        195                 200                 205

Asp Ser Ala Leu Ile His Asp Asp Asn Thr Val Ser Leu Gly Phe Gln
```

```
                   210                 215                 220
Gln Val Arg Leu His Pro Leu Leu
225                 230

<210> SEQ ID NO 36
<211> LENGTH: 168
<212> TYPE: PRT
<213> ORGANISM: Citrobacter rodentium

<400> SEQUENCE: 36

Tyr Phe Asn Glu Ser Pro Asn Val Tyr Asp Lys Lys Tyr Ile Ser Gly
1               5                   10                  15

Val Thr Arg Gly Val Ala Glu Leu Lys Gln Glu Gly Phe Ile Asn Glu
            20                  25                  30

Lys Ala Arg Arg Leu Ala Tyr Met Gln Ala Met Tyr Ser Val Cys Pro
        35                  40                  45

Glu Glu Phe Lys Pro Ile Ser Arg Asn Glu Ala Ser Thr Pro Glu Gly
    50                  55                  60

Ser Trp Leu Thr Val Ile Ser Gly Lys Arg Pro Met Gly Gln Phe Ser
65                  70                  75                  80

Val Asp Ser Leu Tyr His Pro Asp Leu His Ala Leu Cys Glu Leu Pro
                85                  90                  95

Asp Ile Cys Cys Lys Ile Phe Pro Lys Glu Asn Asn Asp Phe Leu Tyr
            100                 105                 110

Ile Val Ile Val Tyr Arg Asn Asp Ser Pro Leu Gly Glu Gln Arg Ala
        115                 120                 125

Asn Arg Phe Ile Glu Leu Tyr Asn Ile Lys Arg Asp Ile Met Gln Glu
    130                 135                 140

Leu Asn Tyr Glu Ser Pro Glu Leu Lys Ala Val Lys Ser Glu Met Ile
145                 150                 155                 160

Ile Ala Arg Glu Met Gly Glu Ile
                165

<210> SEQ ID NO 37
<211> LENGTH: 154
<212> TYPE: PRT
<213> ORGANISM: Citrobacter rodentium

<400> SEQUENCE: 37

Asn Val Tyr Asp Lys Lys Tyr Ile Ser Gly Val Thr Arg Gly Val Ala
1               5                   10                  15

Glu Leu Lys Gln Glu Gly Phe Ile Asn Glu Lys Ala Arg Arg Leu Ala
            20                  25                  30

Tyr Met Gln Ala Met Tyr Ser Val Cys Pro Glu Glu Phe Lys Pro Ile
        35                  40                  45

Ser Arg Asn Glu Ala Ser Thr Pro Glu Gly Ser Trp Leu Thr Val Ile
    50                  55                  60

Ser Gly Lys Arg Pro Met Gly Gln Phe Ser Val Asp Ser Leu Tyr His
65                  70                  75                  80

Pro Asp Leu His Ala Leu Cys Glu Leu Pro Asp Ile Cys Cys Lys Ile
                85                  90                  95

Phe Pro Lys Glu Asn Asn Asp Phe Leu Tyr Ile Val Ile Val Tyr Arg
            100                 105                 110

Asn Asp Ser Pro Leu Gly Glu Gln Arg Ala Asn Arg Phe Ile Glu Leu
        115                 120                 125

Tyr Asn Ile Lys Arg Asp Ile Met Gln Glu Leu Asn Tyr Glu Ser Pro
    130                 135                 140
```

```
Glu Leu Lys Ala Val Lys Ser Glu Met Ile
145                 150
```

<210> SEQ ID NO 38
<211> LENGTH: 224
<212> TYPE: PRT
<213> ORGANISM: Enteropathogenic E. coli

<400> SEQUENCE: 38

```
Met Ile Asn Pro Val Thr Asn Thr Gln Gly Val Ser Pro Ile Asn Thr
1               5                   10                  15

Lys Tyr Ala Glu His Val Val Lys Asn Ile Tyr Pro Lys Ile Lys His
            20                  25                  30

Asp Tyr Phe Asn Glu Ser Pro Asn Ile Tyr Asp Lys Lys Tyr Ile Ser
        35                  40                  45

Gly Ile Thr Arg Gly Val Ala Glu Leu Lys Gln Glu Glu Phe Val Asn
    50                  55                  60

Glu Lys Ala Arg Arg Phe Ser Tyr Met Lys Thr Met Tyr Ser Val Cys
65                  70                  75                  80

Pro Glu Ala Phe Glu Pro Ile Ser Arg Asn Glu Ala Ser Thr Pro Glu
                85                  90                  95

Gly Ser Trp Leu Thr Val Ile Ser Gly Lys Arg Pro Met Gly Gln Phe
            100                 105                 110

Ser Val Asp Ser Leu Tyr Asn Pro Asp Leu His Ala Leu Cys Glu Leu
        115                 120                 125

Pro Asp Ile Cys Cys Lys Ile Phe Pro Lys Glu Asn Asn Asp Phe Leu
    130                 135                 140

Tyr Ile Val Val Tyr Arg Asn Asp Ser Pro Leu Gly Glu Gln Arg
145                 150                 155                 160

Ala Asn Arg Phe Ile Glu Leu Tyr Asn Ile Lys Arg Asp Ile Met Gln
                165                 170                 175

Glu Leu Asn Tyr Glu Leu Pro Glu Leu Lys Ala Val Lys Ser Glu Met
            180                 185                 190

Ile Ile Ala Arg Glu Met Gly Ile Phe Ser Tyr Met Pro Gly Glu
        195                 200                 205

Ile Asp Ser Tyr Met Lys Tyr Ile Asn Asn Lys Leu Ser Lys Ile Glu
    210                 215                 220
```

<210> SEQ ID NO 39
<211> LENGTH: 224
<212> TYPE: PRT
<213> ORGANISM: Enterohemorrhagic E. coli

<400> SEQUENCE: 39

```
Met Ile Asn Pro Val Thr Asn Thr Gln Gly Val Ser Pro Ile Asn Thr
1               5                   10                  15

Lys Tyr Ala Glu His Val Val Lys Asn Ile Tyr Pro Glu Ile Lys His
            20                  25                  30

Asp Tyr Phe Asn Glu Ser Pro Asn Ile Tyr Asp Lys Lys Tyr Ile Ser
        35                  40                  45

Gly Ile Thr Arg Gly Val Ala Glu Leu Lys Gln Glu Glu Phe Val Asn
    50                  55                  60

Glu Lys Ala Arg Arg Phe Ser Tyr Met Lys Thr Met Tyr Ser Val Cys
65                  70                  75                  80

Pro Glu Ala Phe Glu Pro Ile Ser Arg Asn Glu Ala Ser Thr Pro Glu
                85                  90                  95
```

```
Gly Ser Trp Leu Thr Val Ile Ser Gly Lys Arg Pro Met Gly Gln Phe
            100                 105                 110

Ser Val Asp Ser Leu Tyr Asn Pro Asp Leu His Ala Leu Cys Glu Leu
            115                 120                 125

Pro Asp Ile Cys Cys Lys Ile Phe Pro Lys Glu Asn Asn Asp Phe Leu
130                 135                 140

Tyr Ile Val Val Val Tyr Arg Asn Asp Ser Pro Leu Gly Glu Gln Arg
145                 150                 155                 160

Ala Asn Arg Phe Ile Glu Leu Tyr Asn Ile Lys Arg Asp Ile Met Gln
                165                 170                 175

Glu Leu Asn Tyr Glu Leu Pro Glu Leu Lys Ala Val Lys Ser Glu Met
            180                 185                 190

Ile Ile Ala Arg Glu Met Gly Glu Ile Phe Ser Tyr Met Pro Gly Glu
        195                 200                 205

Ile Asp Ser Tyr Met Lys Tyr Ile Asn Asn Lys Leu Ser Lys Ile Glu
    210                 215                 220
```

<210> SEQ ID NO 40
<211> LENGTH: 188
<212> TYPE: PRT
<213> ORGANISM: Citrobacter rodentium

<400> SEQUENCE: 40

```
Met Leu Pro Thr Ser Gly Ser Ser Ala Asn Leu Tyr Ser Trp Met Tyr
1               5                   10                  15

Ile Ser Gly Lys Glu Asn Pro Ser Thr Pro Glu Ser Val Ser Glu Leu
            20                  25                  30

Asn His Asn His Phe Leu Ser Pro Glu Leu Gln Glu Lys Leu Asp Val
        35                  40                  45

Met Phe Ala Ile Tyr Ser Cys Ala Arg Asn Asn Asp Glu Arg Glu Asn
    50                  55                  60

Ile Tyr Pro Glu Leu Arg Asp Phe Val Ser Ser Leu Met Asp Lys Arg
65                  70                  75                  80

Asn Asn Val Phe Glu Val Ile Asn Glu Asp Thr Asp Glu Val Thr Gly
                85                  90                  95

Ala Leu Arg Ala Gly Met Thr Ile Glu Asp Arg Asp Ser Tyr Ile Arg
            100                 105                 110

Asp Leu Phe Phe Leu His Ser Leu Lys Val Lys Ile Glu Glu Ser Arg
        115                 120                 125

Gln Asp Lys Glu Asp Trp Lys Cys Lys Val Tyr Asp Leu Leu Cys Pro
    130                 135                 140

His His Ser Ser Glu Leu Tyr Gly Asp Leu Arg Ala Ile Lys Cys Leu
145                 150                 155                 160

Val Glu Gly Cys Ser Asp Asp Phe Ser Pro Phe Asp Thr Ile Lys Val
                165                 170                 175

Pro Asp Leu Thr Tyr Asn Lys Gly Ser Leu Gln Cys
            180                 185
```

<210> SEQ ID NO 41
<211> LENGTH: 171
<212> TYPE: PRT
<213> ORGANISM: Citrobacter rodentium

<400> SEQUENCE: 41

```
Ala Asn Leu Tyr Ser Trp Met Tyr Ile Ser Gly Lys Glu Asn Pro Ser
1               5                   10                  15

Thr Pro Glu Ser Val Ser Glu Leu Asn His Asn His Phe Leu Ser Pro
```

```
                    20                  25                  30
Glu Leu Gln Glu Lys Leu Asp Val Met Phe Ala Ile Tyr Ser Cys Ala
                35                  40                  45
Arg Asn Asn Asp Glu Arg Glu Asn Ile Tyr Pro Glu Leu Arg Asp Phe
            50                  55                  60
Val Ser Ser Leu Met Asp Lys Arg Asn Asn Val Phe Glu Val Ile Asn
65                  70                  75                  80
Glu Asp Thr Asp Glu Val Thr Gly Ala Leu Arg Ala Gly Met Thr Ile
                85                  90                  95
Glu Asp Arg Asp Ser Tyr Ile Arg Asp Leu Phe Phe Leu His Ser Leu
            100                 105                 110
Lys Val Lys Ile Glu Glu Ser Arg Gln Asp Lys Glu Asp Trp Lys Cys
        115                 120                 125
Lys Val Tyr Asp Leu Leu Cys Pro His His Ser Ser Glu Leu Tyr Gly
        130                 135                 140
Asp Leu Arg Ala Ile Lys Cys Leu Val Glu Gly Cys Ser Asp Asp Phe
145                 150                 155                 160
Ser Pro Phe Asp Thr Ile Lys Val Pro Asp Leu
                165                 170

<210> SEQ ID NO 42
<211> LENGTH: 189
<212> TYPE: PRT
<213> ORGANISM: Enteropathogenic E. coli

<400> SEQUENCE: 42

Met Leu Pro Thr Ser Gly Ser Ser Ala Asn Leu Tyr Ser Trp Met Tyr
1               5                   10                  15
Val Ser Gly Arg Gly Asn Pro Ser Thr Pro Glu Ser Val Ser Glu Leu
                20                  25                  30
Asn His Asn His Phe Leu Ser Pro Glu Leu Gln Asp Lys Leu Asp Val
            35                  40                  45
Met Val Ser Ile Tyr Ser Cys Ala Arg Asn Asn Asn Glu Leu Glu Glu
        50                  55                  60
Ile Phe Gln Glu Leu Ser Ala Phe Val Ser Gly Leu Met Asp Lys Arg
65                  70                  75                  80
Asn Ser Val Phe Glu Val Arg Asn Glu Asn Thr Asp Glu Val Val Gly
                85                  90                  95
Ala Leu Arg Ala Gly Met Thr Ile Glu Asp Arg Asp Ser Tyr Ile Arg
            100                 105                 110
Asp Leu Phe Phe Leu His Ser Leu Lys Val Lys Ile Glu Glu Ser Arg
        115                 120                 125
Gln Gly Lys Glu Asp Ser Lys Cys Lys Val Tyr Asn Leu Leu Cys Pro
        130                 135                 140
His His Ser Ser Glu Leu Tyr Gly Asp Leu Arg Ala Met Lys Cys Leu
145                 150                 155                 160
Val Glu Gly Cys Ser Asp Asp Phe Asn Pro Phe Asp Ile Ile Arg Val
                165                 170                 175
Pro Asp Leu Thr Tyr Asn Lys Gly Ser Leu Gln Cys Gly
            180                 185

<210> SEQ ID NO 43
<211> LENGTH: 189
<212> TYPE: PRT
<213> ORGANISM: Enterohemorrhagic E. coli

<400> SEQUENCE: 43
```

```
Met Leu Pro Thr Ser Gly Ser Ser Ala Asn Leu Tyr Ser Trp Met Tyr
1               5                   10                  15

Val Ser Gly Arg Gly Asn Pro Ser Thr Pro Glu Ser Val Ser Glu Leu
                20                  25                  30

Asn His Asn His Phe Leu Ser Pro Glu Leu Gln Asp Lys Leu Asp Val
            35                  40                  45

Met Val Ser Ile Tyr Ser Cys Ala Arg Asn Asn Asn Glu Leu Glu Glu
    50                  55                  60

Ile Phe Gln Glu Leu Ser Ala Phe Val Ser Gly Leu Met Asp Lys Arg
65                  70                  75                  80

Asn Ser Val Phe Glu Val Arg Asn Glu Asn Thr Asp Glu Val Val Gly
                85                  90                  95

Ala Leu Arg Ala Gly Met Thr Ile Glu Asp Arg Asp Ser Tyr Ile Arg
            100                 105                 110

Asp Leu Phe Phe Leu His Ser Leu Lys Val Lys Ile Glu Glu Ser Arg
            115                 120                 125

Gln Gly Lys Glu Asp Ser Lys Cys Lys Val Tyr Asn Leu Leu Cys Pro
        130                 135                 140

His His Ser Ser Glu Leu Tyr Gly Asp Leu Arg Ala Met Lys Cys Leu
145                 150                 155                 160

Val Glu Gly Cys Ser Asp Asp Phe Asn Pro Phe Asp Ile Ile Arg Val
                165                 170                 175

Pro Asp Leu Thr Tyr Asn Lys Gly Ser Leu Gln Cys Gly
            180                 185

<210> SEQ ID NO 44
<211> LENGTH: 40
<212> TYPE: DNA
<213> ORGANISM: Artificial Sequence
<220> FEATURE:
<223> OTHER INFORMATION: primer Z6024F

<400> SEQUENCE: 44
agatctgaag gagatattat gaacattcaa ccgaccatac                40

<210> SEQ ID NO 45
<211> LENGTH: 34
<212> TYPE: DNA
<213> ORGANISM: Artificial Sequence
<220> FEATURE:
<223> OTHER INFORMATION: primer Z6024R

<400> SEQUENCE: 45
ctcgaggact cttgtttctt cgattatatc aaag                34

<210> SEQ ID NO 46
<211> LENGTH: 28
<212> TYPE: DNA
<213> ORGANISM: Artificial Sequence
<220> FEATURE:
<223> OTHER INFORMATION: primer NT10

<400> SEQUENCE: 46
ccggtacctc taaccattga cgcactcg                28

<210> SEQ ID NO 47
<211> LENGTH: 29
<212> TYPE: DNA
<213> ORGANISM: Artificial Sequence
<220> FEATURE:
<223> OTHER INFORMATION: primer NT11
```

```
<400> SEQUENCE: 47
aacctgcaga actaggtatc tctaatgcc                              29

<210> SEQ ID NO 48
<211> LENGTH: 29
<212> TYPE: DNA
<213> ORGANISM: Artificial Sequence
<220> FEATURE:
<223> OTHER INFORMATION: primer NT12

<400> SEQUENCE: 48
aacctgcagc tgactatcct cgtatatgg                              29

<210> SEQ ID NO 49
<211> LENGTH: 27
<212> TYPE: DNA
<213> ORGANISM: Artificial Sequence
<220> FEATURE:
<223> OTHER INFORMATION: primer NT13

<400> SEQUENCE: 49
ccgagctcag gtaatgagac tgtcagc                                27

<210> SEQ ID NO 50
<211> LENGTH: 22
<212> TYPE: DNA
<213> ORGANISM: Artificial Sequence
<220> FEATURE:
<223> OTHER INFORMATION: primer del1F

<400> SEQUENCE: 50
ggtaccacca cacagaataa tc                                     22

<210> SEQ ID NO 51
<211> LENGTH: 26
<212> TYPE: DNA
<213> ORGANISM: Artificial Sequence
<220> FEATURE:
<223> OTHER INFORMATION: primer del1R

<400> SEQUENCE: 51
cgctagccta tatactgctg ttggtt                                 26

<210> SEQ ID NO 52
<211> LENGTH: 28
<212> TYPE: DNA
<213> ORGANISM: Artificial Sequence
<220> FEATURE:
<223> OTHER INFORMATION: primer del2F

<400> SEQUENCE: 52
gctagctgac aggcaactct tggactgg                               28

<210> SEQ ID NO 53
<211> LENGTH: 29
<212> TYPE: DNA
<213> ORGANISM: Artificial Sequence
<220> FEATURE:
<223> OTHER INFORMATION: primer del2R

<400> SEQUENCE: 53
gagctcaaca taatttgatg gattatgat                              29

<210> SEQ ID NO 54
<211> LENGTH: 24
```

```
<212> TYPE: DNA
<213> ORGANISM: Artificial Sequence
<220> FEATURE:
<223> OTHER INFORMATION: primer

<400> SEQUENCE: 54
ttccatatga acattcaacc gacc                                              24

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ggaattcaat aatagctgcc atcc                                              24

<210> SEQ ID NO 56
<211> LENGTH: 135
<212> TYPE: PRT
<213> ORGANISM: Salmonella

<400> SEQUENCE: 56
```

Met Glu Ser Lys Asn Ser Asp Tyr Val Ile Pro Asp Ser Val Lys Asn
1               5                   10                  15

Tyr Asn Gly Glu Pro Leu Tyr Ile Leu Val Ser Leu Trp Cys Lys Leu
            20                  25                  30

Gln Glu Lys Trp Ile Ser Arg Asn Asp Ile Ala Glu Ala Phe Gly Ile
        35                  40                  45

Asn Leu Arg Arg Ala Ser Phe Ile Ile Thr Tyr Ile Ser Arg Arg Lys
    50                  55                  60

Glu Lys Ile Ser Phe Arg Val Arg Tyr Val Ser Tyr Gly Asn Leu His
65                  70                  75                  80

Tyr Lys Arg Leu Glu Ile Phe Ile Tyr Asn Val Asn Leu Glu Ala Ala
                85                  90                  95

Pro Thr Glu Ser His Val Ser Thr Gly Pro Lys Arg Lys Thr Leu Arg
            100                 105                 110

Val Gly Asn Gly Ile Val Gly Gln Ser Ser Ile Trp Asn Glu Met Ile
        115                 120                 125

Met Arg Arg Lys Lys Glu Ser
    130                 135

```
<210> SEQ ID NO 57
<211> LENGTH: 131
<212> TYPE: PRT
<213> ORGANISM: Enterobacteriaceae

<400> SEQUENCE: 57
```

Met Cys Glu Gly Tyr Val Glu Lys Pro Leu Tyr Leu Leu Ile Ala Glu
1               5                   10                  15

Trp Met Met Ala Glu Asn Arg Trp Val Ile Ala Arg Glu Ile Ser Ile
            20                  25                  30

His Phe Asp Ile Glu His Ser Lys Ala Val Asn Thr Leu Thr Tyr Ile
        35                  40                  45

Leu Ser Glu Val Thr Gly Ile Ser Cys Glu Val Lys Met Ile Pro Asn
    50                  55                  60

Lys Leu Glu Gly Arg Gly Cys Gln Cys Gln Arg Leu Val Lys Val Val
65                  70                  75                  80

Asp Ile Asp Glu Gln Ile Tyr Ala Arg Leu Arg Asn Asn Ser Arg Glu

```
                    85                  90                  95
Lys Leu Val Gly Val Arg Lys Thr Pro Arg Ile Pro Ala Val Pro Leu
                100                 105                 110
Thr Glu Leu Asn Arg Glu Gln Lys Trp Gln Met Met Leu Ser Lys Ser
            115                 120                 125
Met Arg Arg
        130

<210> SEQ ID NO 58
<211> LENGTH: 170
<212> TYPE: PRT
<213> ORGANISM: Citrobacter rodentium

<400> SEQUENCE: 58

Met Cys Pro Asp Asn Thr His Ala Lys Lys Gln Tyr Leu Thr Pro Gly
1               5                   10                  15
Asn Asp Ile His Tyr Pro Gly Gln Thr Asn His Asp Ala Cys Phe Ile
            20                  25                  30
Pro Val Ser Val Arg Gln Tyr Ala Gly Glu Pro Leu Tyr Ile Ile Val
        35                  40                  45
Ala His Trp Cys Leu Leu Gln Gln Asn Trp Val Gln Arg Asn Gln Ile
    50                  55                  60
Ala Glu Ala Phe His Ile Thr Ala Arg Arg Ala Ser Tyr Leu Ile Ala
65                  70                  75                  80
Tyr Leu Arg Ser Lys Thr Ser Arg Val Val Ser Ile Cys Arg His Gln
                85                  90                  95
Thr Leu Pro Asn Lys Ala Arg Arg Tyr Glu Ile Tyr Val Ile Arg Val
                100                 105                 110
Leu Asp Ser Pro Thr Pro Ser Thr Arg Arg Glu Lys Ala Gly Pro Pro
            115                 120                 125
Leu Val Ser Lys Arg Arg Val Gly Asn Gly Asp Arg Ser Met Ala Asn
        130                 135                 140
Glu Leu Trp Asn Arg Leu Cys Ser Asn Arg Asn Ala Gly Lys Ile Leu
145                 150                 155                 160
Lys Lys Lys Glu Asp Glu Asp Asp Gly Thr
                165                 170

<210> SEQ ID NO 59
<211> LENGTH: 12
<212> TYPE: PRT
<213> ORGANISM: Citrobacter rodentium
<220> FEATURE:
<221> NAME/KEY: MISC_FEATURE
<222> LOCATION: (9)..(9)
<223> OTHER INFORMATION: Xaa = Ile or Leu

<400> SEQUENCE: 59

Gln Gln Glu Asn Ala Pro Ser Ser Xaa Gln Thr Arg
1               5                   10

<210> SEQ ID NO 60
<211> LENGTH: 981
<212> TYPE: DNA
<213> ORGANISM: Enterohemorrhagic E. coli

<400> SEQUENCE: 60
atgctttcac cgataaggac aactttccat aactcagtaa atatagtgca gagttcaccc      60
tgtcaaacgg tttcttttgc aggaaaggaa tatgagttaa aggtcattga tgaaaaaacg     120
cctattcttt ttcagtggtt tgaacctaat cctgaacgat ataagaaaga tgaggttcca     180
```

```
atagttaata ctaagcagca tccctattta gataatgtca caaatgcggc aaggatagag    240
agtgatcgta tgataggtat ttttgttgat ggcgattttt cagtcaacca aaagactgct    300
ttttcaaaat tggaacgaga ttttgaaaat gtaatgataa tctatcggga agatgttgac    360
ttcagtatgt atgacagaaa actatcagat atttatcatg atattatatg tgaacaaagg    420
ttacgaactg aagacaaaag atgaatatac ttgttgaatc tgttagagaa agagctgagg    480
gaaatttcaa aggcgcagga ttctttgatt tctatgtatg caaagaaaag aaatcatgca    540
tggtttgatt tcttcagaaa tttagcctta ttaaaagcag agagatatt caggtgcaca     600 tataatacaa agaatcacgg tatttcattc ggggaggggt gtatctatct tgatatggat    660
atgatactta caggtaagct tggtacaata tatgctcctg atggaatttc aatgcatgtg    720
gatcgtcgta atgatagtgt aaatattgaa aatagtgcaa taattgttaa ccgtagtaat    780
catcctgctc tacttgaggg actttctttt atgcatagta agtagatgc tcatccatat     840 tatgatggtt tggggaaagg agttaagaaa tattttaatt ttacaccatt acataattat    900
aatcattttt gtgactttat tgagtttaac caccctaata taatcatgaa cacaagtcag    960
tatacatgca gttcatggta a                                              981
```

<210> SEQ ID NO 61
<211> LENGTH: 531
<212> TYPE: DNA
<213> ORGANISM: Enterohemorrhagic E. coli

<400> SEQUENCE: 61

```
atgaatgtcc ttcgagctca agtagcatct agcggtcgag gggagtttac attaggtaat     60
gagactgtca gcattgtatt taatgaaacc gatgggcgtt ttctatccag cggcagtagt    120
gggggattgc ttactgagtt attcctttat gggtttaata acggccctga agctcttcgc    180
gataggatgc tcagtatgct ttcggactca ggtgaagcac aatcgcaaga gagtattcag    240
gacaaaatat ctcaatgtaa gtttcctgtt agttcaggaa atttccagtg cccgccagag    300
tctattcagt gtccaattac actagagaga cccgaagaag gagtgtttgt caaaaattca    360
gatagttcgg cagtatgctg cttatttgat tttgatgcat ttttctcgttt agctagtgaa    420 ggctcatatc atccactgac ccgagaacca ataacggcat caatgattat aagtcctgat    480
aaatgtgttt atgatcctat caagggaaac ttcattataa aagatagtta a              531
```

<210> SEQ ID NO 62
<211> LENGTH: 912
<212> TYPE: DNA
<213> ORGANISM: Enterohemorrhagic E. coli

<400> SEQUENCE: 62

```
atgttatcgc cctcttctat aaatttggga tgttcatgga attctttaac cagaaacctg     60
acttcgcctg ataatcgtgt tttatcctct gtaagggatg ctgctgttca ctctgatagc    120
gggacgcaag taacggttgg caacagaaca tatcgtgttg tggtcactga taataagttt    180
tgcgttacaa gagaaagtca tagtggttgt tttactaatc tgttgcacag gttgggatgg    240
cctaagggag agattagcag aaaaattgag gctatgctga atacatcgcc agtgagcacg    300
actatagaaa gaggctctgt tcattcgaac agacctgatt tacctccagt ggattatgcg    360
cagccggagt tacctccagc ggattatact caatcagagt tgccgagggt tagcaacaat    420
aaatcacccg tgccaggtaa tgttattggt aaaggtggta atgctgtcgt gtatgaagat    480
atggaagata caacaaaagt gttgaagatg tttactatat ctcaaagcca tgaagaggtg    540
```

```
acaagcgaag ttcgttgttt caatcagtat tatggttccg ggagtgcaga gaaaatatat      600
aatgataatg gaaatgttat tggtattaga atgaataaaa taaatgggga atctcttttg      660
gatattccat cattaccagc acaagctgaa caggctattt acgatatgtt tgacagactg      720
gagaaaaaag gaattctttt tgttgataca acagaaacaa atgttttata tgatcgtatg      780
agaaatgaat ttaatccaat agatatatca tcttataatg tttctgatat ttcatggagt      840
gaacatcaag tcatgcaatc ttatcacgga ggaaagctgg atcttattag tgtagtatta      900
agtaagatat aa                                                         912
```

```
<210> SEQ ID NO 63
<211> LENGTH: 882
<212> TYPE: DNA
<213> ORGANISM: Enterohemorrhagic E. coli

<400> SEQUENCE: 63
atgttatcgc catattctgt aaatttggga tgttcatgga attctttaac cagaaacctg       60
acttcgcctg ataatcgtgt tttatcctct gtaagggatg ctgccgttca ttctgataat      120
ggggcgcaag taaaggttgg caacagaaca tatcgtgttg ttgccaccga taataagttt      180
tgcgttacaa gagaaagtca tagtggttgt tttactaatc tgttgcacag gctgggatgg      240 cctaagggg agattagcag gaaaattgag gtcatgctga atgcatcacc agtgagcgct      300
gctatggaaa gaggcattgt tcattcgaac agacctgatt tacctcctgt tgattatgca      360
ccgccagagt taccgagtgt ggactataac aggttgtcag tacctggtaa tgttattggc      420
aaagggggga acgctgtagt atatgaagat gctgaggatg caacaaaagt cctgaagatg      480
tttactacat ctcaaagcaa tgaagaggtg acaagcgaag ttcgttgctt caaccaatat      540
tatggtgccg ggagtgcaga aaaaatatat ggcaataatg gtgatattat tggtattaga      600
atggataaaa taaatggaga atcgctttta aatatttcgt ccttgccagc acaggctgag      660
catgctattt acgatatgtt tgatagactg gagcaaaaag gaattctttt tgtcgataca      720
acagagacaa atgtcttata tgaccgcgcg aagaatgagt ttaatccaat agatatatca      780
tcttataatg tttccgaccg ttcatggagt gaaagtcaaa taatgcaatc ttatcatggc      840
ggaaagcaag atcttattag tgtggtatta agtaaaattt ag                        882
```

```
<210> SEQ ID NO 64
<211> LENGTH: 153
<212> TYPE: DNA
<213> ORGANISM: Enterohemorrhagic E. coli

<400> SEQUENCE: 64
atggtaatgc ctggattagt atcatatata tcatcgactt cattcgcgaa tgagatggcg       60
gagatgcgtc agcaggtaat ggaagggcag attggtggat ttctcctggg aggggagaga      120
gttagagttt cttatttatt tcaattgcat taa                                   153
```

```
<210> SEQ ID NO 65
<211> LENGTH: 576
<212> TYPE: DNA
<213> ORGANISM: Enterohemorrhagic E. coli

<400> SEQUENCE: 65
atgccattaa cctcagatat tagatcacat tcatttaatc ttggggtgga ggttgttcgt       60
gcccgaattg tagccaatgg gcgcggagat attacagtcg gtggtgaaac tgtcagtatt      120
gtgtatgatt ctactaatgg gcgcttttca tccagtggcg gtaatggcgg attgctttct      180
```

```
gagttattgc ttttgggatt taatagtggt cctcgagccc ttggtgagag aatgctaagt    240
atgctttcgg actcaggtga agcacaatcg caagagagta ttcagaacaa aatatctcaa    300
tgtaagtttt ctgtttgtcc agagagactt cagtgcccgc ttgaggctat tcagtgtcca    360
attacactgg agcagcctga aaaaggtatt tttgtgaaga attcagatgg ttcagatgta    420
tgtactttat ttgatgccgc tgcattttct cgtttggttg gtgaaggctt accccaccca    480
ctgacccggg aaccaataac ggcatcaata attgtaaaac atgaagaatg catttatgac    540
gataccagag gaaacttcat tataaagggt aattga                              576
```

<210> SEQ ID NO 66
<211> LENGTH: 630
<212> TYPE: DNA
<213> ORGANISM: Enterohemorrhagic E. coli
<220> FEATURE:
<221> NAME/KEY: misc_feature
<222> LOCATION: (439)..(439)
<223> OTHER INFORMATION: n = any nucleotide

<400> SEQUENCE: 66

```
atgcctgtta ccaccttaag tatcccaagt atatctcaat tatctcctgc aagagtacag     60
tctttgcagg atgcagccag acttgaaagt ggaataagaa tatccattgg tagtggccaa    120
tattctgttc actatgtcca actactggat ggattttcag ttgaaccggt gagaggaggc    180
ttactggata ggctattggg gcgtgagcat cgaatggata aagggctgt ggctctggaa     240 aggcaattaa atggaggtgt cgattttta agtagtgtta ataactattt tcagagtgtc    300
atggcagaac acagagaaaa taaaacaggt aataaaatat aatggaaaa aataaattct    360 tgtgtatttg gaacggattc taatcacttt tcttgcccgg agtcattttt gacatgcccg    420
ataacgctgg acacacctna gactggagtg ttcatgagaa actcacgagg tgctgagata    480
tgctctctat atgataagga tgcgttagtg caacttgttg aaactggtgg aactcatcct    540
ctgagtcgag aacctataac agaatcaatg attatgagaa aagacgaatg tcactttgat    600
gcaaaaagag aagcttttg ttgtaagtga                                      630
```

<210> SEQ ID NO 67
<211> LENGTH: 642
<212> TYPE: DNA
<213> ORGANISM: Enterohemorrhagic E. coli

<400> SEQUENCE: 67

```
atgcctgtag atttaacgcc ttatatttta cctggggtta gttttttgtc tgacattcct     60
caagaaacct tgtctgagat acgtaatcag actattcgtg gagaagctca gtaagactg    120 ggtgagttga tggtgtcaat acgacctatg caggtaaatg gatattttat gggaagtctt    180
aaccaggatg gtttatcgaa tgataacatc cagattggcc ttcaatatat agaacatatt    240
gaacgtacac ttaatcatgg tagtttgaca agccgtgaag ttacagtact gcgtgaaatt    300
gagatgctcg aaaatatgga attgctttct aactaccagt tagaggagtt gttagataaa    360
attgaagtat gtgcatttaa tgtggagcat gcacaattgc aagtgccaga gagcttacga    420
acatgccctg ttacattatg tgaaccagaa gatggggtat ttatgaggaa ttcaatgaat    480
tcaaatgttt gtatgttgta tgataaaatg tcattaatat atcttgttaa aacaagggcg    540
gctcatcctt tgagcaggga atcaatcgca gtttcaatga ttgtaggaag agataattgt    600
gcttttgact ctgacagagg taacttcgtt ttaaaaaatt aa                        642
```

```
<210> SEQ ID NO 68
<211> LENGTH: 642
<212> TYPE: DNA
<213> ORGANISM: Enterohemorrhagic E. coli

<400> SEQUENCE: 68
atgcctgtag atttaacgcc ttatatttta cctggggtta gttttttgtc tgacattcct     60
caagaaacct tgtctgagat acgtaatcag actattcgtg gagaagctca ataagactg     120 ggtgagttga tggtgtcaat acgacctatg caggtaaatg atatttat gggaagtctt     180 aaccaggatg gtttatcgaa tgataatatc cagattggcc ttcaatatat agaacatatt    240
gaacgtacac ttaatcatgg tagtttgaca agccgtgaag ttacagtact gcgtgaaatt    300
gagatgctcg aaaatatgga tttgcttctt aactaccagt tagaggagtt gttagataaa    360
attgaagtat gtgcatttaa tgtggagcat gcacaattgc aagtgccaga gagcttacga    420
acatgccctg ttacattatg tgaaccagaa gatggggtat ttatgaggaa ttcaatgaat    480
tcaaatgttt gtatgttgta tgataaaatg cattaatac atcttgttaa aacaaggggcg    540 gctcatcctt tgagcaggga atcaatcgca gtttcaatga ttgtaggaag agataattgt    600
gcttttgacc ctgacagagg taacttcgtt ttaaaaaatt aa                       642

<210> SEQ ID NO 69
<211> LENGTH: 630
<212> TYPE: DNA
<213> ORGANISM: Enterohemorrhagic E. coli

<400> SEQUENCE: 69
atgcctgtta ccaccttaag tatcccaagt atatctcaat tatctcctgc aggagtacag     60
tctttgcagg atgctgccag acttgaaagt ggaataagaa tatccattgg tagtggccaa    120
tattctgttc actatgtcca gctactggat ggattttcag ttgaaccggt gagaggaggc    180
ttactggata gctattggg gcgtgagcat cgaatggaga aagggctgt ggctctggaa      240 aggcaattaa atggaggtgt cgatttttta agtagtgtta ataactattt tcagagtgtc    300
atggcagaac acagagaaaa taaacaagt aataaaatat aatgaaaaa ataaattct       360 tgtttattta gacctgattc taatcactt tcttgcccgg agtcattttt gacatgcccg     420
ataacgctgg acacacctga gactggggtg ttcatgagaa actcacgagg tgctgagata    480
tgctctctat atgataagga cgcgttagtg caacttgttg aaactggtgg agctcatcct    540
ctgagtcgag aacctataac agaatcaatg attatgagaa aagatgaatg tcactttgat    600
acaaaaagag aagcttttg ttgtaagtga                                      630

<210> SEQ ID NO 70
<211> LENGTH: 576
<212> TYPE: DNA
<213> ORGANISM: Enterohemorrhagic E. coli

<400> SEQUENCE: 70
atgccattaa cctcagatat tagatcacat tcatttaatc ttggggtgga ggttgttcgt     60
gcccgaattg tagccaatgg gcgcggagat attacagtcg gtggtgaaac tgtcagtatt    120
gtgtatgatt ctactaatgg gcgcttttca tccagtggcg gtaatggcgg attgctttct    180
gagttattgc ttttgggatt taatagtggt cctcgagccc ttggtgagag aatgctaagt    240 atgcttttcgg actcaggtga agcacaatcg caagagagta ttcagaacaa atatctcaa    300 tgtaagttt ctgtttgtcc agagagactt cagtgcccgc ttgaggctat tcartgtcca    360
attacactgg agcagcctga aaaaggtatt tttgtgaaga attcagatgg ttcagatgta   420
```

-continued

```
tgtactttat tgatgccgc tgcattttct cgtttggttg gtgaaggctt acccccaccca    480 ctgacccggg aaccaataac ggcatcaata attgtaaaac atgaagaatg catttatgac    540
gataccagag gaaacttcgt tataaagggt aattga                              576
```

<210> SEQ ID NO 71
<211> LENGTH: 510
<212> TYPE: DNA
<213> ORGANISM: Enterohemorrhagic E. coli

<400> SEQUENCE: 71

```
atggacgctt ttattgtaga tcctgttcaa ggggaactat attcgggttt aagccataca    60
gaactagccg atatcattag attggctgat tctgttgaaa atcaattgaa tggaggcaat   120
tcatttcttg atgtattcag tacatatatg gggcaggtta tttctgaatt tatgcatagt   180
aatgataaca gaattgaatt gttacagcgg cgattacatt catgttcatt tttagttaat   240
attgaagaaa tgtcttacat agatgaagca ttacagtgcc cgattacgct ggcaattcct   300
caacgaggtg tttttttaag aaatgctgaa ggttccagag tatgtagttt atatgatgaa   360
atggctcttt ctcgtataat taatgatggg atgcatcacc cactaagcag agagccaata   420
acattatcaa tgcttgtggc cagagagcag tgtgagtttg attgcagtat cggtcacttt   480
acggtgagga gtgattgtta ttcagtgtag                                    510
```

<210> SEQ ID NO 72
<211> LENGTH: 231
<212> TYPE: DNA
<213> ORGANISM: Enterohemorrhagic E. coli

<400> SEQUENCE: 72

```
atggcagacc gcaaacagca ccgcgctatc gcggagcgtc gtcacatcca gactgaaatc    60
aaccgcagac tttcccgcgc atcacgcgtc gcgcaaatca tgcacatcaa tatgctgcat   120
gagcgcagcc acgcactatc aaacatttat tccgcctctg ttttcagcta tctggcggat   180
gatctgcacg agtttcaaca gctcatccag cagcaaaaca aactccatta a            231
```

<210> SEQ ID NO 73
<211> LENGTH: 176
<212> TYPE: PRT
<213> ORGANISM: Enterohemorrhagic E. coli

<400> SEQUENCE: 73

```
Met Asn Val Leu Arg Ala Gln Val Ala Ser Ser Gly Arg Gly Glu Phe
1               5                   10                  15

Thr Leu Gly Asn Glu Thr Val Ser Ile Val Phe Asn Glu Thr Asp Gly
            20                  25                  30

Arg Phe Leu Ser Ser Gly Ser Ser Gly Gly Leu Leu Thr Glu Leu Phe
        35                  40                  45

Leu Tyr Gly Phe Asn Asn Gly Pro Glu Ala Leu Arg Asp Arg Met Leu
    50                  55                  60

Ser Met Leu Ser Asp Ser Gly Glu Ala Gln Ser Gln Glu Ser Ile Gln
65                  70                  75                  80

Asp Lys Ile Ser Gln Cys Lys Phe Pro Val Ser Gly Asn Phe Gln
                85                  90                  95

Cys Pro Pro Glu Ser Ile Gln Cys Pro Ile Thr Leu Glu Arg Pro Glu
            100                 105                 110

Glu Gly Val Phe Val Lys Asn Ser Asp Ser Ser Ala Val Cys Cys Leu
        115                 120                 125
```

```
Phe Asp Phe Asp Ala Phe Ser Arg Leu Ala Ser Glu Gly Ser Tyr His
            130                 135                 140

Pro Leu Thr Arg Glu Pro Ile Thr Ala Ser Met Ile Ile Ser Pro Asp
145                 150                 155                 160

Lys Cys Val Tyr Asp Pro Ile Lys Gly Asn Phe Ile Ile Lys Asp Ser
                165                 170                 175

<210> SEQ ID NO 74
<211> LENGTH: 303
<212> TYPE: PRT
<213> ORGANISM: Enterohemorrhagic E. coli

<400> SEQUENCE: 74

Met Leu Ser Pro Ser Ile Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Ser Gly Thr Gln Val Thr Val Gly Asn
        35                  40                  45

Arg Thr Tyr Arg Val Val Thr Asp Asn Lys Phe Cys Val Thr Arg
50                  55                  60

Glu Ser His Ser Gly Cys Phe Thr Asn Leu Leu His Arg Leu Gly Trp
65                  70                  75                  80

Pro Lys Gly Glu Ile Ser Arg Lys Ile Glu Ala Met Leu Asn Thr Ser
                85                  90                  95

Pro Val Ser Thr Thr Ile Glu Arg Gly Ser Val His Ser Asn Arg Pro
            100                 105                 110

Asp Leu Pro Pro Val Asp Tyr Ala Gln Pro Glu Leu Pro Pro Ala Asp
        115                 120                 125

Tyr Thr Gln Ser Glu Leu Pro Arg Val Ser Asn Asn Lys Ser Pro Val
130                 135                 140

Pro Gly Asn Val Ile Gly Lys Gly Gly Asn Ala Val Val Tyr Glu Asp
145                 150                 155                 160

Met Glu Asp Thr Thr Lys Val Leu Lys Met Phe Thr Ile Ser Gln Ser
                165                 170                 175

His Glu Glu Val Thr Ser Glu Val Arg Cys Phe Asn Gln Tyr Tyr Gly
            180                 185                 190

Ser Gly Ser Ala Glu Lys Ile Tyr Asn Asp Asn Gly Asn Val Ile Gly
        195                 200                 205

Ile Arg Met Asn Lys Ile Asn Gly Glu Ser Leu Leu Asp Ile Pro Ser
210                 215                 220

Leu Pro Ala Gln Ala Glu Gln Ala Ile Tyr Asp Met Phe Asp Arg Leu
225                 230                 235                 240

Glu Lys Lys Gly Ile Leu Phe Val Asp Thr Thr Glu Thr Asn Val Leu
                245                 250                 255

Tyr Asp Arg Met Arg Asn Glu Phe Asn Pro Ile Asp Ile Ser Ser Tyr
            260                 265                 270

Asn Val Ser Asp Ile Ser Trp Ser Glu His Gln Val Met Gln Ser Tyr
        275                 280                 285

His Gly Gly Lys Leu Asp Leu Ile Ser Val Val Leu Ser Lys Ile
    290                 295                 300

<210> SEQ ID NO 75
<211> LENGTH: 293
<212> TYPE: PRT
<213> ORGANISM: Enterohemorrhagic E. coli
```

<400> SEQUENCE: 75

```
Met Leu Ser Pro Tyr Ser Val Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Asn Gly Ala Gln Val Lys Val Gly Asn
        35                  40                  45

Arg Thr Tyr Arg Val Val Ala Thr Asp Asn Lys Phe Cys Val Thr Arg
    50                  55                  60

Glu Ser His Ser Gly Cys Phe Thr Asn Leu Leu His Arg Leu Gly Trp
65                  70                  75                  80

Pro Lys Gly Glu Ile Ser Arg Lys Ile Glu Val Met Leu Asn Ala Ser
                85                  90                  95

Pro Val Ser Ala Ala Met Glu Arg Gly Ile Val His Ser Asn Arg Pro
            100                 105                 110

Asp Leu Pro Pro Val Asp Tyr Ala Pro Pro Glu Leu Pro Ser Val Asp
        115                 120                 125

Tyr Asn Arg Leu Ser Val Pro Gly Asn Val Ile Gly Lys Gly Gly Asn
    130                 135                 140

Ala Val Val Tyr Glu Asp Ala Glu Asp Ala Thr Lys Val Leu Lys Met
145                 150                 155                 160

Phe Thr Thr Ser Gln Ser Asn Glu Glu Val Thr Ser Glu Val Arg Cys
                165                 170                 175

Phe Asn Gln Tyr Tyr Gly Ala Gly Ser Ala Glu Lys Ile Tyr Gly Asn
            180                 185                 190

Asn Gly Asp Ile Ile Gly Ile Arg Met Asp Lys Ile Asn Gly Glu Ser
        195                 200                 205

Leu Leu Asn Ile Ser Ser Leu Pro Ala Gln Ala Glu His Ala Ile Tyr
    210                 215                 220

Asp Met Phe Asp Arg Leu Glu Gln Lys Gly Ile Leu Phe Val Asp Thr
225                 230                 235                 240

Thr Glu Thr Asn Val Leu Tyr Asp Arg Ala Lys Asn Glu Phe Asn Pro
                245                 250                 255

Ile Asp Ile Ser Ser Tyr Asn Val Ser Asp Arg Ser Trp Ser Glu Ser
            260                 265                 270

Gln Ile Met Gln Ser Tyr His Gly Gly Lys Gln Asp Leu Ile Ser Val
        275                 280                 285

Val Leu Ser Lys Ile
    290
```

<210> SEQ ID NO 76
<211> LENGTH: 50
<212> TYPE: PRT
<213> ORGANISM: Enterohemorrhagic E. coli

<400> SEQUENCE: 76

```
Met Val Met Pro Gly Leu Val Ser Tyr Ile Ser Ser Thr Ser Phe Ala
1               5                   10                  15

Asn Glu Met Ala Glu Met Arg Gln Gln Val Met Glu Gly Gln Ile Gly
            20                  25                  30

Gly Phe Leu Leu Gly Gly Glu Arg Val Arg Val Ser Tyr Leu Phe Gln
        35                  40                  45

Leu His
    50
```

<210> SEQ ID NO 77
<211> LENGTH: 191
<212> TYPE: PRT
<213> ORGANISM: Enterohemorrhagic E. coli

<400> SEQUENCE: 77

```
Met Pro Leu Thr Ser Asp Ile Arg Ser His Ser Phe Asn Leu Gly Val
1               5                   10                  15

Glu Val Val Arg Ala Arg Ile Val Ala Asn Gly Arg Gly Asp Ile Thr
            20                  25                  30

Val Gly Gly Glu Thr Val Ser Ile Val Tyr Asp Ser Thr Asn Gly Arg
        35                  40                  45

Phe Ser Ser Ser Gly Gly Asn Gly Gly Leu Leu Ser Glu Leu Leu Leu
    50                  55                  60

Leu Gly Phe Asn Ser Gly Pro Arg Ala Leu Gly Glu Arg Met Leu Ser
65                  70                  75                  80

Met Leu Ser Asp Ser Gly Glu Ala Gln Ser Gln Glu Ser Ile Gln Asn
                85                  90                  95

Lys Ile Ser Gln Cys Lys Phe Ser Val Cys Pro Glu Arg Leu Gln Cys
            100                 105                 110

Pro Leu Glu Ala Ile Gln Cys Pro Ile Thr Leu Glu Gln Pro Glu Lys
        115                 120                 125

Gly Ile Phe Val Lys Asn Ser Asp Gly Ser Asp Val Cys Thr Leu Phe
    130                 135                 140

Asp Ala Ala Ala Phe Ser Arg Leu Val Gly Glu Gly Leu Pro His Pro
145                 150                 155                 160

Leu Thr Arg Glu Pro Ile Thr Ala Ser Ile Ile Val Lys His Glu Glu
                165                 170                 175

Cys Ile Tyr Asp Asp Thr Arg Gly Asn Phe Ile Ile Lys Gly Asn
            180                 185                 190
```

<210> SEQ ID NO 78
<211> LENGTH: 209
<212> TYPE: PRT
<213> ORGANISM: Enterohemorrhagic E. coli
<220> FEATURE:
<221> NAME/KEY: MISC_FEATURE
<222> LOCATION: (147)..(147)
<223> OTHER INFORMATION: Xaa = any amino acid

<400> SEQUENCE: 78

```
Met Pro Val Thr Thr Leu Ser Ile Pro Ser Ile Ser Gln Leu Ser Pro
1               5                   10                  15

Ala Arg Val Gln Ser Leu Gln Asp Ala Ala Arg Leu Glu Ser Gly Ile
            20                  25                  30

Arg Ile Ser Ile Gly Ser Gly Gln Tyr Ser Val His Tyr Val Gln Leu
        35                  40                  45

Leu Asp Gly Phe Ser Val Glu Pro Val Arg Gly Gly Leu Leu Asp Arg
    50                  55                  60

Leu Leu Gly Arg Glu His Arg Met Asp Arg Arg Ala Val Ala Leu Glu
65                  70                  75                  80

Arg Gln Leu Asn Gly Gly Val Asp Phe Leu Ser Ser Val Asn Asn Tyr
                85                  90                  95

Phe Gln Ser Val Met Ala Glu His Arg Glu Asn Lys Thr Gly Asn Lys
            100                 105                 110
```

```
Ile Leu Met Glu Lys Ile Asn Ser Cys Val Phe Gly Thr Asp Ser Asn
            115                 120                 125

His Phe Ser Cys Pro Glu Ser Phe Leu Thr Cys Pro Ile Thr Leu Asp
        130                 135                 140

Thr Pro Xaa Thr Gly Val Phe Met Arg Asn Ser Arg Gly Ala Glu Ile
145                 150                 155                 160

Cys Ser Leu Tyr Asp Lys Asp Ala Leu Val Gln Leu Val Glu Thr Gly
                165                 170                 175

Gly Thr His Pro Leu Ser Arg Glu Pro Ile Thr Glu Ser Met Ile Met
                180                 185                 190

Arg Lys Asp Glu Cys His Phe Asp Ala Lys Arg Glu Ala Phe Cys Cys
            195                 200                 205

Lys
```

```
<210> SEQ ID NO 79
<211> LENGTH: 213
<212> TYPE: PRT
<213> ORGANISM: Enterohemorrhagic E. coli

<400> SEQUENCE: 79
```

```
Met Pro Val Asp Leu Thr Pro Tyr Ile Leu Pro Gly Val Ser Phe Leu
1               5                   10                  15

Ser Asp Ile Pro Gln Glu Thr Leu Ser Glu Ile Arg Asn Gln Thr Ile
            20                  25                  30

Arg Gly Glu Ala Gln Val Arg Leu Gly Glu Leu Met Val Ser Ile Arg
        35                  40                  45

Pro Met Gln Val Asn Gly Tyr Phe Met Gly Ser Leu Asn Gln Asp Gly
    50                  55                  60

Leu Ser Asn Asp Asn Ile Gln Ile Gly Leu Gln Tyr Ile Glu His Ile
65                  70                  75                  80

Glu Arg Thr Leu Asn His Gly Ser Leu Thr Ser Arg Glu Val Thr Val
                85                  90                  95

Leu Arg Glu Ile Glu Met Leu Glu Asn Met Glu Leu Leu Ser Asn Tyr
            100                 105                 110

Gln Leu Glu Glu Leu Leu Asp Lys Ile Glu Val Cys Ala Phe Asn Val
        115                 120                 125

Glu His Ala Gln Leu Gln Val Pro Glu Ser Leu Arg Thr Cys Pro Val
    130                 135                 140

Thr Leu Cys Glu Pro Glu Asp Gly Val Phe Met Arg Asn Ser Met Asn
145                 150                 155                 160

Ser Asn Val Cys Met Leu Tyr Asp Lys Met Ser Leu Ile Tyr Leu Val
                165                 170                 175

Lys Thr Arg Ala Ala His Pro Leu Ser Arg Glu Ser Ile Ala Val Ser
            180                 185                 190

Met Ile Val Gly Arg Asp Asn Cys Ala Phe Asp Ser Asp Arg Gly Asn
        195                 200                 205

Phe Val Leu Lys Asn
    210
```

```
<210> SEQ ID NO 80
<211> LENGTH: 213
<212> TYPE: PRT
<213> ORGANISM: Enterohemorrhagic E. coli
```

```
<400> SEQUENCE: 80

Met Pro Val Asp Leu Thr Pro Tyr Ile Leu Pro Gly Val Ser Phe Leu
1               5                   10                  15

Ser Asp Ile Pro Gln Glu Thr Leu Ser Glu Ile Arg Asn Gln Thr Ile
            20                  25                  30

Arg Gly Glu Ala Gln Ile Arg Leu Gly Glu Leu Met Val Ser Ile Arg
        35                  40                  45

Pro Met Gln Val Asn Gly Tyr Phe Met Gly Ser Leu Asn Gln Asp Gly
    50                  55                  60

Leu Ser Asn Asp Asn Ile Gln Ile Gly Leu Gln Tyr Ile Glu His Ile
65                  70                  75                  80

Glu Arg Thr Leu Asn His Gly Ser Leu Thr Ser Arg Glu Val Thr Val
                85                  90                  95

Leu Arg Glu Ile Glu Met Leu Glu Asn Met Asp Leu Leu Ser Asn Tyr
            100                 105                 110

Gln Leu Glu Glu Leu Leu Asp Lys Ile Glu Val Cys Ala Phe Asn Val
        115                 120                 125

Glu His Ala Gln Leu Gln Val Pro Glu Ser Leu Arg Thr Cys Pro Val
130                 135                 140

Thr Leu Cys Glu Pro Glu Asp Gly Val Phe Met Arg Asn Ser Met Asn
145                 150                 155                 160

Ser Asn Val Cys Met Leu Tyr Asp Lys Met Ala Leu Ile His Leu Val
                165                 170                 175

Lys Thr Arg Ala Ala His Pro Leu Ser Arg Glu Ser Ile Ala Val Ser
            180                 185                 190

Met Ile Val Gly Arg Asp Asn Cys Ala Phe Asp Pro Asp Arg Gly Asn
        195                 200                 205

Phe Val Leu Lys Asn
    210

<210> SEQ ID NO 81
<211> LENGTH: 209
<212> TYPE: PRT
<213> ORGANISM: Enterohemorrhagic E. coli

<400> SEQUENCE: 81

Met Pro Val Thr Thr Leu Ser Ile Pro Ser Ile Ser Gln Leu Ser Pro
1               5                   10                  15

Ala Gly Val Gln Ser Leu Gln Asp Ala Ala Arg Leu Glu Ser Gly Ile
            20                  25                  30

Arg Ile Ser Ile Gly Ser Gly Gln Tyr Ser Val His Tyr Val Gln Leu
        35                  40                  45

Leu Asp Gly Phe Ser Val Glu Pro Val Arg Gly Gly Leu Leu Asp Arg
    50                  55                  60

Leu Leu Gly Arg Glu His Arg Met Glu Arg Arg Ala Val Ala Leu Glu
65                  70                  75                  80

Arg Gln Leu Asn Gly Gly Val Asp Phe Leu Ser Ser Val Asn Asn Tyr
                85                  90                  95

Phe Gln Ser Val Met Ala Glu His Arg Glu Asn Lys Thr Ser Asn Lys
            100                 105                 110

Ile Leu Met Glu Lys Ile Asn Ser Cys Leu Phe Arg Pro Asp Ser Asn
        115                 120                 125

His Phe Ser Cys Pro Glu Ser Phe Leu Thr Cys Pro Ile Thr Leu Asp
    130                 135                 140
```

```
Thr Pro Glu Thr Gly Val Phe Met Arg Asn Ser Arg Gly Ala Glu Ile
145                 150                 155                 160

Cys Ser Leu Tyr Asp Lys Asp Ala Leu Val Gln Leu Val Glu Thr Gly
                165                 170                 175

Gly Ala His Pro Leu Ser Arg Glu Pro Ile Thr Glu Ser Met Ile Met
            180                 185                 190

Arg Lys Asp Glu Cys His Phe Asp Thr Lys Arg Glu Ala Phe Cys Cys
        195                 200                 205

Lys

<210> SEQ ID NO 82
<211> LENGTH: 191
<212> TYPE: PRT
<213> ORGANISM: Enterohemorrhagic E. coli

<400> SEQUENCE: 82

Met Pro Leu Thr Ser Asp Ile Arg Ser His Ser Phe Asn Leu Gly Val
1               5                   10                  15

Glu Val Val Arg Ala Arg Ile Val Ala Asn Gly Arg Gly Asp Ile Thr
            20                  25                  30

Val Gly Gly Glu Thr Val Ser Ile Val Tyr Asp Ser Thr Asn Gly Arg
        35                  40                  45

Phe Ser Ser Ser Gly Gly Asn Gly Gly Leu Leu Ser Glu Leu Leu Leu
    50                  55                  60

Leu Gly Phe Asn Ser Gly Pro Arg Ala Leu Gly Glu Arg Met Leu Ser
65                  70                  75                  80

Met Leu Ser Asp Ser Gly Glu Ala Gln Ser Gln Glu Ser Ile Gln Asn
                85                  90                  95

Lys Ile Ser Gln Cys Lys Phe Ser Val Cys Pro Glu Arg Leu Gln Cys
            100                 105                 110

Pro Leu Glu Ala Ile Gln Cys Pro Ile Thr Leu Glu Gln Pro Glu Lys
        115                 120                 125

Gly Ile Phe Val Lys Asn Ser Asp Gly Ser Asp Val Cys Thr Leu Phe
    130                 135                 140

Asp Ala Ala Ala Phe Ser Arg Leu Val Gly Glu Gly Leu Pro His Pro
145                 150                 155                 160

Leu Thr Arg Glu Pro Ile Thr Ala Ser Ile Ile Val Lys His Glu Glu
                165                 170                 175

Cys Ile Tyr Asp Asp Thr Arg Gly Asn Phe Val Ile Lys Gly Asn
            180                 185                 190

<210> SEQ ID NO 83
<211> LENGTH: 169
<212> TYPE: PRT
<213> ORGANISM: Enterohemorrhagic E. coli

<400> SEQUENCE: 83

Met Asp Ala Phe Ile Val Asp Pro Val Gln Gly Glu Leu Tyr Ser Gly
1               5                   10                  15

Leu Ser His Thr Glu Leu Ala Asp Ile Ile Arg Leu Ala Asp Ser Val
            20                  25                  30

Glu Asn Gln Leu Asn Gly Gly Asn Ser Phe Leu Asp Val Phe Ser Thr
        35                  40                  45

Tyr Met Gly Gln Val Ile Ser Glu Phe Met His Ser Asn Asp Asn Arg
    50                  55                  60

Ile Glu Leu Leu Gln Arg Arg Leu His Ser Cys Ser Phe Leu Val Asn
65                  70                  75                  80
```

-continued

```
Ile Glu Glu Met Ser Tyr Ile Asp Glu Ala Leu Gln Cys Pro Ile Thr
                 85                  90                  95

Leu Ala Ile Pro Gln Arg Gly Val Phe Leu Arg Asn Ala Glu Gly Ser
            100                 105                 110

Arg Val Cys Ser Leu Tyr Asp Glu Met Ala Leu Ser Arg Ile Ile Asn
        115                 120                 125

Asp Gly Met His His Pro Leu Ser Arg Glu Pro Ile Thr Leu Ser Met
    130                 135                 140

Leu Val Ala Arg Glu Gln Cys Glu Phe Asp Cys Ser Ile Gly His Phe
145                 150                 155                 160

Thr Val Arg Ser Asp Cys Tyr Ser Val
                165

<210> SEQ ID NO 84
<211> LENGTH: 76
<212> TYPE: PRT
<213> ORGANISM: Enterohemorrhagic E. coli

<400> SEQUENCE: 84

Met Ala Asp Arg Lys Gln His Arg Ala Ile Ala Glu Arg Arg His Ile
1               5                   10                  15

Gln Thr Glu Ile Asn Arg Arg Leu Ser Arg Ala Ser Arg Val Ala Gln
            20                  25                  30

Ile Met His Ile Asn Met Leu His Glu Arg Ser His Ala Leu Ser Asn
        35                  40                  45

Ile Tyr Ser Ala Ser Val Phe Ser Tyr Leu Ala Asp Asp Leu His Glu
    50                  55                  60

Phe Gln Gln Leu Ile Gln Gln Asn Lys Leu His
65                  70                  75
```